US010676475B2

(12) United States Patent
Slaugenhaupt et al.

(10) Patent No.: US 10,676,475 B2
(45) Date of Patent: Jun. 9, 2020

(54) COMPOUNDS FOR IMPROVING MRNA SPLICING

(71) Applicants: The General Hospital Corporation, Boston, MA (US); The United States of America, as Represented by the Secretary, Department of Health and Human Services, Bethesda, MD (US)

(72) Inventors: Susan A. Slaugenhaupt, Hignham, MA (US); Graham Johnson, Sanbornton, NH (US); William D. Paquette, Amsterdam, NY (US); Wei Zhang, Schenectady, NY (US); Juan Marugan, Gaithersburg, MD (US)

(73) Assignees: The General Hospital Corporation, Boston, MA (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/543,826

(22) PCT Filed: Jan. 15, 2016

(86) PCT No.: PCT/US2016/013553
§ 371 (c)(1),
(2) Date: Jul. 14, 2017

(87) PCT Pub. No.: WO2016/115434
PCT Pub. Date: Jul. 21, 2016

(65) Prior Publication Data
US 2018/0118748 A1    May 3, 2018

Related U.S. Application Data

(60) Provisional application No. 62/104,547, filed on Jan. 16, 2015, provisional application No. 62/180,380, filed on Jun. 16, 2015.

(51) Int. Cl.
| | | |
|---|---|---|
| *C07D 473/34* | (2006.01) | |
| *C07D 405/12* | (2006.01) | |
| *C07D 417/12* | (2006.01) | |
| *C07D 495/04* | (2006.01) | |
| *C07D 513/04* | (2006.01) | |
| *C07D 473/16* | (2006.01) | |
| *C07D 471/04* | (2006.01) | |
| *C07D 487/04* | (2006.01) | |
| *A61P 25/28* | (2006.01) | |

(52) U.S. Cl.
CPC ............ *C07D 473/34* (2013.01); *A61P 25/28* (2018.01); *C07D 405/12* (2013.01); *C07D 417/12* (2013.01); *C07D 471/04* (2013.01); *C07D 473/16* (2013.01); *C07D 487/04* (2013.01); *C07D 495/04* (2013.01); *C07D 513/04* (2013.01)

(58) Field of Classification Search
CPC .. C07D 473/34; C07D 405/12; C07D 417/12; C07D 471/04; C07D 473/16; C07D 495/04; C07D 513/04
See application file for complete search history.

(56) References Cited

U.S. PATENT DOCUMENTS

| | | |
|---|---|---|
| 3,037,980 A | 6/1962 | Hitchings et al. |
| 7,737,110 B2 | 6/2010 | Slaugenhaupt et al. |
| 8,258,144 B2 * | 9/2012 | Song .................... C07D 239/48 |
| | | 514/265.1 |
| 8,729,025 B2 | 5/2014 | Slaugenhaupt et al. |
| 2005/0153989 A1 | 7/2005 | Grotzfeld et al. |
| 2007/0191293 A1 | 8/2007 | Langston et al. |
| 2014/0330006 A1 | 11/2014 | Hanson et al. |

FOREIGN PATENT DOCUMENTS

| | | |
|---|---|---|
| EP | 3020829 | 5/2016 |
| JP | 2011-136925 | * 7/2011 |
| WO | WO 2005/03290 | 4/2005 |
| WO | WO 2008/006547 | 1/2008 |
| WO | WO 2010/038060 | 4/2010 |
| WO | WO 2010/090764 | 8/2010 |
| WO | WO 2010/118367 | 10/2010 |
| WO | WO 2011/041655 | 4/2011 |
| WO | WO 2014/124458 | 8/2014 |
| WO | WO 2016/011394 | 1/2016 |

OTHER PUBLICATIONS

Axelrod et al., "Kinetin improves IKBKAP mRNA splicing in patients with familial dysautonomia," Pediatric Research, Nov. 2011, 70(5):480-483.
Gold-von Simson et al., "Kinetin in Familial Dysautonomia Carriers: Implications for a New Therapeutic Strategy Targeting mRNA Splicing," Pediatric Research, 2009, 65(3):341-346.
International Preliminary Report on Patentability in International Application No. PCT/US2016/013553, dated Jul. 18, 2017, 7 pages.
International Search Report and Written Opinion in International Application No. PCT/US2016/013553, dated Jun. 17, 2017, 14 pages.
PubChem, Substance Record for SID 163507406, Create Date; Jun. 10, 2013. [retrieved on Mar. 16, 2016]. Retrieved from the Internet. <URL: https://pubchem.ncbi.nlm.nih.gov/substance/163507406> 5 pages.
Shetty et al., "Specific correction of a splice defect in brain by nutritional supplementation," Human Molecular Genetics, 2011, 20(21):4093-4101.
Yoshida et al., "Rectifier of aberrant mRNA splicing recovers tRNA modification in familial dysautonomia," PNAS, 2015, 112(9):2764-2769.

(Continued)

*Primary Examiner* — Rebecca L Anderson
(74) *Attorney, Agent, or Firm* — Fish & Richardson P.C.

(57) ABSTRACT

Provided herein are compounds useful for improving mRNA splicing in a cell. Exemplary compounds provided herein are useful for improving mRNA splicing in genes comprising at least one exon ending in the nucleotide sequence CAA. Methods for preparing the compounds and methods of treating diseases of the central nervous system are also provided.

5 Claims, 8 Drawing Sheets

Specification includes a Sequence Listing.

(56) References Cited

European Search Report in Application No. 16737944.5, dated Aug. 17, 2018, 18 pages.
Office Action in Israeli Application No. 253291, dated May 10, 2018, 8 pages.
Rivkin et al., "Purine derivatives as potent y-secretase modulators," Bioorganic & Medicinal Chemistry Letters, Apr. 2010, 20: 2279-2282.
Jorda et al., "Anti-leishmanial activity of disubstituted purines and related pyrazolo [4,3-d] pyrimidines," Bioorg Med Chem Lett. 2011, 21(14):4233-7.
Taiwan Search Report in Taiwanese Appln. No. 105101315, dated Dec. 13, 2019, 2 pages (with English translation).

* cited by examiner

```
                        SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: EXON19 Forward primer

<400> SEQUENCE: 1
cctgagcagc aatcatgtg                                                  19

<210> SEQ ID NO 2
<211> LENGTH: 20
<212> TYPE: DNA
<213> ORGANISM: Artificial Sequence
<220> FEATURE:
<223> OTHER INFORMATION: EXON23 Reverse primer

<400> SEQUENCE: 2
tacatggtct tcgtgacatc                                                 20

<210> SEQ ID NO 3
<211> LENGTH: 9801
<212> TYPE: DNA
<213> ORGANISM: Artificial Sequence
<220> FEATURE:
<223> OTHER INFORMATION: pcDNA3.1/V5HisTOPO with Renilla-Familial
```

Dysautonomia-Firefly

<400> SEQUENCE: 3

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttggt accgagctcg gatccggtac tgttggtaaa gccaccatgg cttccaaggt     960 gtacgaccc gagcaacgca aacgcatgat cactgggcct cagtggtggg ctcgctgcaa    1020
gcaaatgaac gtgctggact ccttcatcaa ctactatgat ccgagaagc acgccgagaa    1080 cgccgtgatt tttctgcatg gtaacgctgc ctccagctac ctgtggaggc acgtcgtgcc    1140
tcacatcgag cccgtggcta gatgcatcat ccctgatctg atcggaatgg gtaagtccgg    1200
caagagcggg aatggctcat atcgcctcct ggatcactac aagtacctca ccgcttggtt    1260
cgagctgctg aaccttccaa agaaaatcat ctttgtgggc cacgactggg gggcttgtct    1320 ggccttcac tactcctacg agcaccaaga caagatcaag gccatcgtcc atgctgagag    1380
tgtcgtggac gtgatcgagt cctgggacga gtggcctgac atcgaggagg atatcgccct    1440
gatcaagagc gaagagggcg agaaaatggt gcttgagaat aacttcttcg tcgagaccat    1500
gctcccaagc aagatcatgc ggaaactgga gcctgaggag ttcgctgcct acctggagcc    1560
attcaaggag aagggcgagg ttagacggcc taccctctcc tggcctcgcg agatccctct    1620
cgttaaggga ggcaagcccg acgtcgtcca gattgtccgc aactacaacg cctaccttcg    1680
ggccagcgac gatctgccta gatgttcat cgagtccgac cctgggttct tttccaacgc    1740
tattgtcgag ggagctaaga gttccctaa caccgagttc gtgaaggtga agggcctcca    1800
cttcagccag gaggacgctc cagatgaaat gggtaagtac atcaagagct tcgtggagcg    1860
cgtgctgaag aacgagcagg gatccactag tccaatgtgg tggaattgcc cttcattaca    1920
ggccggcctg agcagcaatc atgtgtccca tgggaagtt ctgcggaaag tggagagggg    1980
ttcacggatt gtcactgttg tgccccagga cacaaagctt gtattacagg taagctggtt    2040
tttcagacaa gatagatagt ctgattgtca ttcagccaag taccaagcat aattcttgca    2100
ggttgtattt taggctttct tattctttgt atcgtttatt gtaaaccttt ccttgatagt    2160
tttctgttag ctttattcaa aggagtgttg atacaggctg tgaccataag gctcaaagcg    2220
aaacttttct tgaaagtcaa gataaatata gagaacaaca agattctgct aaaagtgtgc    2280
```

```
tgatttttaga gagttgtggt aattctctgt gaagagttag gtaaaatggt gtatcctggc    2340
tatttaaatg tttctactt aattaaaaat gttactgctt taatttattt aagatgccaa    2400
ggggaaactt agaagttgtt catcatcgag ccctggtttt agctcagatt cggaagtggt    2460
tggacaagta agcgccattg tactgttttgc gactagttag cttgtgattt atgtgtgaag    2520
acaataagta ttttattaca atttcgagaa cttaaaatta tgaaaagccc tcattaccta    2580
tatcatcaat cagattctta gaggctcttt tttttttttt taacttttt actttaatgc    2640 agtattttgt agtggagatt cctagcagaa agaatcgtga cactcatcat ataaaggagg    2700
gcttctctta acctgaggga acacatgtgg gttttaggtg gcctgtgaac ccagggagat    2760
tgtacacacc aaaccttgtc tttgtgtatt tattcaagta gaaagcccac agctttcaat    2820
agatttacag cggggcctat gacccagaaa agcctgagct actcttgtga aggaaatgac    2880
tgattttctg aacctatttg gaggaaactt tgtattggaa agatctatac taatgttttg    2940
tttaaaaagt agacctgaat tccatgatga ttttctttgt ttttttttg agacagagtc    3000 ttgctctgtc acccaggctg gagtacagtg gcgcaatctc ggcttactgc aacctctgcc    3060
ttctgggttc aagcaatcct cccacttcag cctcccgcat agctaggatt acaggtgtgc    3120
accacgcctg gctaattttt tttttgtat tttcagtaga cagggtttt caccatgttg    3180 gccaggctgg tctcaaactc ctgacctcaa gtgttctgcc cacctcggcc tcccaaagtg    3240
ctaggattac aggtgtgaac caccgtgccc gggcttctgt aatgattttc tgttgtatgt    3300
atgtgaagat gtagttctca gacagtcatg atgactaaat tacacctttt aagaaggtaa    3360
atgaatgtgg tacctgattt ttttattctg taatttcaga gtagaaatcc agtgatagca    3420
gcttggcatt ggggctgtaa tctgattata actggttgt atcataatga aaatatgctg    3480
ggcccatgga gctcagtttt tgtgaatatc ttttctattc tttctctgtc ttctcacaga    3540
cttatgttta aagaggcatt tgaatgcatg agaaagctga gaatcaatct caatctgatt    3600
tatgatcata accctaagct ggaagatgcc aaaaacatta agaagggccc agcgccattc    3660
tacccactcg aagacgggac cgccggcgag cagctgcaca aagccatgaa gcgctacgcc    3720
ctggtgcccg gcaccatcgc ctttaccgac gcacatatcg aggtggacat tacctacgcc    3780
gagtacttcg agatgagcgt tcggctggca gaagctatga gcgctatgg gctgaataca    3840 aaccatcgga tcgtggtgtg cagcgagaat agcttgcagt tcttcatgcc cgtgttgggt    3900
gccctgttca tcggtgtggc tgtggcccca gctaacgaca tctacaacga gcgcgagctg    3960
ctgaacagca tgggcatcag ccagcccacc gtcgtattcg tgagcaagaa agggctgcaa    4020
aagatcctca acgtgcaaaa gaagctaccg atcatacaaa agatcatcat catggatagc    4080
aagaccgact accagggctt ccaaagcatg tacacctcg tgacttccca tttgccaccc    4140
ggcttcaacg agtacgactt cgtgcccgag agcttcgacc gggacaaaac catcgccctg    4200
atcatgaaca gtagtggcag taccggattg cccaagggcg tagccctacc gcaccgcacc    4260
gcttgtgtcc gattcagtca tgcccgcgac cccatcttcg gcaaccagat catccccgac    4320
accgctatcc tcagcgtggt gccatttcac cacggcttcg gcatgttcac cacgctgggc    4380
tacttgatct gcggctttcg ggtcgtgctc atgtaccgct tcgaggagga gctattcttg    4440
cgcagcttgc aagactataa gattcaatct gccctgctgg tgcccacact atttagcttc    4500
ttcgctaaga gcactctcat cgacaagtac gacctaagca acttgcacga gatcgccagc    4560
ggcggggcgc cgctcagcaa ggaggtaggt gaggccgtgg ccaaacgctt ccacctacca    4620
```

```
ggcatccgcc agggctacgg cctgacagaa acaaccagcg ccattctgat caccccgaa   4680
ggggacgaca agcctggcgc agtaggcaag gtggtgccct tcttcgaggc taaggtggtg   4740
gacttggaca ccggtaagac actgggtgtg aaccagcgcg gcgagctgtg cgtccgtggc   4800
cccatgatca tgagcggcta cgttaacaac cccgaggcta caaacgctct catcgacaag   4860
gacggctggc tgcacagcgg cgacatcgcc tactgggacg aggacgagca cttcttcatc   4920
gtggaccggc tgaagagcct gatcaaatac aagggctacc aggtagcccc agccgaactg   4980
gagagcatcc tgctgcaaca ccccaacatc ttcgacgccg gggtcgccgg cctgcccgac   5040
gacgatgccg cgagctgcc cgccgcagtc gtcgtgctgg aacacggtaa aaccatgacc   5100
gagaaggaga tcgtggacta tgtggccagc caggttacaa ccgccaagaa gctgcgcggt   5160
ggtgttgtgt tcgtggacga ggtgcctaaa ggactgaccg gcaagttgga cgcccgcaag   5220
atccgcgaga ttctcattaa ggccaagaag ggcggcaaga tcgccgtgta ataattctag   5280
agggcccgcg gttcgaaggt aagcctatcc ctaaccctct cctcggtctc gattctacgc   5340
gtaccggtca tcatcaccat caccattgag tttaaacccg ctgatcagcc tcgactgtgc   5400
cttctagttg ccagccatct gttgtttgcc cctcccccgt gccttccttg accctggaag   5460
gtgccactcc cactgtcctt tcctaataaa atgaggaaat tgcatcgcat tgtctgagta   5520
ggtgtcattc tattctgggg ggtggggtgg ggcaggacag caaggggagg attgggaag a   5580
acaatagcag gcatgctggg gatgcggtgg gctctatggc ttctgaggcg aaagaacca    5640
gctgggggctc taggggtat ccccacgcgc cctgtagcgg cgcattaagc gcggcgggtg    5700
tggtggttac gcgcagcgtg accgctacac ttgccagcgc cctagcgccc gctcctttcg    5760
ctttcttccc ttccttttctc gccacgttcg ccggcttttcc ccgtcaagct ctaaatcggg   5820
gcatcccttt agggttccga tttagtgctt tacggcacct cgaccccaaa aaacttgatt   5880
agggtgatgg ttcacgtagt gggccatcgc cctgatagac ggtttttcgc cctttgacgt   5940
tggagtccac gttctttaat agtggactct tgttccaaac tggaacaaca ctcaacccta   6000
tctcggtcta ttcttttgat ttataaggga ttttggggat ttcggcctat tggttaaaaa   6060
atgagctgat ttaacaaaaa tttaacgcga attaattctg tggaatgtgt gtcagttagg   6120
gtgtggaaag tccccaggct ccccaggcag gcagaagtat gcaaagcatg catctcaatt   6180
agtcagcaac caggtgtgga aagtccccag gctccccagc aggcagaagt atgcaaagca   6240
tgcatctcaa ttagtcagca accatagtcc cgcccctaac tccgcccatc ccgcccctaa   6300
ctccgcccag ttccgcccat tctccgcccc atggctgact aatttttttt atttatgcag   6360
aggccgaggc cgcctctgcc tctgagctat tccagaagta gtgaggaggc ttttttggag   6420
gcctaggctt ttgcaaaaag ctcccgggag cttgtatatc catttttcgga tctgatcaag   6480
agacaggatg aggatcgttt cgcatgattg aacaagatgg attgcacgca ggttctccgg   6540
ccgcttgggt ggagaggcta ttcggctatg actgggcaca acagacaatc ggctgctctg   6600
atgccgccgt gttccggctg tcagcgcagg ggcgcccggt tctttttgtc aagaccgacc   6660
tgtccggtgc cctgaatgaa ctgcaggacg aggcagcgcg gctatcgtgg ctggccacga   6720
cgggcgttcc ttgcgcagct gtgctcgacg ttgtcactga agcgggaagg gactggctgc   6780
tattgggcga agtgccgggg caggatctcc tgtcatctca ccttgctcct gccgagaaag   6840
tatccatcat ggctgatgca atgcggcggc tgcatacgct tgatccggct acctgcccat   6900
tcgaccacca agcgaaacat cgcatcgagc gagcacgtac tcggatgaa gccggtcttg   6960
tcgatcagga tgatctggac gaagagcatc aggggctcgc gccagccgaa ctgttcgcca   7020
```

```
ggctcaaggc gcgcatgccc gacggcgagg atctcgtcgt gacccatggc gatgcctgct    7080
tgccgaatat catggtggaa aatggccgct tttctggatt catcgactgt ggccggctgg    7140
gtgtggcgga ccgctatcag gacatagcgt tggctacccg tgatattgct gaagagcttg    7200
gcggcgaatg gctgaccgc ttcctcgtgc tttacggtat cgccgctccc gattcgcagc     7260
gcatcgcctt ctatcgcctt cttgacgagt tcttctgagc gggactctgg ggttcgcgaa    7320
atgaccgacc aagcgacgcc caacctgcca tcacgagatt tcgattccac cgccgccttc    7380
tatgaaaggt tgggcttcgg aatcgttttc cgggacgccg gctggatgat cctccagcgc    7440
ggggatctca tgctggagtt cttcgcccac cccaacttgt ttattgcagc ttataatggt    7500
tacaaataaa gcaatagcat cacaaatttc acaaataaag cattttttc actgcattct     7560 agttgtggtt tgtccaaact catcaatgta tcttatcatg tctgtatacc gtcgacctct    7620
agctagagct tggcgtaatc atggtcatag ctgtttcctg tgtgaaattg ttatccgctc    7680
acaattccac acaacatacg agccggaagc ataaagtgta aagccggggg tgcctaatga    7740
gtgagctaac tcacattaat tgcgttgcgc tcactgcccg ctttccagtc gggaaacctg    7800
tcgtgccagc tgcattaatg aatcggccaa cgcgcgggga gaggcggttt gcgtattggg    7860
cgctcttccg cttcctcgct cactgactcg ctgcgctcgg tcgttcggct gcggcgagcg    7920
gtatcagctc actcaaaggc ggtaatacgg ttatccacag aatcagggga taacgcagga    7980
aagaacatgt gagcaaaagg ccagcaaaag gccaggaacc gtaaaaaggc cgcgttgctg    8040 gcgttttttcc ataggctccg ccccctgac gagcatcaca aaaatcgacg ctcaagtcag    8100
aggtggcgaa acccgacagg actataaaga taccaggcgt ttccccctgg aagctccctc    8160
gtgcgctctc ctgttccgac cctgccgctt accggatacc tgtccgcctt tctcccttcg    8220
ggaagcgtgg cgctttctca atgctcacgc tgtaggtatc tcagttcggt gtaggtcgtt    8280
cgctccaagc tgggctgtgt gcacgaaccc ccgttcagc ccgaccgctg cgccttatcc      8340
ggtaactatc gtcttgagtc aacccggta agacacgact tatcgccact ggcagcagcc     8400
actggtaaca ggattagcag agcgaggtat gtaggcggtg ctacagagtt cttgaagtgg    8460
tggcctaact acggctacac tagaaggaca gtatttggta tctgcgctct gctgaagcca    8520
gttaccttcg gaaaaagagt tggtagctct tgatccggca aacaaaccac cgctggtagc    8580
ggtggttttt ttgtttgcaa gcagcagatt acgcgcagaa aaaaggatc tcaagaagat     8640 cctttgatct tttctacggg gtctgacgct cagtggaacg aaaactcacg ttaagggatt    8700
ttggtcatga gattatcaaa aaggatcttc acctagatcc ttttaaatta aaaatgaagt    8760
tttaaatcaa tctaaagtat atatgagtaa acttggtctg acagttacca atgcttaatc    8820
agtgaggcac ctatctcagc gatctgtcta tttcgttcat ccatagttgc ctgactcccc    8880
gtcgtgtaga taactacgat acgggagggc ttaccatctg gccccagtgc tgcaatgata    8940
ccgcgagacc cacgctcacc ggctccagat ttatcagcaa taaaccagcc agccggaagg    9000
gccgagcgca gaagtggtcc tgcaacttta tccgcctcca tccagtctat taattgttgc    9060
cgggaagcta gagtaagtag ttcgccagtt aatagtttgc gcaacgttgt tgccattgct    9120
acaggcatcg tggtgtcacg ctcgtcgttt ggtatggctt cattcagctc cggttcccaa    9180
cgatcaaggc gagttacatg atcccccatg ttgtgcaaaa aagcggttag ctccttcggt    9240
cctccgatcg ttgtcagaag taagttggcc gcagtgttat cactcatggt tatggcagca    9300
ctgcataatt ctcttactgt catgccatcc gtaagatgct tttctgtgac tggtgagtac    9360
```

-continued

```
tcaaccaagt cattctgaga atagtgtatg cggcgaccga gttgctcttg cccggcgtca   9420
atacgggata ataccgcgcc acatagcaga actttaaaag tgctcatcat tggaaaacgt   9480 tcttcgggc gaaaactctc aaggatctta ccgctgttga gatccagttc gatgtaaccc    9540
actcgtgcac ccaactgatc ttcagcatct tttactttca ccagcgtttc tgggtgagca   9600
aaaacaggaa ggcaaaatgc cgcaaaaaag ggaataaggg cgacacggaa atgttgaata   9660
ctcatactct cctttttca atattattga agcatttatc agggttattg tctcatgagc    9720
ggatacatat ttgaatgtat ttagaaaaat aaacaaatag gggttccgcg cacatttccc   9780
cgaaaagtgc cacctgacgt c                                             9801
```

```
<210> SEQ ID NO 4
<211> LENGTH: 20
<212> TYPE: DNA
<213> ORGANISM: Artificial Sequence
<220> FEATURE:
<223> OTHER INFORMATION: T7 promoter/priming site

<400> SEQUENCE: 4
taatacgact cactataggg                                                 20

<210> SEQ ID NO 5
<211> LENGTH: 19
<212> TYPE: DNA
<213> ORGANISM: Artificial Sequence
<220> FEATURE:
<223> OTHER INFORMATION: Primer (Luciferase) 146Rev

<400> SEQUENCE: 5
ctcggcgtag gtaatgtcc                                                  19

<210> SEQ ID NO 6
<211> LENGTH: 19
<212> TYPE: DNA
<213> ORGANISM: Artificial Sequence
<220> FEATURE:
<223> OTHER INFORMATION: Primer (Luciferase) 146Rev On Sequence

<400> SEQUENCE: 6
ggacattacc tacgccgag                                                  19

<210> SEQ ID NO 7
<211> LENGTH: 116
<212> TYPE: DNA
<213> ORGANISM: Homo sapiens
<220> FEATURE:
<221> NAME/KEY: misc_feature
<223> OTHER INFORMATION: Exon 19

<400> SEQUENCE: 7
cattacaggc cggcctgagc agcaatcatg tgtcccatgg ggaagttctg cggaaagtgg    60 agagggttc acgattgtc actgttgtgc cccaggacac aaagcttgta ttacag         116

<210> SEQ ID NO 8
<211> LENGTH: 363
<212> TYPE: DNA
<213> ORGANISM: Homo sapiens
<220> FEATURE:
<221> NAME/KEY: misc_feature
<223> OTHER INFORMATION: Intron between Exon 19 and Exon 20

<400> SEQUENCE: 8
taagctggtt tttcagacaa gatagatagt ctgattgtca ttcagccaag taccaagcat    60
```

```
aattcttgca ggttgtatttt taggctttct tattctttgt atcgtttatt gtaaacettt    120 cottgatagt tttctgttag ctttattcaa aggagtgttg atacaggctg tgaccataag    180
gctcaaagcg aaacttttct tgaaagtcaa gataaatata gagaacaaca agattctgct    240
aaaagtgtgc tgattttaga gagttgtggt aattctctgt gaagagttag gtaaaatggt    300
gtatcctggc tatttaaatg ttttctactt aattaaaaat gttactgctt taatttattt    360
aag                                                                  363
```

<210> SEQ ID NO 9
<211> LENGTH: 74
<212> TYPE: DNA
<213> ORGANISM: Homo sapiens
<220> FEATURE:
<221> NAME/KEY: misc_feature
<223> OTHER INFORMATION: Exon 20

<400> SEQUENCE: 9

```
atgccaaggg gaaacttaga agttgttcat catcgagccc tggttttagc tcagattcgg    60
aagtggttgg acaa                                                      74
```

<210> SEQ ID NO 10
<211> LENGTH: 1072
<212> TYPE: DNA
<213> ORGANISM: Homo sapiens
<220> FEATURE:
<221> NAME/KEY: misc_feature
<223> OTHER INFORMATION: Intron between Exon 20 and Exon 21

<400> SEQUENCE: 10

```
gtaagcgcca ttgtactgtt tgcgactagt tagcttgtga tttatgtgtg aagacaataa    60
gtattttatt acaatttcga gaacttaaaa ttatgaaaag ccctcattac ctatatcatc    120
aatcagattc ttagaggctc tttttttttt ttttaacttt tttactttaa tgcagtattt    180
tgtagtggag attcctagca gaaagaatcg tgacactcat catataaagg agggcttctc    240
ttaacctgag ggaacacatg tgggttttag gtggcctgtg aacccaggga gattgtacac    300 accaaaccett gtctttgtgt attttattcaa gtagaaagcc cacagctttc aatagattta    360
cagcggggcc tatgacccag aaaagcctga gctactcttg tgaaggaaat gactgatttt    420
ctgaacctat ttggaggaaa cttttgtattg gaaagatcta tactaatgtt ttgtttaaaa    480
agtagacctg aattccatga tgatttttctt tgttttttttt ttgagacaga gtcttgctct    540
gtcacccagg ctggagtaca gtggcgcaat ctcggcttac tgcaacctct gccttctggg    600
ttcaagcaat cctcccactt cagcctcccg catagctagg attacaggtg tgcaccacgc    660
ctggctaatt ttttttttttg tattttcagt agagacaggg tttcaccatg ttggccaggc    720
tggtctcaaa ctcctgacct caagtgttct gcccacctcg gcctcccaaa gtgctaggat    780
tacaggtgtg aaccaccgtg cccgggcttc tgtaatgatt ttctgttgta tgtatgtgaa    840
gatgtagttc tcagacagtc atgatgacta aattcacect tttaagaagg taaatgaatg    900
tggtacctga ttttttttatt ctgtaatttc agagtagaaa tccagtgata gcagcttggc    960
attggggctg taatctgatt ataactggtt tgtatcataa tgaaaatatg ctgggcccat    1020
ggagctcagt ttttgtgaat atcttttcta ttctttctct gtcttctcac ag            1072
```

<210> SEQ ID NO 11
<211> LENGTH: 79
<212> TYPE: DNA

<213> ORGANISM: Homo sapiens
<220> FEATURE:
<221> NAME/KEY: misc_feature
<223> OTHER INFORMATION: Exon 21

<400> SEQUENCE: 11

```
acttatgttt aaagaggcat ttgaatgcat gagaaagctg agaatcaatc tcaatctgat    60
ttatgatcat aaccctaag                                                 79
```

<210> SEQ ID NO 12
<211> LENGTH: 269
<212> TYPE: DNA
<213> ORGANISM: Homo sapiens
<220> FEATURE:
<221> NAME/KEY: misc_feature
<223> OTHER INFORMATION: Exons 19-20-21

<400> SEQUENCE: 12

```
cattacaggc cggcctgagc agcaatcatg tgtcccatgg ggaagttctg cggaaagtgg    60
agaggggttc acggattgtc actgttgtgc cccaggacac aaagcttgta ttacagatgc   120
caaggggaaa cttagaagtt gttcatcatc gagccctggt tttagctcag attcggaagt   180
ggttggacaa acttatgttt aaagaggcat ttgaatgcat gagaaagctg agaatcaatc   240
tcaatctgat ttatgatcat aaccctaag                                    269
```

<210> SEQ ID NO 13
<211> LENGTH: 939
<212> TYPE: DNA
<213> ORGANISM: Renilla reniformis
<220> FEATURE:
<221> NAME/KEY: misc_feature
<223> OTHER INFORMATION: RENILLA LUCIFERASE

<400> SEQUENCE: 13

```
atggcttcca aggtgtacga ccccgagcaa cgcaaacgca tgatcactgg gcctcagtgg    60
tgggctcgct gcaagcaaat gaacgtgctg gactccttca tcaactacta tgattccgag   120
aagcacgccg agaacgccgt gattttttctg catggtaacg ctgcctccag ctacctgtgg   180
aggcacgtcg tgcctcacat cgagcccgtg gctagatgca tcatccctga tctgatcgga   240
atgggtaagt ccggcaagag cgggaatggc tcatatcgcc tcctggatca ctacaagtac   300
ctcaccgctt ggttcgagct gctgaacctt ccaaagaaaa tcatctttgt gggccacgac   360
tggggggctt gtctggcctt tcactactcc tacgagcacc aagacaagat caaggccatc   420
gtccatgctg agagtgtcgt ggacgtgatc gagtcctggg acgagtggcc tgacatcgag   480
gaggatatcg ccctgatcaa gagcgaagag ggcgagaaaa tggtgcttga gaataacttc   540
ttcgtcgaga ccatgctccc aagcaagatc atgcggaaac tggagcctga ggagttcgct   600
gcctacctgg agccattcaa ggagaagggc gaggttagac ggcctaccct ctcctggcct   660
cgcgagatcc ctctcgttaa gggaggcaag cccgacgtcg tccagattgt ccgcaactac   720
aacgcctacc ttcgggccag cgacgatctg cctaagatgt tcatcgagtc cgaccctggg   780
ttcttttcca acgctattgt cgagggagct aagaagttcc ctaacaccga gttcgtgaag   840
gtgaagggcc tccacttcag ccaggaggac gctccagatg aaatgggtaa gtacatcaag   900
agcttcgtgg agcgcgtgct gaagaacgag cagggatcc                          939
```

<210> SEQ ID NO 14
<211> LENGTH: 1653
<212> TYPE: DNA

<213> ORGANISM: Artificial Sequence
<220> FEATURE:
<223> OTHER INFORMATION: FIREFLY LUCIFERASE (with Mutation ATG-CTG base 3619)

<400> SEQUENCE: 14

```
ctggaagatg ccaaaaacat taagaagggc ccagcgccat tctacccact cgaagacggg      60
accgccggcg agcagctgca caaagccatg aagcgctacg ccctggtgcc cggcaccatc     120
gcctttaccg acgcacatat cgaggtggac attacctacg ccgagtactt cgagatgagc     180
gttcggctgg cagaagctat gaagcgctat gggctgaata caaaccatcg gatcgtggtg     240
tgcagcgaga atagcttgca gttcttcatg cccgtgttgg gtgccctgtt catcggtgtg     300
gctgtggccc cagctaacga catctacaac gagcgcgagc tgctgaacag catgggcatc     360
agccagccca ccgtcgtatt cgtgagcaag aaagggctgc aaaagatcct caacgtgcaa     420
aagaagctac cgatcataca aaagatcatc atcatggata gcaagaccga ctaccagggc     480
ttccaaagca tgtacacctt cgtgacttcc catttgccac ccggcttcaa cgagtacgac     540
ttcgtgcccg agagcttcga ccgggacaaa accatcgccc tgatcatgaa cagtagtggc     600
agtaccggat tgcccaaggg cgtagcccta ccgcaccgca ccgcttgtgt ccgattcagt     660
catgcccgcg accccatctt cggcaaccag atcatccccg acaccgctat cctcagcgtg     720
gtgccatttc accacggctt cggcatgttc accacgctgg gctacttgat ctgcggcttt     780
cgggtcgtgc tcatgtaccg cttcgaggag gagctattct gcgcagcttt gcaagactat     840
aagattcaat ctgccctgct ggtgcccaca ctatttagct tcttcgctaa gagcactctc     900
atcgacaagt acgacctaag caacttgcac gagatcgcca gcggcggggc gccgctcagc     960
aaggaggtag gtgaggccgt ggccaaacgc ttccacctac caggcatccg ccagggctac    1020
ggcctgacag aaacaaccag cgccattctg atcaccccgg aagggacga caagcctggc    1080
gcagtaggca aggtggtgcc cttcttcgag gctaaggtgg tggacttgga caccggtaag    1140
acactgggtg tgaaccagcg cggcgagctg tgcgtccgtg gccccatgat catgagcggc    1200
tacgttaaca accccgaggc tacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380
caccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg gtggtgttgt gttcgtggac    1560
gaggtgccta aaggactgac cggcaagttg gacgcccgca agatccgcga gattctcatt    1620
aaggccaaga agggcggcaa gatcgccgtg taa                                1653
```

COMPOUNDS FOR IMPROVING MRNA SPLICING

CROSS REFERENCE TO RELATED APPLICATIONS

This application is a 371 U.S. National Phase Application of PCT/US2016/013553, filed on Jan. 15, 2016, which claims the benefit of United States Provisional Application Nos. 62/104,547, filed Jan. 16, 2015, and 62/180,380, filed Jun. 16, 2015, the disclosures of each of which are incorporated herein by reference in their entirety.

FEDERALLY SPONSORED RESEARCH OR DEVELOPMENT

This invention was made with Government support under Grant No. U01NS078025, awarded by the National Institutes of Health. The Government has certain rights in the invention.

TECHNICAL FIELD

The present disclosure relates to compounds for treating disorders associated with misspliced mRNA, and more particularly to kinetin derivatives for treating familial dysautonomia in a patient in need thereof.

BACKGROUND

Familial dysautonomia (FD) (MIM #2239001), also known as Riley Day syndrome or hereditary sensory and autonomic neuropathy III (HSAN-III), is the best-known and most common member of a group of congenital sensory and autonomic neuropathies (HSAN) characterized by widespread sensory and variable autonomic dysfunction. FD affects neuronal development and is associated with progressive neuronal degeneration. Multiple systems are impacted resulting in a markedly reduced quality of life and premature death. FD is caused by mutations in the IKBKAP gene and all cases described to date involve an intron 20 mutation that results in a unique pattern of tissue-specific exon skipping.

See also, for example, Shetty et al. *Human Molecular Genetics,* 2011, 20(21):4093-4101; Axelrod et al. *Pediatric Research,* 2011, 70(5):480-483; Gold-von Simson et al. *Pediatric Research,* 2009, 65(3):341-346; Yoshida et al. *PNAS,* 2015, 112(9):2764-2769; and International Patent Application Nos. WO 2015/005491, WO 2010/118367, and WO 2014/124458, the disclosures of each of which are incorporated by reference herein in their entireties.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

SUMMARY

The present application provides compounds of Formula (I):

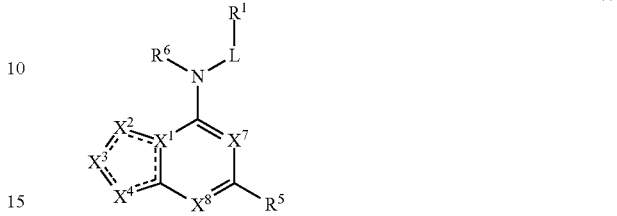

or a pharmaceutically acceptable salt thereof, wherein:
$X^1$ is N or C;
$X^2$ is selected from the group consisting of S, N, $NR^2$, $CR^2$, and $CHR^2$;
$X^3$ is selected from the group consisting of S, N, $NR^3$, $CR^3$, and $CHR^3$;
$X^4$ is selected from the group consisting of S, N, $NR^4$, $CR^4$, and $CHR^4$;
$X^7$ is N or $CR^7$;
$X^8$ is N or $CR^8$;
L is absent or selected from the group consisting of $C_{1-6}$ alkylene, $C_{2-6}$ alkenylene, and $C_{2-6}$ alkynylene, wherein the $C_{1-6}$ alkylene, $C_{2-6}$ alkenylene, and $C_{2-6}$ alkynylene are each optionally substituted by 1, 2, 3, or 4 independently selected $R^{20}$ groups;
$R^1$ is selected from the group consisting of a $C_{6-10}$ aryl, 2-benzofuranyl, 4-quinolinyl, a 5-6 member heteroaryl, and a 5-6 member heterocycloalkyl, each optionally substituted by 1, 2, 3, or 4 independently selected $R^{1A}$ groups;
each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;
$R^2$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a2}$, C(=O)$R^{b2}$, C(=O)$OR^{b2}$, $NR^{c2}R^{d2}$, C(=O)$NR^{c2}R^{d2}$, —OC(=O)$NR^{c2}R^{d2}$, $NR^{c2}$C(=O)$R^{b2}$, $NR^{c2}$C(=O)$OR^{b2}$, $NR^{c2}$C(=O)$NR^{c2}R^{d2}$, $NR^{c2}S(=O)_2R^{b2}$, $NR^{c2}S(=O)_2NR^{c2}R^{d2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;
$R^3$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a3}$, $SR^{a3}$, C(=O)$R^{b3}$, C(=O)$OR^{b3}$, $NR^{c3}R^{d3}$, C(=O)$NR^{c3}R^{d3}$, —OC(=O) $NR^{c3}R^{d3}$, $NR^{c3}$C(=O)$R^{b3}$, $NR^{c3}$C(=O)$OR^{b3}$, $NR^{c3}$C (=O)$NR^{c3}R^{d3}$, $NR^{c3}S(=O)_2R^{b3}$, $NR^{c3}S(=O)_2NR^{c3}R^{d3}$, $S(O)NR^{c3}R^{d3}$, and $S(O)_2NR^{c3}R^{d3}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;
$R^4$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a4}$, C(=O)$R^{b4}$, C(=O) $OR^{b4}$, $NR^{c4}R^{d4}$, C(=O)$NR^{c4}R^{d4}$, —OC(=O)$NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(O)NR^{c4}R^{d4}$, and $S(O)_2NR^{c4}R^{d4}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^5$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a5}$, $SR^{a5}$, $C(=O)R^{b5}$, $C(=O)OR^{b5}$, $NR^{c5}R^{d5}$, $C(=O)NR^{c5}R^{d5}$, $-OC(=O)NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(O)NR^{c5}R^{d5}$, and $S(O)_2NR^{c5}R^{d5}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^6$ is selected from the group consisting of H, $C_{1-6}$ alkyl, $C_{1-6}$ haloalkyl, $C_{1-6}$ hydroxyalkyl, and $C_{1-6}$ alkoxy;

$R^7$ is selected from the group consisting of H, $C_{1-6}$ alkyl, CN, $NO_2$, $OR^{a7}$, $C(=O)R^{b7}$, $C(=O)OR^{b7}$, $NR^{c7}R^{d7}$, $C(=O)NR^{c7}R^{d7}$, $-OC(=O)NR^{c7}R^{d7}$, $NR^{c7}C(=O)R^{b7}$, $NR^{c7}C(=O)OR^{b7}$, $NR^{c7}C(=O)NR^{c7}R^{d7}$, $NR^{c7}S(=O)_2R^{b7}$, and $NR^{c7}S(=O)_2NR^{c7}R^{d7}$;

$R^8$ is selected from the group consisting of H, $C_{1-6}$ alkyl, CN, $NO_2$, $OR^{a8}$, $C(=O)R^{b8}$, $C(=O)OR^{b8}$, $NR^{c8}R^{d8}$, $C(=O)NR^{c8}R^{d8}$, $-OC(=O)NR^{c8}R^{d8}$, $NR^{c8}C(=O)R^{b8}$, $NR^{c8}C(=O)OR^{b8}$, $NR^{c8}C(=O)NR^{c8}R^{d8}$, $NR^{c8}S(=O)_2R^{b8}$, and $NR^{c8}S(=O)_2NR^{c8}R^{d8}$;

each $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a7}$, $R^{b7}$, $R^{c7}$, $R^{d7}$, $R^{a8}$, $R^{b8}$, $R^{c8}$, and $R^{d8}$ is independently selected from the group consisting of H, $C_{1-6}$ alkyl, $C_{2-6}$ alkenyl, $C_{2-6}$ alkynyl, $C_{1-6}$ hydroxyalkyl, $C_{1-6}$ haloalkyl, $C_{1-6}$ alkoxy, $-(C_{1-6}$ alkylene)-$C_{1-6}$ alkoxy, $C_{3-10}$ cycloalkyl, $-(C_{1-6}$ alkylene)-$C_{3-10}$ cycloalkyl, $C_{6-10}$ aryl, 5-10 membered heteroaryl, 4-10 membered heterocycloalkyl, wherein the $C_{1-6}$ alkyl, $C_{2-6}$ alkenyl, $C_{2-6}$ alkynyl, $C_{3-10}$ cycloalkyl, $-(C_{1-6}$ alkylene)-$C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

or $R^{c2}$ and $R^{d2}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c3}$ and $R^{d3}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c4}$ and $R^{d4}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, $-(C_{1-4}$ alkyl)-$(C_{1-4}$ alkoxy), $-(C_{1-4}$ alkoxy)-$(C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamoyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino;

wherein the ring comprising $X^1$, $X^2$, $X^3$, and $X^4$ forms a cycloalkyl, heteroaryl or heterocycloalkyl ring;

with the proviso that when the 9-membered ring comprising $X^1$, $X^2$, $X^3$, $X^4$, $X^7$, and $X^8$ forms Ring A:

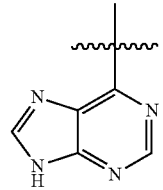

Ring A then -L-$R^1$ does not form the following groups:

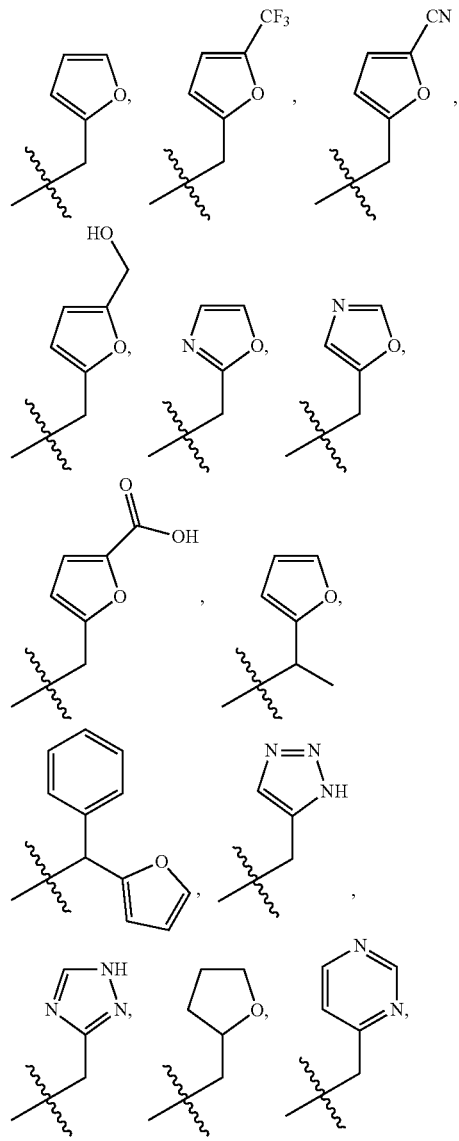

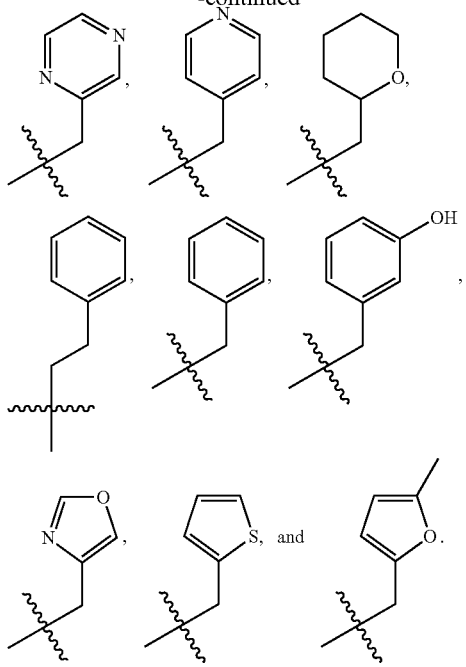

In some embodiments, $X^1$ is N. In some embodiments, $X^1$ is C.

In some embodiments, $X^2$ is N. In some embodiments, $X^2$ is $NR^2$. In some embodiments, $X^2$ is $CR^2$. In some embodiments, $X^2$ is $CHR^2$.

In some embodiments, $X^3$ is N. In some embodiments, $X^3$ is $NR^3$. In some embodiments, $X^3$ is $CR^3$. In some embodiments, $X^3$ is $CHR^3$.

In some embodiments, $X^4$ is S. In some embodiments, $X^4$ is N. In some embodiments, $X^4$ is $NR^4$. In some embodiments, $X^4$ is $CR^4$. In some embodiments, $X^4$ is $CHR^4$.

In some embodiments, $X^7$ is N. In some embodiments, $X^7$ is $CR^7$.

In some embodiments, $X^8$ is N. In some embodiments, $X^8$ is $CR^8$.

In some embodiments, L is $C_{1-6}$ alkylene optionally substituted by 1, 2, 3, or 4 independently selected $R^{20}$ groups. In some embodiments, L is unsubstituted $C_{1-6}$ alkylene. In some embodiments, L is unsubstituted methylene or unsubstituted ethylene.

In some embodiments, $R^1$ is selected from the group consisting of $C_{6-10}$ aryl, 5-6 membered heteroaryl, and 5-6 membered heterocycloalkyl, each optionally substituted by 1, 2, 3, or 4 independently selected $R^{14}$ groups. In some embodiments, $R^1$ is 2-benzofuranyl or 4-quinolinyl, each optionally substituted by 1, 2, 3, or 4 independently selected $R^{14}$ groups. In some embodiments, $R^1$ is selected from the group consisting of 2-benzofuranyl, 4-quinolinyl, phenyl, 5-6 membered heteroaryl, and 5-6 membered heterocycloalkyl, each optionally substituted by 1 or 2 independently selected $R^{14}$ groups. In some embodiments, $R^1$ is selected from the group consisting of 2-benzofuranyl, 4-quinolinyl, 5-6 membered heteroaryl, and 5-6 membered heterocycloalkyl, each optionally substituted by 1 or 2 independently selected $R^{14}$ groups. In some embodiments, $R^1$ is selected from the group consisting of:

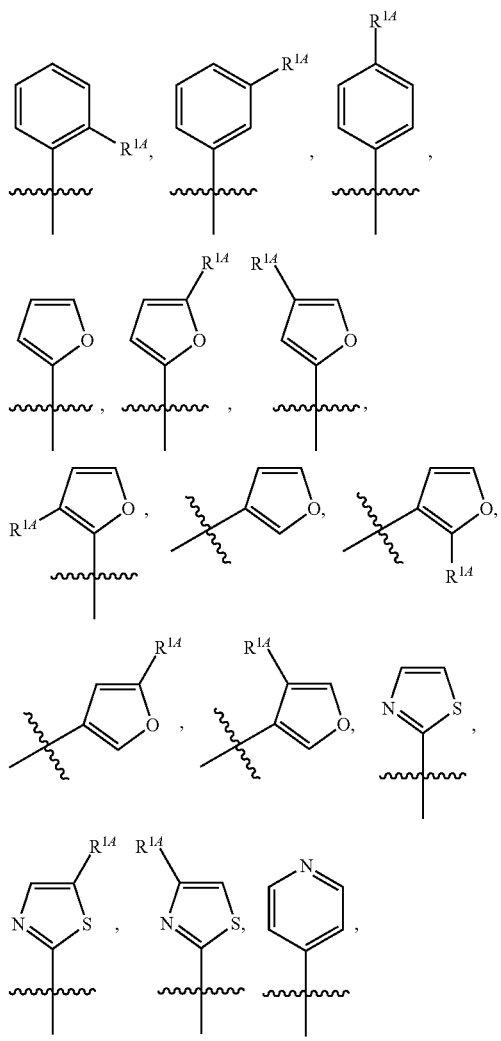

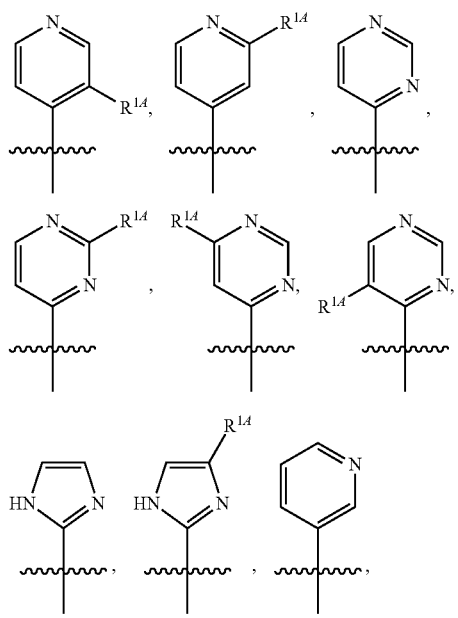

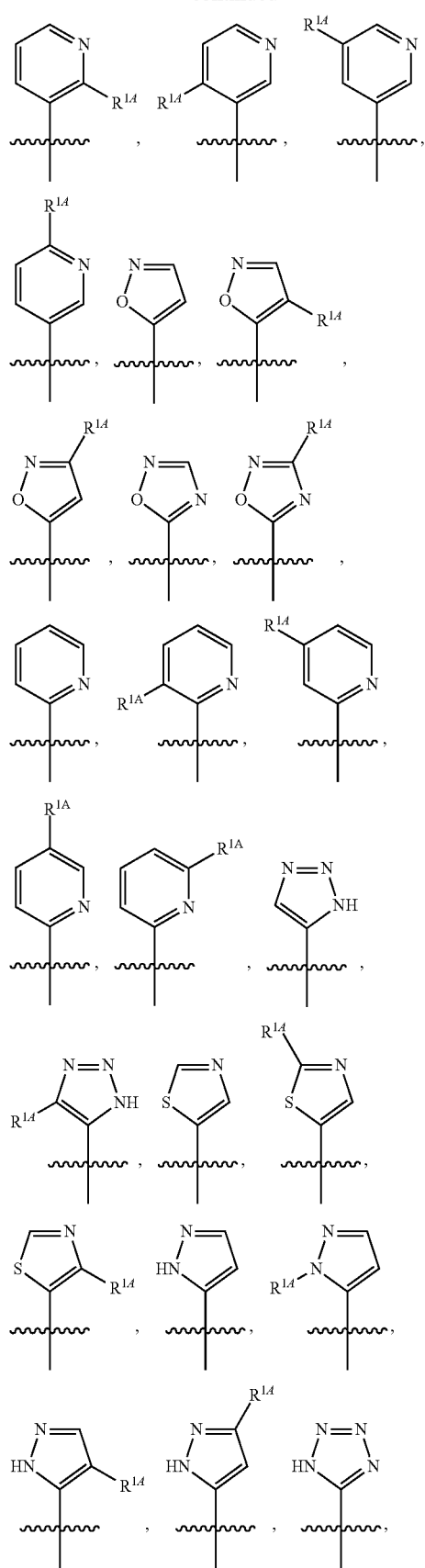
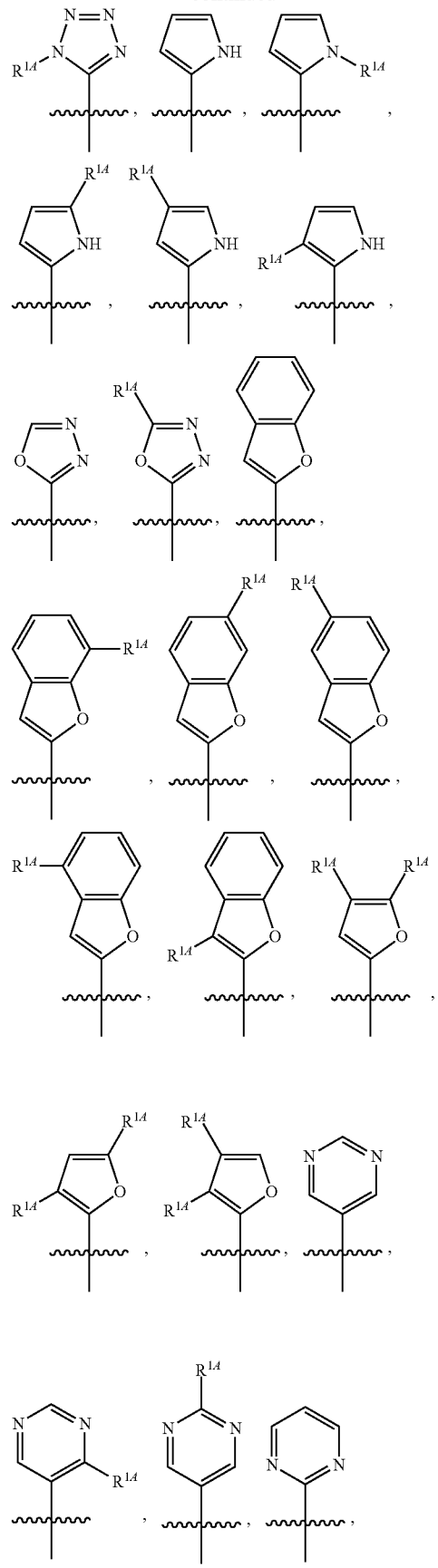

-continued
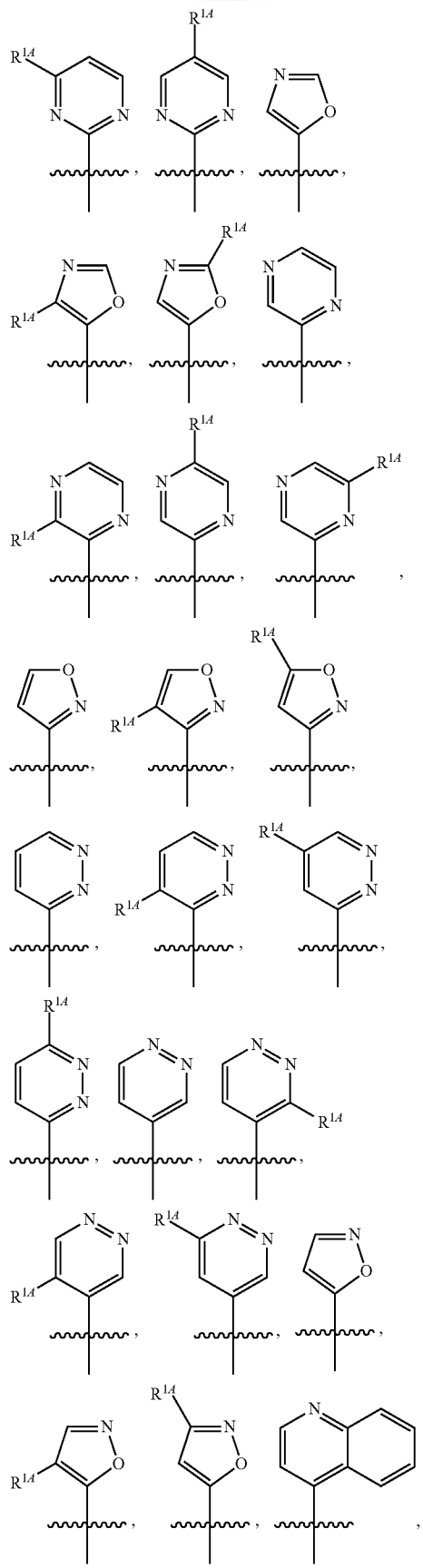
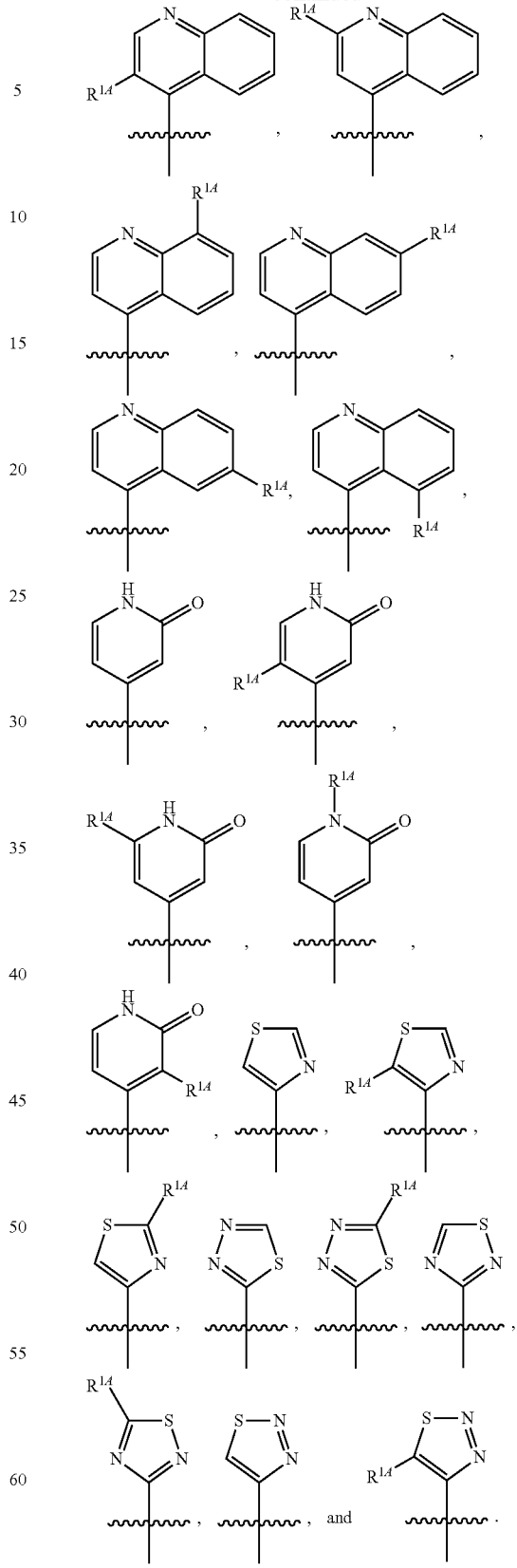
In some embodiments, each $R^{1A}$ is independently selected from the group consisting of halo, CN, $C_{1-6}$ alkyl, $C_{1-6}$ haloalkyl, $C_{1-6}$ alkoxy, and —C(=O)OH. In some embodiments, each $R^{1A}$ is independently selected from the group consisting of CN, fluoro, chloro, methyl, trifluoromethyl, methoxy, and —C(=O)OH.

In some embodiments, $R^1$ is selected from the group consisting of unsubstituted phenyl, unsubstituted 5-6 membered heteroaryl, and unsubstituted 5-6 membered heterocycloalkyl.

In some embodiments, $R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups. In some embodiments, $R^2$ is selected from the group consisting of H, oxo, chloro, fluoro, bromo, CN, methyl, —CH$_2$OH, —CH$_2$OCH$_3$, —CH$_2$NHCH$_3$, —CH$_2$N(CH$_3$)$_2$, NH$_2$, —NHCH$_3$, —N(CH$_3$)$_2$, phenyl, 4-pyridinyl, C(=O)OCH$_3$, C(=O)NH$_2$, C(=O)NHCH$_3$,

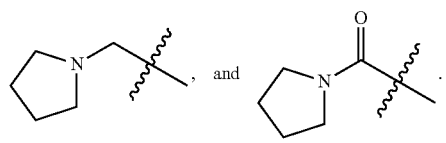 [SMILES: *CN1CCCC1 ; *C(=O)N1CCCC1]

and

In some embodiments, $R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$, wherein the $C_{1-6}$ alkyl, $C_{3-6}$ cycloalkyl, phenyl, 5-6 membered heteroaryl, 5-6 membered heterocycloalkyl, are each optionally substituted by 1, 2, 3, or 4 independently selected $R^{20}$ groups. In some embodiments, $R^3$ is selected from the group consisting of H, azido, CN, methyl, cyclopropyl, cyclobutyl, phenyl, 3-pyridinyl, N-morpholino, methoxy, ethoxy, n-propoxy, isopropoxy, n-butoxy, —OCH$_2$CH$_2$OH, —OCH$_2$CH$_2$CH$_2$OH, —OCH$_2$CH$_2$OCH$_3$, —OCH$_2$CH$_2$CH$_2$OCH$_3$, —ONHCH$_3$, —OCH$_2$CHF$_2$, —OCH$_2$CF$_3$, —OCH$_2$CH$_2$CF$_3$, —OCH$_2$CHF$_2$CH$_3$, —OCH$_2$CH$_2$NHC(=O)CH$_3$, cyclobutoxy, —OCH$_2$CH$_2$—O-phenyl, —SCH$_3$, —NH$_2$, —NHCH$_3$, —NHCH$_2$CH$_3$, —N(CH$_3$)$_2$, —NHCH$_2$CH$_2$OH, —CH$_2$OCH$_3$, —CH$_2$OH, —CH$_2$NHCH$_3$, —CH$_2$N(CH$_3$)$_2$, —C(=O)OCH$_3$, —C(=O)NH$_2$, —C(=O)NHCH$_3$, —C(=O)N(CH$_3$)$_2$, —NHCH$_2$CH$_2$OH, —C(=O)NHCH$_2$CH$_2$OH, —OC(=O)CH$_3$, —OCH$_2$-azetidinyl, —OCH$_2$-oxetanyl,

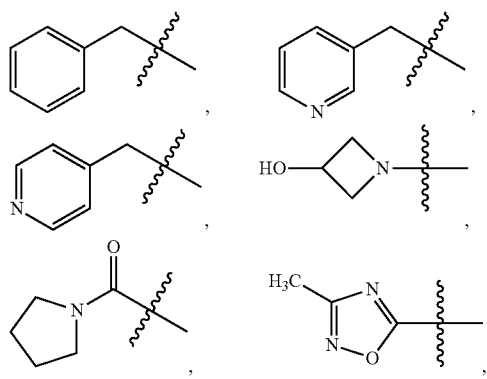

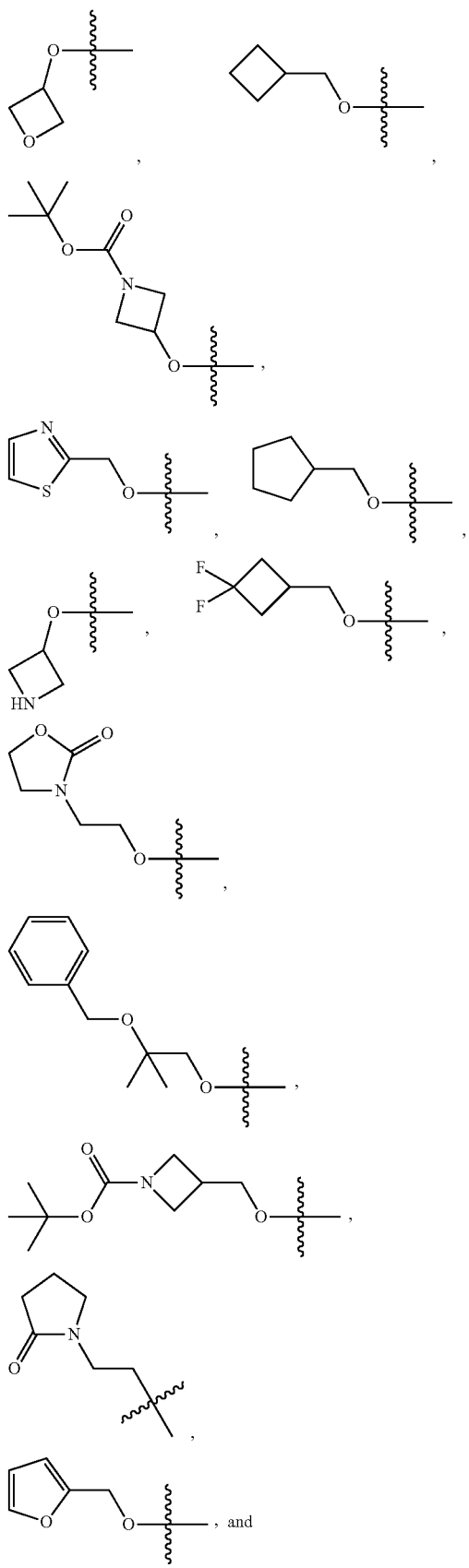

In some embodiments, $R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups. In some embodiments, $R^4$ is selected from the group consisting of H, halo, methyl, —$CH_2CH_2F$, —$CH_2CH_2CF_3$, —$CH_2CH_2OH$, —$CH_2CH_2CH_2OH$, —$CH_2CH_2OCH_3$, —$CH_2C(=O)OH$, —$CH_2C(=O)NH(CH_3)$, —$CH_2C(=O)N(CH_3)_2$, —$CH_2CH_2NHC(=O)CH_3$, —$CH_2CH_2NHCH_3$, —$CH_2CH_2N(CH_3)_2$, In some embodiments, $R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl. In some embodiments, $R^5$ is selected from the group consisting of H, fluoro, chloro, bromo, iodo, CN, methyl, isopropyl, OH, $OCH_3$, $NH_2$, —$NHCH_3$, —$N(CH_3)_2$, —$SCH_3$, phenyl, cyclopropyl, and In some embodiments, $R^5$ is chloro or fluoro.
In some embodiments, $R^7$ is selected from the group consisting of H, CN, and $C(=O)NR^{c7}R^{d7}$.
In some embodiments, $R^7$ is selected from the group consisting of H, CN, and $C(=O)NH_2$.
In some embodiments, $R^6$ is H.
In some embodiments, $R^8$ is H.
In some embodiments:
$X^1$ is N or C;
$X^2$ is N, $NR^2$, $CR^2$, or $CHR^2$;
$X^3$ is N, $NR^3$, $CR^3$, or $CHR^3$;
$X^4$ is S, N, $NR^4$, $CR^4$, or $CHR^4$;
$X^7$ is N or $CR^7$;
$X^8$ is N or $CR^8$;
L is unsubstituted $C_{1-6}$ alkylene;
$R^1$ is selected from the group consisting of 2-benzofuranyl, 4-quinolinyl, $C_{6-10}$ aryl, 5-6 membered heteroaryl, 5-6 membered heterocycloalkyl, optionally substituted by 1, 2, 3, or 4 independently selected $R^{1A}$ groups;
each $R^{1A}$ is independently selected from the group consisting of halo, CN, $C_{1-6}$ alkyl, $C_{1-6}$ haloalkyl, $C_{1-6}$ alkoxy, and —$C(=O)OH$;
$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, $C(=O)OR^{a2}$, and $C(=O)NR^{c2}R^{d2}$, wherein the $C_{1-6}$ alkyl and 4-10 membered heterocycloalkyl are each optionally substituted by 1, 2, 3, or 4 independently selected $R^{20}$ groups;
$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, $C(=O)OR^{a3}$, —$C(=O)NR^{c3}R^{d3}$, —$OC(=O)R^{b3}$, wherein the $C_{1-6}$ alkyl, $C_{3-6}$ cycloalkyl, phenyl, 5-6 membered heteroaryl, 5-6 membered heterocycloalkyl, are each optionally substituted by 1, 2, 3, or 4 independently selected $R^{20}$ groups;
$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;
$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;
$R^6$ is H;
$R^7$ is selected from the group consisting of H, CN, and $C(=O)NR^{c7}R^{d7}$; and
$R^8$ is H.
In some embodiments:
$X^1$ is N or C;
$X^2$ is selected from the group consisting of N, $NR^2$, $CR^2$, and $CH_2$;
$X^3$ is selected from the group consisting of N, $NR^3$, $CR^3$, and $CH_2$;
$X^4$ is selected from the group consisting of S, N, $NR^4$, $CR^4$, and $CH_2$;
$X^7$ is N or $CR^7$;
$X^8$ is N or $CR^8$;

L is unsubstituted methylene or unsubstituted ethylene;

$R^1$ is selected from the group consisting of 2-furanyl, 4-quinolinyl, $C_{6-10}$ aryl, 5-6 membered heteroaryl, and 5-6 membered heterocycloalkyl, optionally substituted by 1, 2, 3, or 4 independently selected $R^{1A}$ groups;

each $R^{1A}$ is independently selected from the group consisting of halo, CN, $C_{1-6}$ alkyl, $C_{1-6}$ haloalkyl, $C_{1-6}$ alkoxy, and —C(=O)OH;

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and C(=O)$NR^{c7}R^{d7}$; and $R^8$ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

$R^1$ is selected from the group consisting of 2-furanyl, 4-quinolinyl, phenyl, 5-6 membered heteroaryl, and 5-6 membered heterocycloalkyl, each optionally substituted by 1, 2, 3, or 4 independently selected $R^{1A}$ groups;

each $R^{1A}$ is independently selected from the group consisting of halo, CN, $C_{1-6}$ alkyl, $C_{1-6}$ haloalkyl, $C_{1-6}$ alkoxy, and —C(=O)OH;

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and C(=O)$NR^{c7}R^{d7}$; and $R^8$ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

R[1] is selected from the group consisting of unsubstituted 2-furanyl, unsubstituted 4-quinolinyl, unsubstituted phenyl, unsubstituted 5-6 membered heteroaryl;

R[2] is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, $C(=O)OR^{a2}$, and $C(=O)NR^{c2}R^{d2}$, wherein the $C_{1-6}$ alkyl and 4-10 membered heterocycloalkyl are each optionally substituted by 1, 2, 3, or 4 independently selected $R^{20}$ groups;

R[3] is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, $C(=O)OR^{a3}$, $—C(=O)NR^{c3}R^{d3}$, $—OC(=O)R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

R[4] is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

R[5] is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

R[6] is H;

R[7] is selected from the group consisting of H, CN, and $C(=O)NR^{c7}R^{d7}$; and R[8] is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

R[1] is selected from the group consisting of:

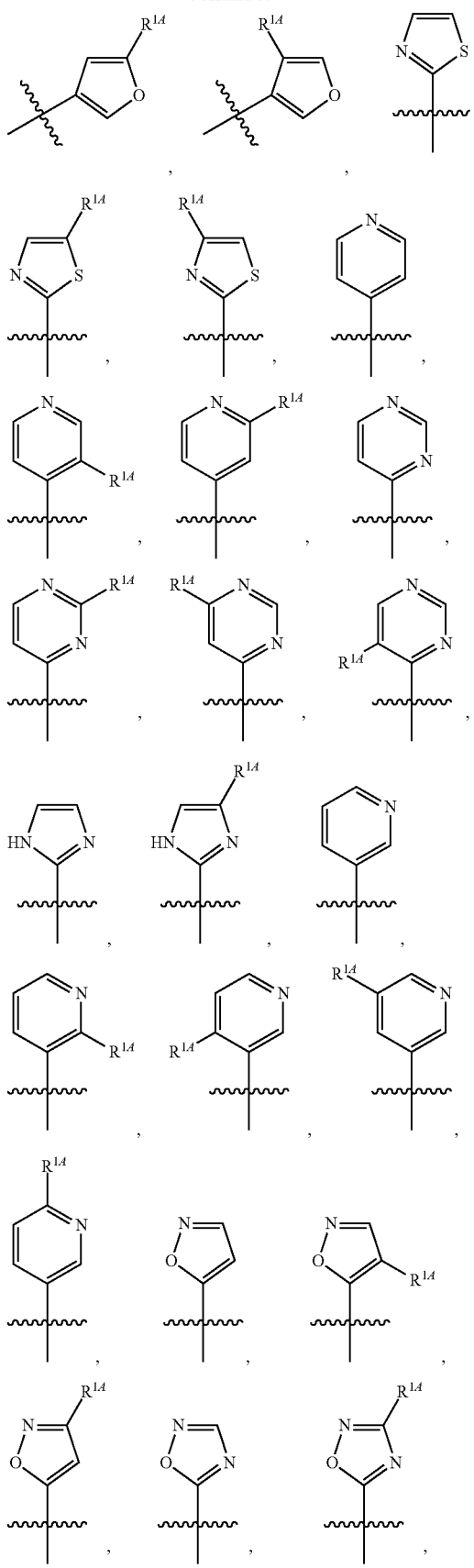

-continued
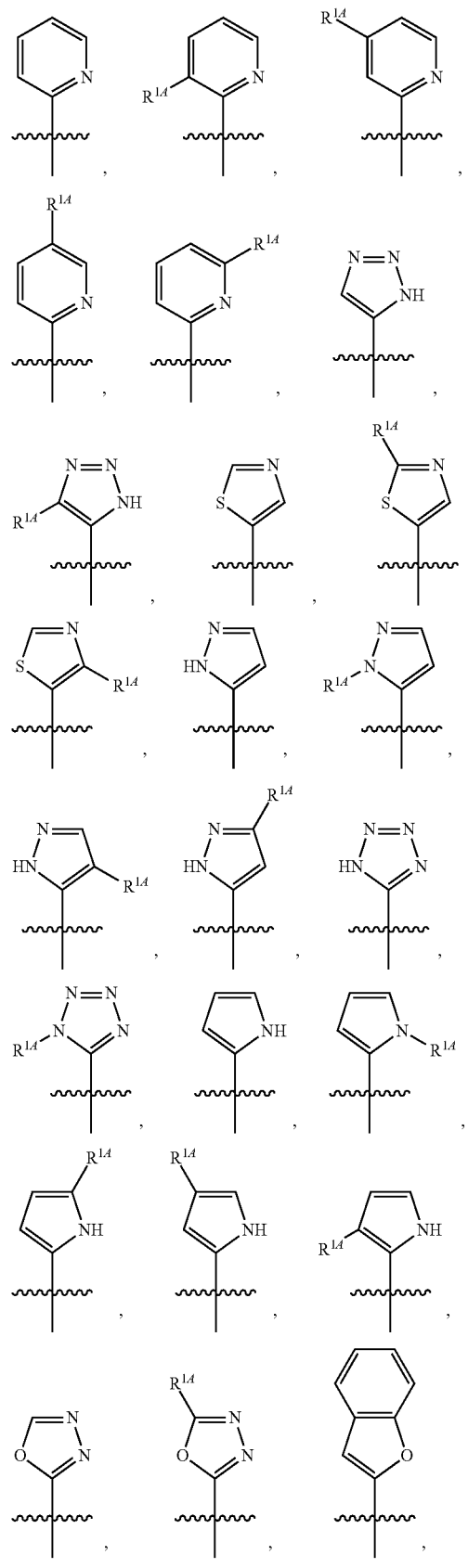
-continued
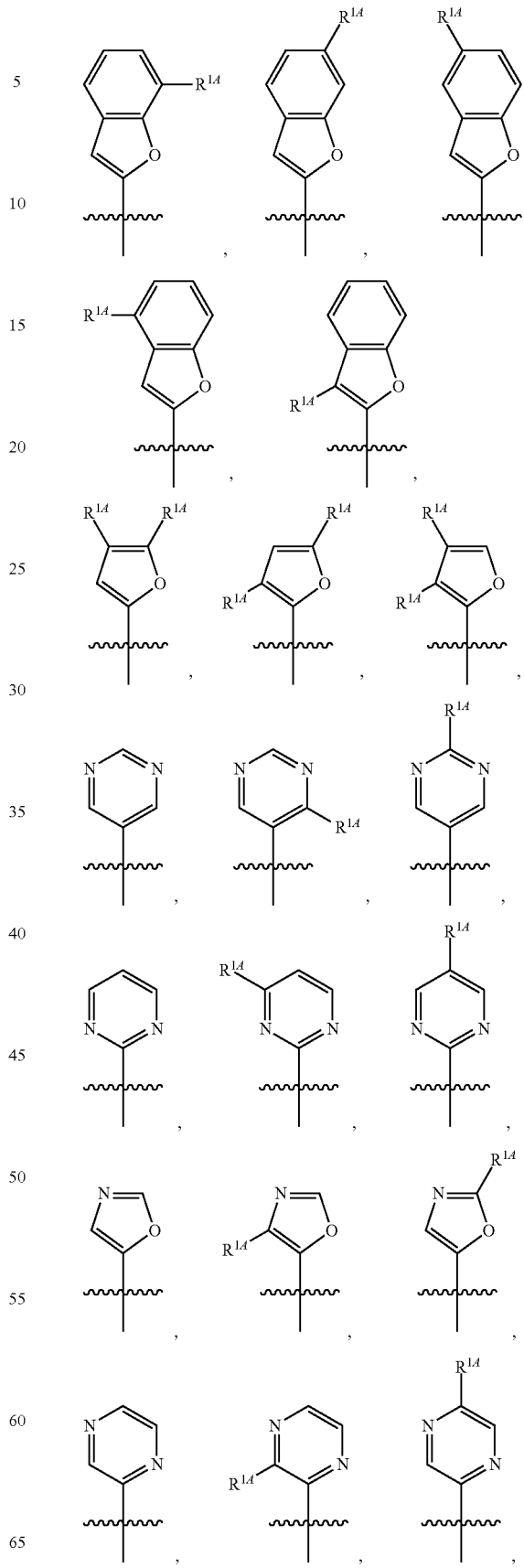

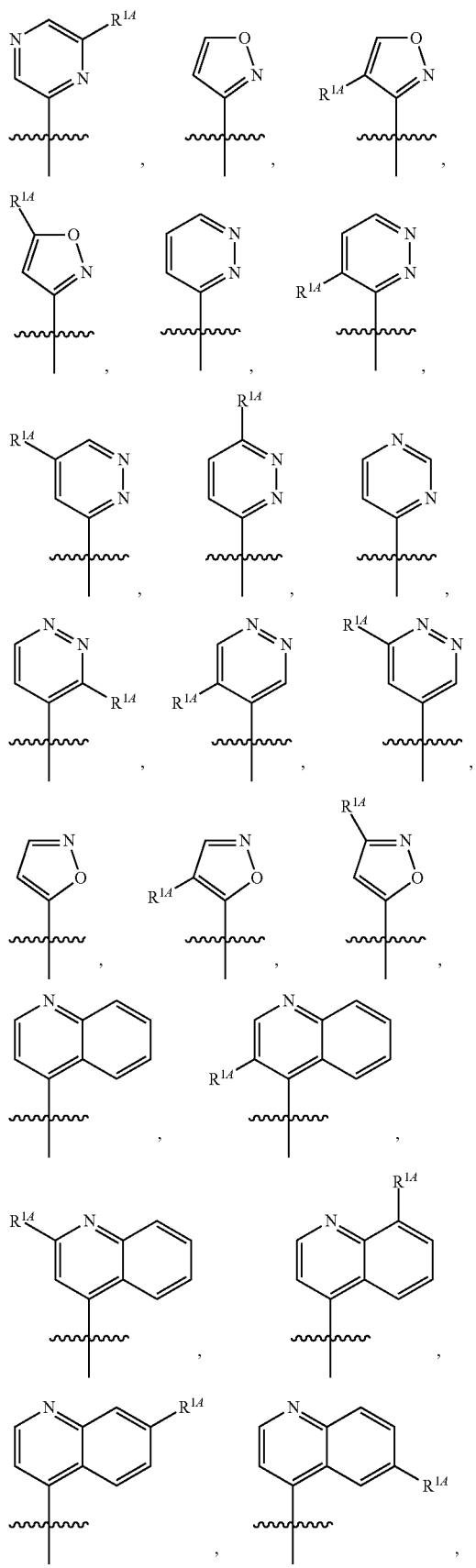

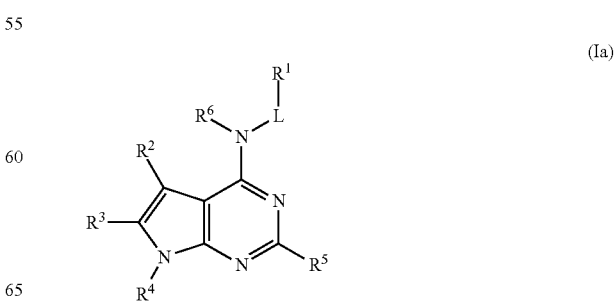

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, $C(=O)OR^{a2}$, and $C(=O)NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, $C(=O)OR^{a3}$, $-C(=O)NR^{c3}R^{d3}$, $-OC(=O)R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and $C(=O)NR^{c7}R^{d7}$; and $R^8$ is H.

In some embodiments, the compound of Formula (I) is a compound of Formula (Ia):

or a pharmaceutically acceptable salt thereof.

In some embodiments, the compound of Formula (I) is a compound of Formula (Ib):

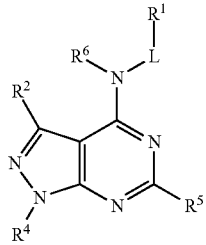

(Ib)

or a pharmaceutically acceptable salt thereof.

In some embodiments, the compound of Formula (I) is a compound of Formula (Ic):

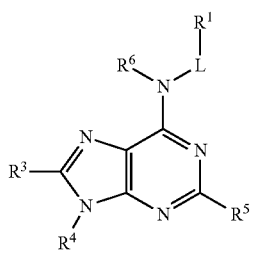

(Ic)

or a pharmaceutically acceptable salt thereof.

In some embodiments, the compound of Formula (I) is a compound of Formula (Id):

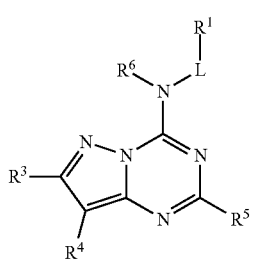

(Id)

or a pharmaceutically acceptable salt thereof.

In some embodiments, the compound of Formula (I) is a compound of Formula (Ie):

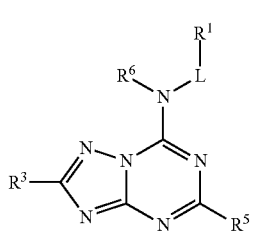

(Ie)

or a pharmaceutically acceptable salt thereof.

In some embodiments, the compound of Formula (I) is a compound of Formula (If):

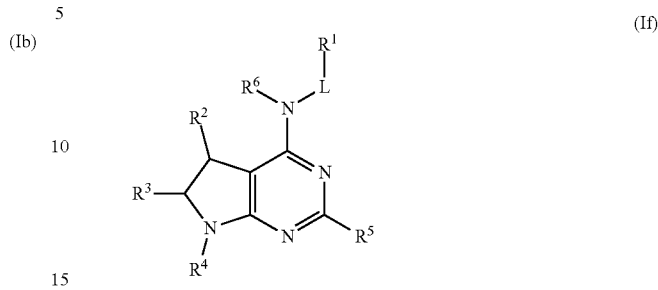

(If)

or a pharmaceutically acceptable salt thereof.

In some embodiments, the compound of Formula (I) is a compound of Formula (Ig):

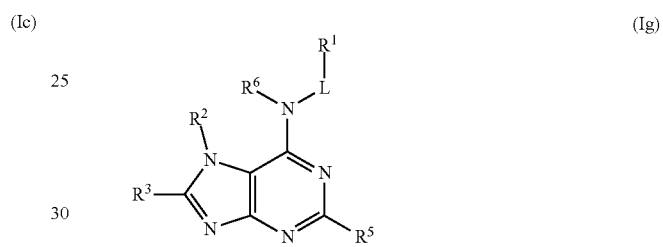

(Ig)

or a pharmaceutically acceptable salt thereof.

In some embodiments, the compound of Formula (I) is a compound of Formula (Ih):

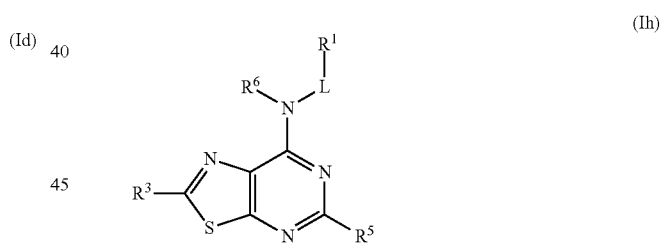

(Ih)

or a pharmaceutically acceptable salt thereof.

In some embodiments, the compound of Formula (I) is a compound of Formula (Ij):

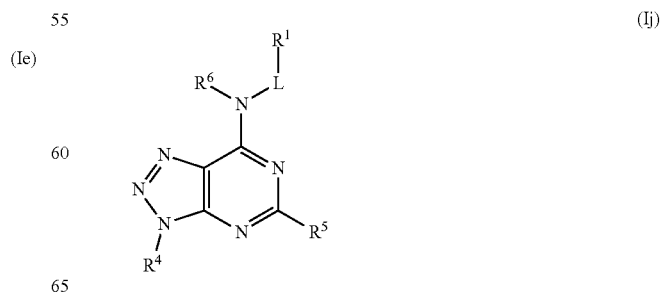

(Ij)

or a pharmaceutically acceptable salt thereof.

In some embodiments, the compound of Formula (I) is a compound of Formula (Ik):

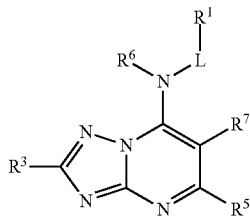

(Ik)

or a pharmaceutically acceptable salt thereof.

In some embodiments, the compound of Formula (I) is a compound of Formula (Im):

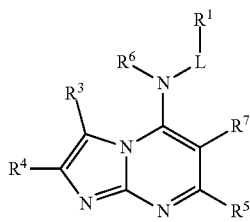

(Im)

or a pharmaceutically acceptable salt thereof.

In some embodiments, the compound of Formula (I) is a compound of Formula (In):

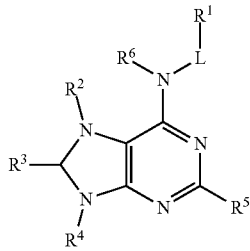

(In)

or a pharmaceutically acceptable salt thereof.

In some embodiments, the compound of Formula (I) is a compound of Formula (Io):

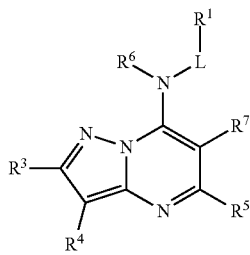

(Io)

or a pharmaceutically acceptable salt thereof.

In some embodiments, the compound of Formula (I) is a compound of Formula (Ip):

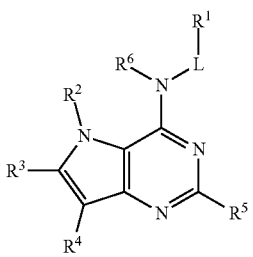

(Ip)

or a pharmaceutically acceptable salt thereof.

In some embodiments, the compound of Formula (I) is a compound of Formula (Iq):

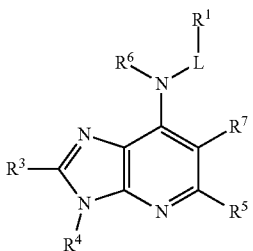

(Iq)

or a pharmaceutically acceptable salt thereof.

In some embodiments, the compound of Formula (I) is a compound of Formula (Ir):

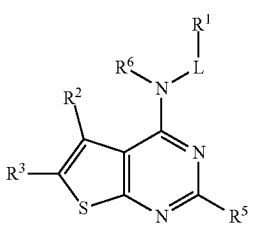

(Ir)

or a pharmaceutically acceptable salt thereof.

In some embodiments, the compound of Formula (I) is a compound of Formula (Is):

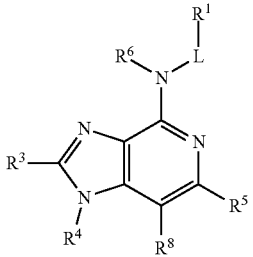

(Is)

or a pharmaceutically acceptable salt thereof.

In some embodiments, the compound of Formula (I) is a compound of Formula (It):

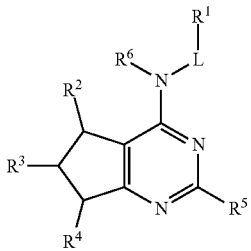

(It)

or a pharmaceutically acceptable salt thereof.

In some embodiments, the compound of Formula (I) is selected from the group of compounds provided in Table A, or a pharmaceutically acceptable salt thereof.

The present application further provides a compound of Formula (II):

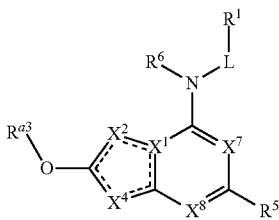

II or a pharmaceutically acceptable salt thereof, wherein:

$X^1$ is N or C;

$X^2$ is selected from the group consisting of S, N, $NR^2$, $CR^2$, and $CHR^2$;

$X^4$ is selected from the group consisting of S, N, $NR^4$, $CR^4$, and $CHR^4$;

$X^7$ is N or $CR^7$;

$X^8$ is N or $CR^8$;

L is absent or selected from the group consisting of $C_{1-6}$ alkylene, $C_{2-6}$ alkenylene, and $C_{2-6}$ alkynylene, wherein the $C_{1-6}$ alkylene, $C_{2-6}$ alkenylene, and $C_{2-6}$ alkynylene are each optionally substituted by 1, 2, 3, or 4 independently selected $R^{20}$ groups;

$R^1$ is selected from the group consisting of a $C_{6-10}$ aryl, $C_{3-10}$ cycloalkyl, 5-10 membered heteroaryl, and a 4-10 membered heterocycloalkyl, each optionally substituted by 1, 2, 3, or 4 independently selected $R^{1A}$ groups;

each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;

$R^2$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a2}$, $C(=O)R^{b2}$, $C(=O)OR^{b2}$, $NR^{c2}R^{d2}$, $C(=O)NR^{c2}R^{d2}$, —OC(=O)$NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^4$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a4}$, $C(=O)R^{b4}$, $C(=O)OR^{b4}$, $NR^{c4}R^{d4}$, $C(=O)NR^{c4}R^{d4}$, —OC(=O)$NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(O)NR^{c4}R^{d4}$, and $S(O)_2NR^{c4}R^{d4}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^5$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a5}$, $SR^{a5}$, $C(=O)R^{b5}$, $C(=O)OR^{b5}$, $NR^{c5}R^{d5}$, $C(=O)NR^{c5}R^{d5}$, —OC(=O)$NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(O)NR^{c5}R^{d5}$, and $S(O)_2NR^{c5}R^{d5}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^6$ is selected from the group consisting of H, $C_{1-6}$ alkyl, $C_{1-6}$ haloalkyl, $C_{1-6}$ hydroxyalkyl, and $C_{1-6}$ alkoxy, wherein the $C_{1-6}$ alkyl is optionally substituted by 1, 2, 3, or 4 independently selected $R^{20}$ groups;

$R^7$ is selected from the group consisting of H, $C_{1-6}$ alkyl, CN, $NO_2$, $OR^{a7}$, $C(=O)R^{b7}$, $C(=O)OR^{b7}$, $NR^{c7}R^{d7}$, $C(=O)NR^{c7}R^{d7}$, —OC(=O)$NR^{c7}R^{d7}$, $NR^{c7}C(=O)R^{b7}$, $NR^{c7}C(=O)OR^{b7}$, $NR^{c7}C(=O)NR^{c7}R^{d7}$ $NR^{c7}S(=O)_2R^{b7}$, and $NR^{c7}S(=O)_2NR^{c7}R^{d7}$;

$R^8$ is selected from the group consisting of H, $C_{1-6}$ alkyl, CN, $NO_2$, $OR^{a8}$, $C(=O)R^{b8}$, $C(=O)OR^{b8}$, $NR^{c8}R^{d8}$, $C(=O)NR^{c8}R^{d8}$, —OC(=O)$NR^{c8}R^{d8}$, $NR^{c8}C(=O)R^{b8}$, $NR^{c8}C(=O)OR^{b8}$, $NR^{c8}C(=O)NR^{c8}R^{d8}$, $NR^{c8}S(=O)_2R^{b8}$, and $NR^{c8}S(=O)_2NR^{c8}R^{d8}$;

$R^{a3}$ is selected from the group consisting of H, $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}C(=O)R^{4e}$, wherein said $C_{1-6}$ alkyl, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups;

each $R^{a2}$, $R^{b2}$, $R^{c2}$, $R^{d2}$, $R^{a4}$, $R^{b4}$, $R^{c4}$, $R^{d4}$, $R^{a5}$, $R^{b5}$, $R^{c5}$, $R^{d5}$, $R^{a7}$, $R^{b7}$, $R^{c7}$, $R^{d7}$, $R^{a8}$, $R^{b8}$, $R^{c8}$, and $R^{d8}$ is independently selected from the group consisting of H, $C_{1-6}$ alkyl, $C_{2-6}$ alkenyl, $C_{2-6}$ alkynyl, $C_{1-6}$ hydroxyalkyl, $C_{1-6}$ haloalkyl, $C_{1-6}$ alkoxy, —($C_{1-6}$ alkylene)-$C_{1-6}$ alkoxy, $C_{3-10}$ cycloalkyl, —($C_{1-6}$ alkylene)-$C_{3-10}$ cycloalkyl, $C_{6-10}$ aryl, 5-10 membered heteroaryl, 4-10 membered heterocycloalkyl, wherein the $C_{1-6}$ alkyl, $C_{2-6}$ alkenyl, $C_{2-6}$ alkynyl, $C_{3-10}$ cycloalkyl, —($C_{1-6}$ alkylene)-$C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

or $R^{c2}$ and $R^{d2}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c4}$ and $R^{d4}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

each $R^{3e}$ and $R^{3f}$ is independently selected from the group consisting of H and $C_{1-6}$ alkyl;

each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino;

wherein the ring comprising $X^1$, $X^2$, and $X^4$ forms a cycloalkyl, heteroaryl or heterocycloalkyl ring.

In some embodiments, $X^1$ is N. In some embodiments, $X^1$ is C.

In some embodiments, $X^2$ is N. In some embodiments, $X^2$ is $NR^2$. In some embodiments, $X^2$ is $CR^2$. In some embodiments, $X^2$ is $CHR^2$.

In some embodiments, $X^4$ is N. In some embodiments, $X^4$ is $NR^4$. In some embodiments, $X^4$ is $CR^4$. In some embodiments, $X^4$ is $CHR^4$.

In some embodiments, $X^7$ is N. In some embodiments, $X^7$ is $CR^7$.

In some embodiments, $X^8$ is N. In some embodiments, $X^8$ is $CR^8$.

In some embodiments, L is $C_{1-6}$ alkylene optionally substituted by 1, 2, 3, or 4 independently selected $R^{20}$ groups. In some embodiments, L is unsubstituted $C_{1-6}$ alkylene. In some embodiments, L is unsubstituted methylene or unsubstituted ethylene.

In some embodiments, $R^1$ is selected from the group consisting of $C_{6-10}$ aryl, 5-6 membered heteroaryl, and 5-6 membered heterocycloalkyl, each optionally substituted by 1, 2, 3, or 4 independently selected $R^{14}$ groups. In some embodiments, $R^1$ is selected from the group consisting of 5-6 membered heteroaryl, and 5-6 membered heterocycloalkyl, each optionally substituted by 1, 2, 3, or 4 independently selected $R^{14}$ groups. In some embodiments, $R^1$ is selected from the group consisting of:

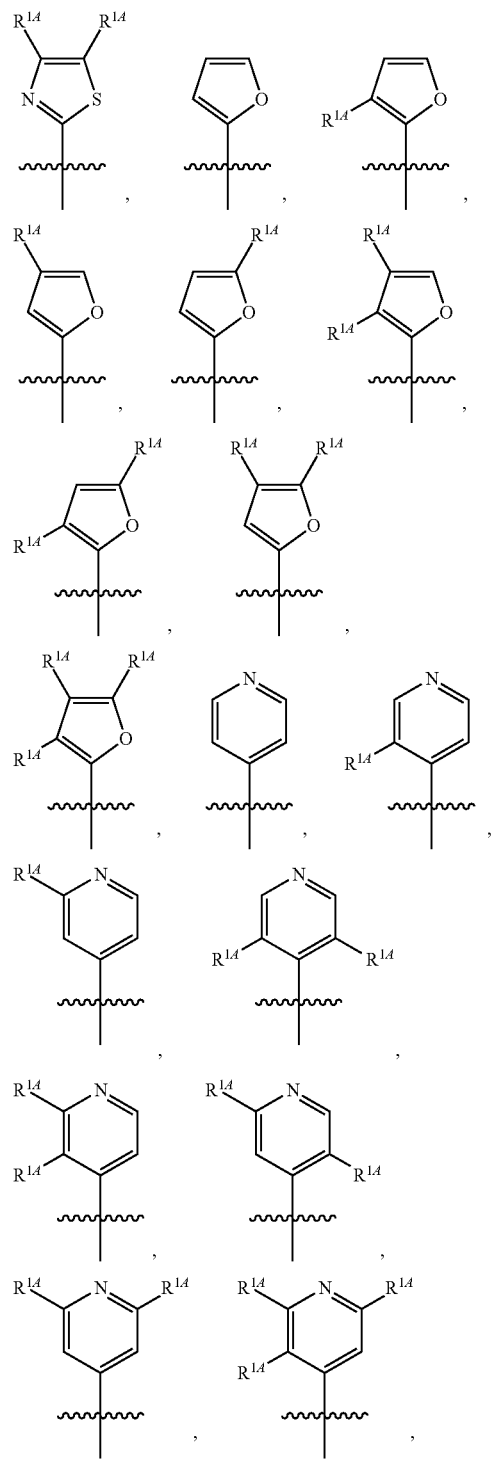

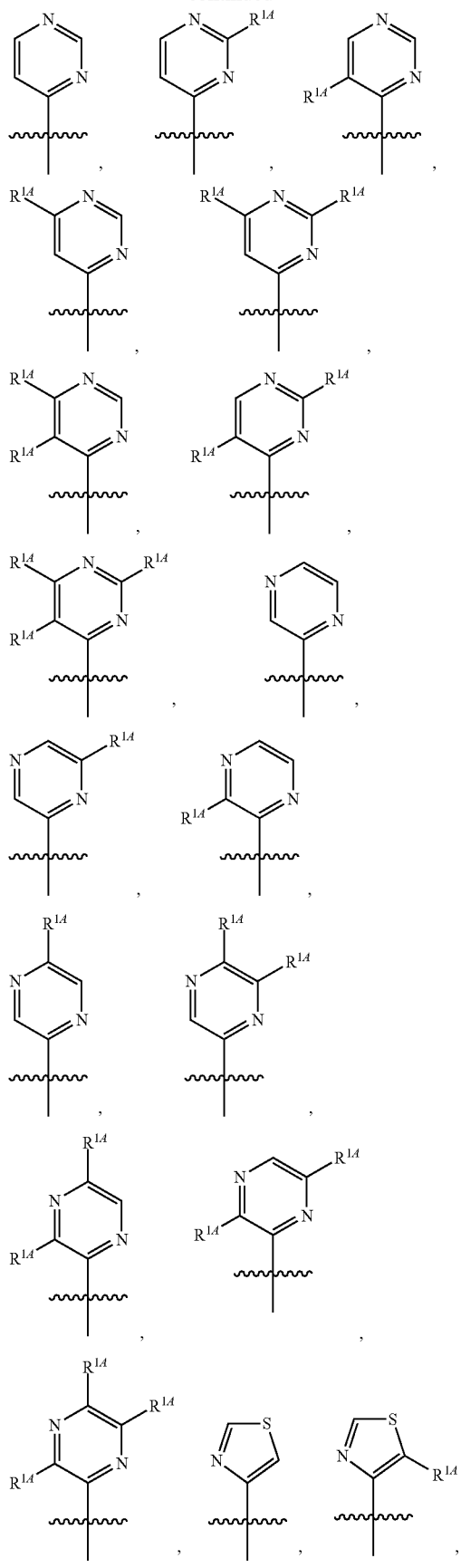
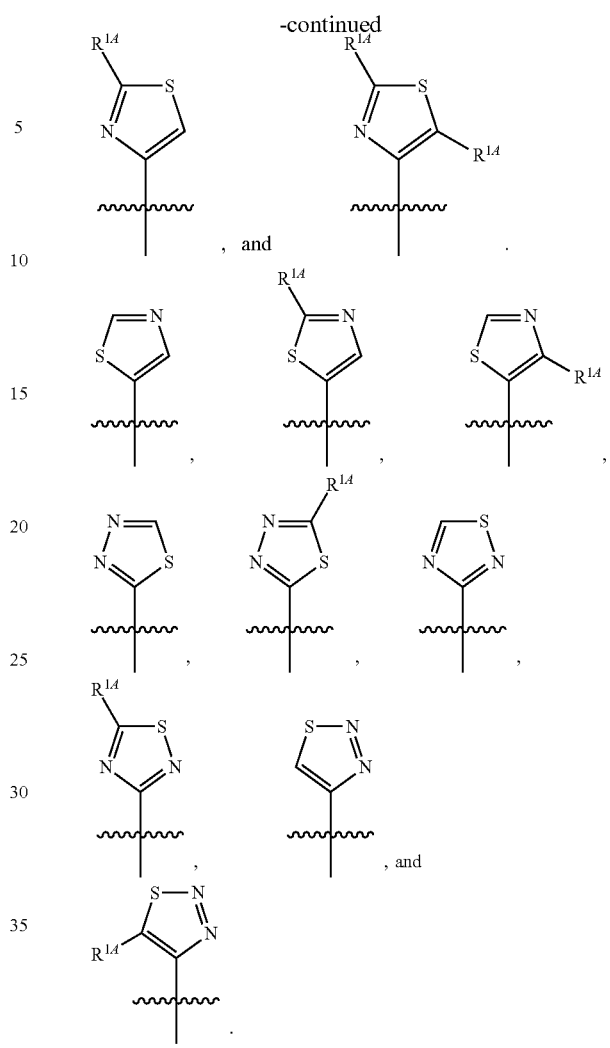
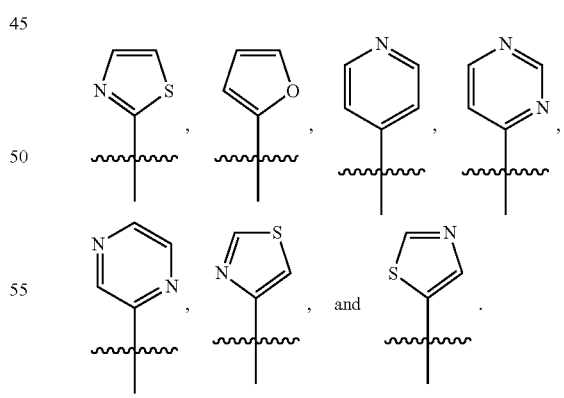
In some embodiments, $R^1$ is selected from the group consisting of:
In some embodiments, $R^2$ is H or $C_{1-6}$ alkyl. In some embodiments, $R^2$ is H or methyl.
In some embodiments, $R^4$ is H or $C_{1-6}$ alkyl, wherein the $C_{1-6}$ alkyl is optionally substituted by 1, 2, 3, or 4 independently selected $R^{20}$ groups. In some embodiments, $R^4$ is H or —CH$_2$CH$_2$OH.

In some embodiments, $R^5$ is selected from the group consisting of H, halo, CN, and $OR^{a4}$. In some embodiments, $R^5$ is selected from the group consisting of H, Cl, CN, and —$OCH_3$.

In some embodiments, $R^6$ is H or $C_{1-6}$ alkyl, wherein the $C_{1-6}$ alkyl is optionally substituted by 1, 2, 3, or 4 independently selected $R^{20}$ groups. In some embodiments, $R^6$ is selected from the group consisting of H, methyl, and —$CH_2CH_2OH$.

In some embodiments, $R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}$C(=O)$R^{4e}$, wherein said $C_{1-6}$ alkyl, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups.

In some embodiments, $R^{a3}$ is selected from the group consisting of H, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}$C(=O)$R^{4e}$, wherein said $C_{1-6}$ alkyl, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups.

In some embodiments, $R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}$C(=O)$R^{4e}$, wherein said $C_{1-6}$ alkyl, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups.

In some embodiments, $R^{a3}$ is selected from the group consisting of $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}$C(=O)$R^{4e}$, wherein said $C_{1-6}$ alkyl, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups.

In some embodiments, $R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{5-6}$ aryloxy, $C_{4-6}$ cycloalkyl, —($C_{1-6}$ alkylene)-$C_{4-6}$ cycloalkyl, —($C_{1-6}$ alkylene)-(5-6 membered heteroaryl), 4-6 membered heterocycloalkyl, -(4-6 membered heterocycloalkyl)-C(=O)$OR^{3f}$, —($C_{1-6}$ alkylene)-(4-6 membered heterocycloalkyl), —$NR^{3e}R^{3f}$, —($C_{1-6}$ alkylene)-$NR^{3e}R^{3f}$, and —($C_{1-6}$ alkylene)-$NR^{3e}$C(=O)$R^{4e}$, wherein the —($C_{1-6}$ alkylene)-$C_{1-6}$ alkoxy is substituted by phenyl.

In some embodiments, $R^{a3}$ is selected from the group consisting of methyl, ethyl, n-propyl, isopropyl, n-butyl, —$CH_2CH_2OH$, —$CH_2CH_2CH_2OH$, —$CH_2CHF_2$, —$CH_2CF_3$, —$CH_2CH_2CF_3$, —$CH_2CHF_2CH_3$, —$CH_2CH_2OCH_3$, —$CH_2CH_2CH_2OCH_3$, —$NHCH_3$, —$CH_2CH_2NHC$(=O)$CH_3$, cyclobutyl, —$CH_2$-cyclobutyl, —$CH_2$-cyclopentyl, —$CH_2CH_2$—O-phenyl, azetidinyl, —$CH_2$-azetidinyl, oxetanyl, —$CH_2$-oxetanyl, —$CH_2$-thiazolyl,

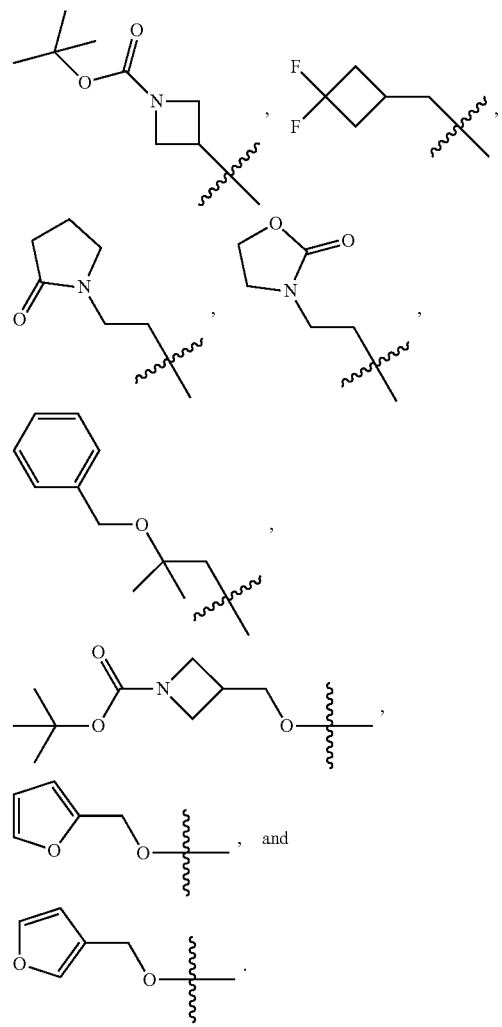

In some embodiments:
$X^1$ is C;
$X^2$ is N or $NR^2$;
$X^4$ N or $NR^4$;
$X^7$ is N; and
$X^8$ is N.

In some embodiments:
$X^1$ is C;
$X^2$ is N or $NR^2$;
$X^4$ N or $NR^4$;
$X^7$ is N;
$X^8$ is N;
L is $C_{1-6}$ alkylene optionally substituted by 1, 2, 3, or 4 independently selected $R^{20}$ groups;
$R^1$ is selected from the group consisting of $C_{6-10}$ aryl, 5-6 membered heteroaryl, and 5-6 membered heterocycloalkyl, each optionally substituted by 1, 2, 3, or 4 independently selected $R^{1A}$ groups;
each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;
$R^2$ is H or $C_{1-6}$ alkyl;
$R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}$C(=O)$R^{4e}$, wherein said $C_{1-6}$ alkyl, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups;
$R^4$ is H or $C_{1-6}$ alkyl, wherein the $C_{1-6}$ alkyl is optionally substituted by 1, 2, 3, or 4 independently selected $R^{20}$ groups;
$R^5$ is selected from the group consisting of H, halo, CN, and $OR^{a4}$;
$R^6$ is H or $C_{1-6}$ alkyl;
each $R^{3e}$ and $R^{3f}$ is independently selected from the group consisting of H and $C_{1-6}$ alkyl; and
each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments:
$X^1$ is C;
$X^2$ is N or $NR^2$;
$X^4$ N or $NR^4$;
$X^7$ is N;
$X^8$ is N;
L is unsubstituted $C_{1-6}$ alkylene;
$R^1$ is selected from the group consisting of 5-6 membered heteroaryl, and 5-6 membered heterocycloalkyl, each optionally substituted by 1, 2, 3, or 4 independently selected $R^{1A}$ groups;
each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;
$R^2$ is H or $C_{1-6}$ alkyl;
$R^4$ is H or $C_{1-6}$ alkyl, wherein the $C_{1-6}$ alkyl is optionally substituted by 1, 2, 3, or 4 independently selected $R^{20}$ groups;
$R^5$ is selected from the group consisting of H, halo, CN, and $OR^{a4}$;
$R^6$ is H or $C_{1-6}$ alkyl, wherein the $C_{1-6}$ alkyl is optionally substituted by 1, 2, 3, or 4 independently selected $R^{20}$ groups;
$R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{5-6}$ aryloxy, $C_{4-6}$ cycloalkyl, —($C_{1-6}$ alkylene)-$C_{4-6}$ cycloalkyl, —($C_{1-6}$ alkylene)-(5-6 membered heteroaryl), 4-6 membered heterocycloalkyl, -(4-6 membered heterocycloalkyl)-C(=O)$OR^{3f}$, —($C_{1-6}$ alkylene)-(4-6 membered heterocycloalkyl), —$NR^{3e}R^{3f}$, —($C_{1-6}$ alkylene)-$NR^{3e}R^{3f}$, and —($C_{1-6}$ alkylene)-$NR^{3e}$C(=O)$R^{4e}$, wherein the —($C_{1-6}$ alkylene)-$C_{1-6}$ alkoxy is substituted by phenyl;
each $R^{3e}$ and $R^{3f}$ is independently selected from the group consisting of H and $C_{1-6}$ alkyl; and
each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments:
$X^1$ is C;
$X^2$ is N or $NR^2$;
$X^4$ is N or $NR^4$;
$X^7$ is N;
$X^8$ is N;
L is unsubstituted methylene or unsubstituted ethylene;
$R^1$ is selected from the group consisting of 5-6 membered heteroaryl, and 5-6 membered heterocycloalkyl;
$R^2$ is H or $C_{1-6}$ alkyl;
$R^4$ is H or $C_{1-6}$ alkyl, wherein the $C_{1-6}$ alkyl is optionally substituted by 1 $R^{20}$ group;
$R^5$ is selected from the group consisting of H, halo, CN, and $OR^{a4}$;
$R^6$ is H or $C_{1-6}$ alkyl, wherein the $C_{1-6}$ alkyl is optionally substituted by 1 $R^{20}$ group;
$R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{5-6}$ aryloxy, $C_{4-6}$ cycloalkyl, —($C_{1-6}$ alkylene)-$C_{4-6}$ cycloalkyl, —($C_{1-6}$ alkylene)-(5-6 membered heteroaryl), 4-6 membered heterocycloalkyl, -(4-6 membered heterocycloalkyl)-C(=O)$OR^{3f}$, —($C_{1-6}$ alkylene)-(4-6 membered heterocycloalkyl), —NR$^{3e}$R$^{3f}$, —(C$_{1-6}$ alkylene)-NR$^{3e}$R$^{3f}$, and —(C$_{1-6}$ alkylene)-NR$^{3e}$C(=O)R$^{4e}$, wherein the —(C$_{1-6}$ alkylene)-C$_{1-6}$ alkoxy is substituted by phenyl;

R$^{a4}$ is C$_{1-6}$ alkyl;

each R$^{3e}$ and R$^{3f}$ is independently selected from the group consisting of H and C$_{1-6}$ alkyl; and each R$^{20}$ is OH.

In some embodiments, the compound of Formula (II) is a compound of Formula (IIa):

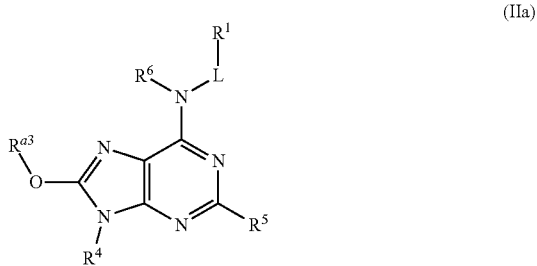

(IIa)

or a pharmaceutically acceptable salt thereof, wherein, R$^{a3}$ is selected from the group consisting of H, C$_{1-6}$ alkyl, C$_{1-6}$ haloalkyl, C$_{1-6}$-hydroxyalkyl, —(C$_{1-6}$ alkylene)-C$_{1-6}$ alkoxy, —(C$_{1-6}$ alkylene)-C$_{6-10}$ aryloxy, C$_{6-10}$-aryl, —(C$_{1-6}$ alkylene)-C$_{6-10}$ aryl, C$_{3-10}$-cycloalkyl, —(C$_{1-6}$-alkylene)-C$_{3-10}$-cycloalkyl, 5-10 membered heteroaryl, —(C$_{1-6}$ alkylene)-(5-10 membered heteroaryl), 4-10 membered heterocycloalkyl, -(4-10 membered heterocycloalkyl)-C(=O)OR$^{3f}$, —(C$_{1-6}$ alkylene)-(4-10 membered heterocycloalkyl), —NR$^{3e}$R$^{3f}$, —(C$_{1-6}$ alkyl)-NR$^{3e}$R$^{3f}$, and —(C$_{1-6}$ alkylene)-NR$^{3e}$C(=O)R$^{4e}$, wherein said C$_{1-6}$ alkyl, C$_{6-10}$ aryl, —(C$_{1-6}$ alkylene)-C$_{6-10}$ aryl, C$_{3-10}$-cycloalkyl, —(C$_{1-6}$ alkylene)-C$_{3-10}$ cycloalkyl, 5-10 membered heteroaryl, —(C$_{1-6}$ alkylene)-(5-10 membered heteroaryl), 4-10 membered heterocycloalkyl, and —(C$_{1-6}$ alkylene)-(4-10 membered heterocycloalkyl) are each optionally substituted by 1, 2, 3, or 4 R$^{20}$ groups.

In some embodiments, the compound of Formula (II) is a compound of Formula (IIb):

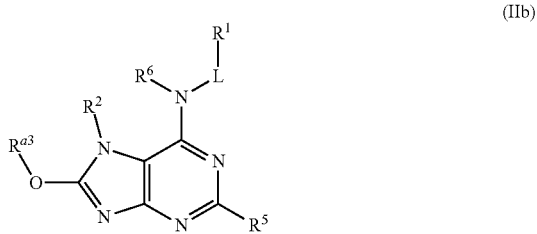

(IIb)

or a pharmaceutically acceptable salt thereof, wherein, R$^{a3}$ is selected from the group consisting of H, C$_{1-6}$ alkyl, C$_{1-6}$ haloalkyl, C$_{1-6}$-hydroxyalkyl, —(C$_{1-6}$ alkylene)-C$_{1-6}$ alkoxy, —(C$_{1-6}$ alkylene)-C$_{6-10}$ aryloxy, C$_{6-10}$-aryl, —(C$_{1-6}$ alkylene)-C$_{6-10}$ aryl, C$_{3-10}$-cycloalkyl, —(C$_{1-6}$-alkylene)-C$_{3-10}$-cycloalkyl, 5-10 membered heteroaryl, —(C$_{1-6}$ alkylene)-(5-10 membered heteroaryl), 4-10 membered heterocycloalkyl, -(4-10 membered heterocycloalkyl)-C(=O)OR$^{3f}$, —(C$_{1-6}$ alkylene)-(4-10 membered heterocycloalkyl), —NR$^{3e}$R$^{3f}$, —(C$_{1-6}$ alkyl)-NR$^{3e}$R$^{3f}$, and —(C$_{1-6}$ alkylene)-NR$^{3e}$C(=O)R$^{4e}$, wherein said C$_{1-6}$ alkyl, C$_{6-10}$ aryl, —(C$_{1-6}$ alkylene)-C$_{6-10}$ aryl, C$_{3-10}$-cycloalkyl, —(C$_{1-6}$ alkylene)-C$_{3-10}$ cycloalkyl, 5-10 membered heteroaryl, —(C$_{1-6}$ alkylene)-(5-10 membered heteroaryl), 4-10 membered heterocycloalkyl, and —(C$_{1-6}$ alkylene)-(4-10 membered heterocycloalkyl) are each optionally substituted by 1, 2, 3, or 4 R$^{20}$ groups.

In some embodiments, the compound of Formula (II) is selected from the group of compounds provided in Table B, or a pharmaceutically acceptable salt thereof.

The present application further provides a pharmaceutical composition comprising a compound provided herein, or a pharmaceutically acceptable salt thereof, and at least one pharmaceutically acceptable carrier.

The present application further provides a method of treating a disease associated with one or more mRNA splicing defects in a subject in need thereof, the method comprising administering to the subject a therapeutically effective amount of a compound provided herein, or a pharmaceutically acceptable salt thereof.

In some embodiments, the disease associated with one or more mRNA splicing defects comprises a disease of the central nervous system. In some embodiments, disease associated with one or more mRNA splicing defects is a disease of the central nervous system. In some embodiments, the methods include delivering the compound to the central nervous system of a subject.

In some embodiments, the disease associated with one or more mRNA splicing defects is selected from the group consisting of amyotrophic lateral sclerosis (ALS), atypical cystic fibrosis, autism, autism spectrum disorders, Charcot-Marie-Tooth disease, CHARGE syndrome, dementia, epilepsy, epileptic encephalopathy, familial dysautonomia (FD), familial isolated growth hormone deficiency type II (IGHD II), Frasier syndrome, frontotemporal dementia and Parkinson's linked to Chromosome 17 (FTDP-17), Huntington's disease, Marfan syndrome, mental retardation, Menkes Disease (MD), muscular dystrophies, myopathies, myotonic dystrophy type 1 (DM1), myotonic dystrophy type 2 (DM2), neurofibromatosis 1 (NF1, von Recklinghausen NF; peripheral NF), occipital horn syndrome, Parkinson's disease, retinoblastoma, schizophrenia, tuberous sclerosis, and the gene-associated diseases listed in Table 1. In some embodiments, the disease associated with one or more mRNA splicing defects is selected from the group consisting of familial dysautonomia and neurofibromatosis 1. In some embodiments, the disease associated with one or more mRNA splicing defects is familial dysautonomia. In some embodiments, the disease associated with one or more mRNA splicing defects is neurofibromatosis 1. In some embodiments, the disease associated with one or more mRNA splicing defects is a disease listed in Table 1.

In some embodiments, the one or more mRNA splicing defects is associated with one or more genes comprising at least one exon comprising the nucleotide sequence CAA. In some embodiments, the one or more mRNA splicing defects is associated with one gene comprising at least one exon comprising the nucleotide sequence CAA. In some embodiments, the one or more mRNA splicing defects is associated with one or more genes selected from the group consisting of BMP2K, ABI2, IKBKAP, FIG4, DNAJC6, WDR45, LRRK2, LRSAM1, SBF2, C19orf12, ARFGEF2, ARH-GEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD7.

In some embodiments, the one or more mRNA splicing defects is associated with one gene selected from the group consisting of BMP2K, ABI2, IKBKAP, FIG4, DNAJC6, WDR45, LRRK2, LRSAM1, SBF2, C19orf12, ARFGEF2, ARHGEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD7. In some embodiments, the one or more genes is selected from the group provided in Table 1. In some embodiments, the gene is selected from the group provided in Table 1. In some embodiments, the gene is associated with a condition listed in Table 1 as associated with a gene provided therein.

The present application further provides, a method of improving mRNA splicing of a gene (e.g., a gene in a cell), comprising contacting a cell expressing the gene with a compound provided herein, or a pharmaceutically acceptable salt thereof. In some embodiments, the gene is selected from the group consisting of BMP2K, ABI2, IKBKAP, FIG4, DNAJC6, WDR45, LRRK2, LRSAM1, SBF2, C19orf12, ARFGEF2, ARHGEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD7. In some embodiments, the gene is selected from the group provided in Table 1. In some embodiments, the contacting the cell is performed in vitro. In some embodiments, the contacting the cell is performed in vivo. In some embodiments, the method of improving mRNA splicing in a gene comprises improving exon inclusion.

The present application further provides a method of improving mRNA splicing in a cell, comprising contacting the cell with an effective amount of a compound provided herein, or a pharmaceutically acceptable salt thereof, wherein the improving comprises improving mRNA splicing in a gene.

The present application further provides a method of improving mRNA splicing in a cell, comprising contacting the cell with a compound provided herein, or a pharmaceutically acceptable salt thereof, wherein the improving comprises improving mRNA splicing in a gene selected from the group consisting of BMP2K, ABI2, IKBKAP, FIG4, DNAJC6, WDR45, LRRK2, LRSAM1, SBF2, C19orf12, ARFGEF2, ARHGEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD7. In some embodiments, the gene is selected from the group provided in Table 1. In some embodiments, the contacting the cell is performed in vitro. In some embodiments, the contacting the cell is performed in vivo. In some embodiments, the method of improving mRNA splicing in a gene comprises improving exon inclusion.

In some embodiments, the methods described herein can include assaying mRNA splicing in a cell in the presence of a compound as provided herein, and detecting an improvement in mRNA splicing (e.g., increasing the rate of exon inclusion) in the cell.

In some embodiments, the methods described herein are practiced on a cell or a subject who has a genetic mutation that causes an mRNA splicing defect, i.e., impaired or abnormal mRNA splicing that differs from mRNA splicing in a wild-type cell. The methods can include identifying a subject who has such a genetic mutation and/or identifying a subject who has a condition associated with an mRNA splicing defect as described herein or known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1A:
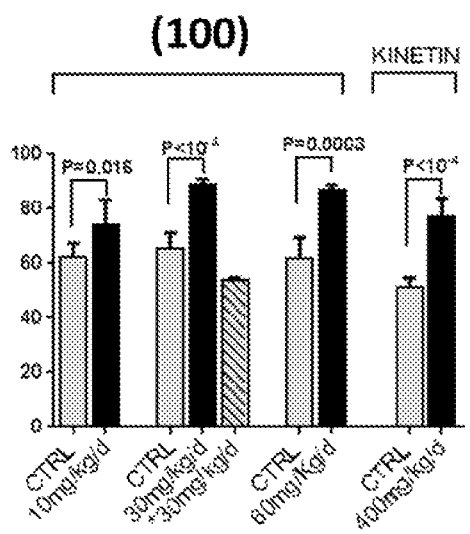
FIG. 1A shows percent exon 20 inclusion in C57Bl6-FD mouse liver after administration of compound (100) at 10 mg/kg/day; 30 mg/kg/day; and 60 mg/kg/day; and administration of kinetin at 400 mg/kg/day.
Figure 1B:
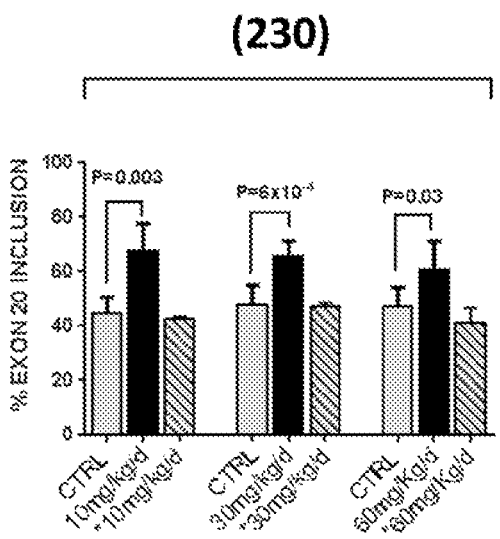
FIG. 1B shows percent exon 20 inclusion in C57Bl6-FD mouse liver after administration of compound (230) at 10 mg/kg/day; 30 mg/kg/day; and 60 mg/kg/day.
Figure 1C:
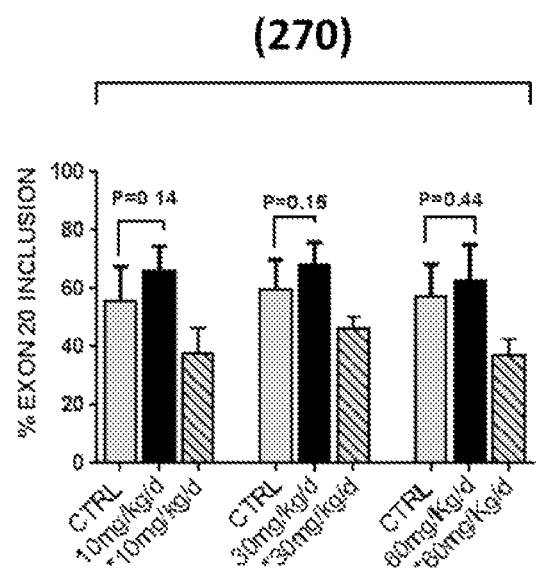
FIG. 1C shows percent exon 20 inclusion in C57Bl6-FD mouse liver after administration of compound (270) at 10 mg/kg/day; 30 mg/kg/day; and 60 mg/kg/day.
Figure 2A:
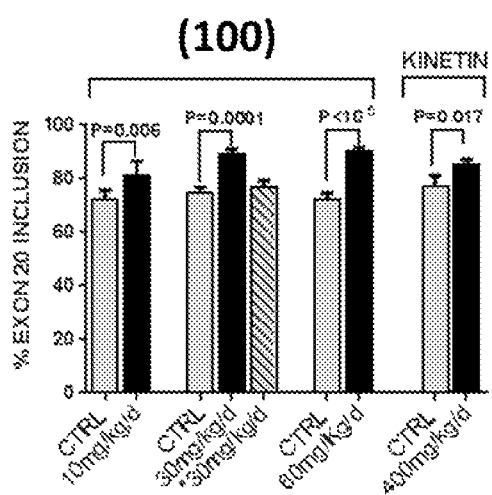
FIG. 2A shows percent exon 20 inclusion in C57Bl6-FD mouse heart after administration of compound (100) at 10 mg/kg/day; 30 mg/kg/day; and 60 mg/kg/day; and administration of kinetin at 400 mg/kg/day.
Figure 2B:
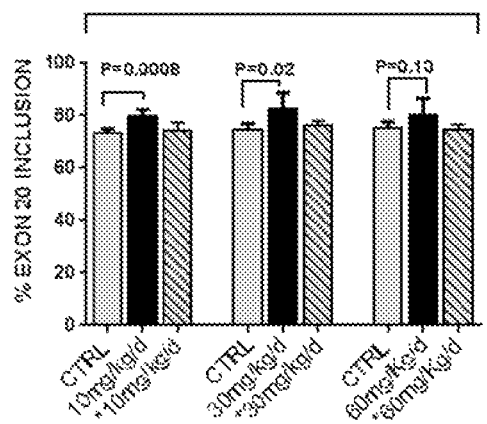
FIG. 2B shows percent exon 20 inclusion in C57Bl6-FD mouse heart after administration of compound (230) at 10 mg/kg/day; 30 mg/kg/day; and 60 mg/kg/day.
Figure 2C:
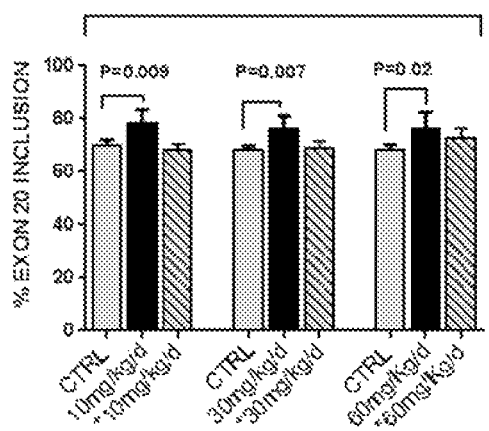
FIG. 2C shows percent exon 20 inclusion in C57Bl6-FD mouse heart after administration of compound (270) at 10 mg/kg/day; 30 mg/kg/day; and 60 mg/kg/day.
Figure 3A:
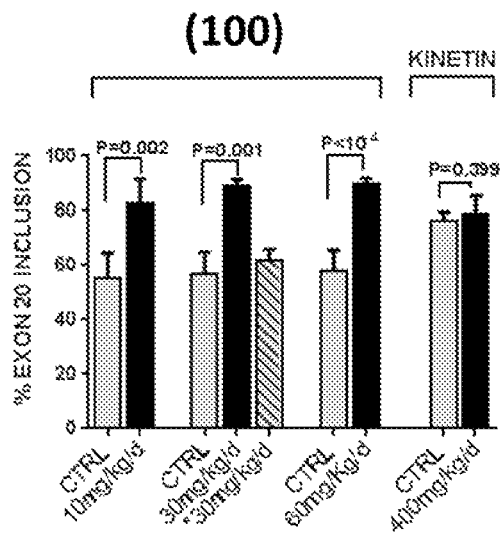
FIG. 3A shows percent exon 20 inclusion in C57Bl6-FD mouse kidney after administration of compound (100) at 10 mg/kg/day; 30 mg/kg/day; and 60 mg/kg/day; and administration of kinetin at 400 mg/kg/day.
Figure 3B:
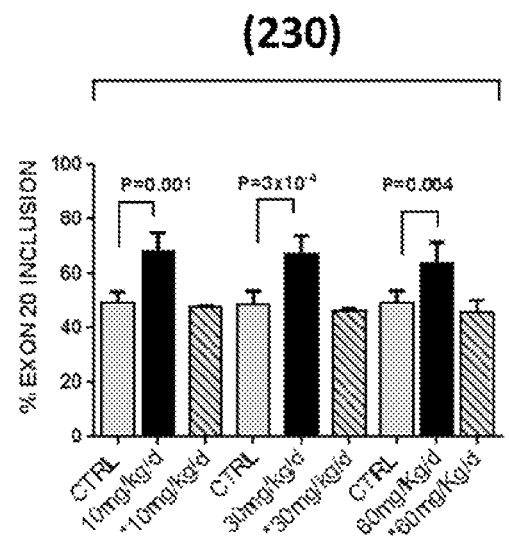
FIG. 3B shows percent exon 20 inclusion in C57Bl6-FD mouse kidney after administration of compound (230) at 10 mg/kg/day; 30 mg/kg/day; and 60 mg/kg/day.
Figure 3C:
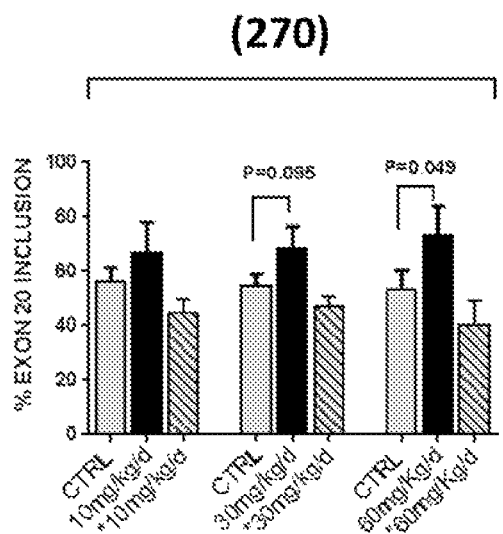
FIG. 3C shows percent exon 20 inclusion in C57Bl6-FD mouse kidney after administration of compound (270) at 10 mg/kg/day; 30 mg/kg/day; and 60 mg/kg/day.

Mutations that alter mRNA splicing have been estimated to account for as many as 20-30% of all disease-causing mutations, and studies have demonstrated that alternatively spliced isoforms are highly prevalent in the brain. These data collectively suggest that defects in alternative splicing may be a driver of neurodegenerative disease.

Oral administration of kinetin ($N^6$-furfuryladenine) in mice (400 mg/kg/day for 7 days) has been shown to improve IKBKAP splicing in vivo in certain tissues, including the brain. Further, preliminary testing in human patients and carriers of familial dysautonomia led to increased normal IKBKAP mRNA in peripheral blood in humans (see e.g., U.S. Pat. Nos. 8,729,025 and 7,737,110, the disclosures of which are each incorporated by reference herein in their entireties). However, high doses were necessary to achieve splicing changes. Accordingly, the present application provides compounds useful for therapeutically targeting mRNA splicing mechanisms.

The present application provides compounds of Formula (I):

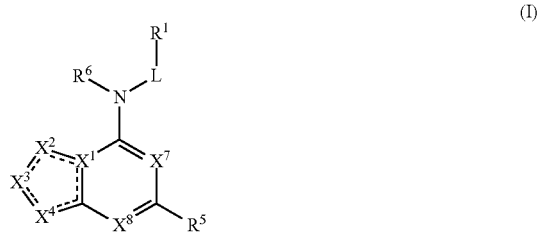

(I)

or a pharmaceutically acceptable salt thereof, wherein:

$X^1$ is N or C;

$X^2$ is selected from the group consisting of S, N, $NR^2$, $CR^2$, and $CHR^2$;

$X^3$ is selected from the group consisting of S, N, $NR^3$, $CR^3$, and $CHR^3$;

$X^4$ is selected from the group consisting of S, N, $NR^4$, $CR^4$, and $CHR^4$;

$X^7$ is N or $CR^7$;

$X^8$ is N or $CR^8$;

L is absent or selected from the group consisting of $C_{1-6}$ alkylene, $C_{2-6}$ alkenylene, and $C_{2-6}$ alkynylene, wherein the $C_{1-6}$ alkylene, $C_{2-6}$ alkenylene, and $C_{2-6}$ alkynylene are each optionally substituted by 1, 2, 3, or 4 independently selected $R^{20}$ groups;

$R^1$ is selected from the group consisting of a $C_{6-10}$ aryl, 2-benzofuranyl, 4-quinolinyl, a 5-6 member heteroaryl, and a 5-6 member heterocycloalkyl, each optionally substituted by 1, 2, 3, or 4 independently selected $R^{14}$ groups;

each $R^{14}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;

$R^2$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a2}$, $C(=O)R^{b2}$, $C(=O)OR^{b2}$, $NR^{c2}R^{d2}$, $C(=O)NR^{c2}R^{d2}$, —$OC(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^3$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a3}$, $SR^{a3}$, $C(=O)R^{b3}$, $C(=O)OR^{b3}$, $NR^{c3}R^{d3}$, $C(=O)NR^{c3}R^{d3}$, —$OC(=O)$ $NR^{c3}R^{d3}$, $NR^{c3}C(=O)R^{b3}$, $NR^{c3}C(=O)OR^{b3}$, $NR^{c3}C(=O)NR^{c3}R^{d3}$, $NR^{c3}S(=O)_2R^{b3}$, $NR^{c3}S(=O)_2NR^{c3}R^{d3}$, $S(O)NR^{c3}R^{d3}$, and $S(O)_2NR^{c3}R^{d3}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^4$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a4}$, $C(=O)R^{b4}$, $C(=O)OR^{b4}$, $NR^{c4}R^{d4}$, $C(=O)NR^{c4}R^{d4}$, —$OC(=O)NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(O)NR^{c4}R^{d4}$, and $S(O)_2NR^{c4}R^{d4}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^5$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a5}$, $SR^{a5}$, $C(=O)R^{b5}$, $C(=O)OR^{b5}$, $NR^{c5}R^{d5}$, $C(=O)NR^{c5}R^{d5}$, —$OC(=O)$ $NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(O)NR^{c5}R^{d5}$, and $S(O)_2NR^{c5}R^{d5}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^6$ is selected from the group consisting of H, $C_{1-6}$ alkyl, $C_{1-6}$ haloalkyl, $C_{1-6}$ hydroxyalkyl, and $C_{1-6}$ alkoxy;

$R^7$ is selected from the group consisting of H, $C_{1-6}$ alkyl, CN, $NO_2$, $OR^{a7}$, $C(=O)R^{b7}$, $C(=O)OR^{b7}$, $NR^{c7}R^{d7}$, $C(=O)NR^{c7}R^{d7}$, —$OC(=O)NR^{c7}R^{d7}$, $NR^{c7}C(=O)R^{b7}$, $NR^{c7}C(=O)OR^{b7}$ $NR^{c7}C(=O)NR^{c7}R^{d7}$, $NR^{c7}S(=O)_2R^{b7}$, and $NR^{c7}S(=O)_2NR^{c7}R^{d7}$;

$R^8$ is selected from the group consisting of H, $C_{1-6}$ alkyl, CN, $NO_2$, $OR^{a8}$, $C(=O)R^{b8}$, $C(=O)OR^{b8}$, $NR^{c8}R^{d8}$, $C(=O)NR^{c8}R^{d8}$, —$OC(=O)NR^{c8}R^{d8}$, $NR^{c8}C(=O)R^{b8}$, $NR^{c8}C(=O)OR^{b8}$, $NR^{c8}C(=O)NR^{c8}R^{d8}$, $NR^{c8}S$ $(=O)_2R^{b8}$, and $NR^{c8}S(=O)_2NR^{c8}R^{d8}$;

each $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, $R^{d5}$, $R^{a7}$, $R^{b7}$, $R^{c7}$, $R^{d7}$, $R^{a8}$, $R^{b8}$, $R^{c8}$, and $R^{d8}$ is independently selected from the group consisting of H, $C_{1-6}$ alkyl, $C_{2-6}$ alkenyl, $C_{2-6}$ alkynyl, $C_{1-6}$ hydroxyalkyl, $C_{1-6}$ haloalkyl, $C_{1-6}$ alkoxy, —($C_{1-6}$ alkylene)-$C_{1-6}$ alkoxy, $C_{3-10}$ cycloalkyl, —($C_{1-6}$ alkylene)-$C_{3-10}$ cycloalkyl, $C_{6-10}$ aryl, 5-10 membered heteroaryl, 4-10 membered heterocycloalkyl, wherein the $C_{1-6}$ alkyl, $C_{2-6}$ alkenyl, $C_{2-6}$ alkynyl, $C_{3-10}$ cycloalkyl, —($C_{1-6}$ alkylene)-$C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

or $R^{c2}$ and $R^{d2}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c3}$ and $R^{d3}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c4}$ and $R^{d4}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino;

wherein the ring comprising $X^1$, $X^2$, $X^3$, and $X^4$ forms a cycloalkyl, heteroaryl or heterocycloalkyl ring;

with the proviso that when the 9-membered ring comprising $X^1$, $X^2$, $X^3$, $X^4$, $X^7$, and $X^8$ forms Ring A:

Ring A

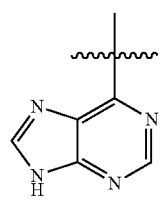

then -L-$R^1$ does not form the following groups:

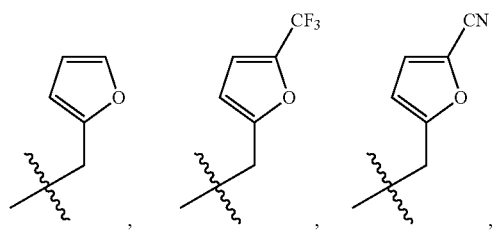

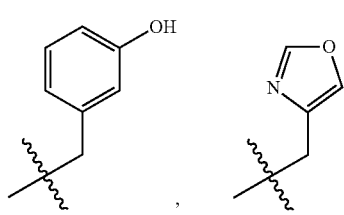

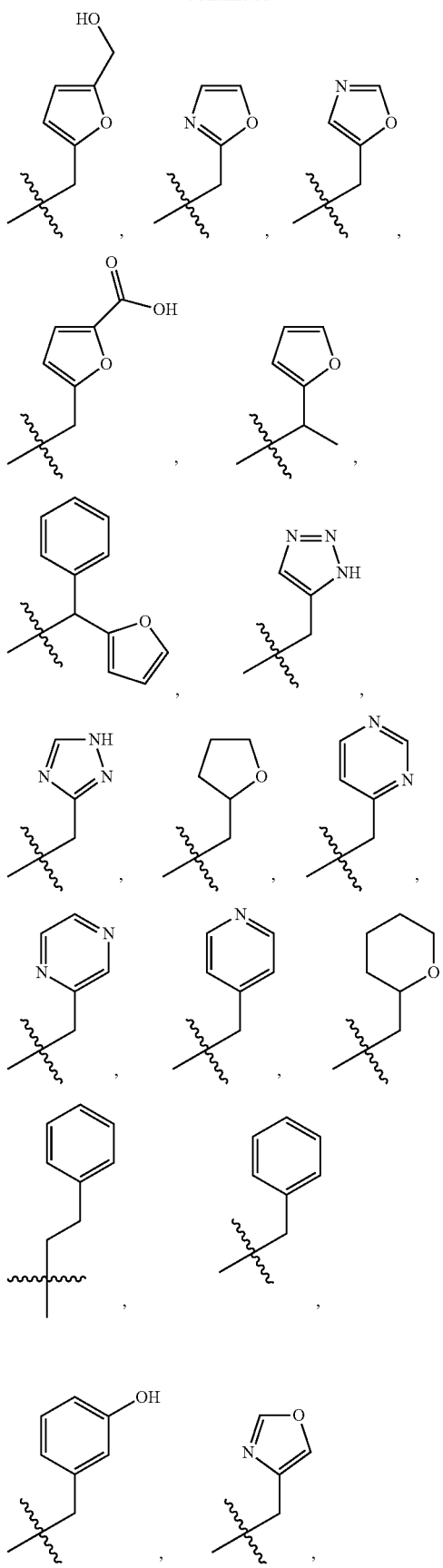

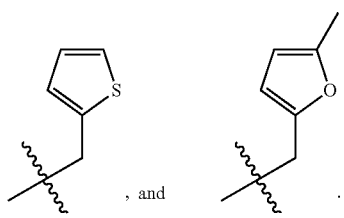

In some embodiments, $X^1$ is N. In some embodiments, $X^1$ is C.

In some embodiments, $X^2$ is S. In some embodiments, wherein $X^2$ is N. In some embodiments, $X^2$ is $NR^2$. In some embodiments, $X^2$ is $CR^2$. In some embodiments, is $CHR^2$.

In some embodiments, $X^3$ is S. In some embodiments, $X^3$ is N. In some embodiments, $X^3$ is $NR^3$. In some embodiments, $X^3$ is $CR^3$. In some embodiments, $X^3$ is $CHR^3$.

In some embodiments, $X^4$ is S. In some embodiments, $X^4$ is N. In some embodiments, $X^4$ is $NR^4$. In some embodiments, $X^4$ is $CR^4$. In some embodiments, is $CHR^4$.

In some embodiments, $X^7$ is N. In some embodiments, $X^7$ is $CR^7$.

In some embodiments, $X^8$ is N. In some embodiments, $X^8$ is $CR^8$. In some embodiments, $X^8$ is CH.

In some embodiments, L is $C_{1-6}$ alkylene optionally substituted by 1, 2, 3, or 4 independently selected $R^{20}$ groups. In some embodiments, L is unsubstituted $C_{1-6}$ alkylene. In some embodiments, L is unsubstituted methylene or unsubstituted ethylene.

In some embodiments, $R^1$ is selected from the group consisting of $C_{6-10}$ aryl, 5-6 membered heteroaryl, and 5-6 membered heterocycloalkyl, each optionally substituted by 1, 2, 3, or 4 independently selected $R^{14}$ groups. In some embodiments, $R^1$ is 2-benzofuranyl or 4-quinolinyl, each optionally substituted by 1, 2, 3, or 4 independently selected $R^{14}$ groups. In some embodiments, $R^1$ is selected from the group consisting of 2-benzofuranyl, 4-quinolinyl, phenyl, 5-6 membered heteroaryl, and 5-6 membered heterocycloalkyl, each optionally substituted by 1 or 2 independently selected $R^{14}$ groups. In some embodiments, $R^1$ is selected from the group consisting of unsubstituted phenyl, unsubstituted 5-6 membered heteroaryl, and unsubstituted 5-6 membered heterocycloalkyl. In some embodiments, $R^1$ is selected from the group consisting of 2-benzofuranyl, 4-quinolinyl, 5-6 membered heteroaryl, and 5-6 membered heterocycloalkyl, each optionally substituted by 1 or 2 independently selected $R^{14}$ groups. In some embodiments, $R^1$ is selected from the group consisting of:

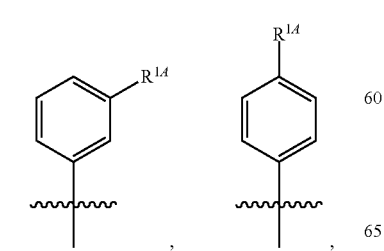

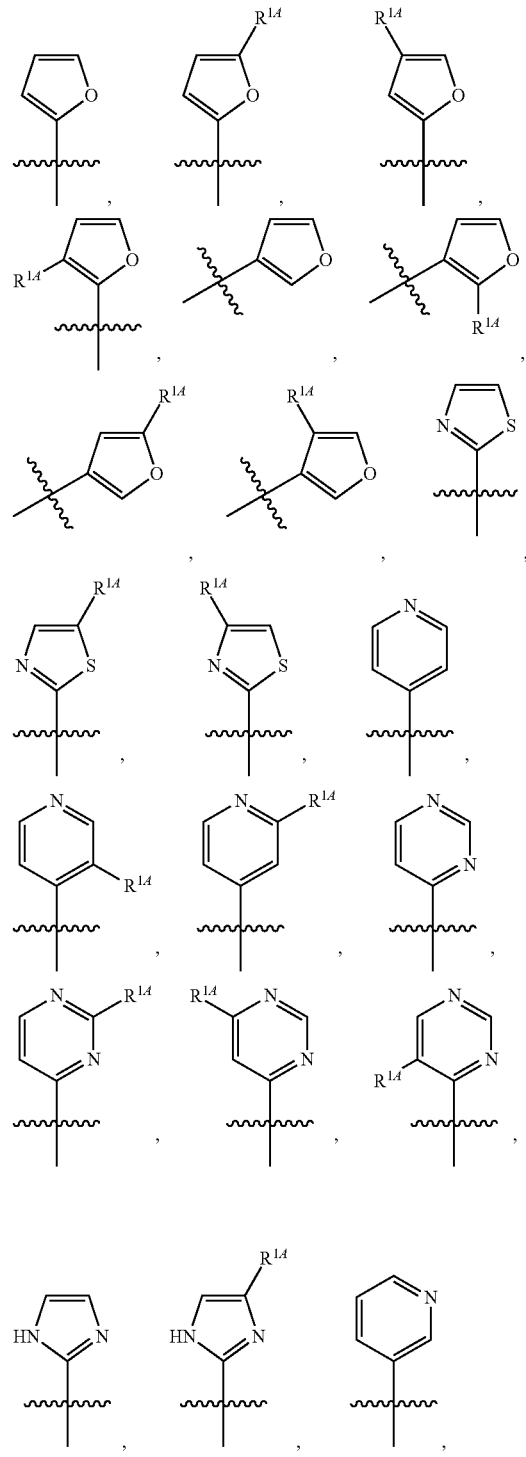

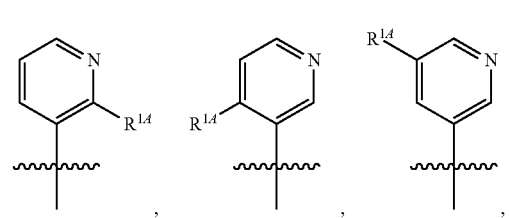

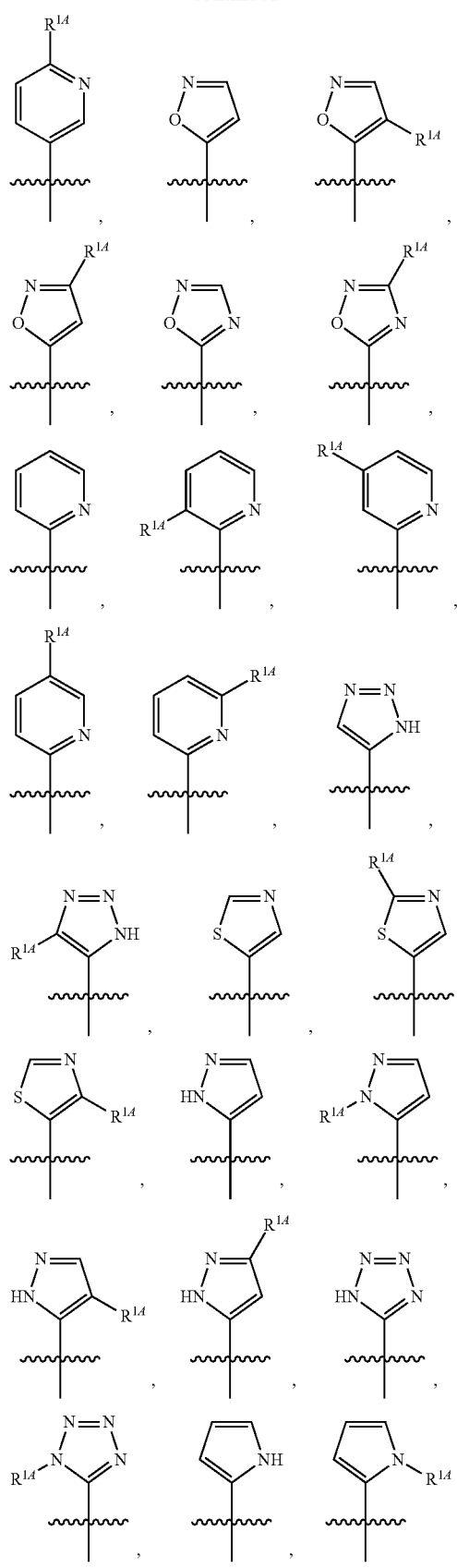

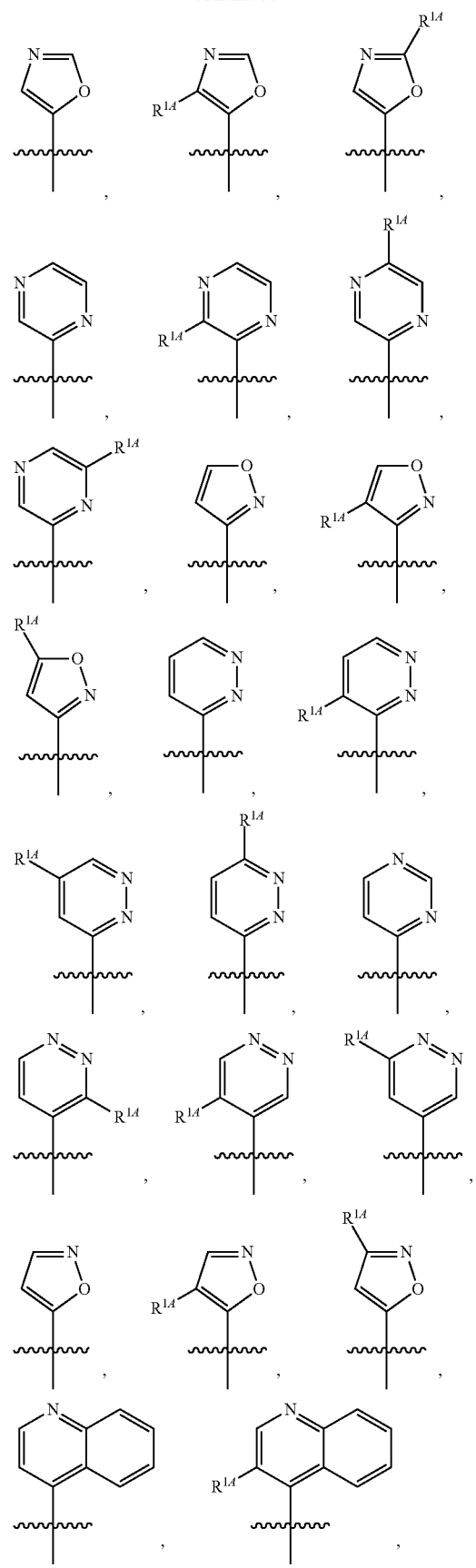
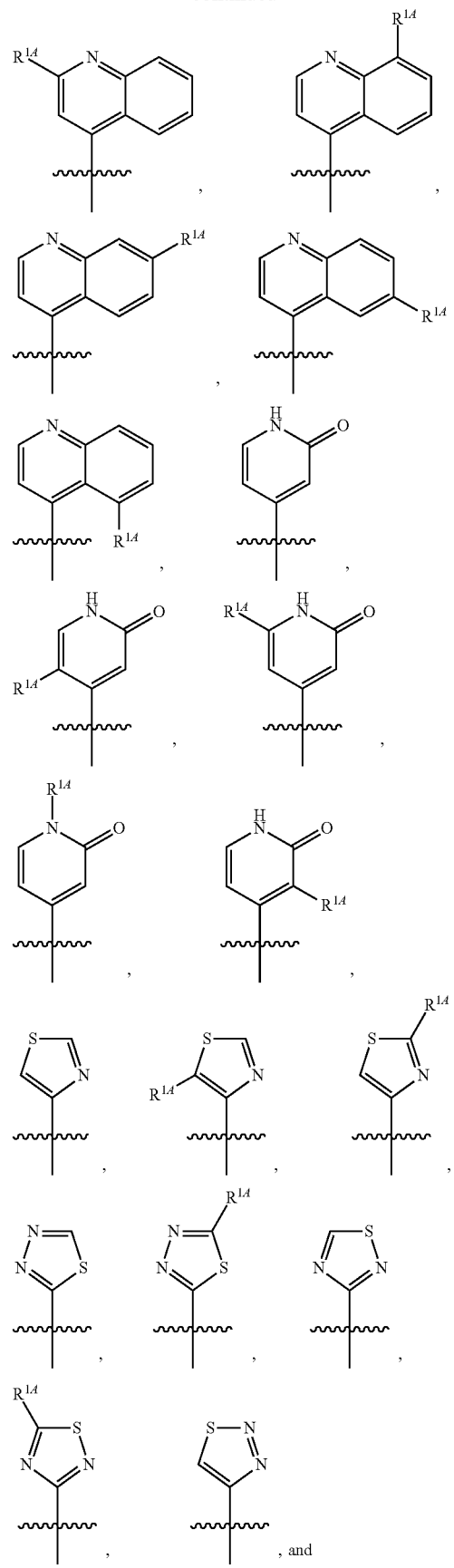

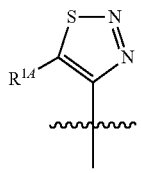

In some embodiments, each $R^{1A}$ is independently selected from the group consisting of halo, CN, $C_{1-6}$ alkyl, $C_{1-6}$ haloalkyl, $C_{1-6}$ alkoxy, and —C(=O)OH. In some embodiments, each $R^{1A}$ is independently selected from the group consisting of CN, fluoro, chloro, methyl, trifluoromethyl, methoxy, and —C(=O)OH.

In some embodiments, $R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups. In some embodiments, $R^2$ is selected from the group consisting of H, oxo, chloro, fluoro, bromo, CN, methyl, —CH$_2$OH, —CH$_2$OCH$_3$, —CH$_2$NHCH$_3$, —CH$_2$N(CH$_3$)$_2$, NH$_2$, —NHCH$_3$, —N(CH$_3$)$_2$, phenyl, 4-pyridinyl, C(=O)OCH$_3$, C(=O)NH$_2$, C(=O)NHCH$_3$,

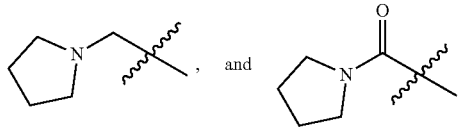

In some embodiments, $R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$ wherein the $C_{1-6}$ alkyl, $C_{3-6}$ cycloalkyl, phenyl, 5-6 membered heteroaryl, 5-6 membered heterocycloalkyl, are each optionally substituted by 1, 2, 3, or 4 independently selected $R^{20}$ groups. In some embodiments, $R^3$ is —$OR^{a3}$. In some embodiments, $R^3$ is selected from the group consisting of H, azido, CN, methyl, cyclopropyl, cyclobutyl, phenyl, 3-pyridinyl, N-morpholino, methoxy, ethoxy, n-propoxy, isopropoxy, n-butoxy, —OCH$_2$CH$_2$OH, —OCH$_2$CH$_2$CH$_2$OH, —OCH$_2$CH$_2$OCH$_3$, —OCH$_2$CH$_2$CH$_2$OCH$_3$, —ONHCH$_3$, —OCH$_2$CHF$_2$, —OCH$_2$CF$_3$, —OCH$_2$CH$_2$CF$_3$, —OCH$_2$CHF$_2$CH$_3$, —OCH$_2$CH$_2$NHC(=O)CH$_3$, cyclobutoxy, —OCH$_2$CH$_2$—O-phenyl, —SCH$_3$, —NH$_2$, —NHCH$_3$, —NHCH$_2$CH$_3$, —N(CH$_3$)$_2$, —NHCH$_2$CH$_2$CH$_2$OH, —CH$_2$OCH$_3$, —CH$_2$OH, —CH$_2$NHCH$_3$, —CH$_2$N(CH$_3$)$_2$, —C(=O)OCH$_3$, —C(=O)NH$_2$, —C(=O)NHCH$_3$, —C(=O)N(CH$_3$)$_2$, —NHCH$_2$CH$_2$OH, —C(=O)NHCH$_2$CH$_2$OH, —OC(=O)CH$_3$, —OCH$_2$-azetidinyl, —OCH$_2$-oxetanyl,

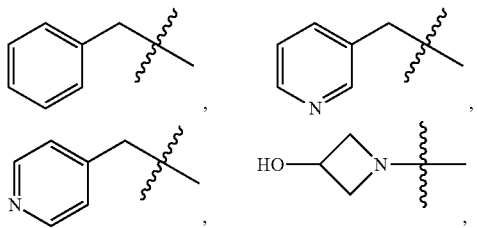

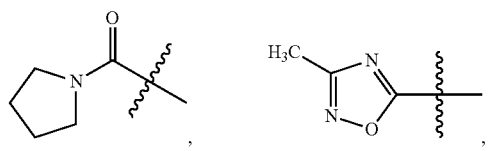

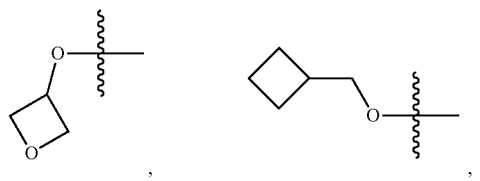

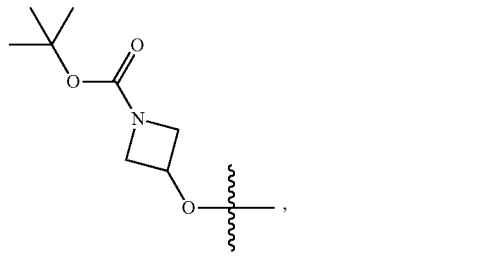

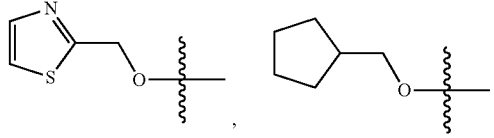

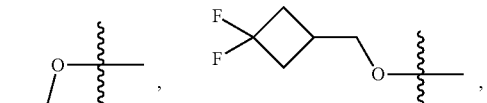

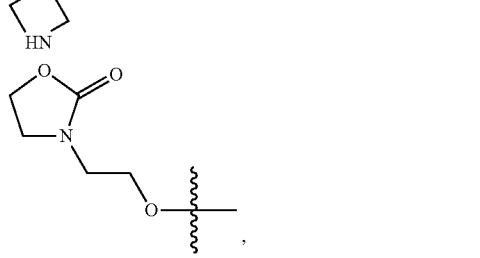

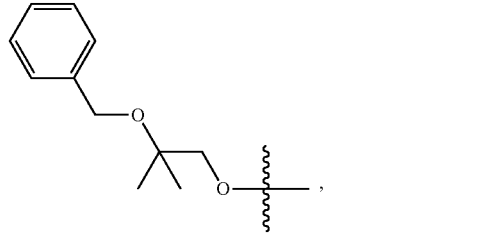

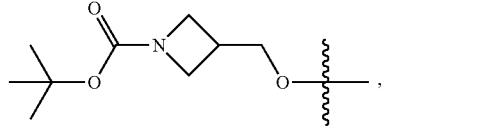

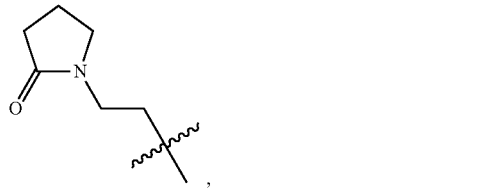

In some embodiments, R⁴ is selected from the group consisting of H, oxo, azido, halo, CN, C₁₋₆ alkyl, OR^{a4}, NR^{c4}R^{d4}, and 4-10 membered heterocycloalkyl, wherein the C₁₋₆ alkyl and 4-10 membered heterocycloalkyl are each optionally substituted by 1, 2, 3, or 4 independently selected R²⁰ groups. In some embodiments, R⁴ is selected from the group consisting of H, halo, methyl, —CH₂CH₂F, —CH₂CH₂CF₃, —CH₂CH₂OH, —CH₂CH₂CH₂OH, —CH₂CH₂OCH₃, —CH₂C(=O)OH, —CH₂C(=O)NH(CH₃), —CH₂C(=O)N(CH₃)₂, —CH₂CH₂NHC(=O)CH₃, —CH₂CH₂NHCH₃, —CH₂CH₂N(CH₃)₂, In some embodiments, R⁵ is selected from the group consisting of H, halo, CN, C₁₋₆ alkyl, C₁₋₆ haloalkyl, OR^{a5}, SR^{a5}, NR^{c5}R^{d5}, C₃₋₆ cycloalkyl, C₆₋₁₀ aryl, and 5-6 membered heteroaryl. In some embodiments, R⁵ is selected from the group consisting of H, fluoro, chloro, bromo, iodo, CN, methyl, isopropyl, OH, OCH₃, NH₂, —NHCH₃, —N(CH₃)₂, —SCH₃, phenyl, cyclopropyl, and In some embodiments, R⁵ is chloro or fluoro. In some embodiments, R⁵ is chloro. In some embodiments, R⁵ is fluoro.

In some embodiments, R⁶ is H or C₁₋₆ alkyl. In some embodiments, R⁶ is H. In some embodiments, R⁶ is C₁₋₆ alkyl. In some embodiments, R⁶ is C₁₋₆ haloalkyl. In some embodiments, R⁶ is C₁₋₆ hydroxyalkyl. In some embodiments, R⁶ is C₁₋₆ alkoxy.

In some embodiments, R⁷ is selected from the group consisting of H, CN, and C(=O)NR^{c7}R^{d7}. In some embodiments, R⁷ is selected from the group consisting of H, CN, and C(=O)NH₂.

In some embodiments, R⁸ is H or C₁₋₆ alkyl. In some embodiments, R⁸ is H.

In some embodiments:
X¹ is N or C;
X² is N, NR², CR², or CHR²;
X³ is N, NR³, CR³, or CHR³;
X⁴ is S, N, NR⁴, CR⁴, or CHR⁴;
X⁷ is N or CR⁷;
X⁸ is N or CR⁸;
L is unsubstituted C₁₋₆ alkylene;
R¹ is selected from the group consisting of 2-benzofuranyl, 4-quinolinyl, C₆₋₁₀ aryl, 5-6 membered heteroaryl, 5-6 membered heterocycloalkyl, optionally substituted by 1, 2, 3, or 4 independently selected R^{1A} groups;
each R^{1A} is independently selected from the group consisting of halo, CN, C₁₋₆ alkyl, C₁₋₆ haloalkyl, C₁₋₆ alkoxy, and —C(=O)OH;
R² is selected from the group consisting of H, oxo, halo, CN, C₁₋₆ alkyl, OR^{a2}, NR^{c2}R^{d2}, 5-6 membered heteroaryl, 5-6 membered heterocycloalkyl, C(=O)OR^{a2}, and C(=O)NR^{c2}R^{d2}, wherein the C₁₋₆ alkyl and 4-10 membered heterocycloalkyl are each optionally substituted by 1, 2, 3, or 4 independently selected R²⁰ groups;
R³ is selected from the group consisting of H, oxo, azido, CN, C₁₋₆ alkyl, C₃₋₆ cycloalkyl, phenyl, 5-6 membered heteroaryl, 5-6 membered heterocycloalkyl, OR^{a3}, SR^{a3}, NR^{c3}R^{d3}, C(=O)OR^{a3}, —C(=O)NR^{c3}R^{d3}, —OC(=O)R^{b3}, wherein the C₁₋₆ alkyl, C₃₋₆ cycloalkyl, phenyl, 5-6 membered heteroaryl, 5-6 membered heterocycloalkyl, are each optionally substituted by 1, 2, 3, or 4 independently selected R²⁰ groups;
R⁴ is selected from the group consisting of H, oxo, azido, halo, CN, C₁₋₆ alkyl, OR^{a4}, NR^{c4}R^{d4}, and 4-10 membered heterocycloalkyl, wherein the C₁₋₆ alkyl and 4-10 membered heterocycloalkyl are each optionally substituted by 1, 2, 3, or 4 independently selected R²⁰ groups;
R⁵ is selected from the group consisting of H, halo, CN, C₁₋₆ alkyl, C₁₋₆ haloalkyl, OR^{a5}, SR^{a5}, NR^{c5}R^{d5}, C₃₋₆ cycloalkyl, C₆₋₁₀ aryl, and 5-6 membered heteroaryl;
R⁶ is H;
R⁷ is selected from the group consisting of H, CN, and C(=O)NR^{c7}R^{d7}; and
R⁸ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

$R^1$ is selected from the group consisting of 2-furanyl, 4-quinolinyl, $C_{6-10}$ aryl, 5-6 membered heteroaryl, and 5-6 membered heterocycloalkyl, optionally substituted by 1, 2, 3, or 4 independently selected $R^{1A}$ groups;

each $R^{1A}$ is independently selected from the group consisting of halo, CN, $C_{1-6}$ alkyl, $C_{1-6}$ haloalkyl, $C_{1-6}$ alkoxy, and —C(=O)OH;

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and C(=O)$NR^{c7}R^{d7}$; and $R^8$ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

$R^1$ is selected from the group consisting of 2-furanyl, 4-quinolinyl, phenyl, 5-6 membered heteroaryl, and 5-6 membered heterocycloalkyl, each optionally substituted by 1, 2, 3, or 4 independently selected $R^{1A}$ groups;

each $R^{1A}$ is independently selected from the group consisting of halo, CN, $C_{1-6}$ alkyl, $C_{1-6}$ haloalkyl, $C_{1-6}$ alkoxy, and —C(=O)OH;

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and C(=O)$NR^{c7}R^{d7}$; and $R^8$ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

$R^1$ is selected from the group consisting of 2-furanyl, 4-quinolinyl, phenyl, 5-6 membered heteroaryl, and 5-6 membered heterocycloalkyl, each optionally substituted by 1 or 2 independently selected $R^{1A}$ groups;

each $R^{1A}$ is independently selected from the group consisting of halo, CN, $C_{1-6}$ alkyl, $C_{1-6}$ haloalkyl, $C_{1-6}$ alkoxy, and —C(=O)OH;

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, C(=O)$OR^{a2}$, and C(=O)$NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, C(=O)$OR^{a3}$, —C(=O)$NR^{c3}R^{d3}$, —OC(=O)$R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and C(=O)$NR^{c7}R^{d7}$; and $R^8$ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

$R^1$ is selected from the group consisting of unsubstituted 2-furanyl, unsubstituted 4-quinolinyl, unsubstituted phenyl, unsubstituted 5-6 membered heteroaryl;

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, $C(=O)OR^{a2}$, and $C(=O)NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, $C(=O)OR^{a3}$, $-C(=O)NR^{c3}R^{d3}$, $-OC(=O)R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and $C(=O)NR^{c7}R^{d7}$; and $R^8$ is H.

In some embodiments:

$X^1$ is N or C;

$X^2$ is selected from the group consisting of N, $NR^2$, $CR^2$, and $CH_2$;

$X^3$ is selected from the group consisting of N, $NR^3$, $CR^3$, and $CH_2$;

$X^4$ is selected from the group consisting of S, N, $NR^4$, $CR^4$, and $CH_2$;

$X^7$ is N or $CR^7$;

$X^8$ is N or $CR^8$;

L is unsubstituted methylene or unsubstituted ethylene;

$R^1$ is selected from the group consisting of:

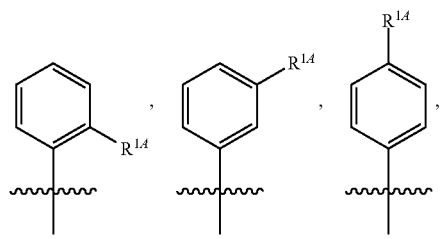

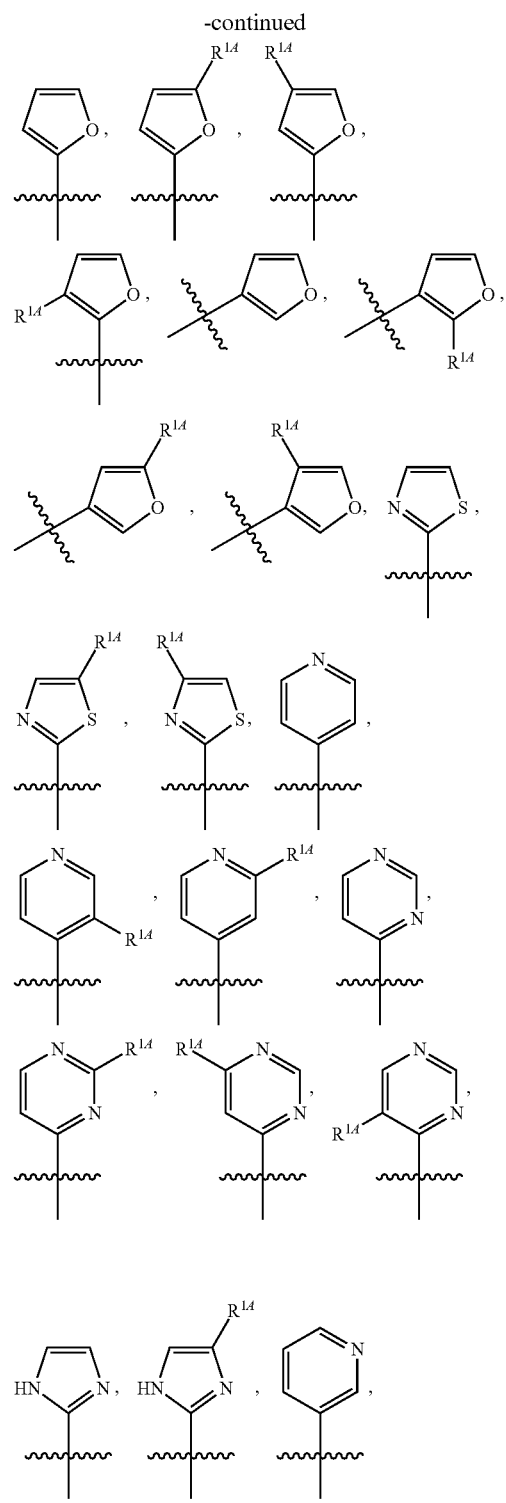

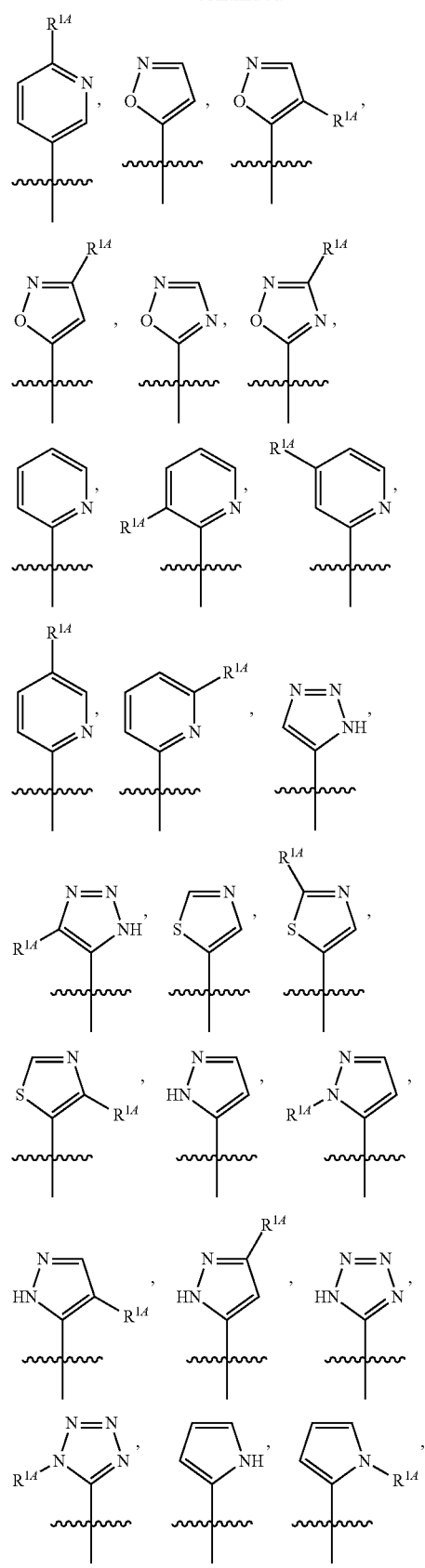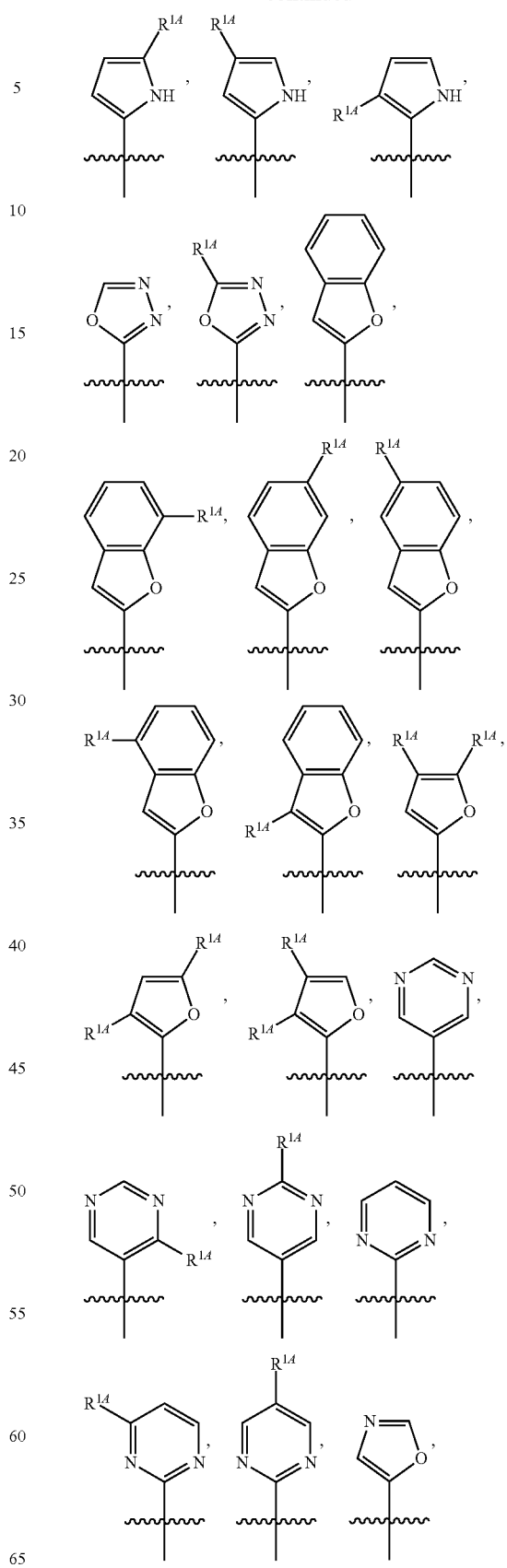

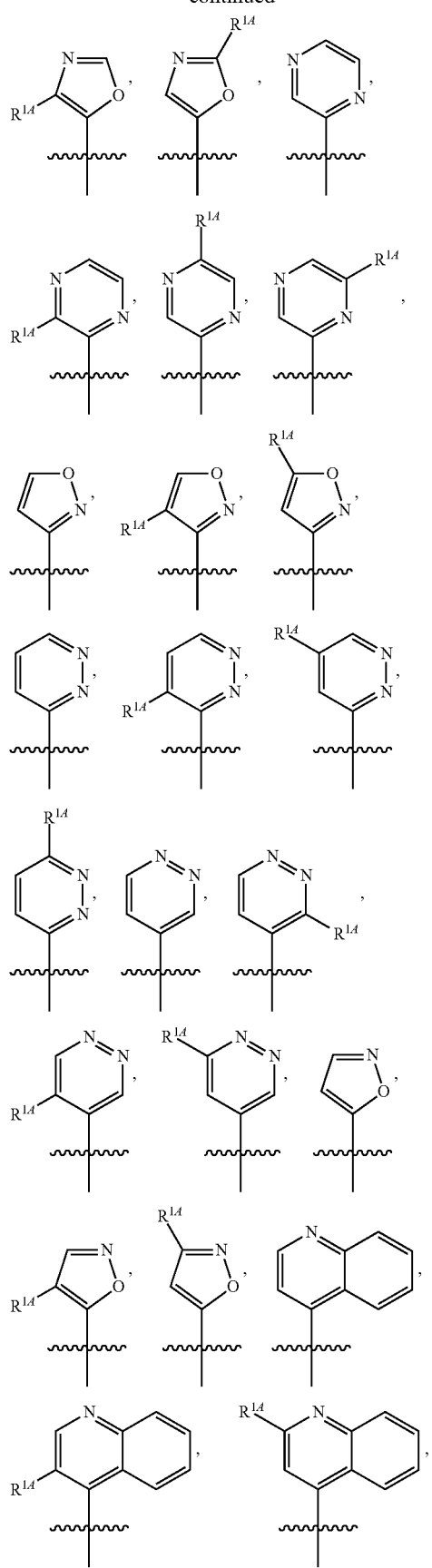
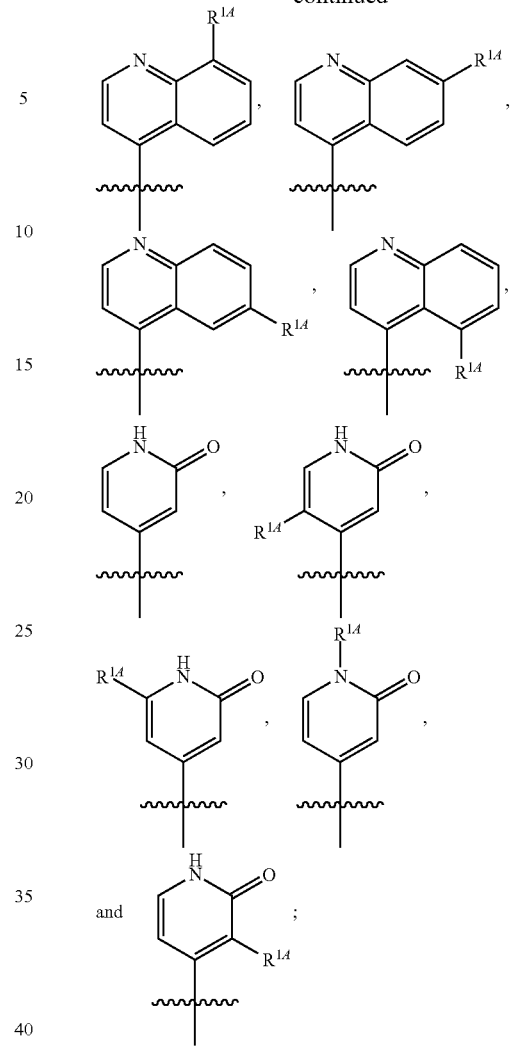

$R^2$ is selected from the group consisting of H, oxo, halo, CN, $C_{1-6}$ alkyl, $OR^{a2}$, $NR^{c2}R^{d2}$, 5-6 membered heteroaryl, 5-6 membered heterocycloalkyl, $C(=O)OR^{a2}$, and $C(=O)NR^{c2}R^{d2}$, wherein the $C_{1-6}$ alkyl and 4-10 membered heterocycloalkyl are each optionally substituted by 1, 2, 3, or 4 independently selected $R^{20}$ groups;

$R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, $OR^{a3}$, $SR^{a3}$, $NR^{c3}R^{d3}$, $C(=O)OR^{a3}$, —$C(=O)NR^{c3}R^{d3}$, —$OC(=O)R^{b3}$, wherein the $C_{1-6}$ alkyl, $C_{3-6}$ cycloalkyl, phenyl, 5-6 membered heteroaryl, 5-6 membered heterocycloalkyl are each optionally substituted by 1, 2, 3, or 4 independently selected $R^{20}$ groups;

$R^4$ is selected from the group consisting of H, oxo, azido, halo, CN, $C_{1-6}$ alkyl, $OR^{a4}$, $NR^{c4}R^{d4}$, and 4-10 membered heterocycloalkyl, wherein the $C_{1-6}$ alkyl and 4-10 membered heterocycloalkyl are each optionally substituted by 1, 2, 3, or 4 independently selected $R^{20}$ groups;

$R^5$ is selected from the group consisting of H, halo, CN, $C_{1-6}$ alkyl, $C_{1-6}$ haloalkyl, $OR^{a5}$, $SR^{a5}$, $NR^{c5}R^{d5}$, $C_{3-6}$ cycloalkyl, $C_{6-10}$ aryl, and 5-6 membered heteroaryl;

$R^6$ is H;

$R^7$ is selected from the group consisting of H, CN, and $C(=O)NR^{c7}R^{d7}$; and $R^8$ is H.

In some embodiments, the compound of Formula (I) is a compound of Formula (Ia):

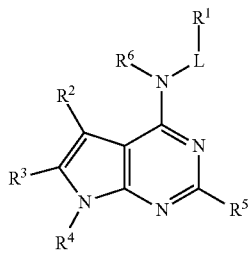

(Ia)

or a pharmaceutically acceptable salt thereof, wherein:

variables L, $R^1$, $R^2$, $R^3$, $R^4$, $R^5$, $R^6$ of Formula (Ia) are defined according to the definitions described herein for compounds of Formula (I).

In some embodiments, L is absent or selected from the group consisting of an unsubstituted $C_{1-6}$ alkylene, an unsubstituted $C_{2-6}$ alkenylene, and a $C_{2-6}$ alkynylene. In some embodiments, L is selected from the group consisting of an unsubstituted $C_{1-6}$ alkylene, an unsubstituted $C_{2-6}$ alkenylene, and a $C_{2-6}$ alkynylene. In some embodiments, L is an unsubstituted $C_{1-6}$ alkylene. In some embodiments, L is an unsubstituted methylene or an unsubstituted ethylene. In some embodiments, L is an unsubstituted methylene.

In some embodiments, $R^1$ is a 5-6 membered heteroaryl or a 5-6 membered heterocycloalkyl, each optionally substituted by 1, 2, 3, or 4 independently selected $R^{1A}$ groups. In some embodiments, $R^1$ is a 5-6 membered heteroaryl optionally substituted by 1, 2, 3, or 4 independently selected $R^{1A}$ groups. In some embodiments, $R^1$ is an unsubstituted 5-6 membered heteroaryl or an unsubstituted 5-6 membered heterocycloalkyl. In some embodiments, $R^1$ is an unsubstituted 5-6 membered heteroaryl.

In some embodiments, $R^2$, $R^3$, and $R^4$ are each independently selected from H and $C_{1-6}$ alkyl. In some embodiments, $R^2$, $R^3$, and $R^4$ are each H.

In some embodiments, $R^5$ is selected from the group consisting of H and halo. In some embodiments, $R^5$ is halo. In some embodiments, $R^5$ is chloro or fluoro. In some embodiments, $R^5$ is chloro.

In some embodiments, $R^6$ is H or $C_{1-6}$ alkyl. In some embodiments, $R^6$ is H.

In some embodiments, the compound of Formula (Ia) is selected from the group consisting of:

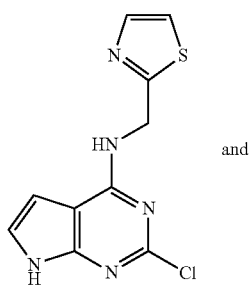

(107)

and

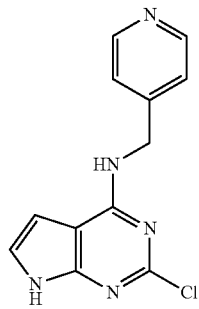

(100)

or a pharmaceutically acceptable salt thereof.

In some embodiments, the compound of Formula (I) is a compound of Formula (Ib):

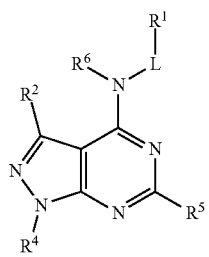

(Ib)

or a pharmaceutically acceptable salt thereof, wherein:

variables L, $R^1$, $R^2$, $R^4$, $R^5$, and $R^6$ of Formula (Ib) are defined according to the definitions described herein for compounds of Formula (I). In some embodiments, $R^6$ is H.

In some embodiments, the compound of Formula (I) is a compound of Formula (Ic):

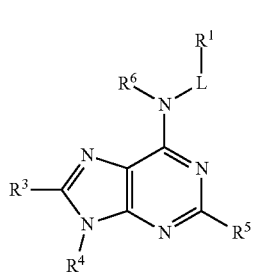

(Ic)

or a pharmaceutically acceptable salt thereof, wherein:

variables L, $R^1$, $R^3$, $R^4$, $R^5$, and $R^6$ of Formula (Ic) are defined according to the definitions described herein for compounds of Formula (I). In some embodiments, $R^6$ is H. In some embodiments, $R^3$ is —$OR^{a3}$.

In some embodiments, the compound of Formula (I) is a compound of Formula (Id):

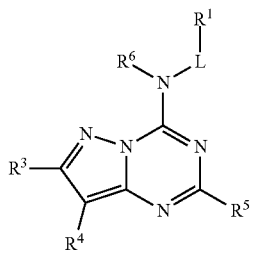

(Id)

or a pharmaceutically acceptable salt thereof, wherein:
variables L, $R^1$, $R^3$, $R^4$, $R^5$, $R^6$ of Formula (Id) are defined according to the definitions described herein for compounds of Formula (I). In some embodiments, $R^6$ is H.

In some embodiments, the compound of Formula (I) is a compound of Formula (Ie):

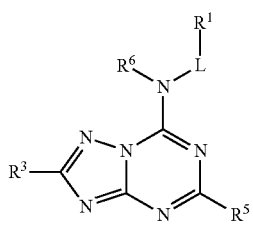

(Ie)

or a pharmaceutically acceptable salt thereof, wherein:
variables L, $R^1$, $R^3$, $R^5$, and $R^6$ of Formula (Ie) are defined according to the definitions described herein for compounds of Formula (I). In some embodiments, $R^6$ is H.

In some embodiments, the compound of Formula (I) is a compound of Formula (If):

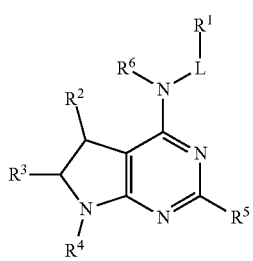

(If)

or a pharmaceutically acceptable salt thereof, wherein:
variables L, $R^1$, $R^2$, $R^3$, $R^4$, $R^5$, and $R^6$ of Formula (If) are defined according to the definitions described herein for compounds of Formula (I). In some embodiments, $R^6$ is H.

In some embodiments, the compound of Formula (I) is a compound of Formula (Ig):

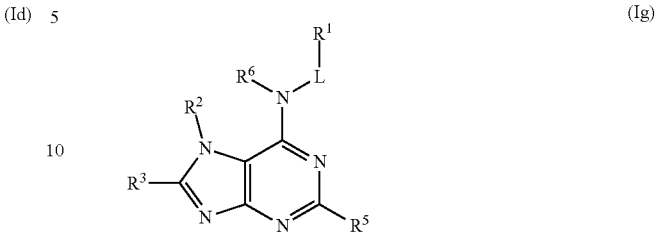

(Ig)

or a pharmaceutically acceptable salt thereof, wherein:
variables L, $R^1$, $R^2$, $R^3$, $R^5$, $R^6$ and $R^7$ of Formula (Ig) are defined according to the definitions described herein for compounds of Formula (I). In some embodiments, $R^6$ is H.

In some embodiments, the compound of Formula (I) is a compound of Formula (Ih):

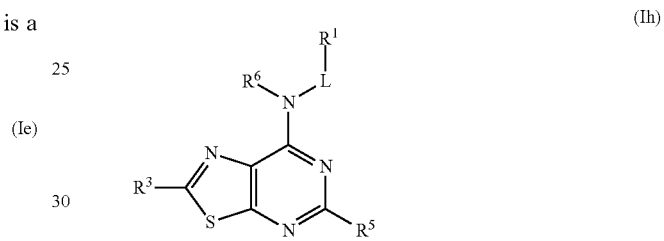

(Ih)

or a pharmaceutically acceptable salt thereof, wherein:
variables L, $R^1$, $R^3$, $R^5$, $R^6$ of Formula (Ih) are defined according to the definitions described herein for compounds of Formula (I). In some embodiments, $R^6$ is H.

In some embodiments, the compound of Formula (I) is a compound of Formula (Ij):

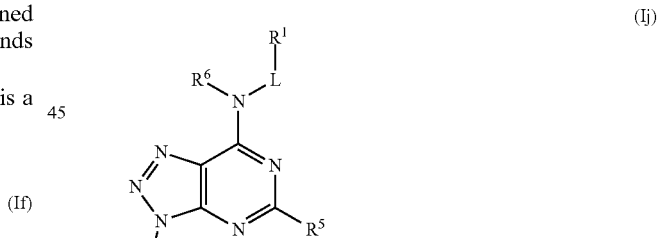

(Ij)

or a pharmaceutically acceptable salt thereof, wherein:
variables L, $R^1$, $R^4$, $R^5$, and $R^6$ of Formula (Ij) are defined according to the definitions described herein for compounds of Formula (I).

In some embodiments, L is absent or selected from the group consisting of an unsubstituted $C_{1-6}$ alkylene, an unsubstituted $C_{2-6}$ alkenylene, and a $C_{2-6}$ alkynylene. In some embodiments, L is selected from the group consisting of an unsubstituted $C_{1-6}$ alkylene, an unsubstituted $C_{2-6}$ alkenylene, and a $C_{2-6}$ alkynylene. In some embodiments, L is an unsubstituted $C_{1-6}$ alkylene. In some embodiments, L is an unsubstituted methylene or an unsubstituted ethylene. In some embodiments, L is an unsubstituted methylene.

In some embodiments, $R^1$ is a 5-6 membered heteroaryl or a 5-6 membered heterocycloalkyl, each optionally substituted by 1, 2, 3, or 4 independently selected $R^{1A}$ groups. In some embodiments, $R^1$ is a 5-6 membered heteroaryl optionally substituted by 1, 2, 3, or 4 independently selected $R^{1A}$ groups. In some embodiments, $R^1$ is an unsubstituted 5-6 membered heteroaryl or an unsubstituted 5-6 membered heterocycloalkyl. In some embodiments, $R^1$ is an unsubstituted 5-6 membered heteroaryl. In some embodiments, $R^1$ is an unsubstituted 5-membered heteroaryl.

In some embodiments, $R^5$ is H or halo. In some embodiments, $R^5$ is halo. In some embodiments, $R^5$ is chloro or fluoro. In some embodiments, $R^5$ is chloro.

In some embodiments, $R^6$ is H or $C_{1-6}$ alkyl. In some embodiments, $R^6$ is H.

In some embodiments, the compound of Formula (Ij) is:

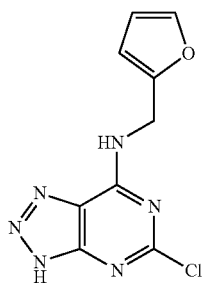

(285)

or a pharmaceutically acceptable salt thereof.

In some embodiments, the compound of Formula (I) is a compound of Formula (Ik):

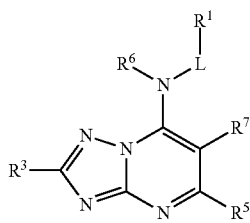

(Ik)

or a pharmaceutically acceptable salt thereof, wherein:
variables L, $R^1$, $R^3$, $R^5$, $R^6$, and $R^7$ of Formula (Ik) are defined according to the definitions described herein for compounds of Formula (I). In some embodiments, $R^6$ is H.

In some embodiments, the compound of Formula (I) is a compound of Formula (Im):

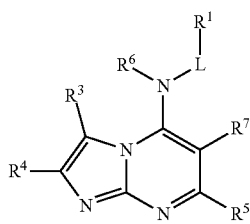

(Im)

or a pharmaceutically acceptable salt thereof, wherein:
variables L, $R^1$, $R^3$, $R^4$, $R^5$, $R^6$, and $R^7$ of Formula (Im) are defined according to the definitions described herein for compounds of Formula (I). In some embodiments, $R^6$ is H.

In some embodiments, the compound of Formula (I) is a compound of Formula (In):

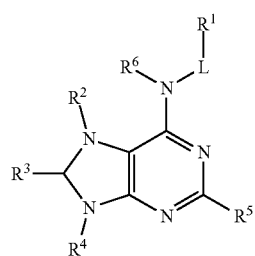

(In)

or a pharmaceutically acceptable salt thereof, wherein:
variables L, $R^1$, $R^2$, $R^3$, $R^4$, $R^5$, and $R^6$ of Formula (In) are defined according to the definitions described herein for compounds of Formula (I). In some embodiments, $R^6$ is H.

In some embodiments, the compound of Formula (I) is a compound of Formula (Io):

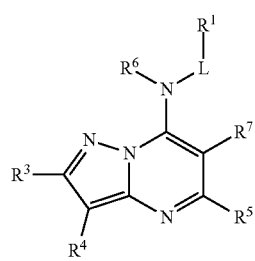

(Io)

or a pharmaceutically acceptable salt thereof, wherein:
variables L, $R^1$, $R^3$, $R^4$, $R^5$, $R^6$, and $R^7$ of Formula (Io) are defined according to the definitions described herein for compounds of Formula (I). In some embodiments, $R^6$ is H.

In some embodiments, the compound of Formula (I) is a compound of Formula (Ip):

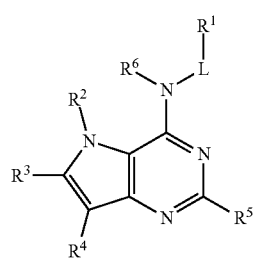

(Ip)

or a pharmaceutically acceptable salt thereof, wherein:
variables L, $R^1$, $R^2$, $R^3$, $R^4$, $R^5$, and $R^6$ of Formula (Ip) are defined according to the definitions described herein for compounds of Formula (I). In some embodiments, $R^6$ is H.

In some embodiments, the compound of Formula (I) is a compound of Formula (Iq):

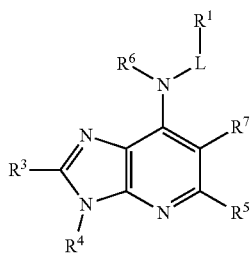
(Iq)

or a pharmaceutically acceptable salt thereof, wherein:

variables L, $R^1$, $R^3$, $R^4$, $R^5$, $R^6$, and $R^7$ of Formula (Iq) are defined according to the definitions described herein for compounds of Formula (I). In some embodiments, $R^6$ is H.

In some embodiments, the compound of Formula (I) is a compound of Formula (Ir):

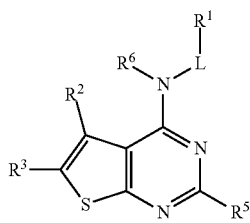
(Ir)

or a pharmaceutically acceptable salt thereof, wherein:

variables L, $R^1$, $R^2$, $R^3$, $R^5$, and $R^6$ of Formula (Ir) are defined according to the definitions described herein for compounds of Formula (I). In some embodiments, $R^6$ is H.

In some embodiments, the compound of Formula (I) is a compound of Formula (Is):

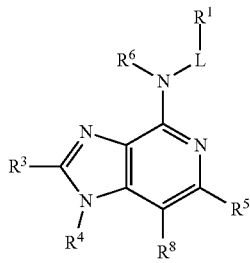
(Is)

or a pharmaceutically acceptable salt thereof, wherein:

variables L, $R^1$, $R^2$, $R^3$, $R^4$, $R^5$, $R^6$, and $R^8$ of Formula (Is) are defined according to the definitions described herein for compounds of Formula (I). In some embodiments, $R^6$ is H. In some embodiments, $R^8$ is H. In some embodiments, $R^6$ and $R^8$ are each H.

In some embodiments, the compound of Formula (I) is a compound of Formula (It):

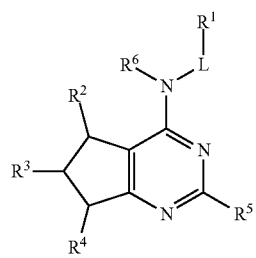
(It)

or a pharmaceutically acceptable salt thereof, wherein:

variables L, $R^1$, $R^2$, $R^3$, $R^4$, $R^5$, $R^6$ of Formula (It) are defined according to the definitions described herein for compounds of Formula (I). In some embodiments, $R^6$ is H. In some embodiments, $R^8$ is H. In some embodiments, $R^6$ and $R^8$ are each H.

In some embodiments, the compound of Formula (I) is selected from the group of compounds provided in Table A, or a pharmaceutically acceptable salt thereof.

TABLE A

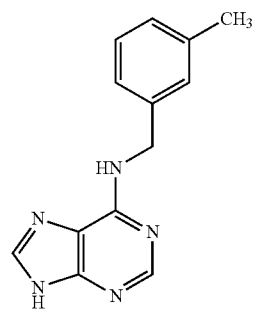 [SMILES: Cc1cccc(CNc2ncnc3[nH]cnc23)c1]
(1)

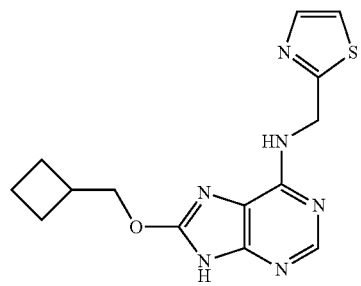 [SMILES: c1csc(CNc2ncnc3[nH]c(OCC4CCC4)nc23)n1]
(2)

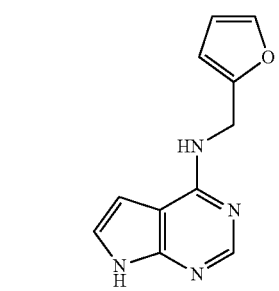 [SMILES: c1coc(CNc2ncnc3[nH]ccc23)c1]
(3)

TABLE A-continued
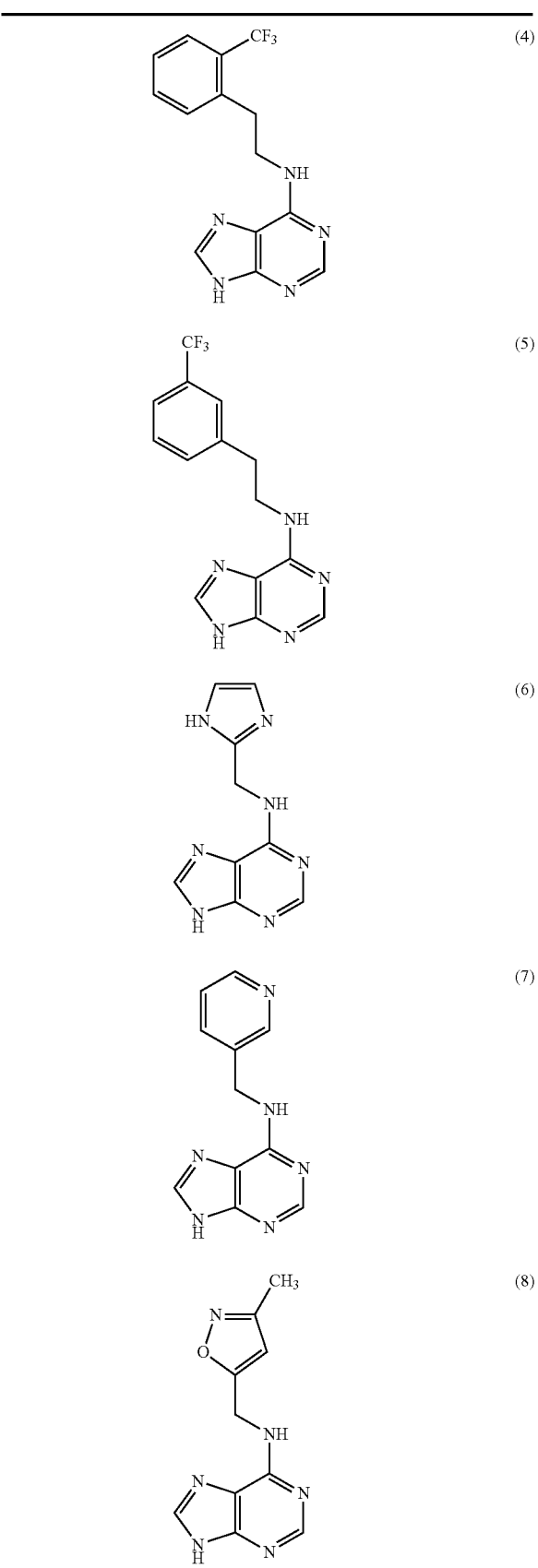
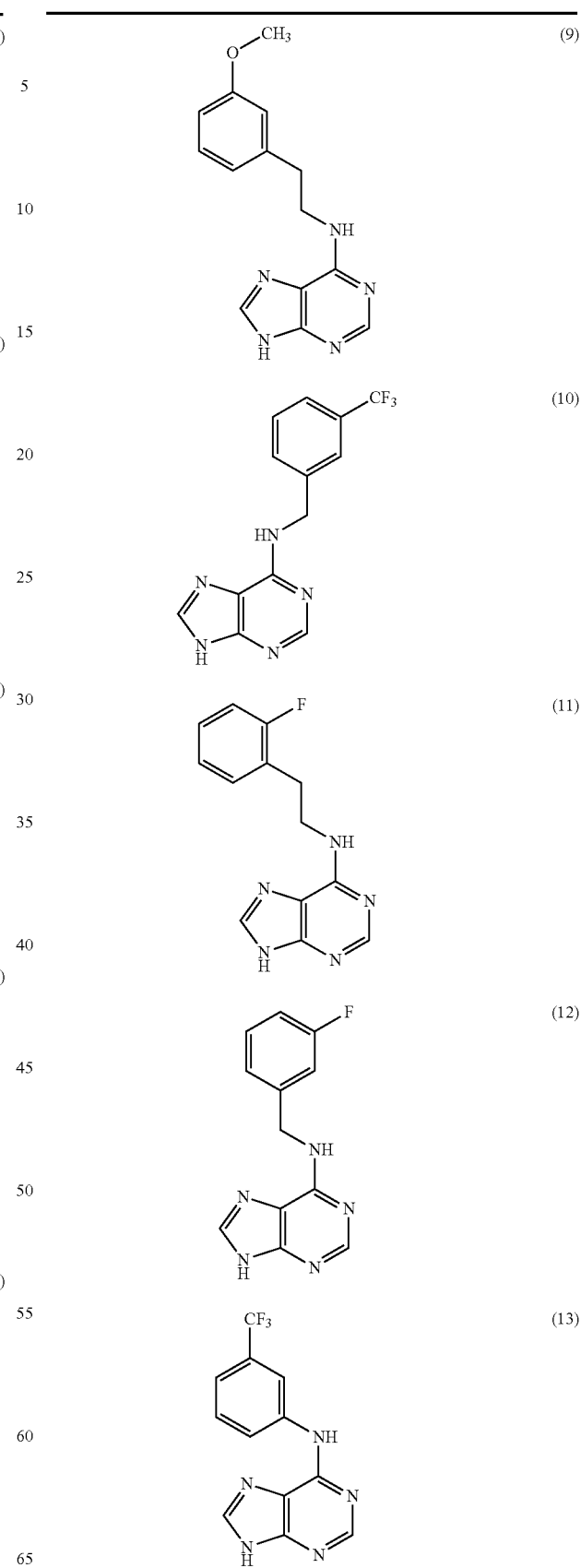

TABLE A-continued
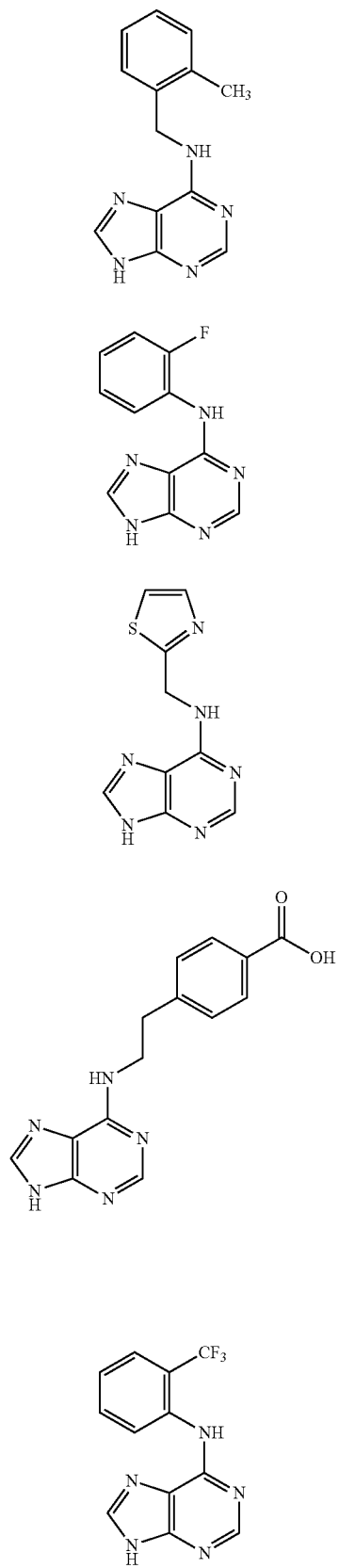
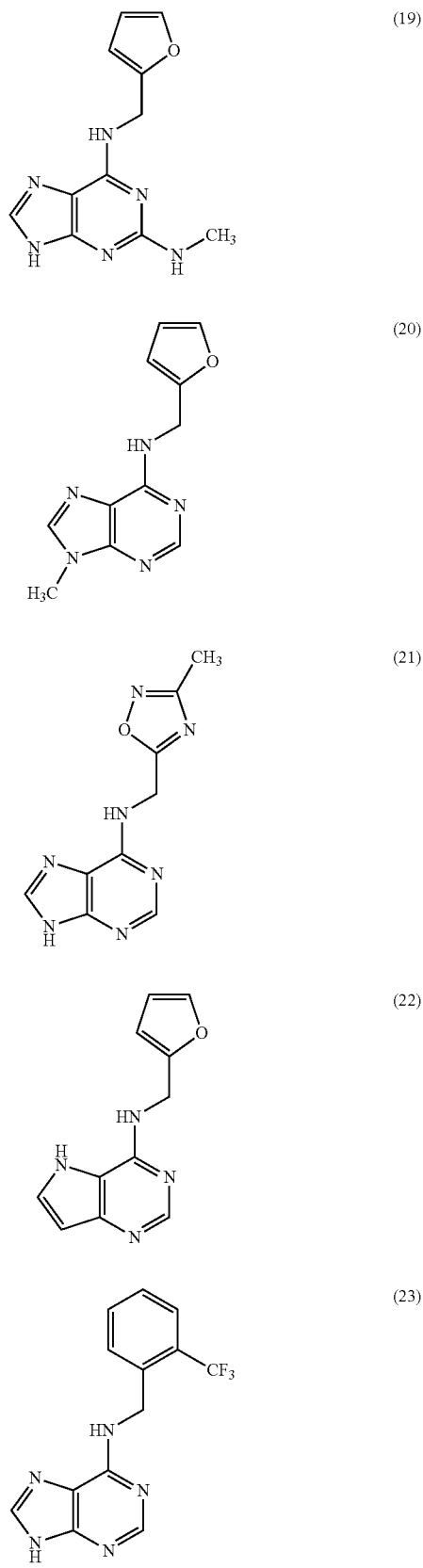

TABLE A-continued
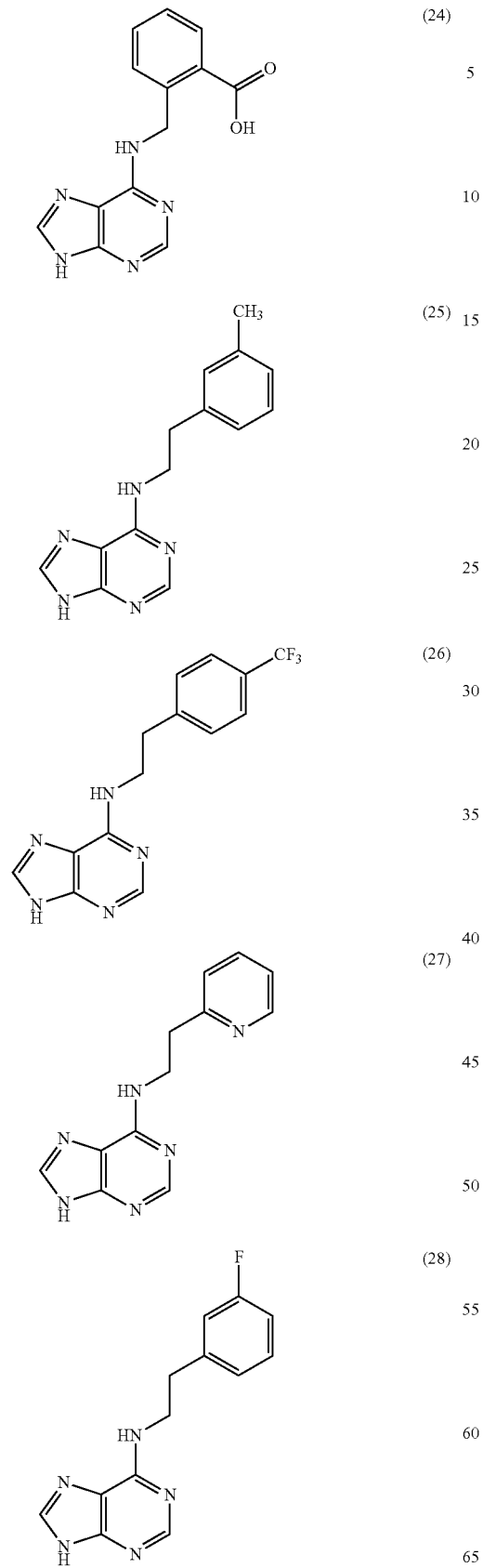
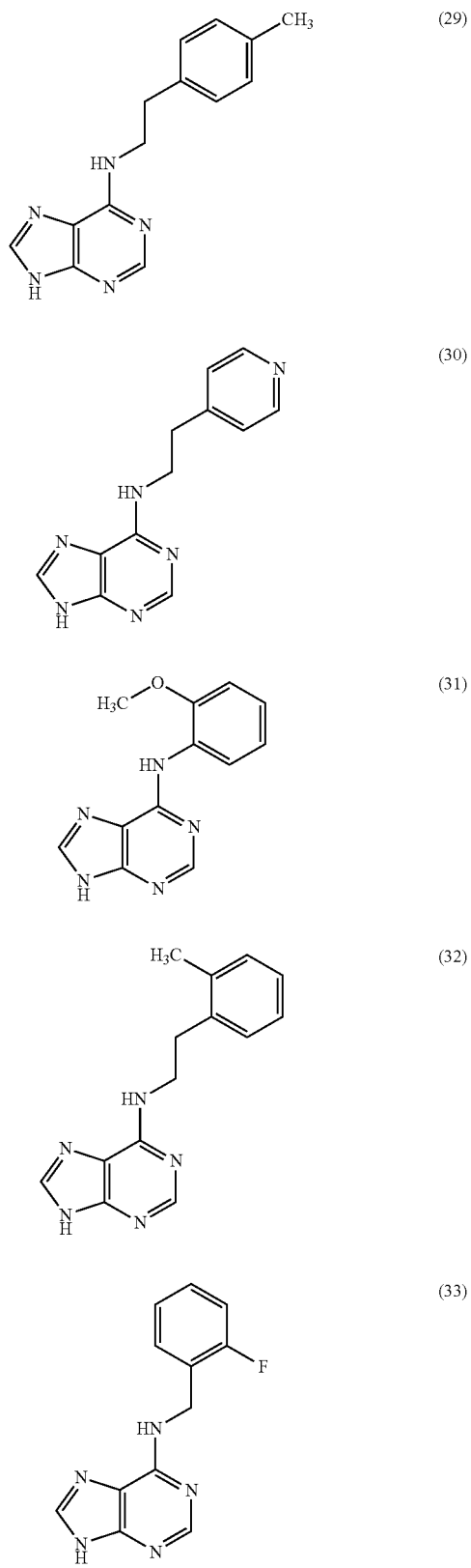

TABLE A-continued
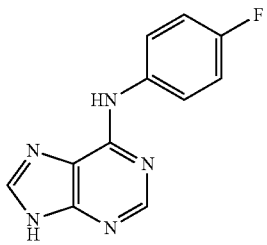 [SMILES: Fc1ccc(Nc2ncnc3[nH]cnc23)cc1]
(34)
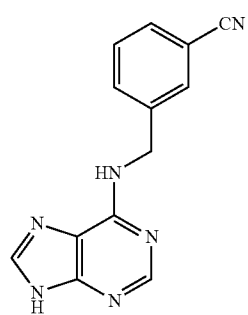 [SMILES: N#Cc1cccc(CNc2ncnc3[nH]cnc23)c1]
(35)
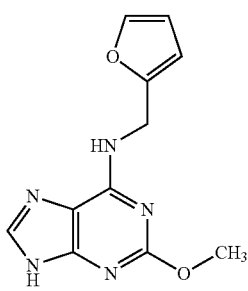 [SMILES: COc1nc(NCc2ccco2)c2nc[nH]c2n1]
(36)
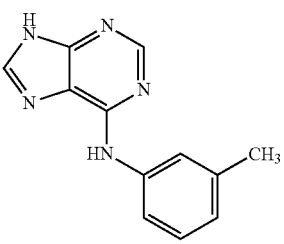 [SMILES: Cc1cccc(Nc2ncnc3[nH]cnc23)c1]
(37)
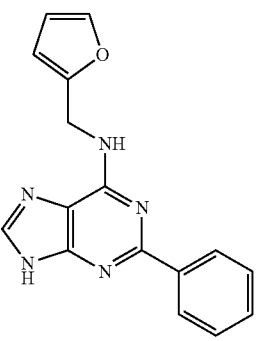 [SMILES: c1ccc(-c2nc(NCc3ccco3)c3nc[nH]c3n2)cc1]
(38)
TABLE A-continued
(39)
(40)
(41)
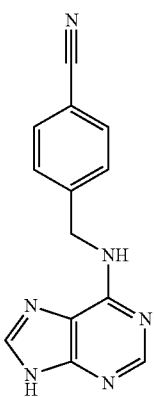 [SMILES: N#Cc1ccc(CNc2ncnc3[nH]cnc23)cc1]
(42)

TABLE A-continued
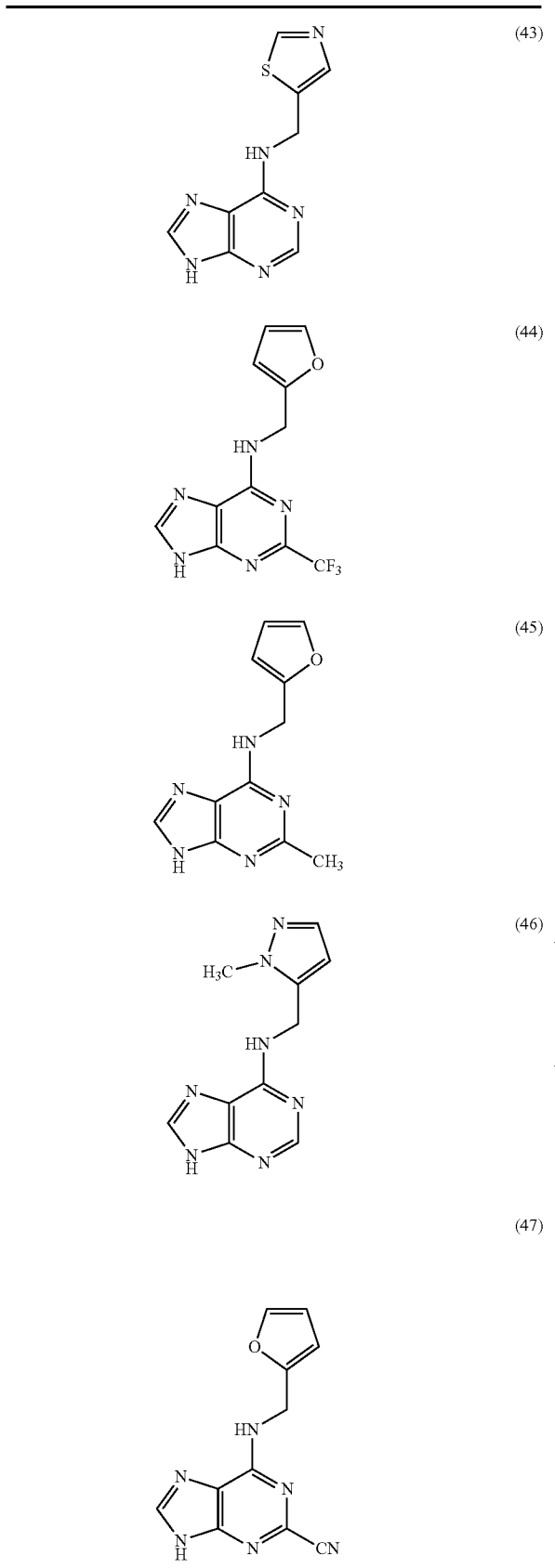
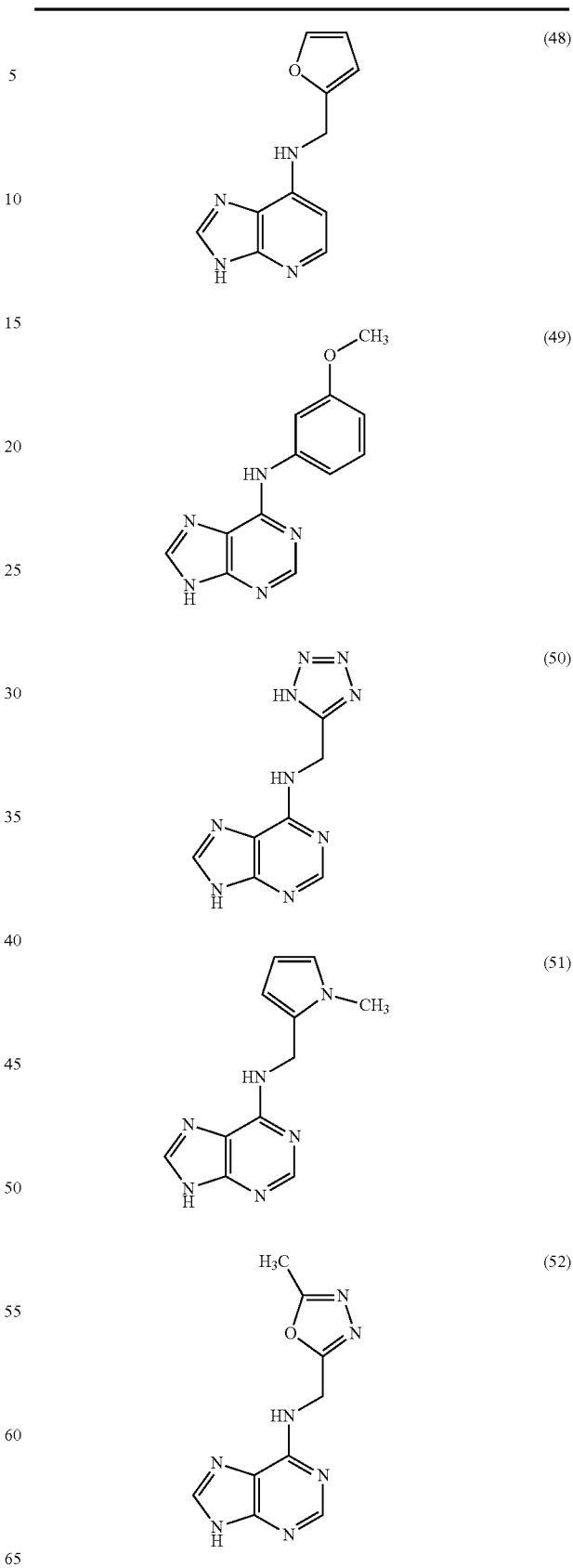

TABLE A-continued
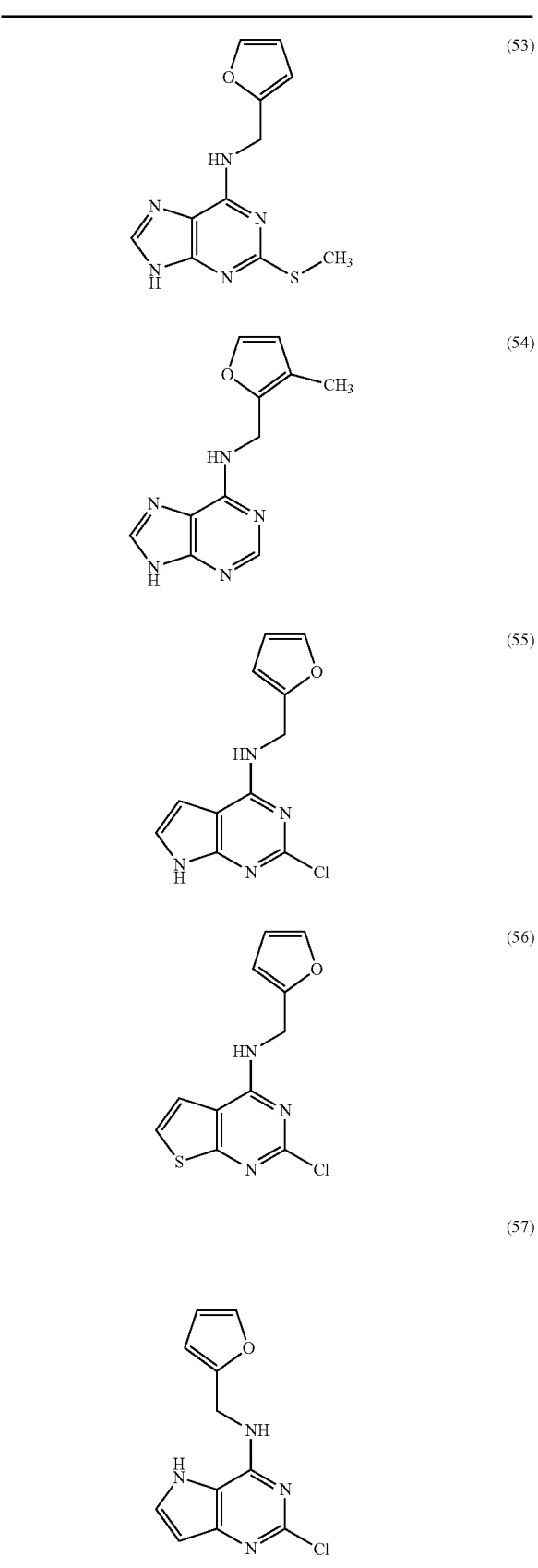
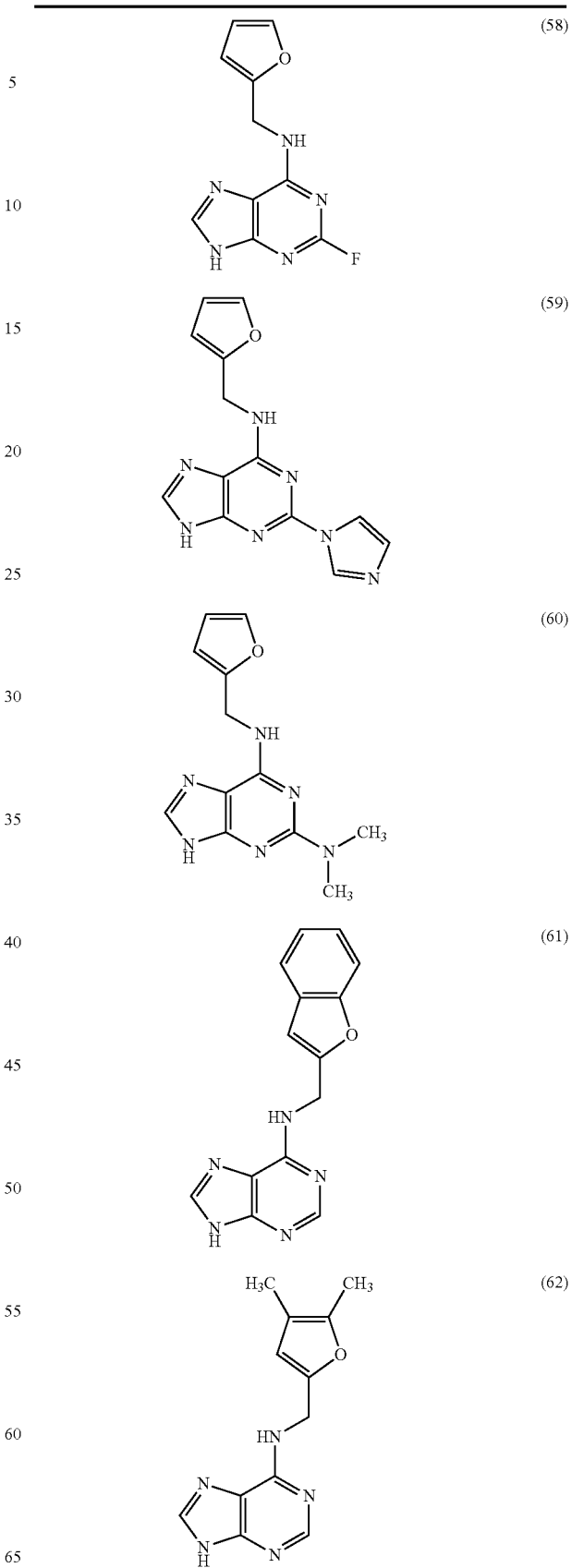

TABLE A-continued
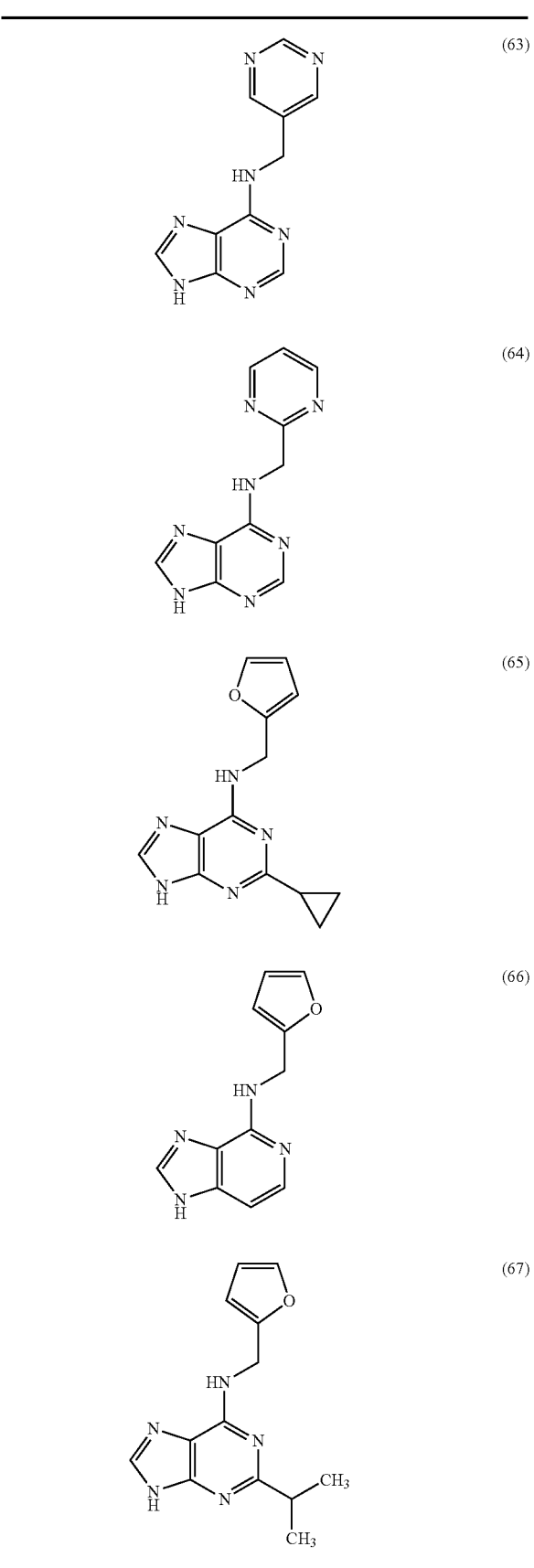

TABLE A-continued
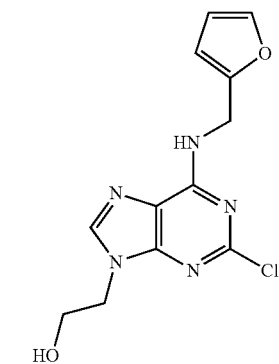 [SMILES: OCCn1cnc2c(NCc3ccco3)nc(Cl)nc21]
(73)
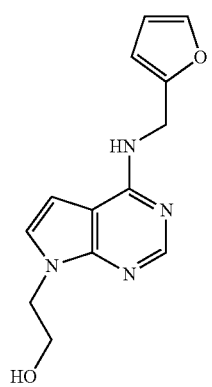
(74)
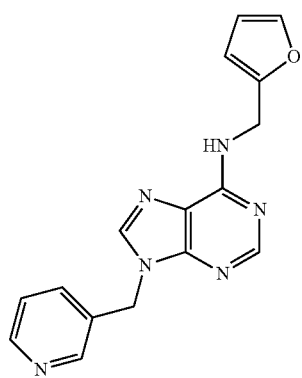 [SMILES: c1cncc(Cn2cnc3c(NCc4ccco4)ncnc32)c1]
(75)
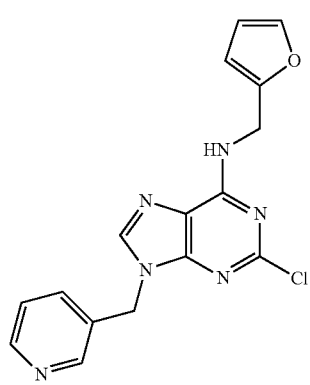 [SMILES: Clc1nc(NCc2ccco2)c2ncn(Cc3cccnc3)c2n1]
(76)
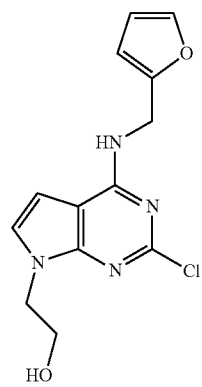
(77)
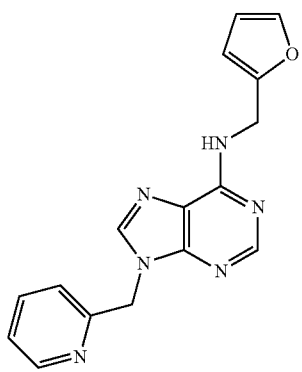 [SMILES: c1ccc(Cn2cnc3c(NCc4ccco4)ncnc32)nc1]
(78)
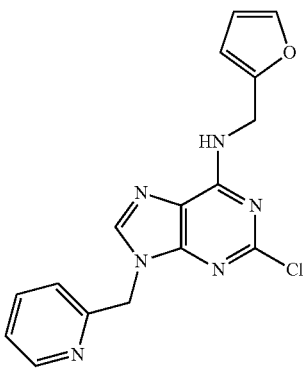 [SMILES: Clc1nc(NCc2ccco2)c2ncn(Cc3ccccn3)c2n1]
(79)
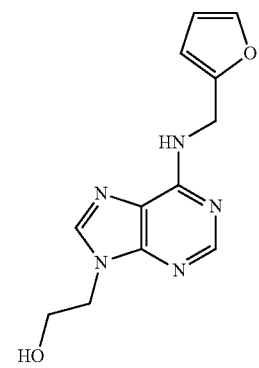 [SMILES: OCCn1cnc2c(NCc3ccco3)ncnc21]
(80)

TABLE A-continued
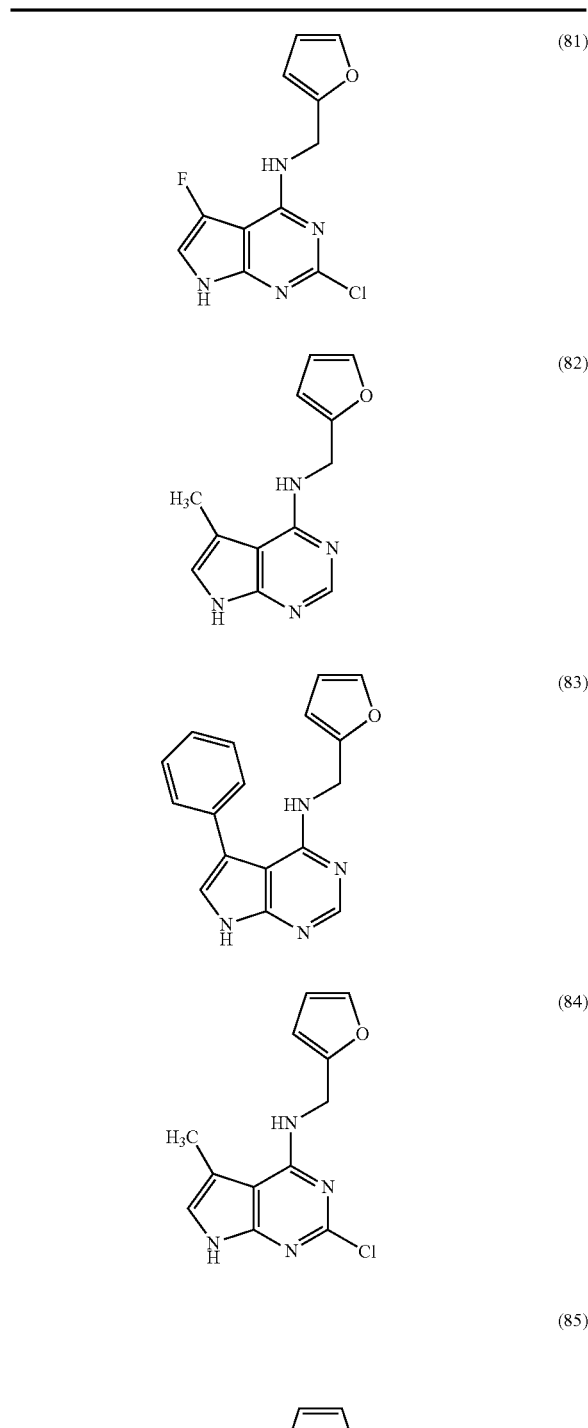
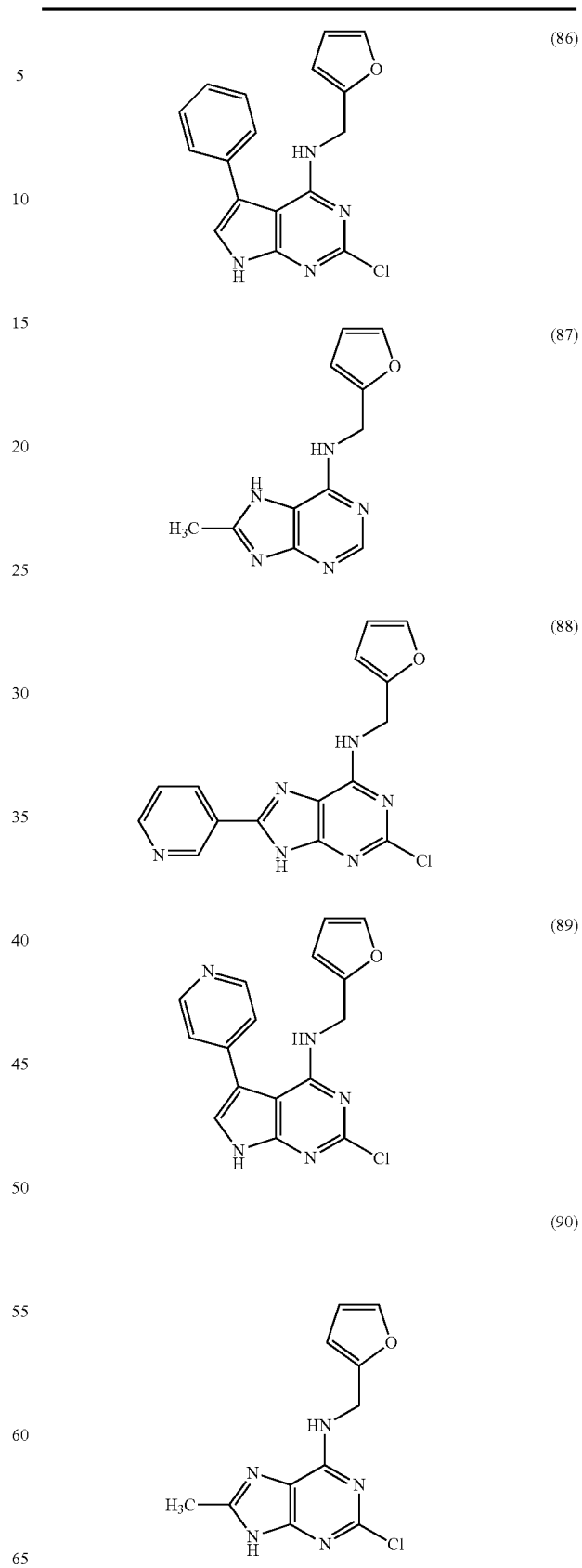

TABLE A-continued
(91) 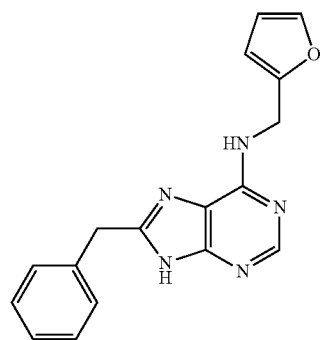 [SMILES: c1ccc(Cc2nc3c(NCc4ccco4)ncnc3[nH]2)cc1]
(92) 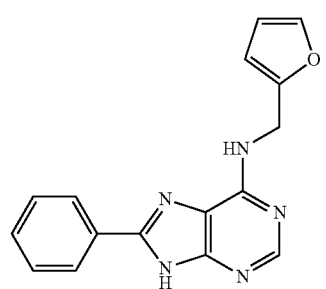 [SMILES: c1ccc(-c2nc3c(NCc4ccco4)ncnc3[nH]2)cc1]
(93) 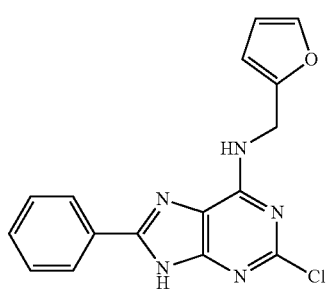 [SMILES: Clc1nc(NCc2ccco2)c2nc(-c3ccccc3)[nH]c2n1]
(94) 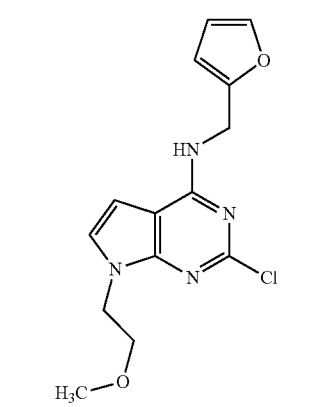 [SMILES: COCCn1ccc2c(NCc3ccco3)nc(Cl)nc21]
(95) 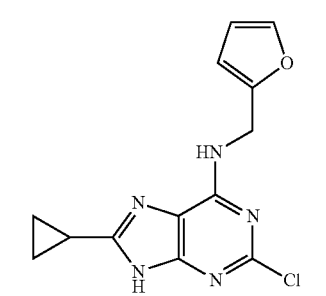 [SMILES: Clc1nc(NCc2ccco2)c2nc(C3CC3)[nH]c2n1]
TABLE A-continued
(96) 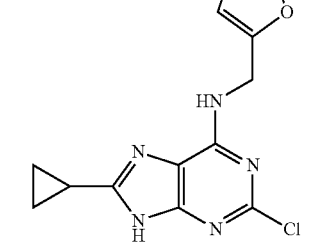
(97) 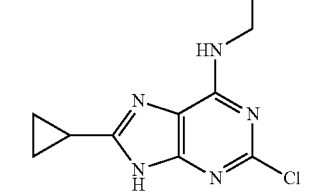
(98) 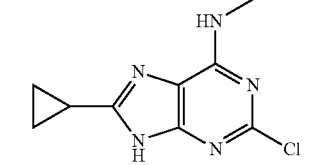
(99) 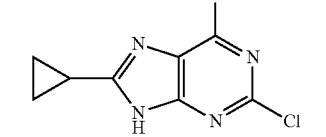
(100) 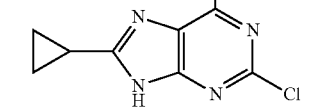

TABLE A-continued
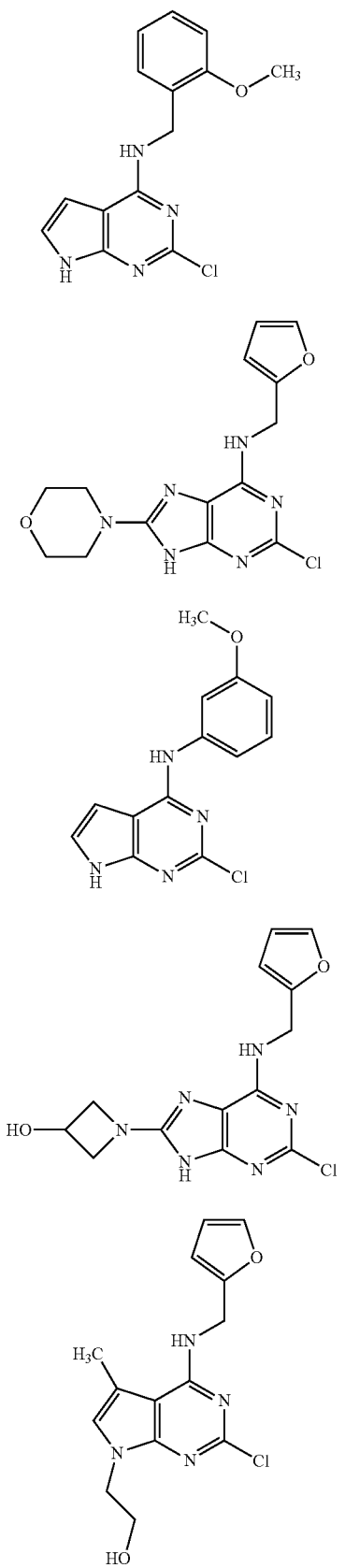
TABLE A-continued
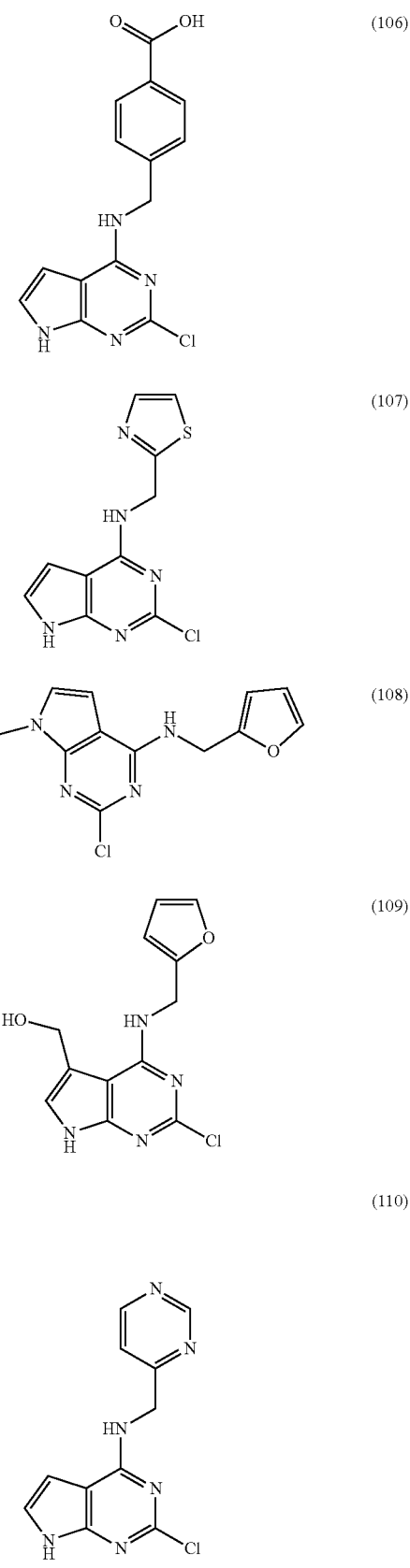

TABLE A-continued
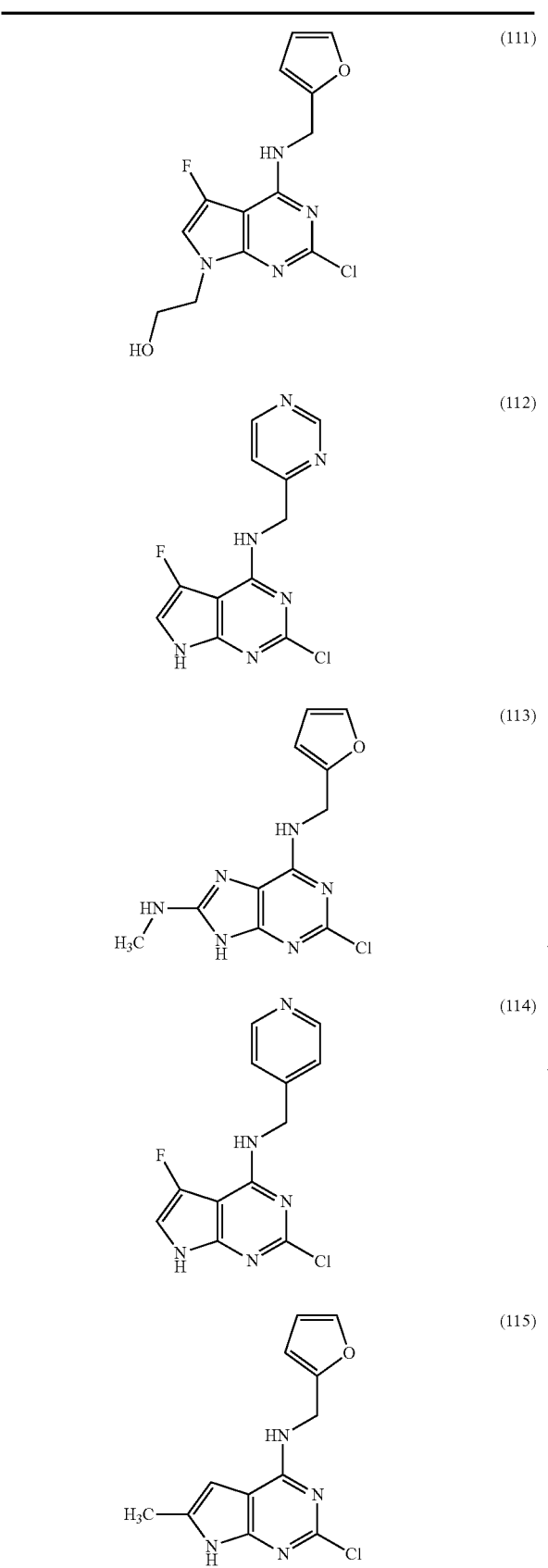
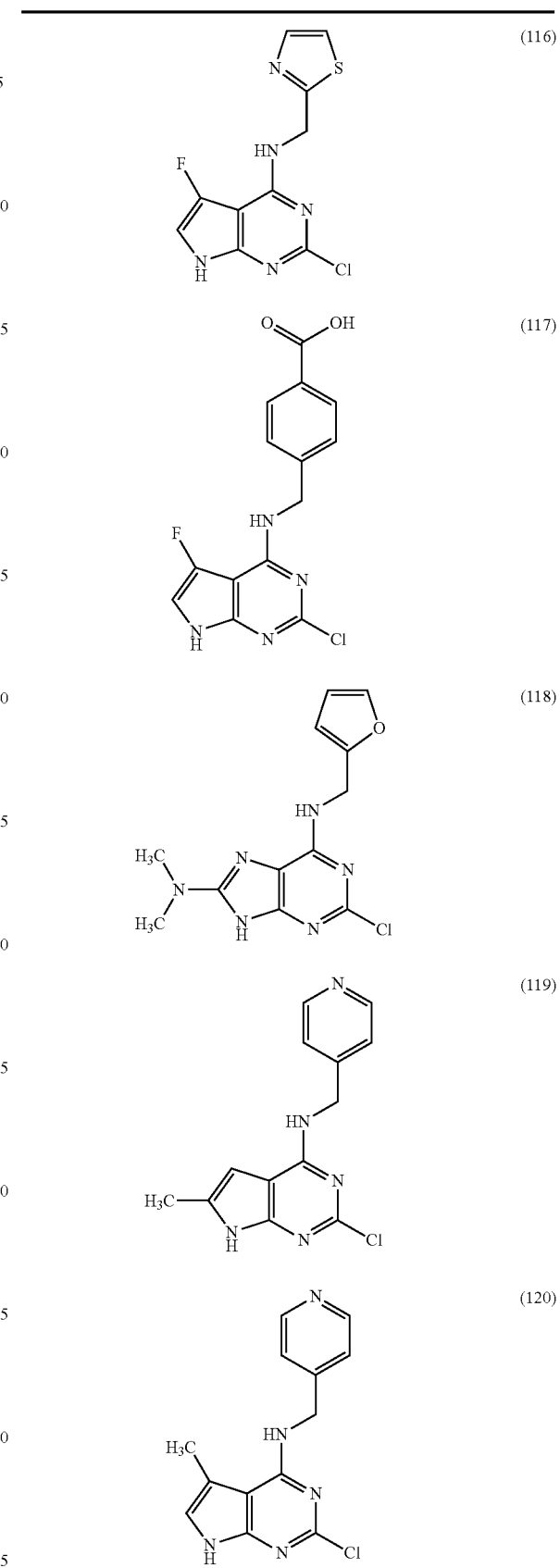

TABLE A-continued
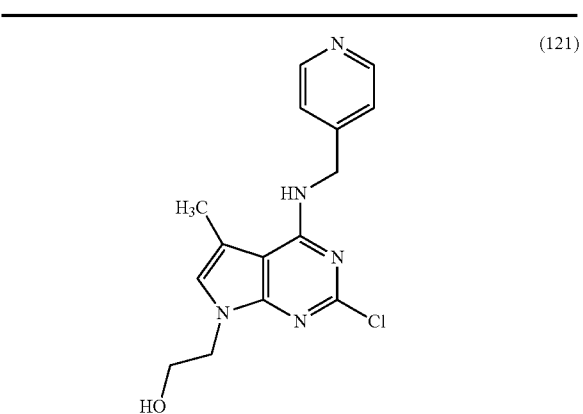 (121)
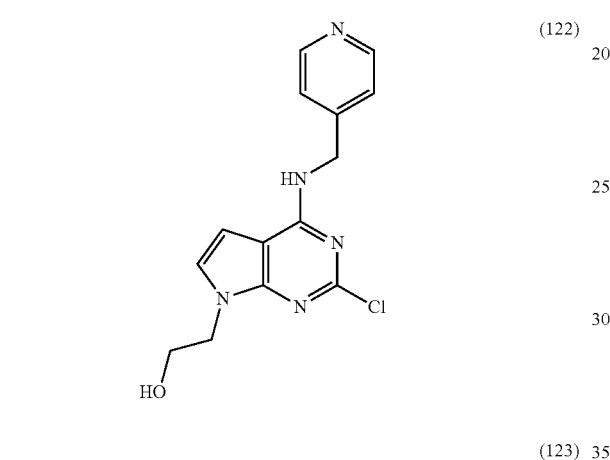 (122)
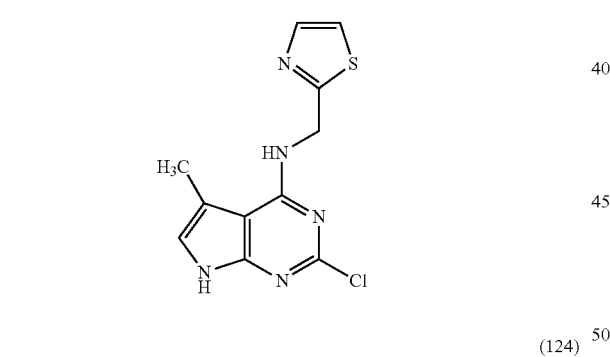 (123)
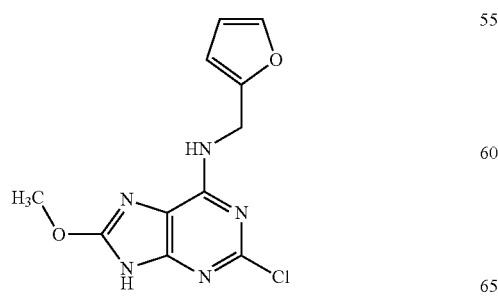 (124)
TABLE A-continued
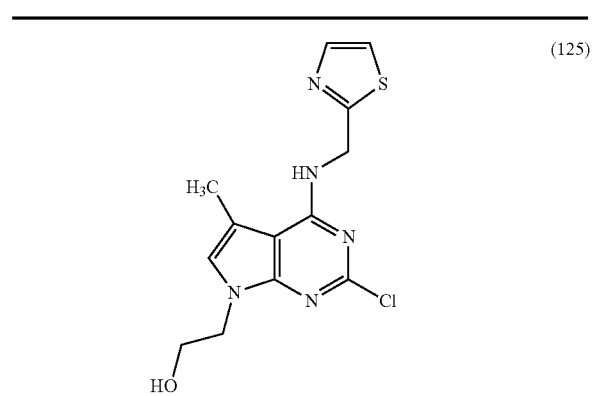 (125)
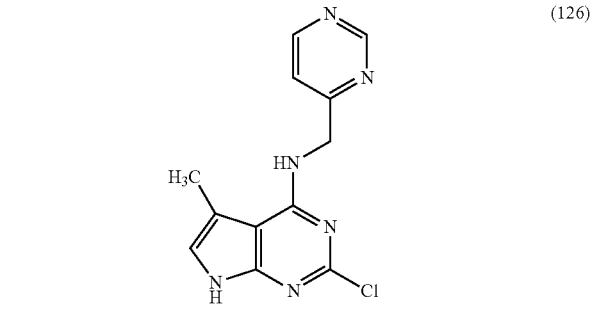 (126)
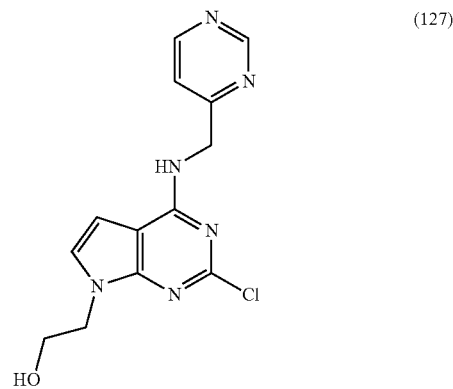 (127)
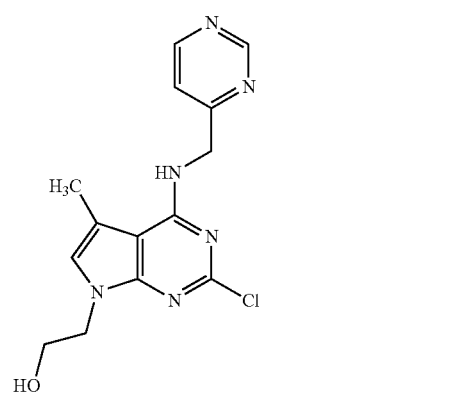 [SMILES: Cc1cn(CCO)c2nc(Cl)nc(NCc3ccncn3)c12] (128)

TABLE A-continued
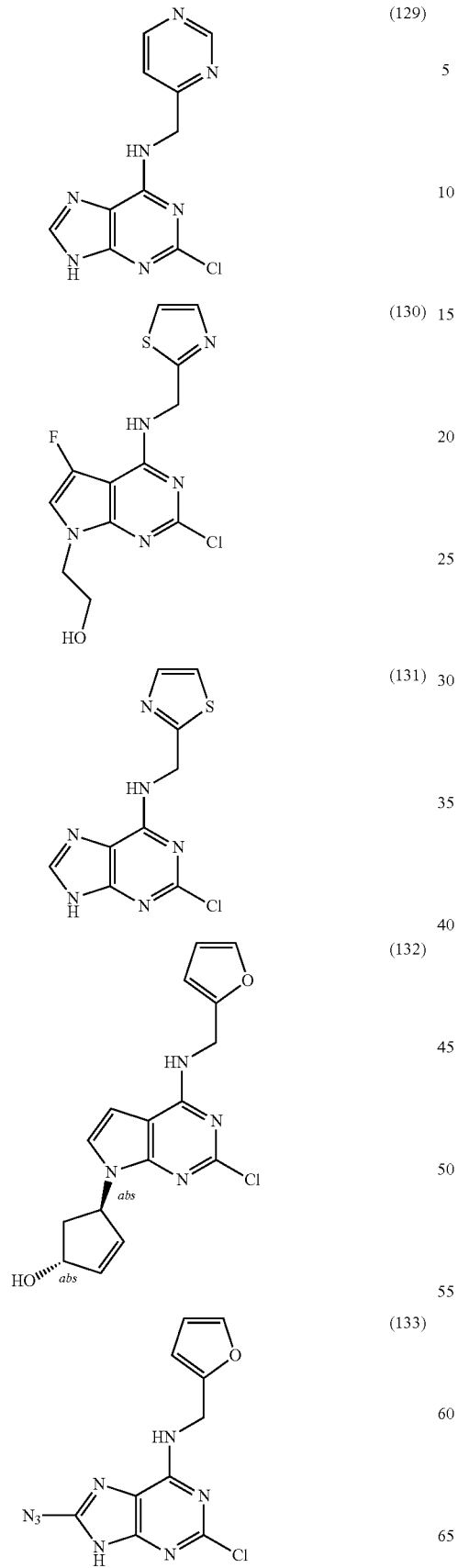
TABLE A-continued
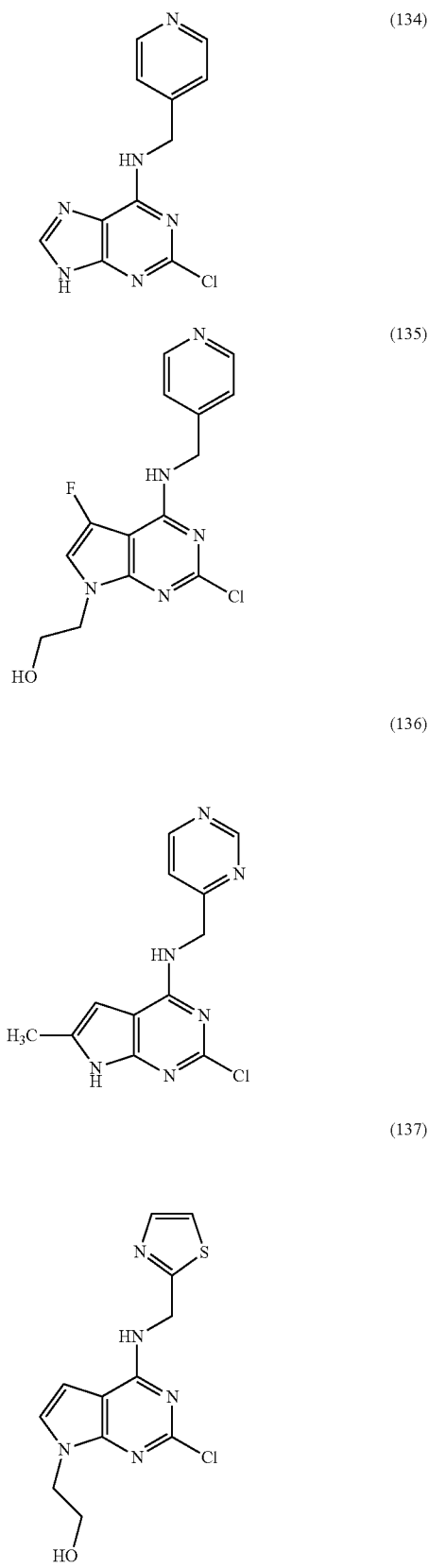

TABLE A-continued
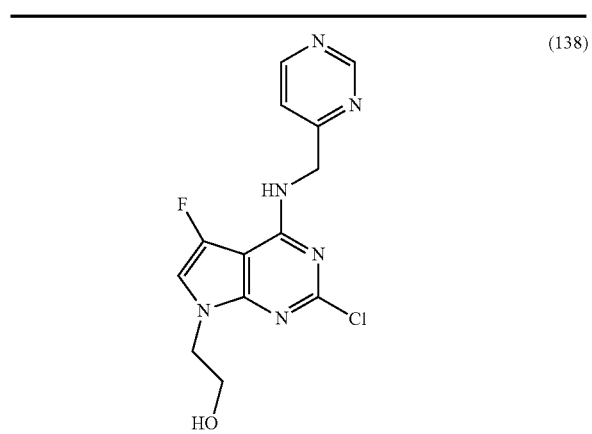 (138)
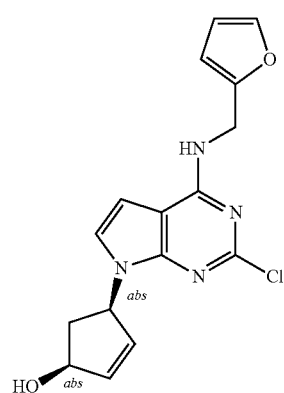 [SMILES: O[C@@H]1C=C[C@H](n2ccc3c(NCc4ccco4)nc(Cl)nc32)C1] (139)
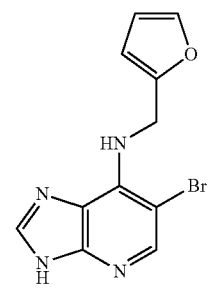 [SMILES: Brc1cnc2[nH]cnc2c1NCc1ccco1] (140)
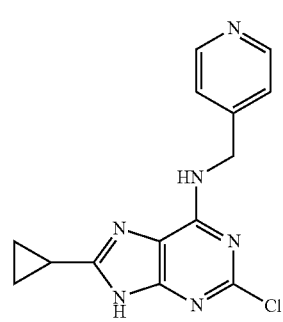 [SMILES: Clc1nc(NCc2ccncc2)c2nc(C3CC3)[nH]c2n1] (141)
TABLE A-continued
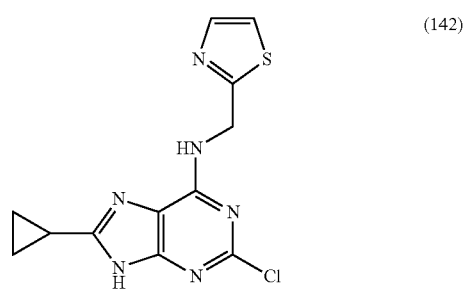 (142)
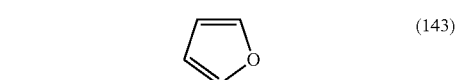 (143)
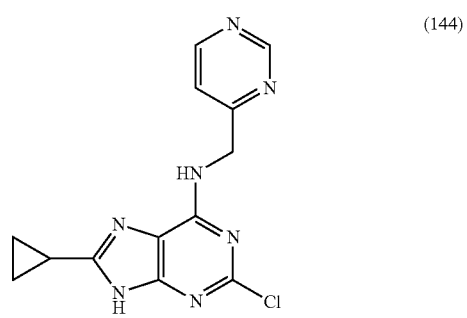 (144)
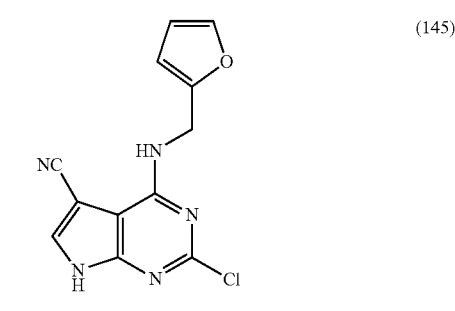 (145)
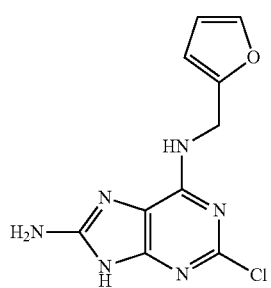 [SMILES: Nc1nc2c(NCc3ccco3)nc(Cl)nc2[nH]1] (146)

TABLE A-continued
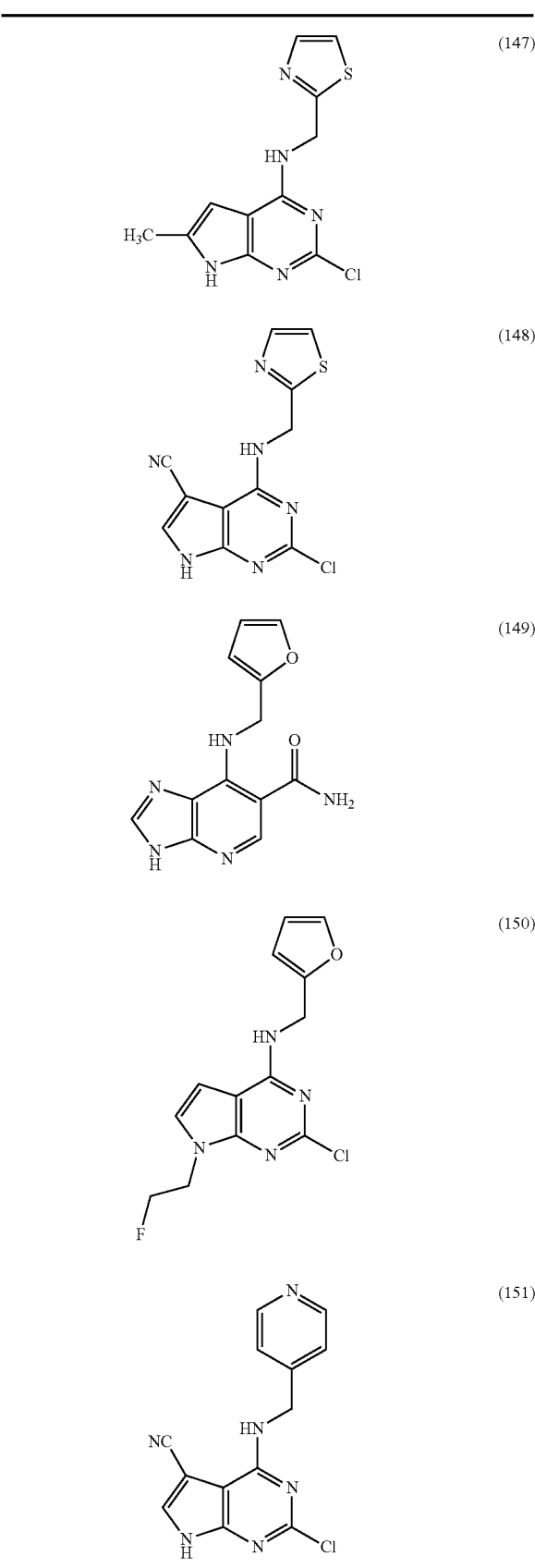
TABLE A-continued
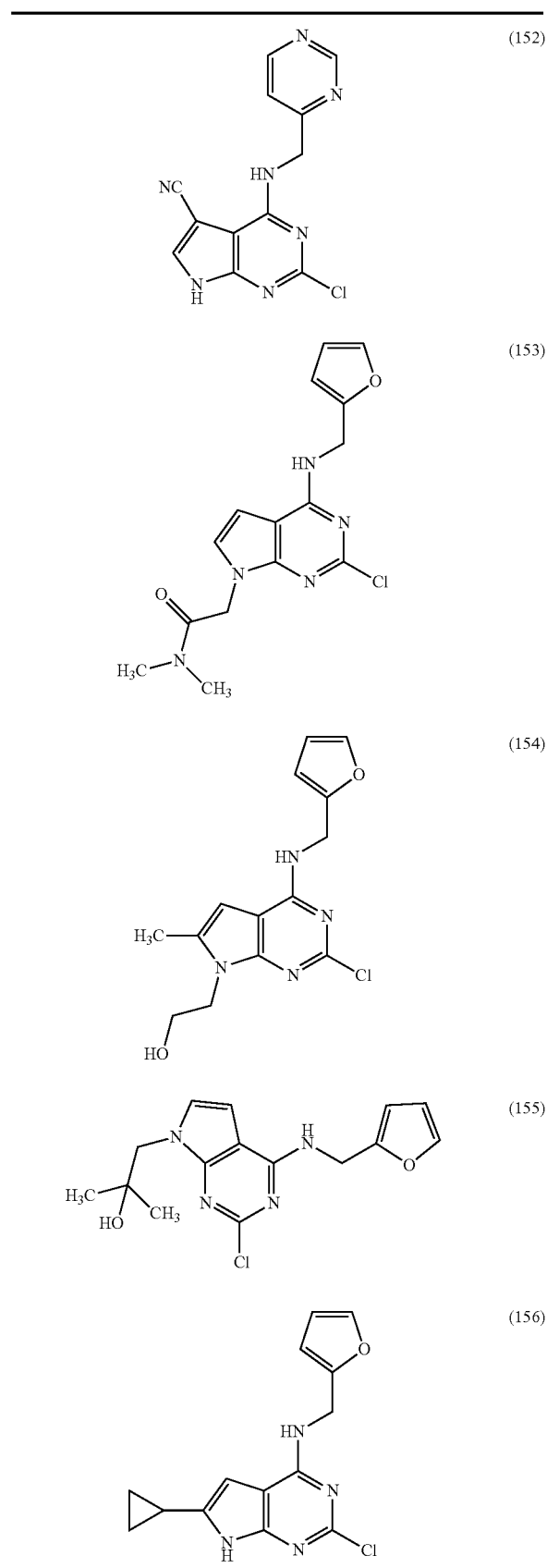

TABLE A-continued
(157) 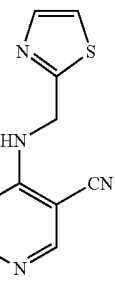
(158) 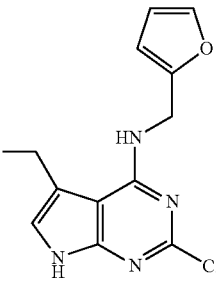
(159) 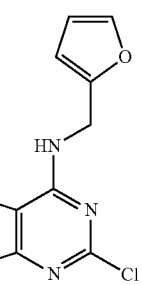
(160) 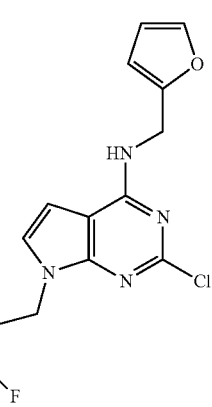
(161) 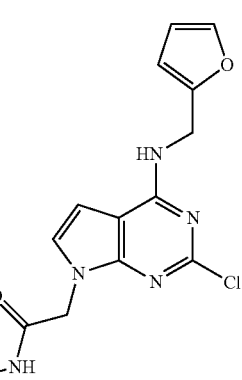
TABLE A-continued
(162) 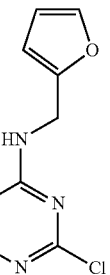
(163) 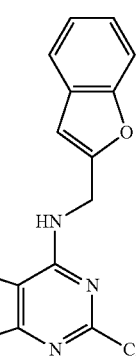
(164) 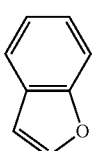
(165) 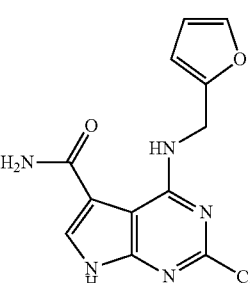
(166) 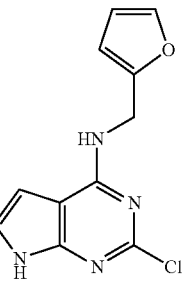

TABLE A-continued
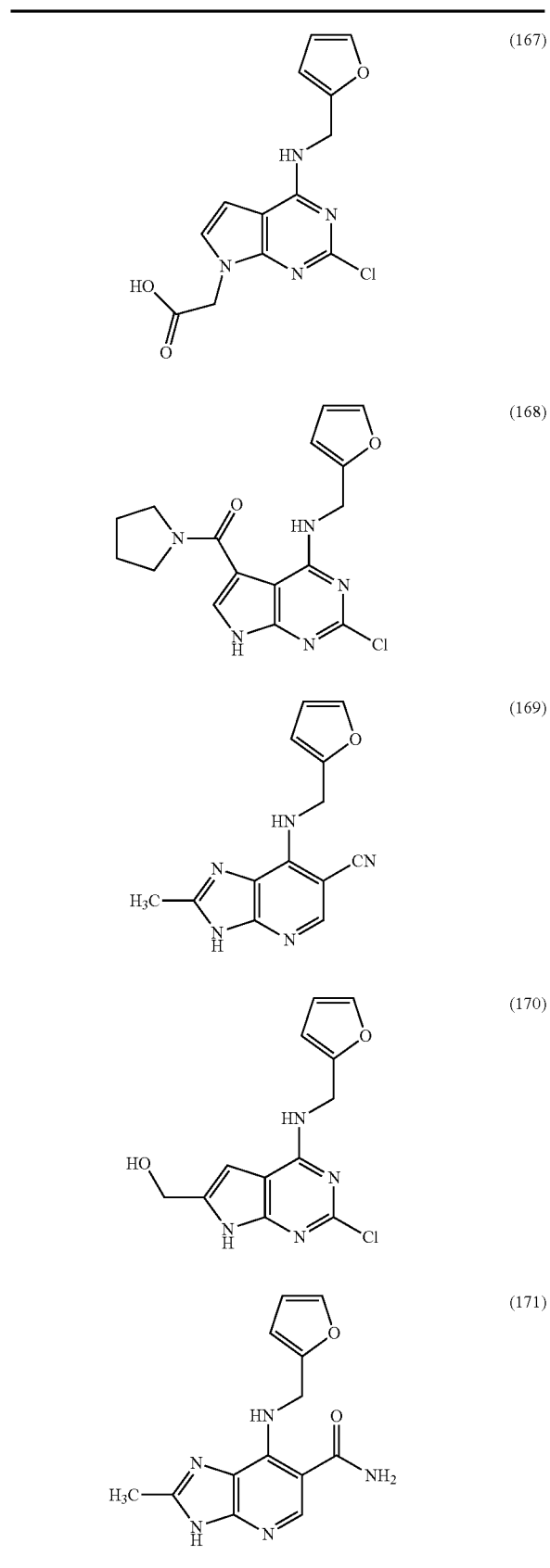
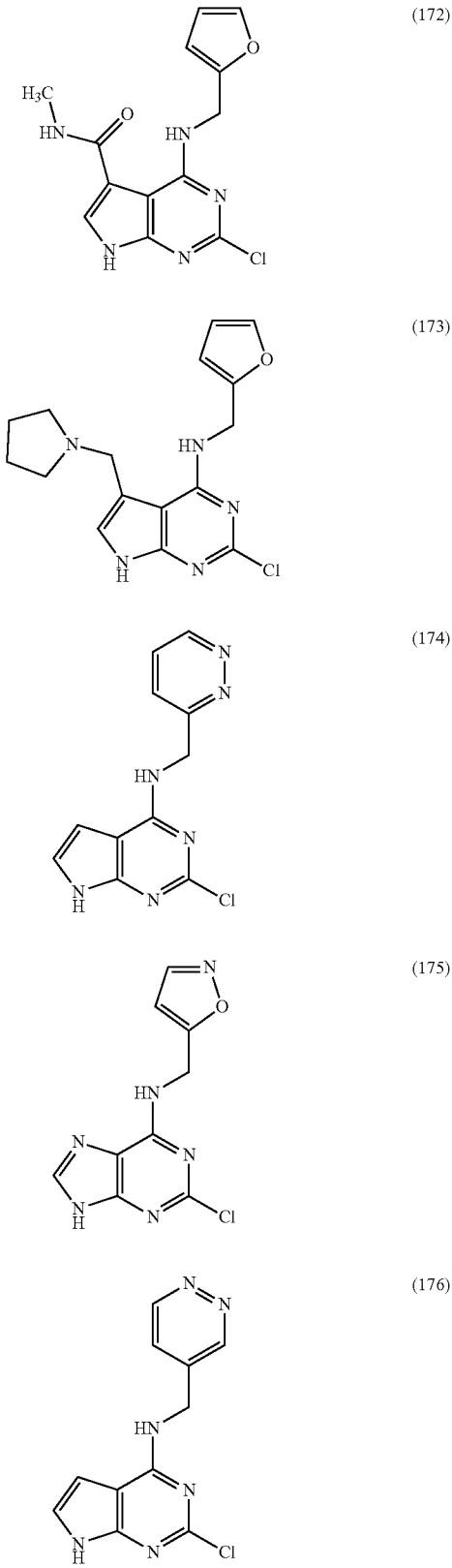

TABLE A-continued
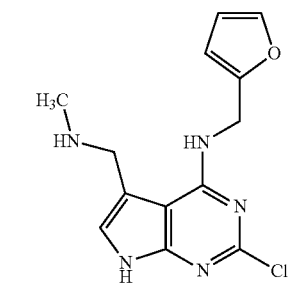
(177)
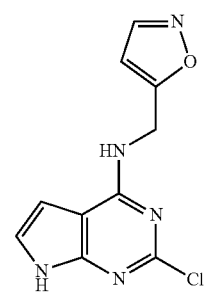
(178)
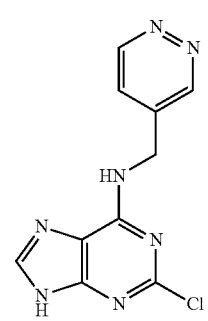 [SMILES: Clc1nc(NCc2ccnnc2)c2cc[nH]c2n1]
(179)
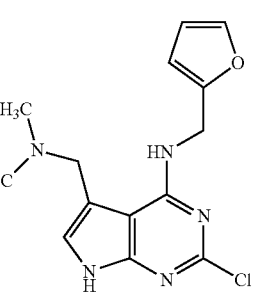
(180)
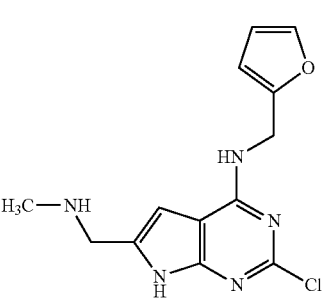 [SMILES: CNCc1cc2c(NCc3ccco3)nc(Cl)nc2[nH]1]
(181)
TABLE A-continued
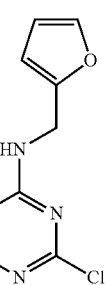
(182)
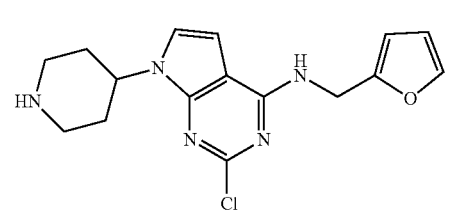 [SMILES: Clc1nc(NCc2ccco2)c2ccn(C3CCNCC3)c2n1]
(183)
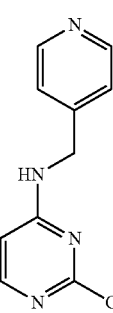
(184)
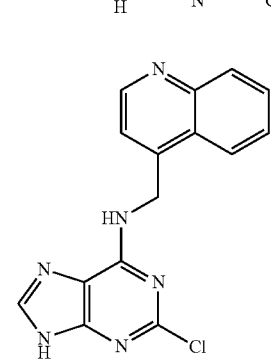
(185)
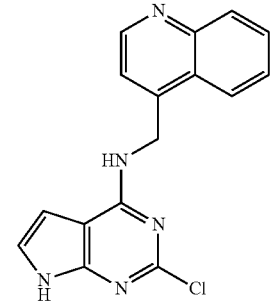 [SMILES: Clc1nc(NCc2ccnc3ccccc23)c2cc[nH]c2n1]
(186)

TABLE A-continued
(187) 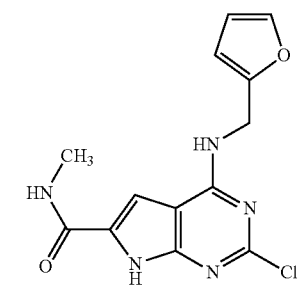 [SMILES: CNC(=O)c1cc2c(NCc3ccco3)nc(Cl)nc2[nH]1]
(188) 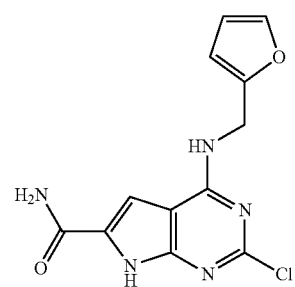 [SMILES: NC(=O)c1cc2c(NCc3ccco3)nc(Cl)nc2[nH]1]
(189) 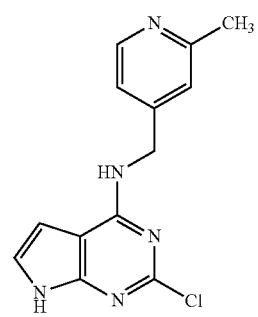 [SMILES: Cc1cc(CNc2nc(Cl)nc3[nH]ccc23)ccn1]
(190) 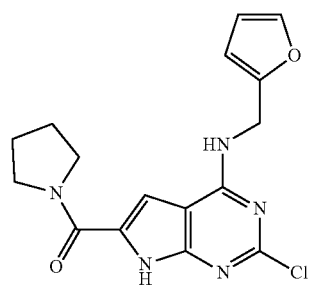 [SMILES: O=C(c1cc2c(NCc3ccco3)nc(Cl)nc2[nH]1)N1CCCC1]
(191) 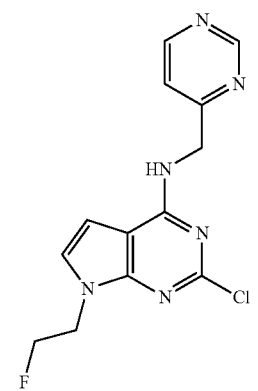
TABLE A-continued
(192) 
(193) 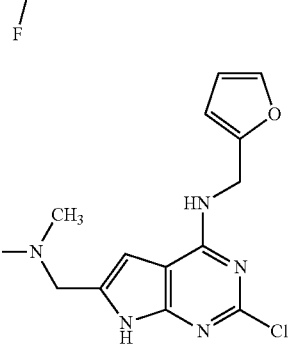
(194) 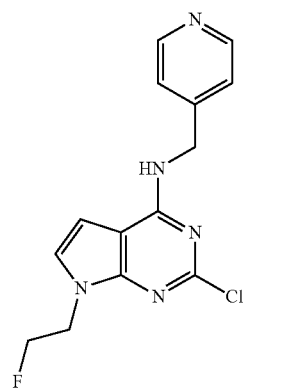 [SMILES: FCCn1ccc2c(NCc3ccncc3)nc(Cl)nc21]
(195) 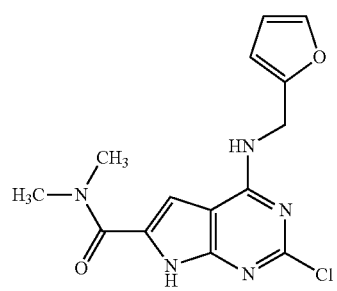 [SMILES: CN(C)C(=O)c1cc2c(NCc3ccco3)nc(Cl)nc2[nH]1]
(196) 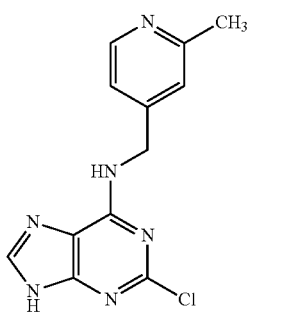 [SMILES: Cc1cc(CNc2nc(Cl)nc3[nH]cnc23)ccn1]

TABLE A-continued
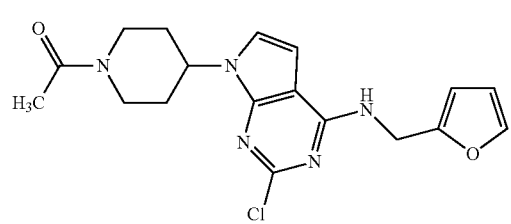 [SMILES: CC(=O)N1CCC(n2ccc3c(NCc4ccco4)nc(Cl)nc32)CC1]
(197)
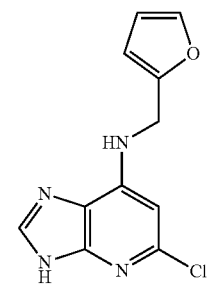
(198)
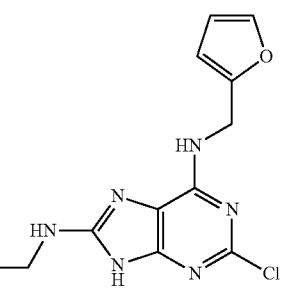
(199)
(200)
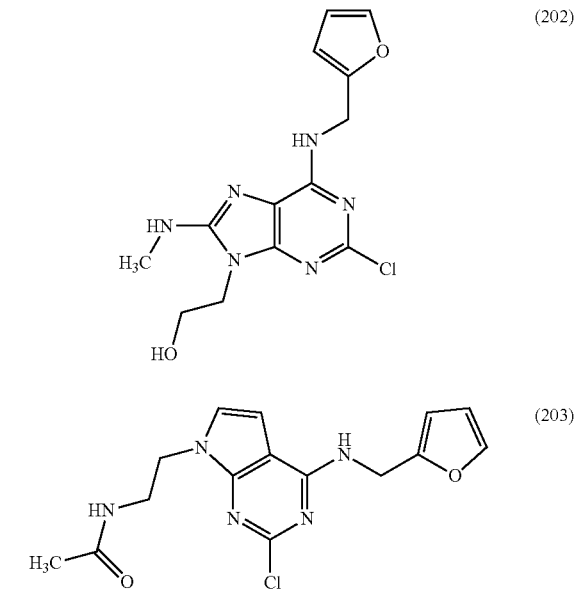
(201)
TABLE A-continued
(202)
(203)
(204)
(205)
(206)

TABLE A-continued
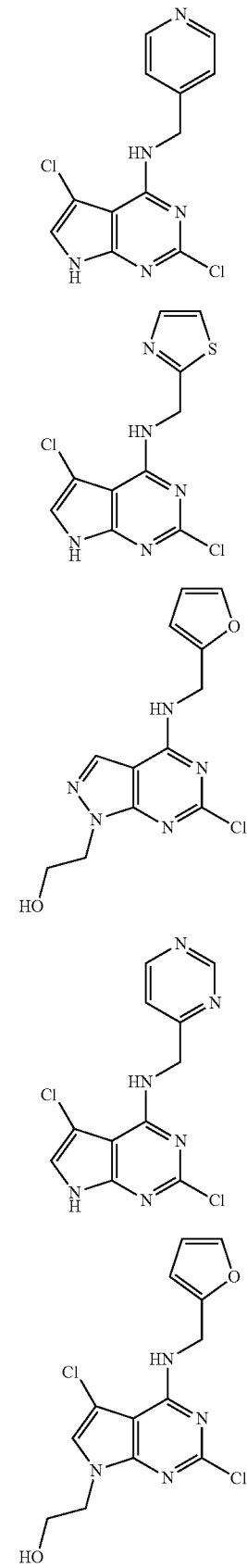
(207)
(208)
(209)
(210)
(211)
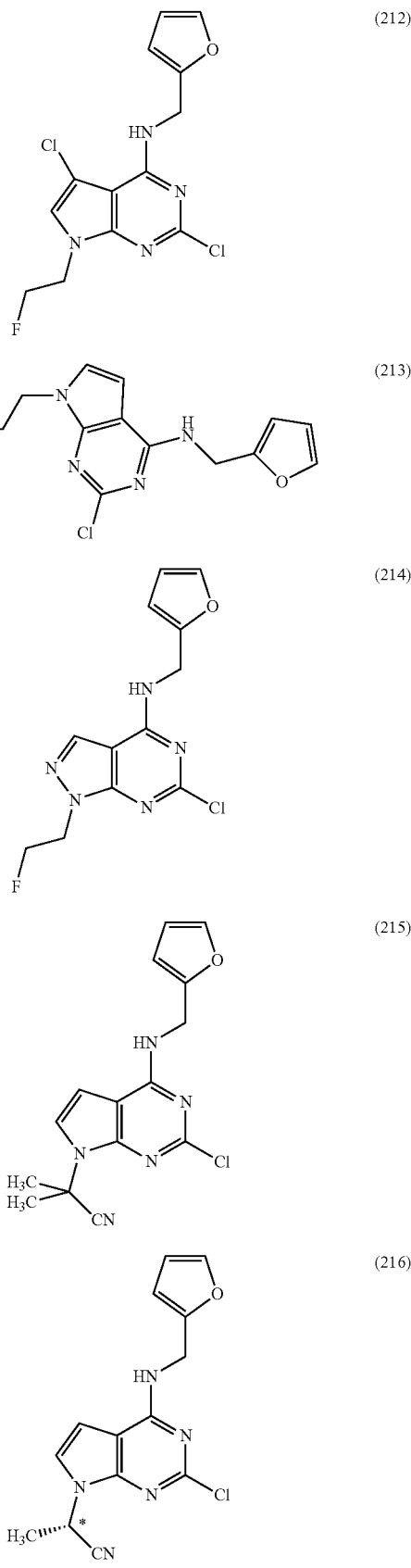
(212)
(213)
(214)
(215)
(216)

TABLE A-continued
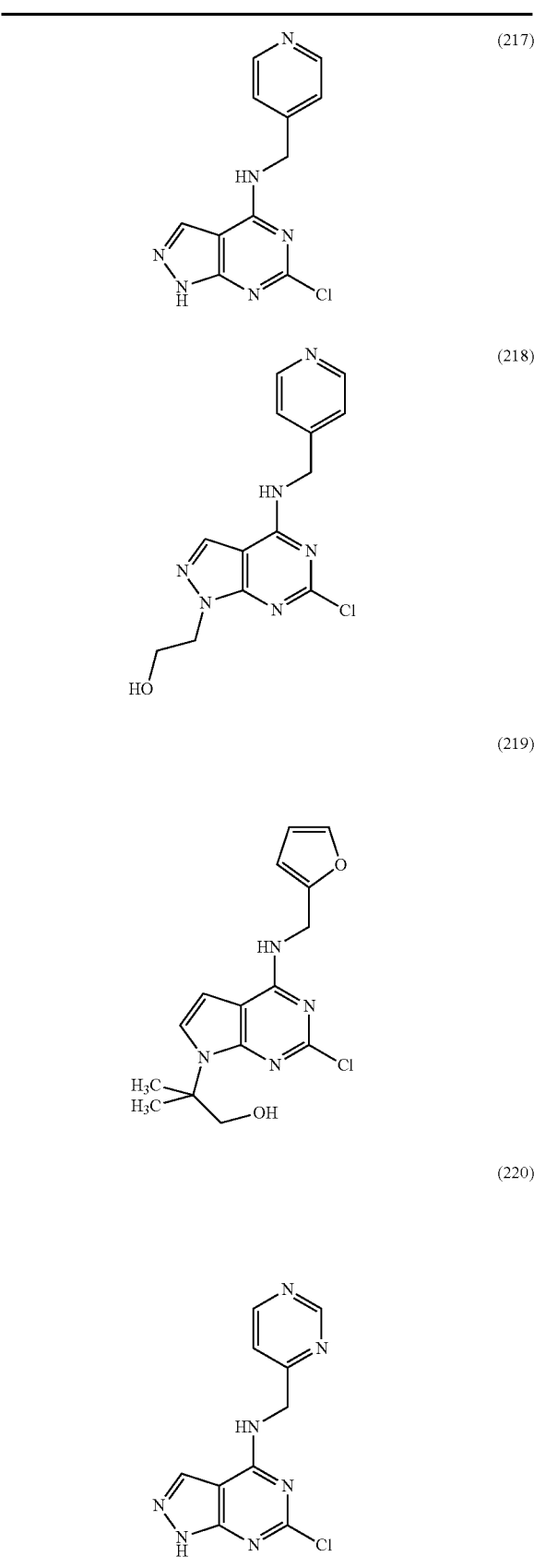
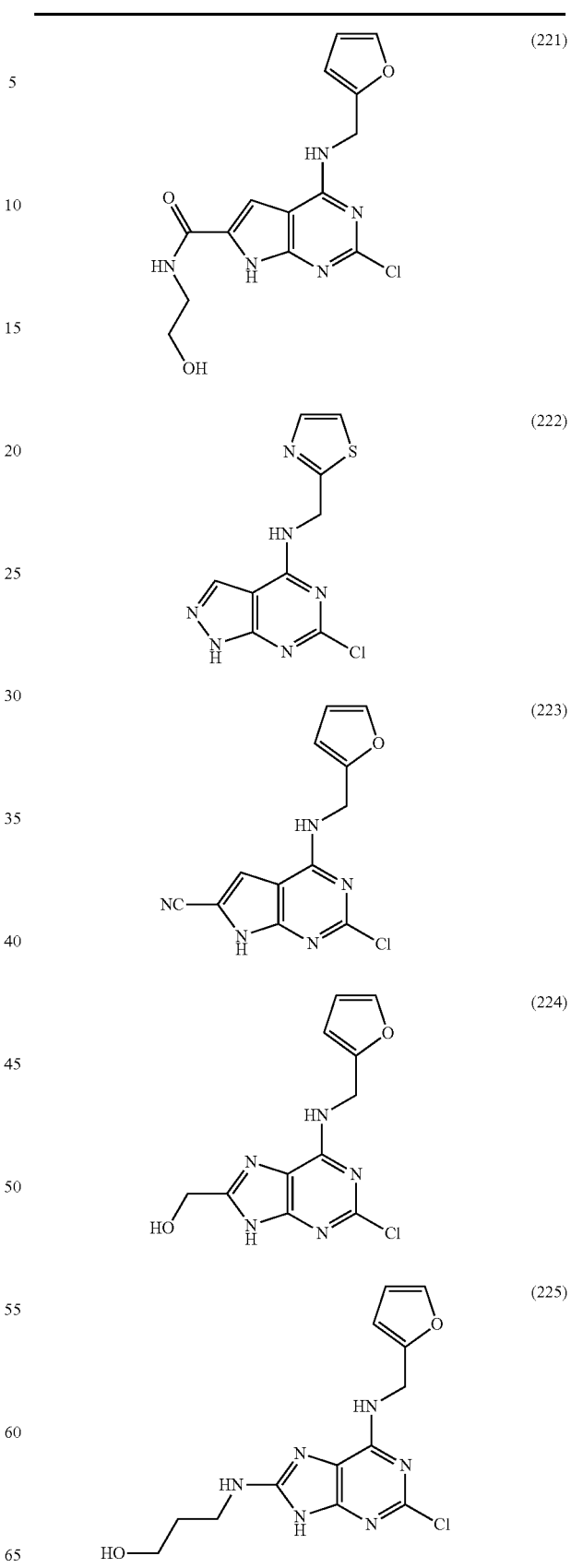

TABLE A-continued
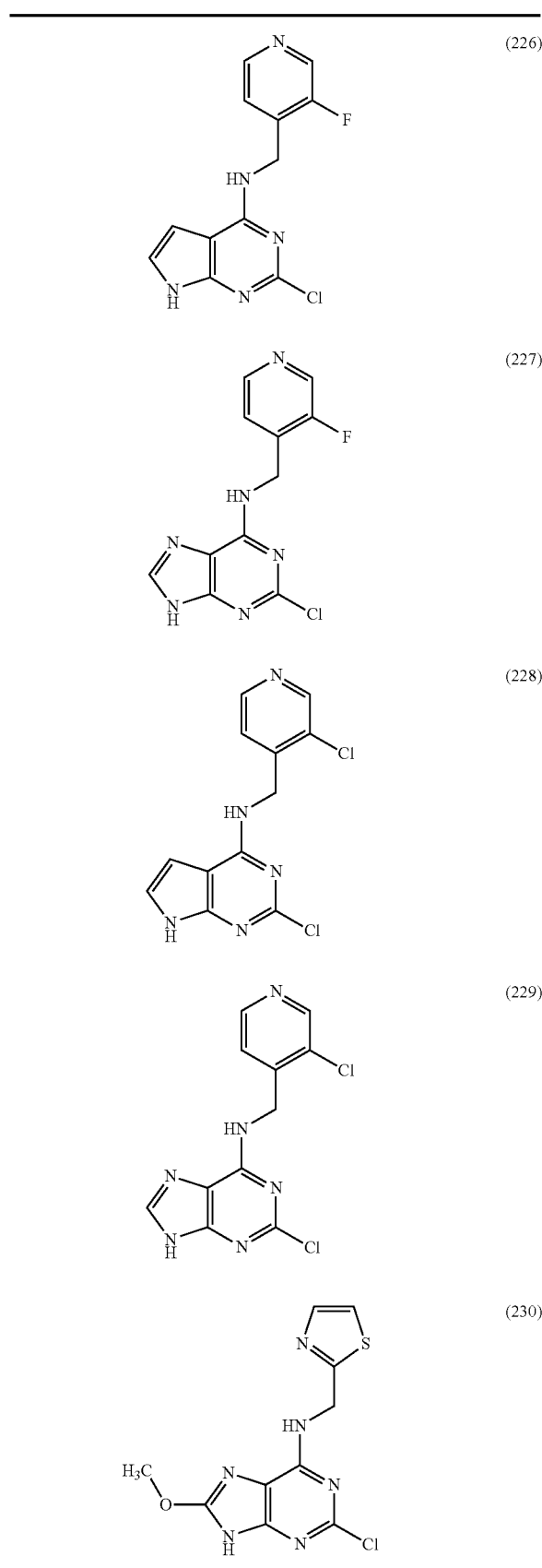
TABLE A-continued
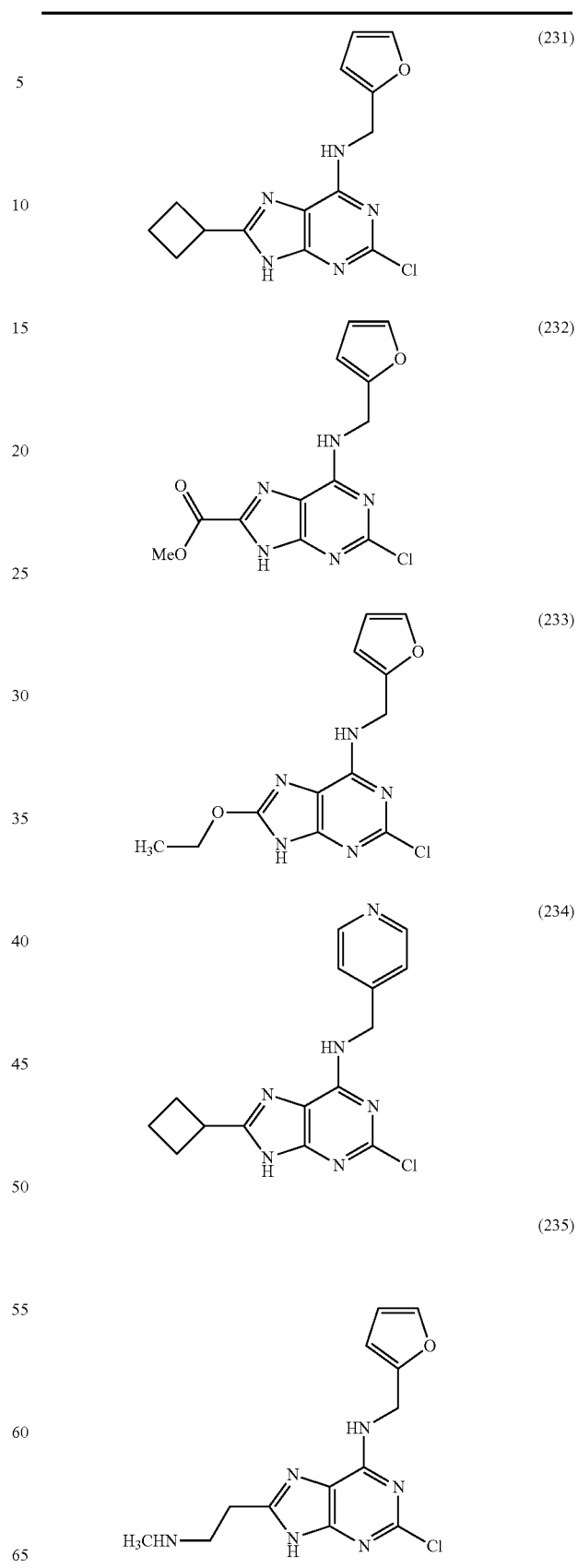

TABLE A-continued
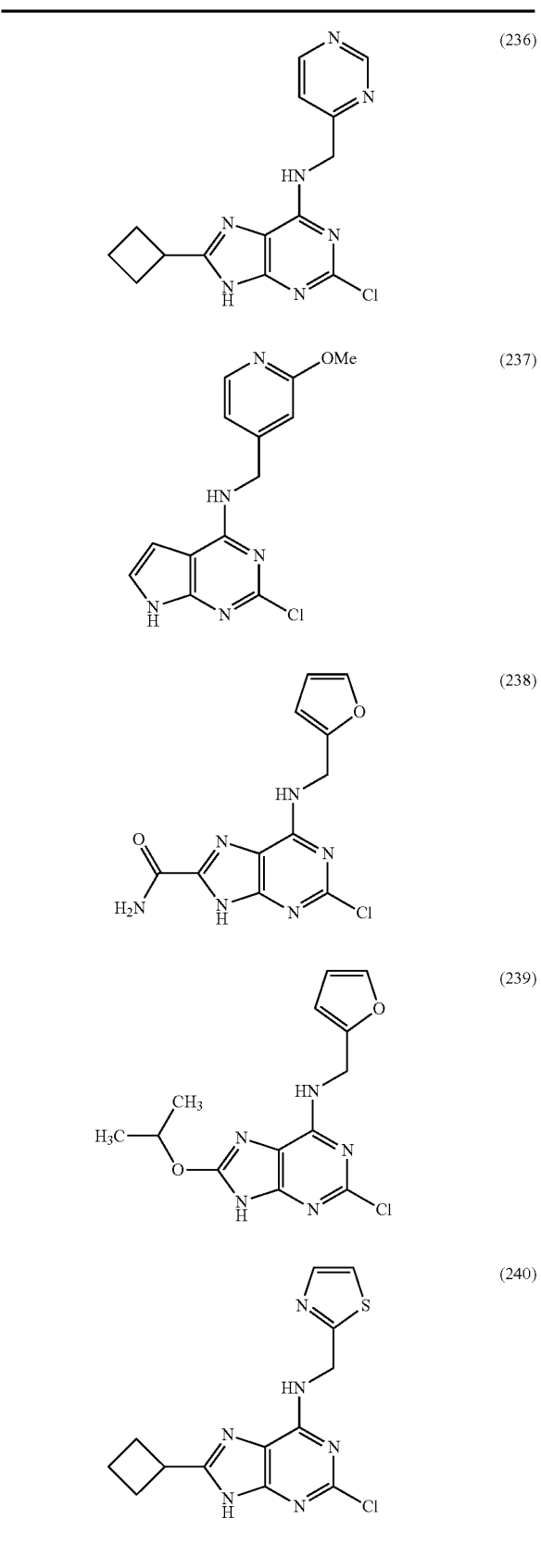
(236)
(237)
(238)
(239)
(240)
TABLE A-continued
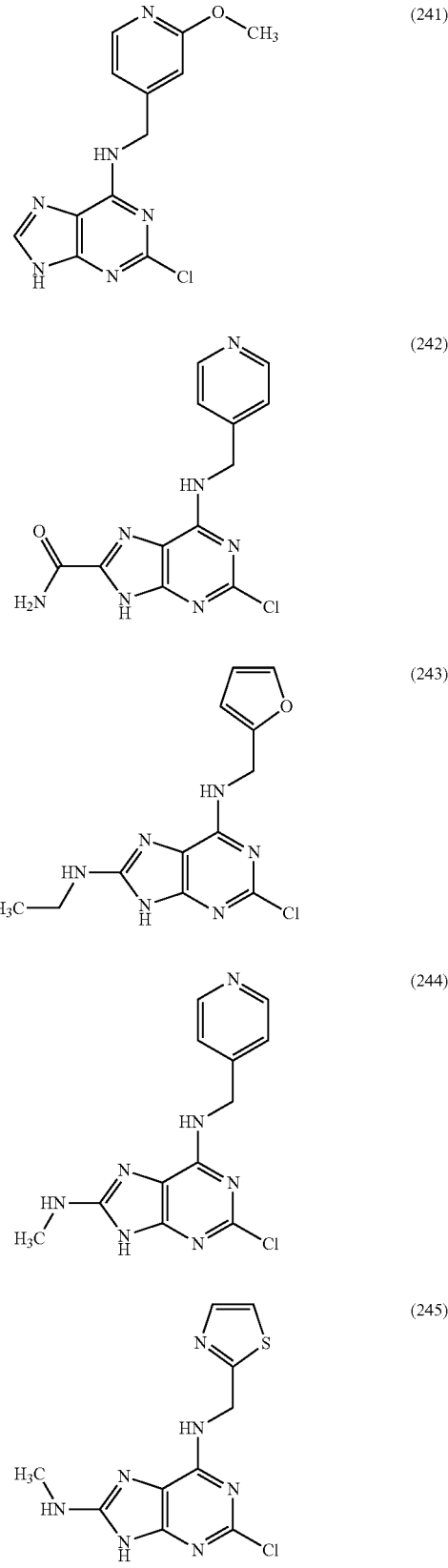
(241)
(242)
(243)
(244)
(245)

TABLE A-continued
| | |
|---|---|
| 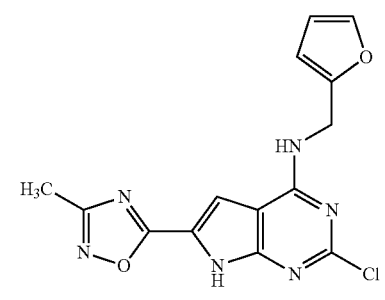 [SMILES: Cc1noc(-c2cc3c(NCc4ccco4)nc(Cl)nc3[nH]2)n1] | (246) |
| 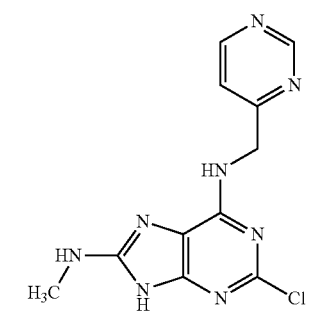 [SMILES: CNc1nc2c(NCc3ccncn3)nc(Cl)nc2[nH]1] | (247) |
| 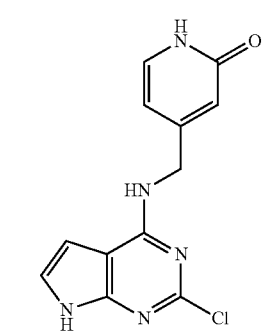 [SMILES: O=c1cc(CNc2nc(Cl)nc3[nH]ccc23)cc[nH]1] | (248) |
| 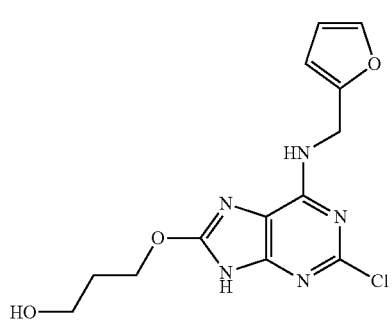 | (249) |
| 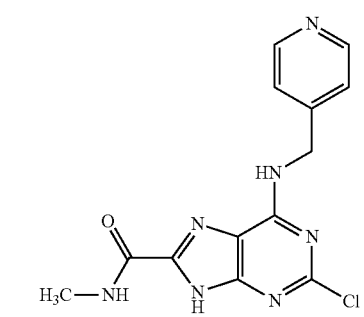 [SMILES: CNC(=O)c1nc2c(NCc3ccncc3)nc(Cl)nc2[nH]1] 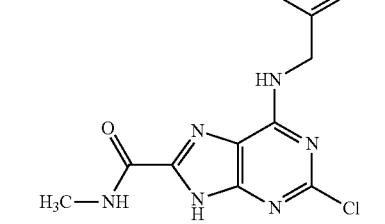 | (250) |
TABLE A-continued
| | |
|---|---|
| 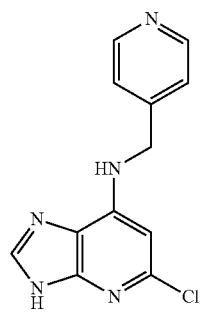 [SMILES: Clc1cc(NCc2ccncc2)c2nc[nH]c2n1] | (251) |
| 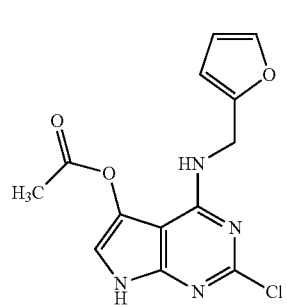 [SMILES: CC(=O)Oc1c[nH]c2nc(Cl)nc(NCc3ccco3)c12] | (252) |
|  | (253) |
|  | (254) |
| 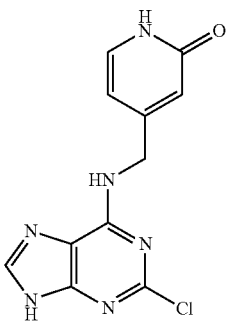 [SMILES: O=c1cc(CNc2nc(Cl)nc3[nH]cnc23)cc[nH]1] | (255) |

TABLE A-continued
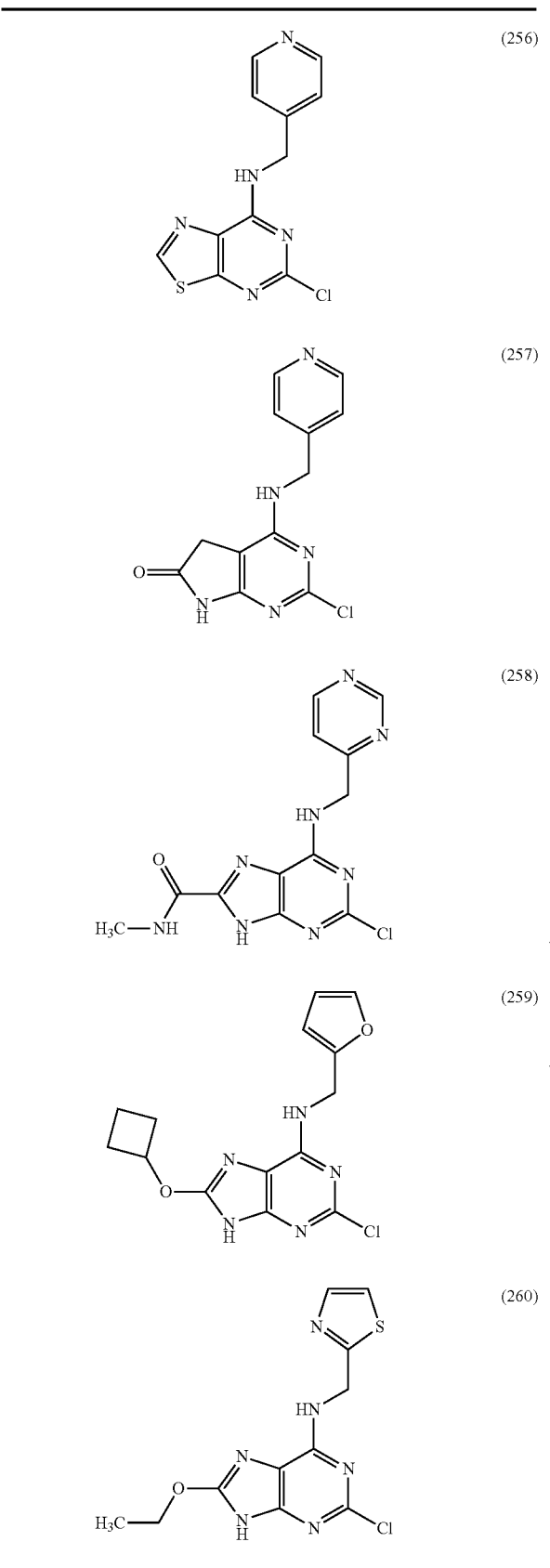
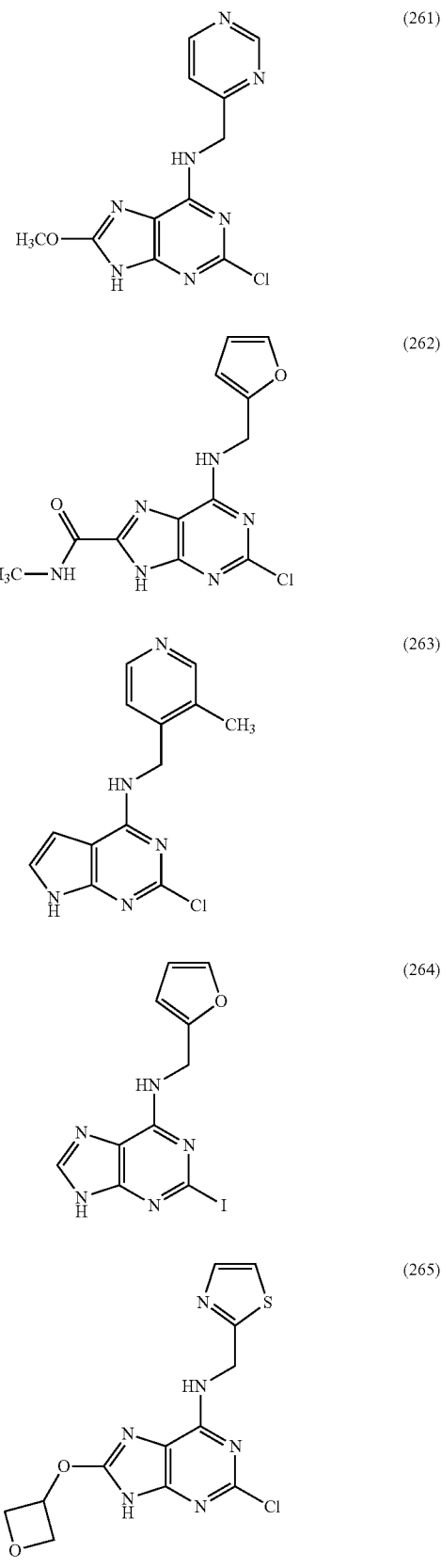

TABLE A-continued
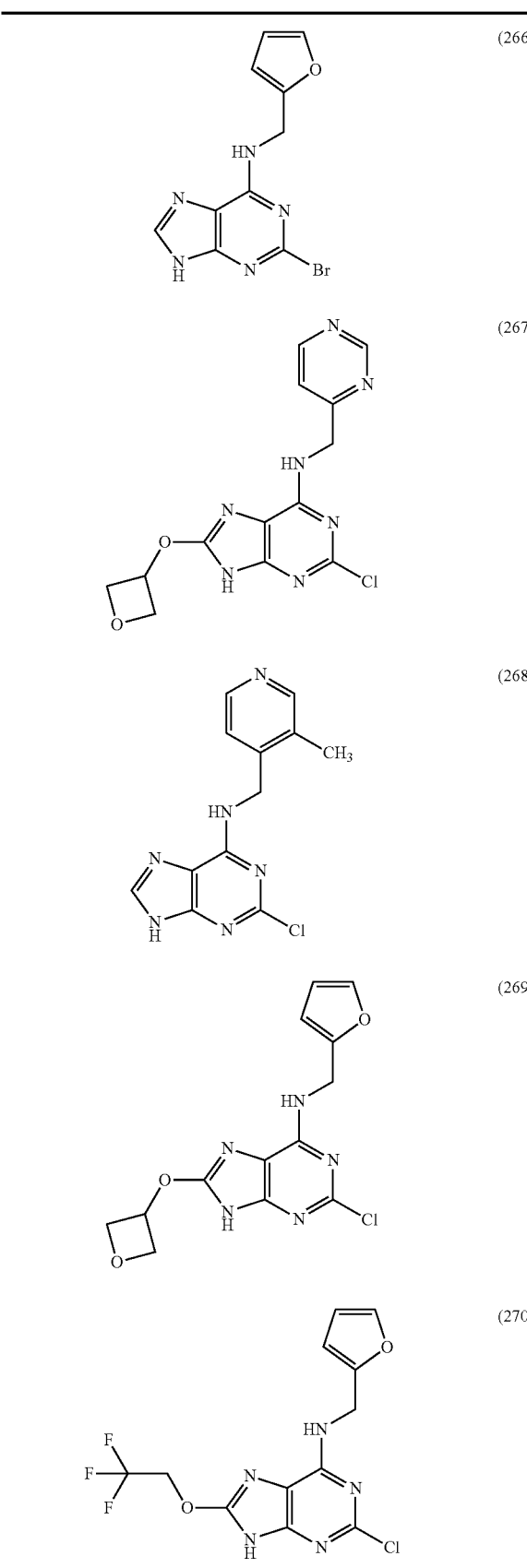
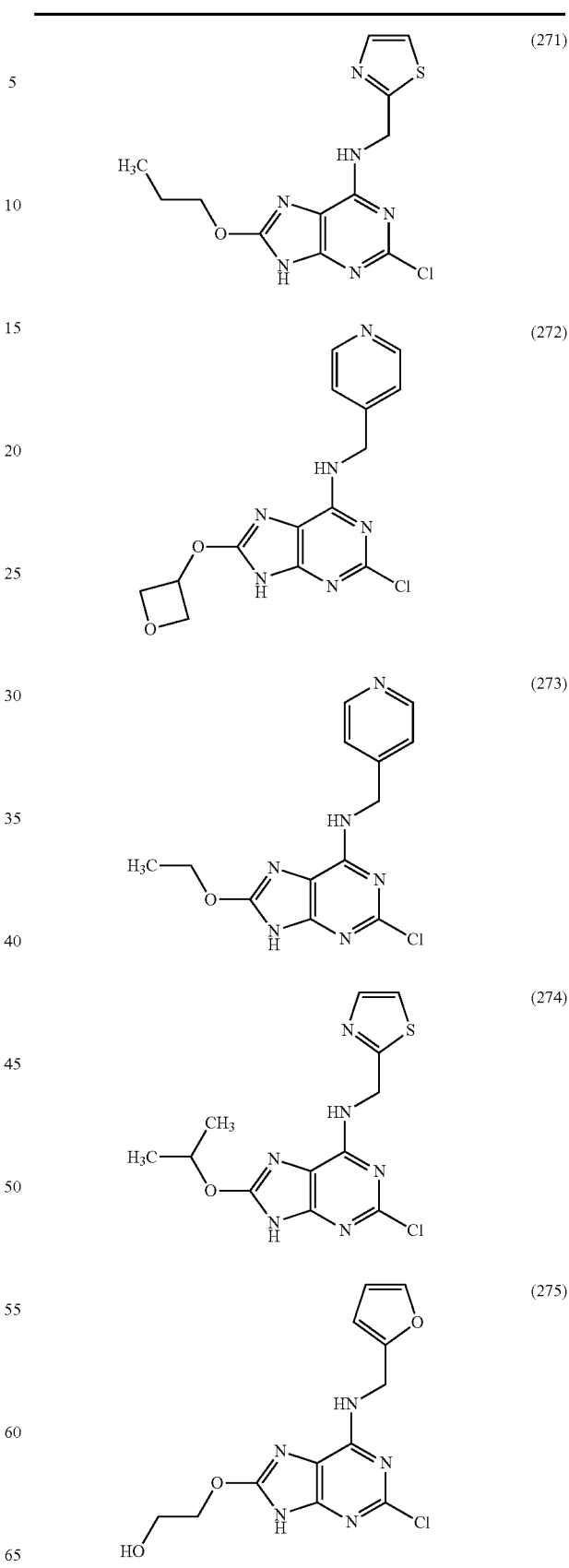

TABLE A-continued
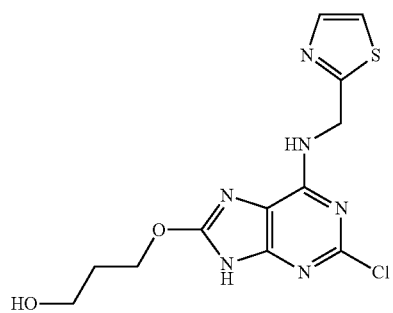 (276)
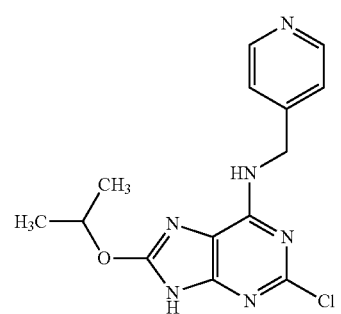 [SMILES: CC(C)Oc1nc2c(NCc3ccncc3)nc(Cl)nc2[nH]1] (277)
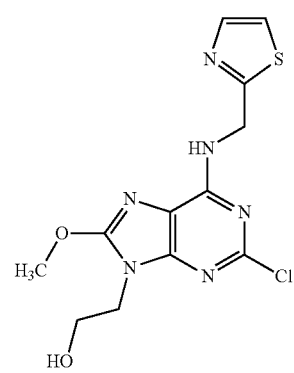 [SMILES: COc1nc2c(NCc3nccs3)nc(Cl)nc2n1CCO] (278)
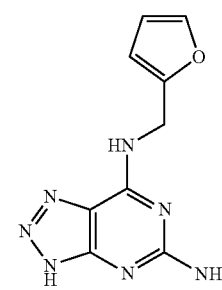 (279)
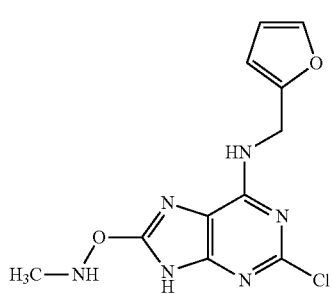 [SMILES: CNOc1nc2c(NCc3ccco3)nc(Cl)nc2[nH]1] (280)
TABLE A-continued
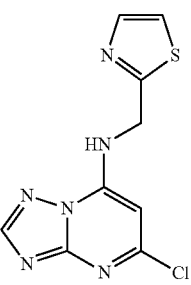 [SMILES: Clc1cc(NCc2nccs2)n2ncnc2n1] (281)
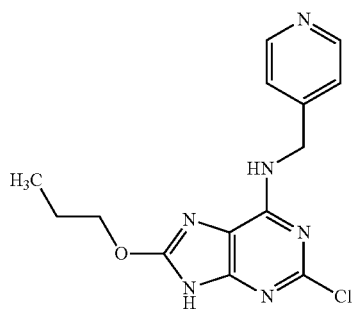 [SMILES: CCCOc1nc2c(NCc3ccncc3)nc(Cl)nc2[nH]1] (282)
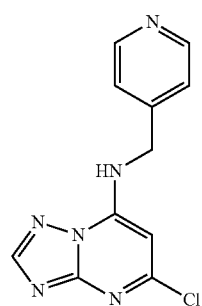 [SMILES: Clc1cc(NCc2ccncc2)n2ncnc2n1] (283)
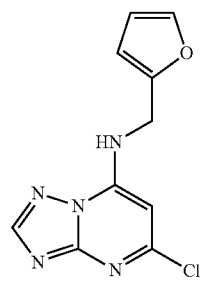 [SMILES: Clc1cc(NCc2ccco2)n2ncnc2n1] (284)
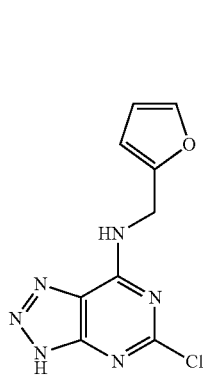 [SMILES: Clc1nc(NCc2ccco2)c2nn[nH]c2n1] (285)

TABLE A-continued
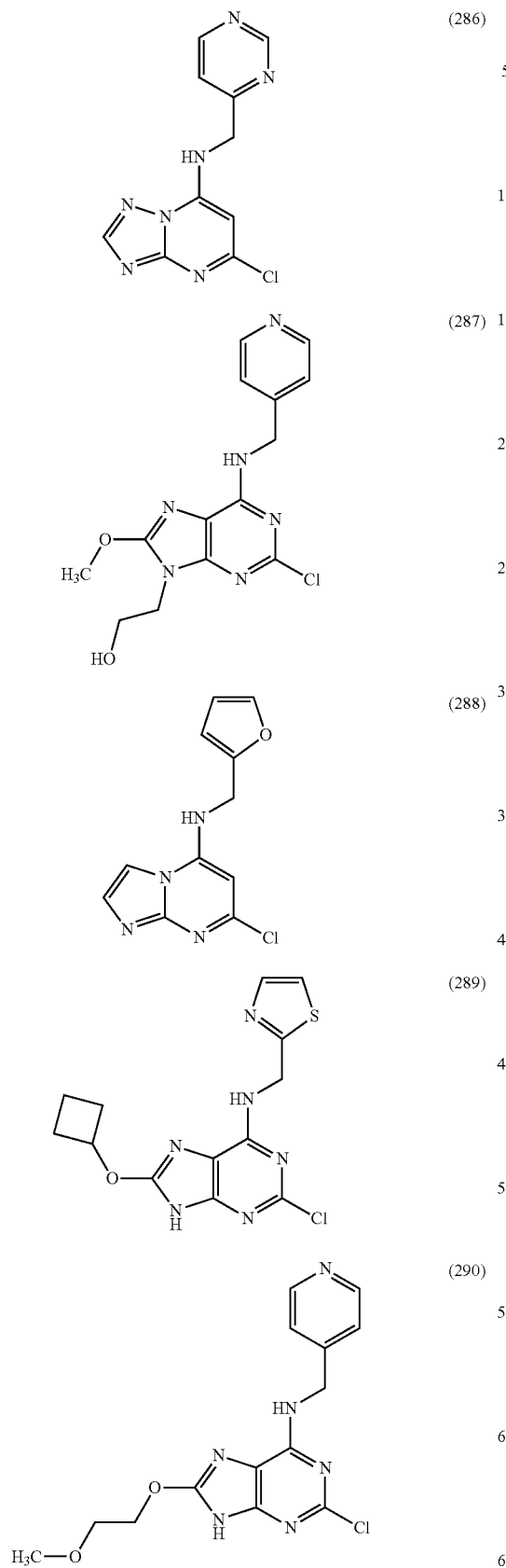
TABLE A-continued
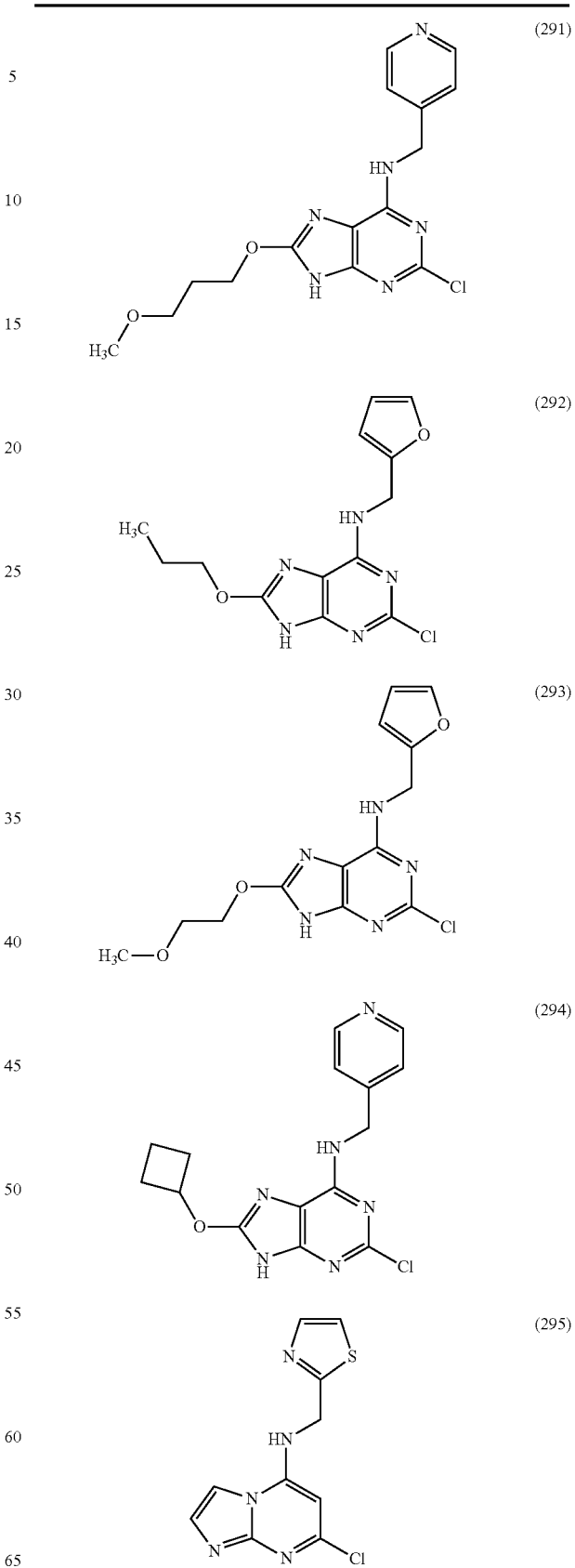

TABLE A-continued
| | |
|---|---|
| 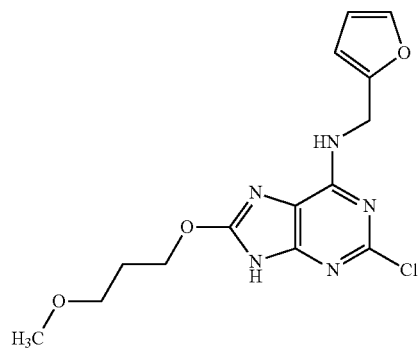 [SMILES: COCCCOc1nc2c(NCc3ccco3)nc(Cl)nc2[nH]1] | (296) |
| 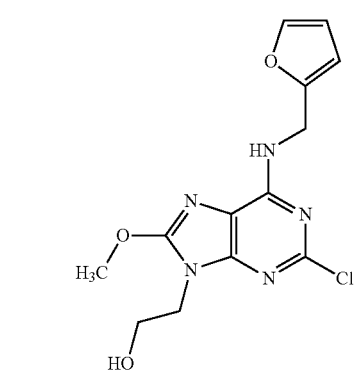 [SMILES: COc1nc2c(NCc3ccco3)nc(Cl)nc2n1CCO] | (297) |
| 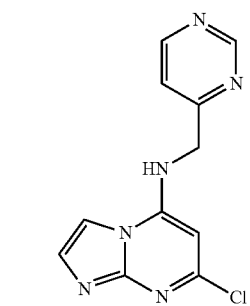 [SMILES: Clc1cc(NCc2ccncn2)n2ccnc2n1] | (298) |
| 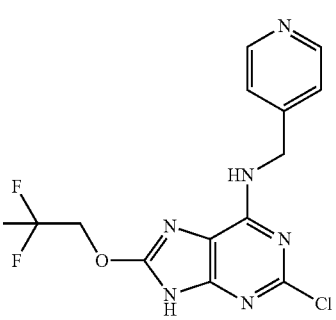 | (299) |
TABLE A-continued
| | |
|---|---|
| 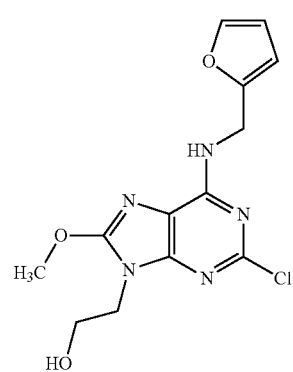 | (300) |
| 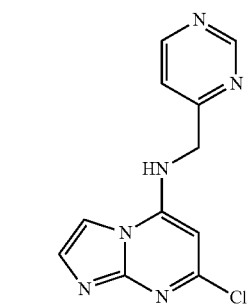 | (301) |
| 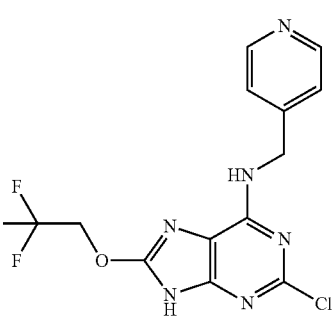 | (302) |
| 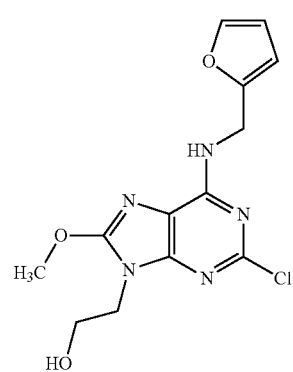 | (303) |
| 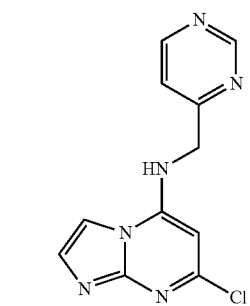 | (304) |

TABLE A-continued
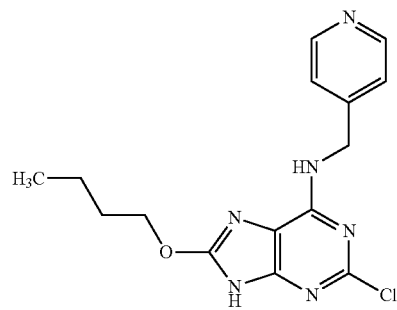 [SMILES: CCCCOc1nc2c(NCc3ccncc3)nc(Cl)nc2[nH]1] (305)
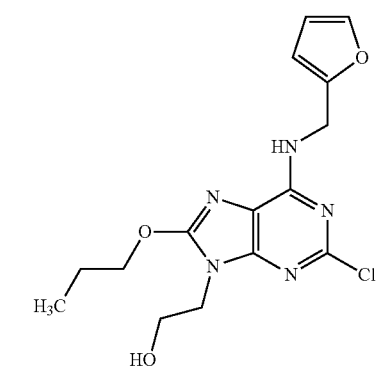 [SMILES: CCCOc1nc2c(NCc3ccco3)nc(Cl)nc2n1CCO] (306)
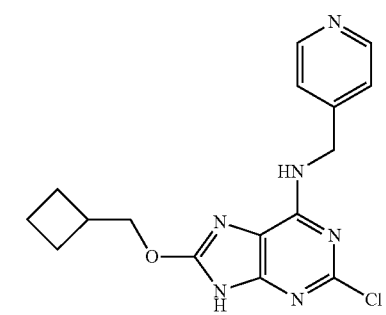 [SMILES: Clc1nc(NCc2ccncc2)c2nc(OCC3CCC3)[nH]c2n1] (307)
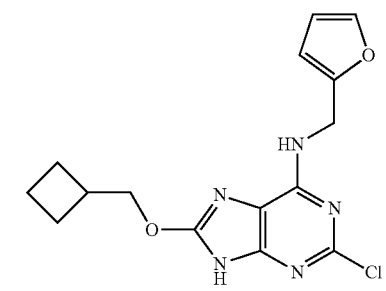 [SMILES: Clc1nc(NCc2ccco2)c2nc(OCC3CCC3)[nH]c2n1] (308)
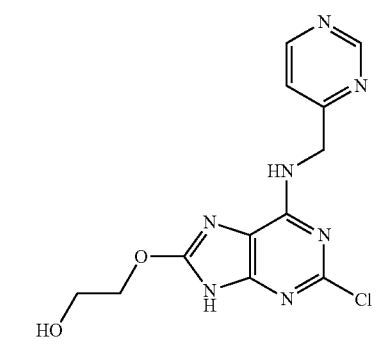 [SMILES: OCCOc1nc2c(NCc3ccncn3)nc(Cl)nc2[nH]1] (309)
TABLE A-continued
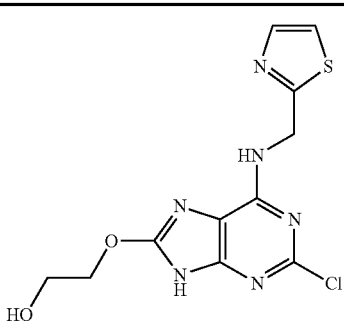 (310)
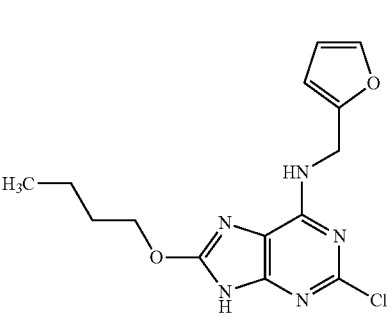 [SMILES: CCCCOc1nc2c(NCc3ccco3)nc(Cl)nc2[nH]1] (311)
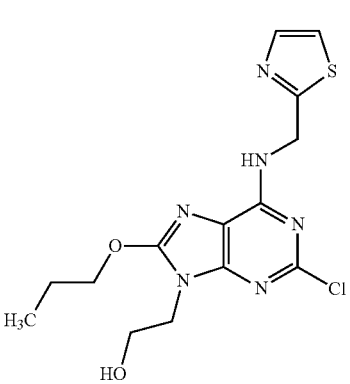 [SMILES: CCCOc1nc2c(NCc3nccs3)nc(Cl)nc2n1CCO] (312)
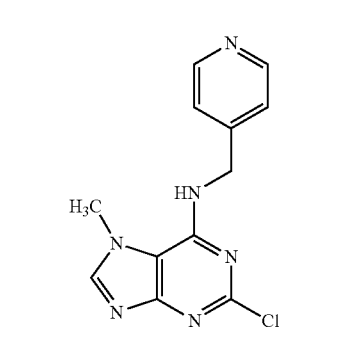 [SMILES: Cn1cnc2nc(Cl)nc(NCc3ccncc3)c21] (313)
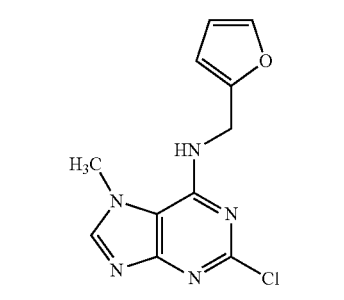 [SMILES: Cn1cnc2nc(Cl)nc(NCc3ccco3)c21] (314)

TABLE A-continued
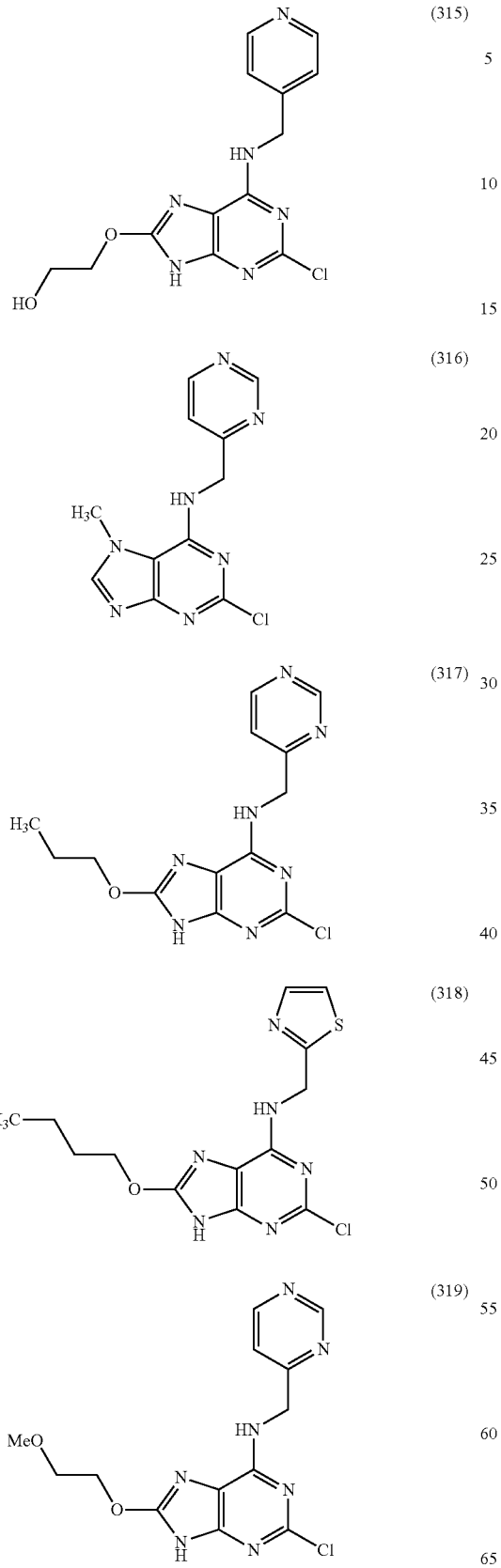
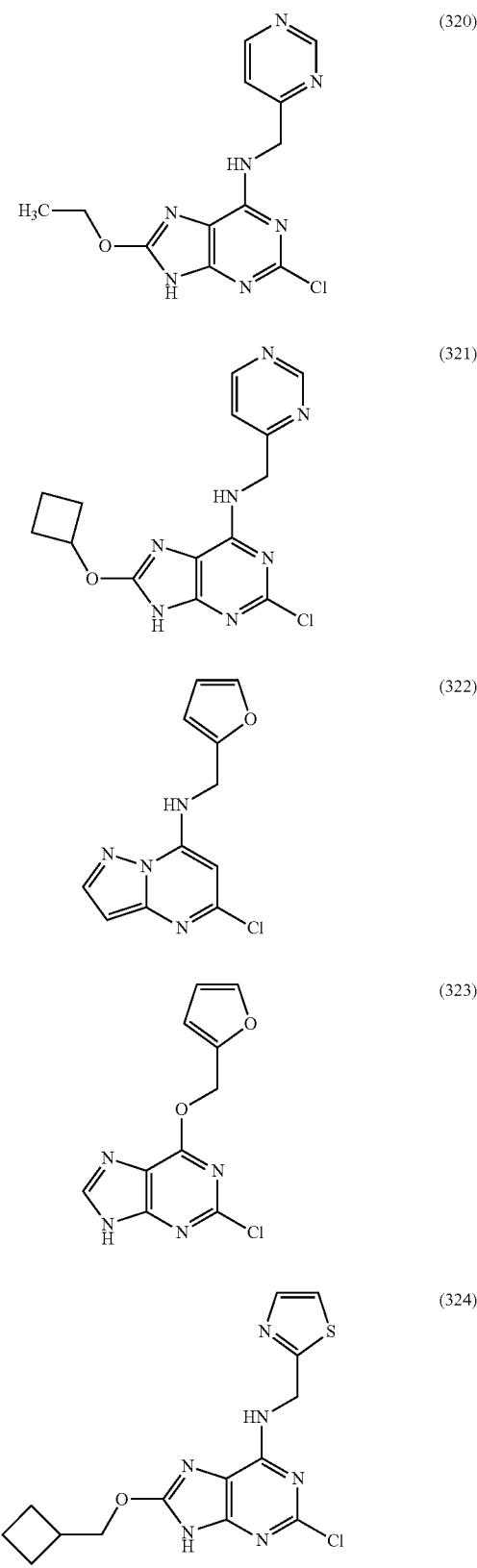

TABLE A-continued
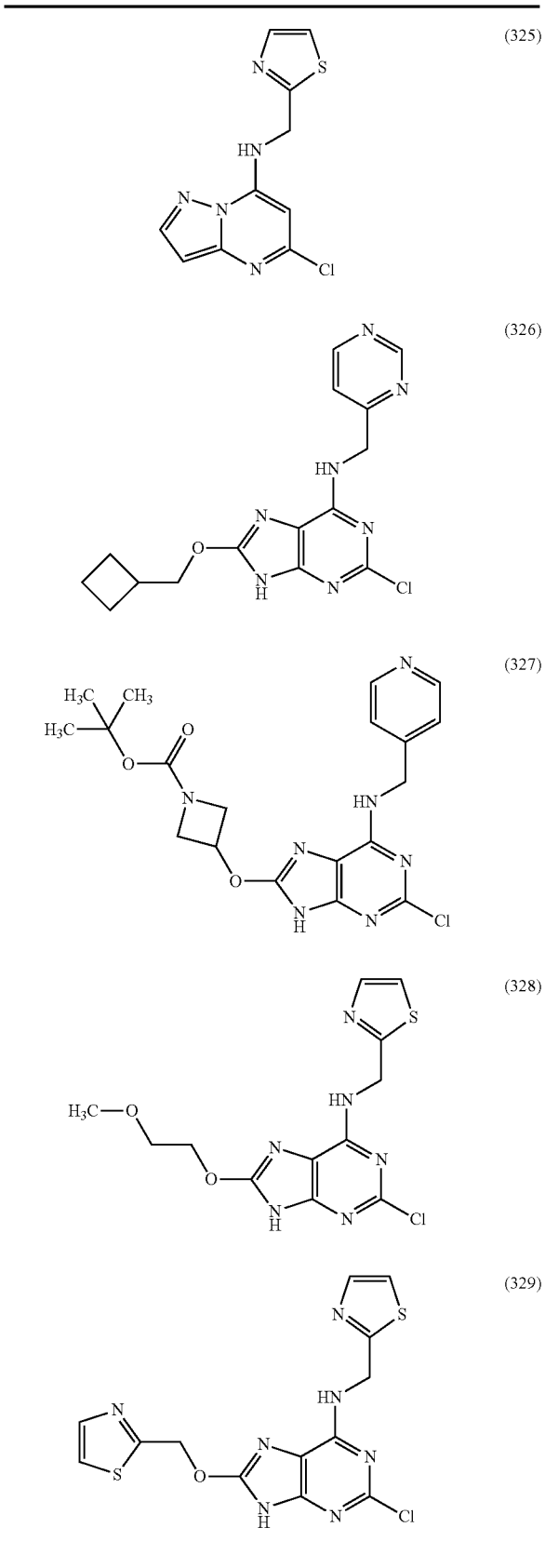
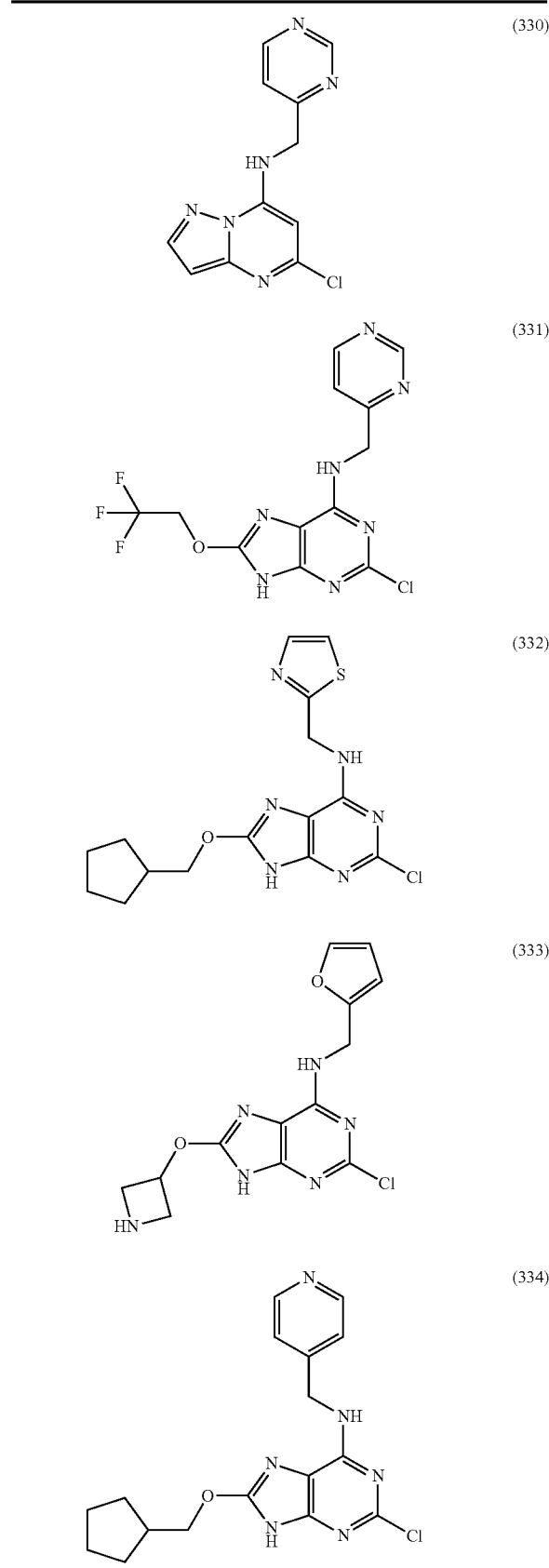

TABLE A-continued
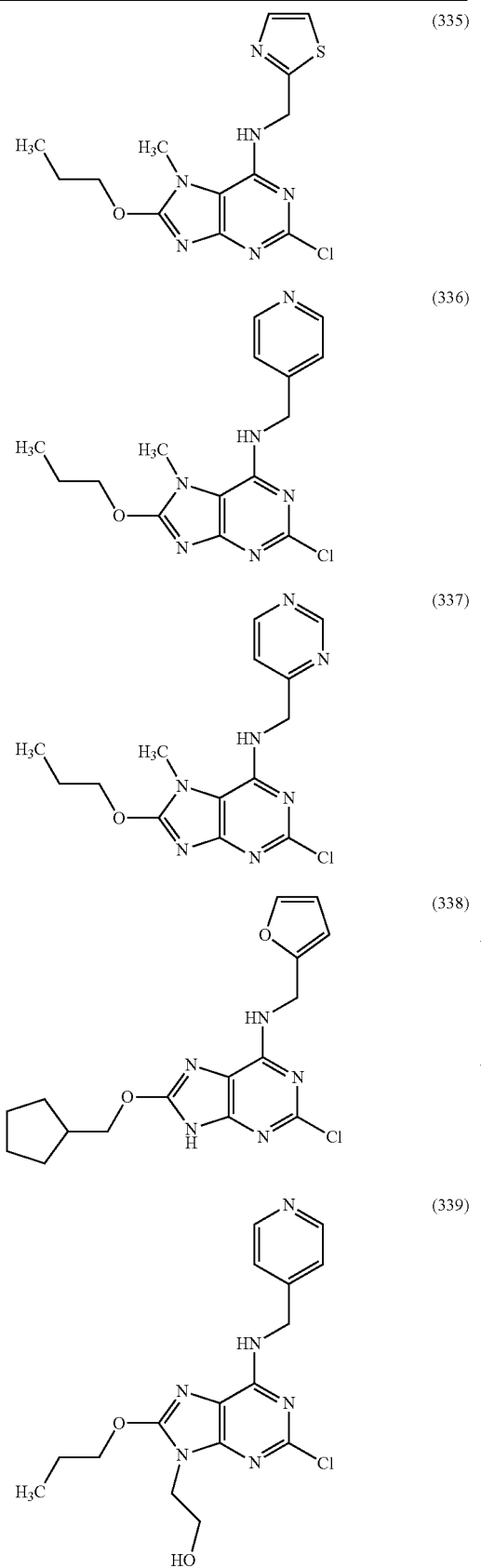

TABLE A-continued
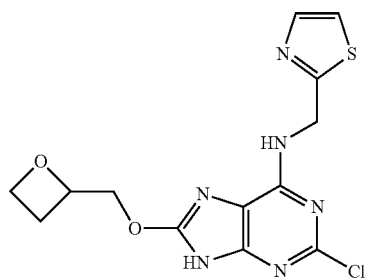 [SMILES: Clc1nc(NCc2nccs2)c2nc(OCC3CCO3)[nH]c2n1] (346)
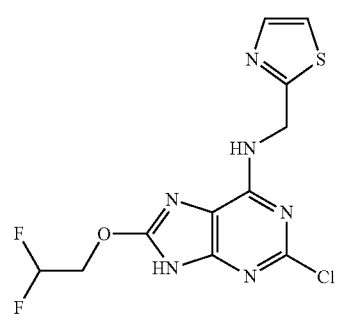 [SMILES: FC(F)COc1nc2c(NCc3nccs3)nc(Cl)nc2[nH]1] (347)
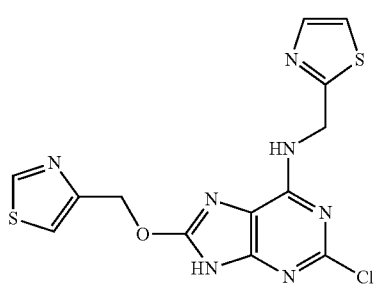 [SMILES: Clc1nc(NCc2nccs2)c2nc(OCc3cscn3)[nH]c2n1] (348)
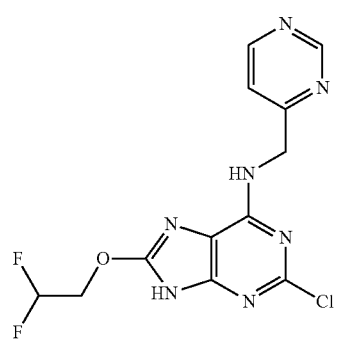 [SMILES: FC(F)COc1nc2c(NCc3ccncn3)nc(Cl)nc2[nH]1] (349)
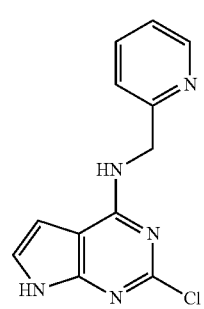 (350)
TABLE A-continued
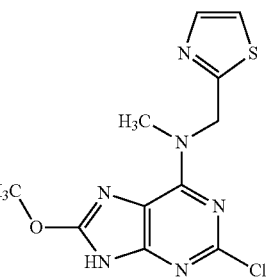 (351)
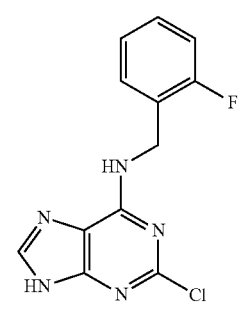 [SMILES: Fc1ccccc1CNc1nc(Cl)nc2[nH]cnc12] (352)
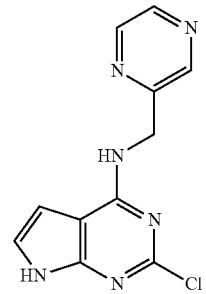 [SMILES: Clc1nc(NCc2cnccn2)c2cc[nH]c2n1] (353)
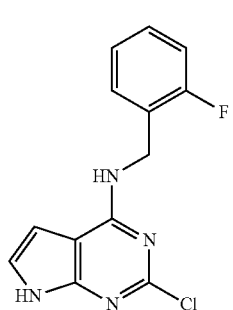 [SMILES: Fc1ccccc1CNc1nc(Cl)nc2[nH]ccc12] (354)
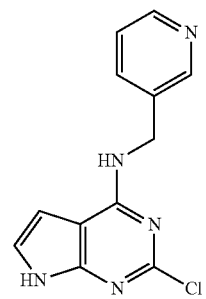 (355)

TABLE A-continued
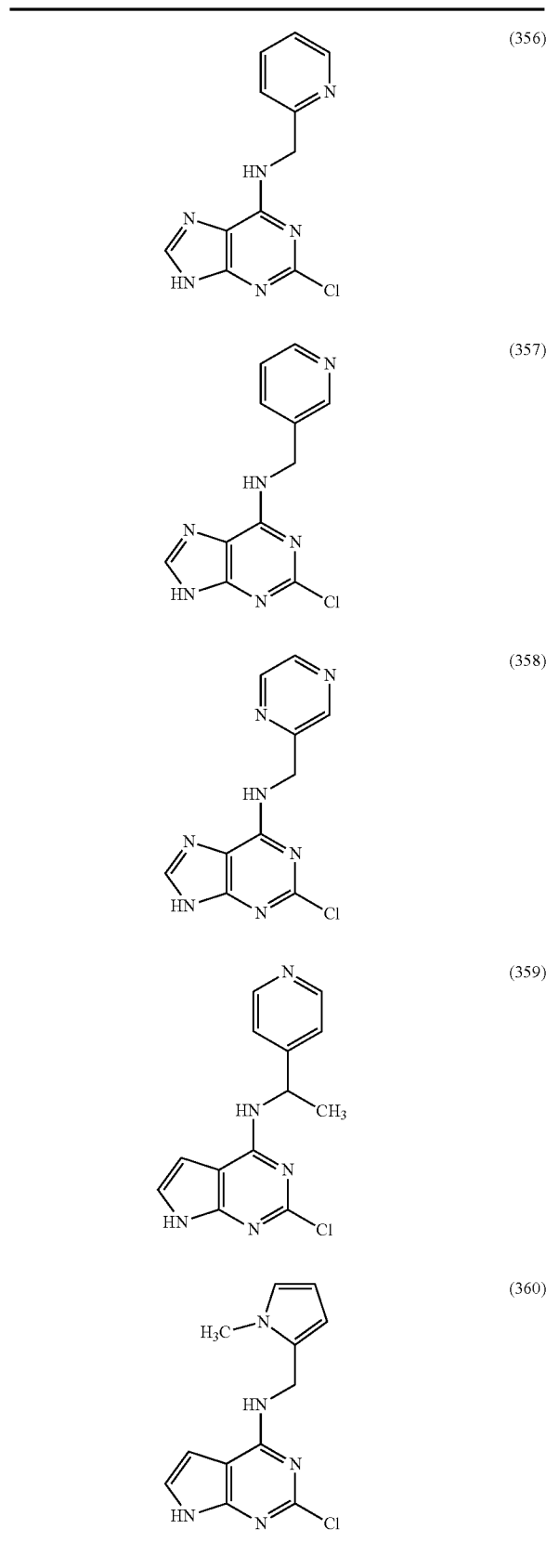
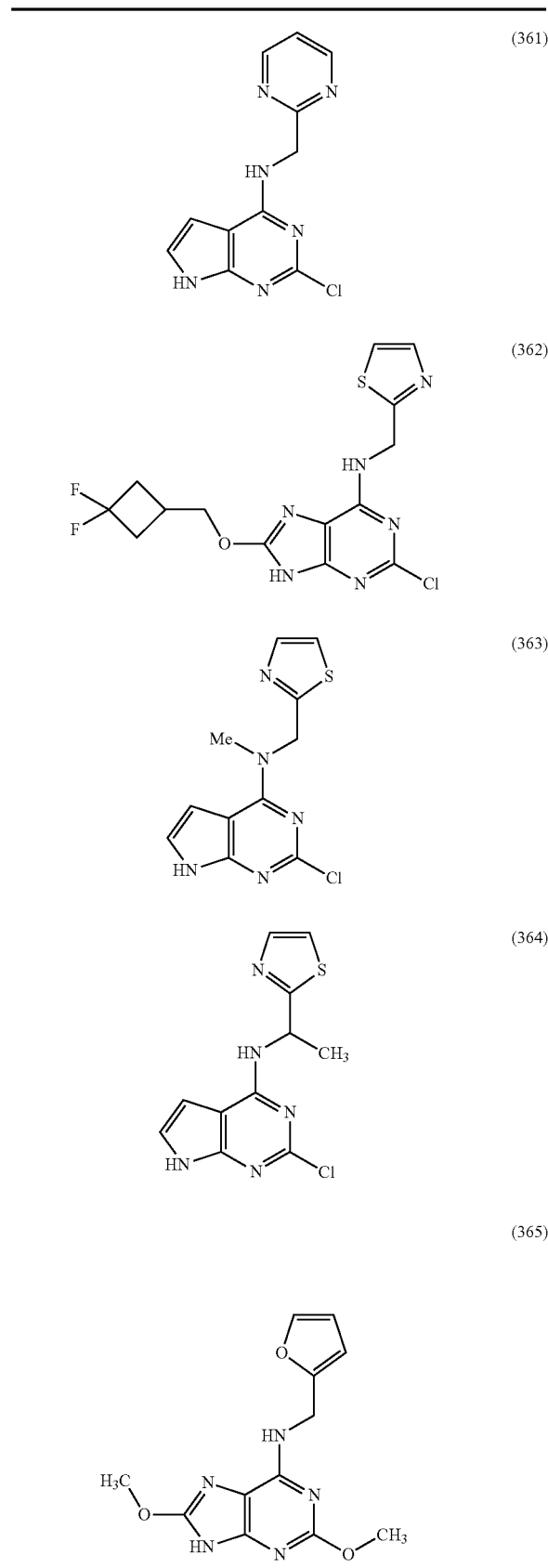

TABLE A-continued
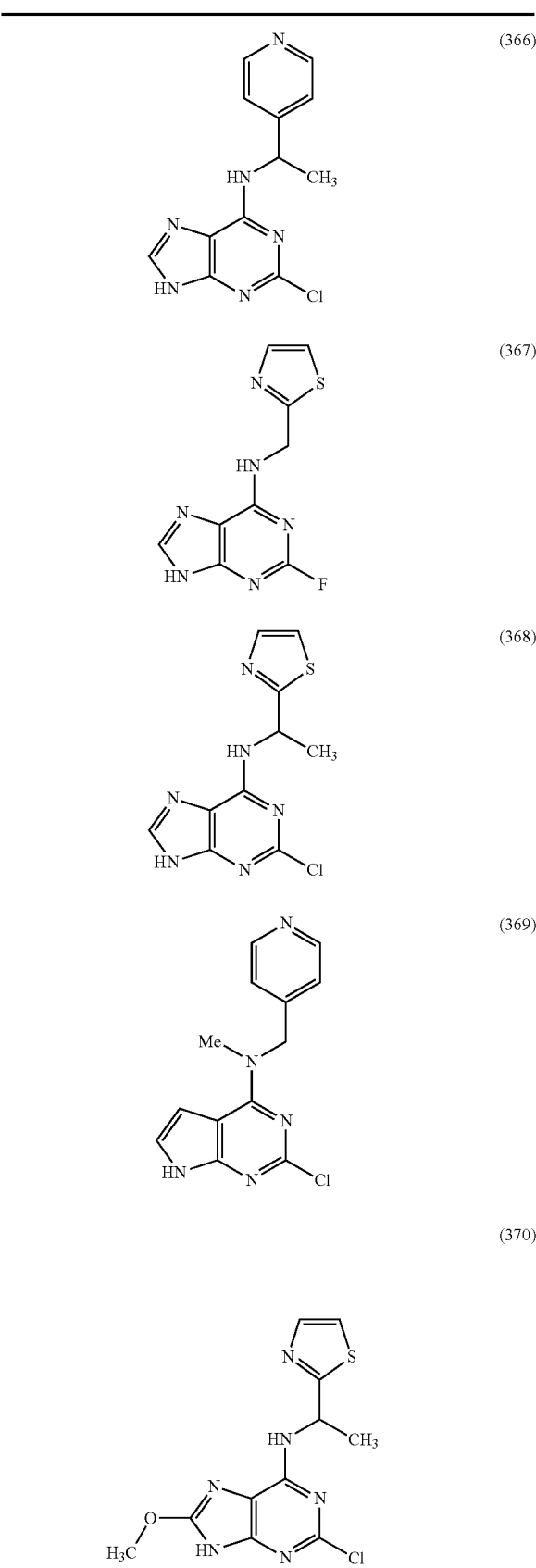
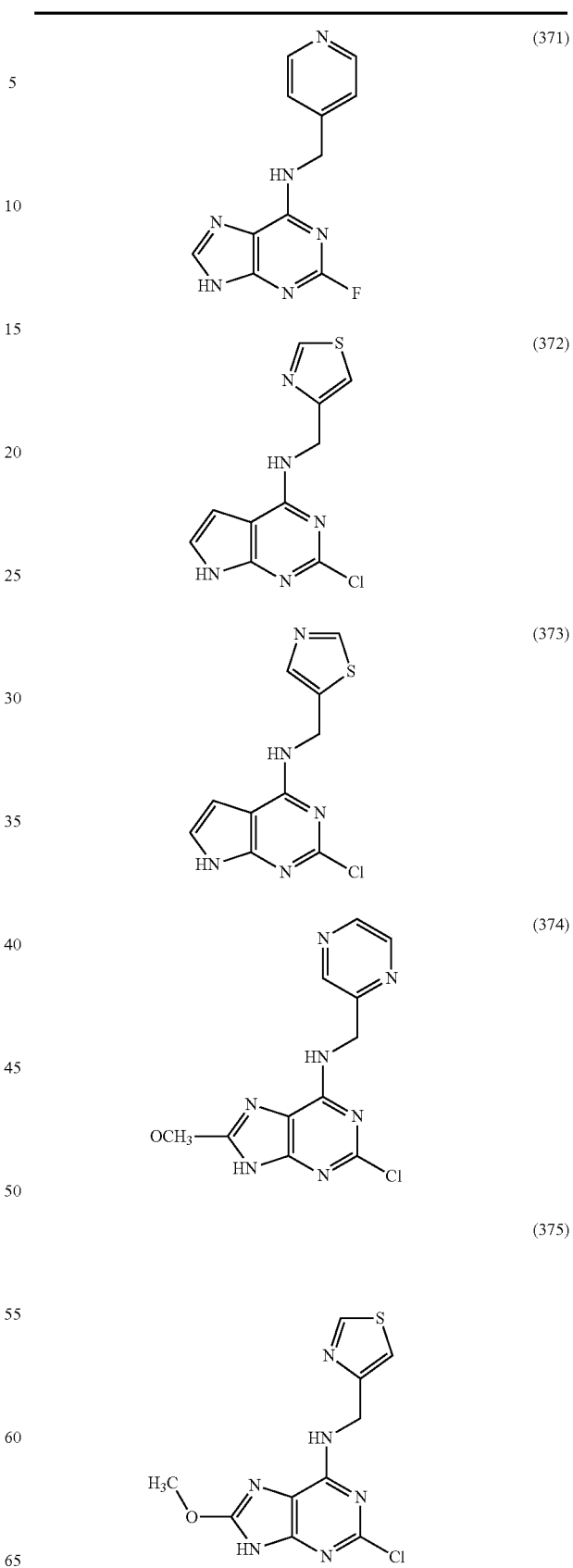

TABLE A-continued
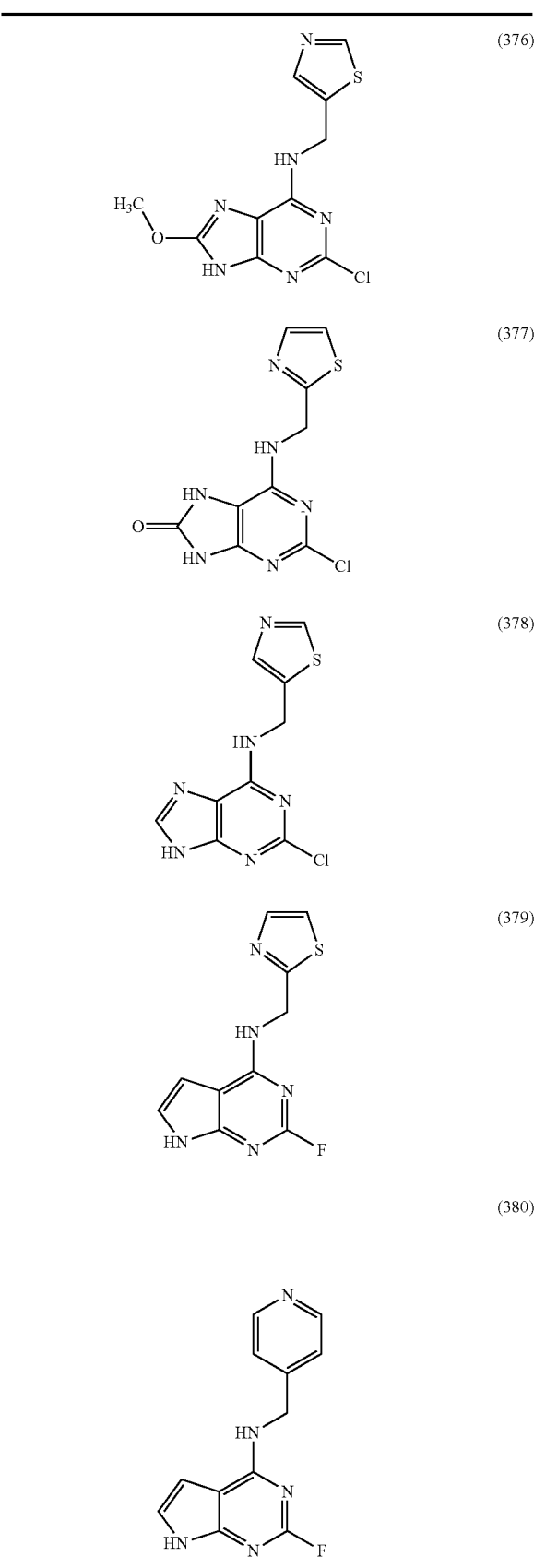
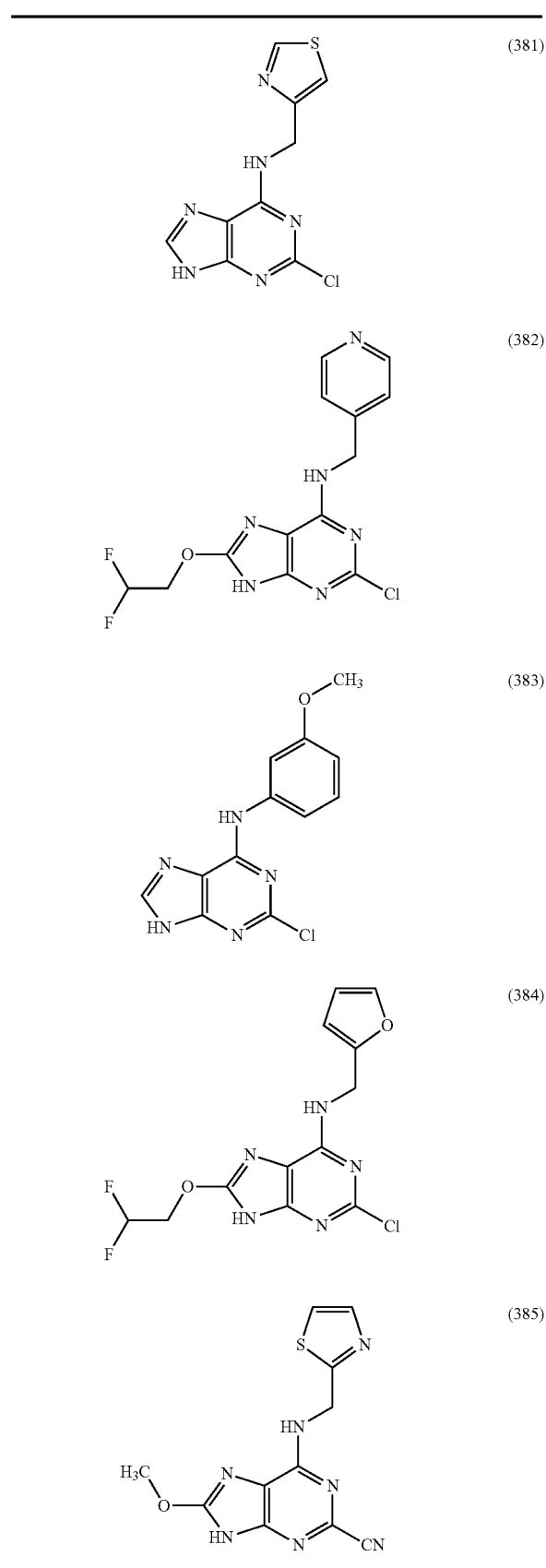

TABLE A-continued
(386) 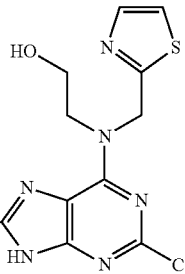
(387) 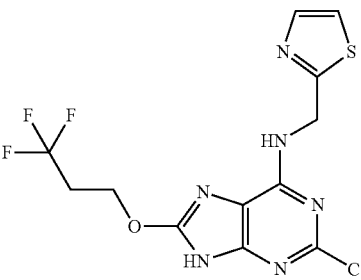
(388) 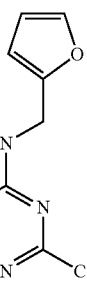
(389) 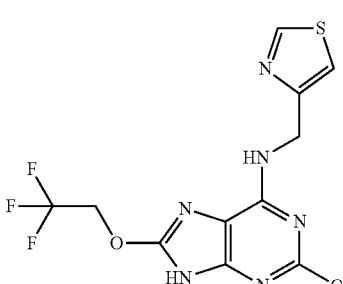
(390) 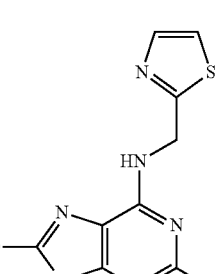
(391) 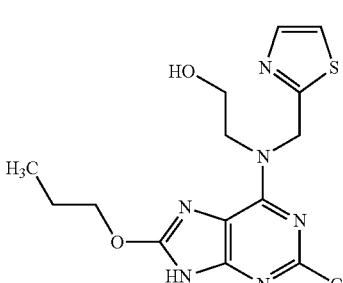
(392) 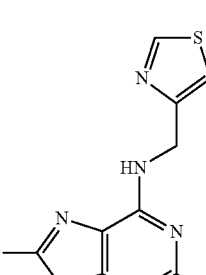
(393) 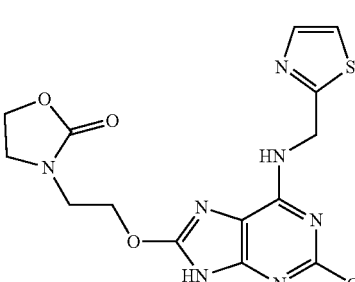
(394) 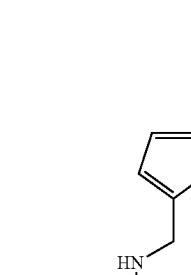
(395) 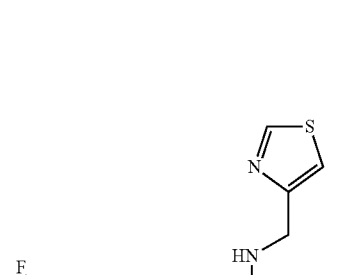

TABLE A-continued
(396) 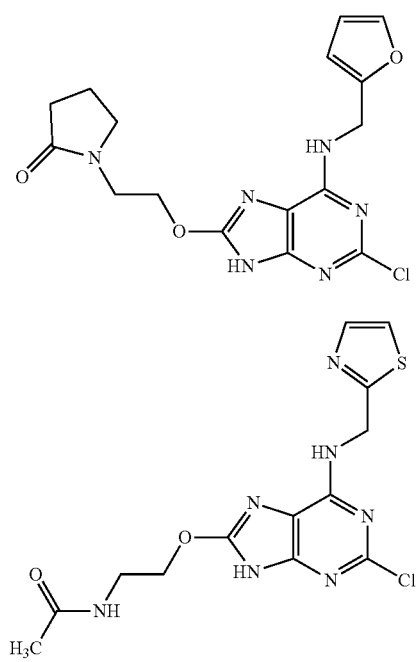
(397) 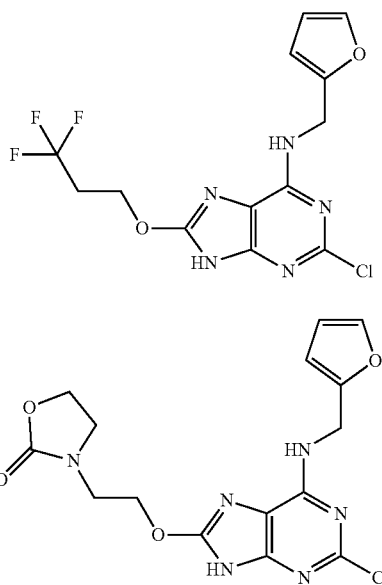
(398) 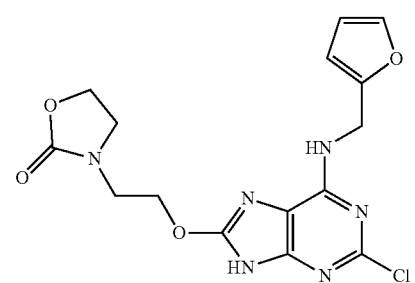 [SMILES: O=C1OCCN1CCOc1nc2c(NCc3ccco3)nc(Cl)nc2[nH]1]
(399) 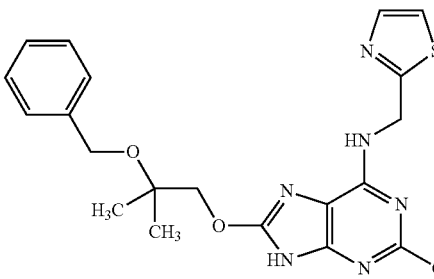
(400) 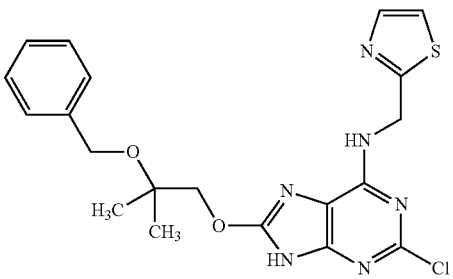 [SMILES: CC(C)(COc1nc2c(NCc3nccs3)nc(Cl)nc2[nH]1)OCc1ccccc1]
TABLE A-continued
(401) 
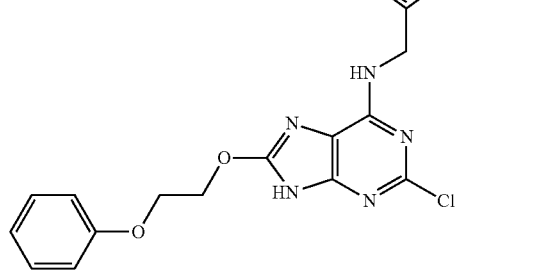
(402) 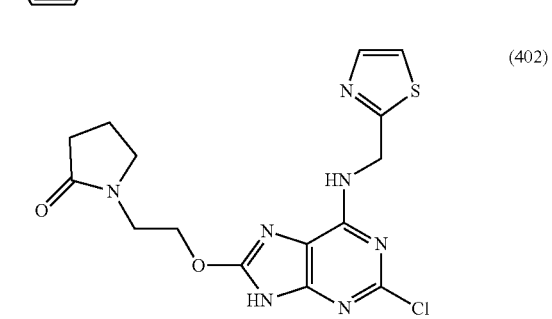
(465) 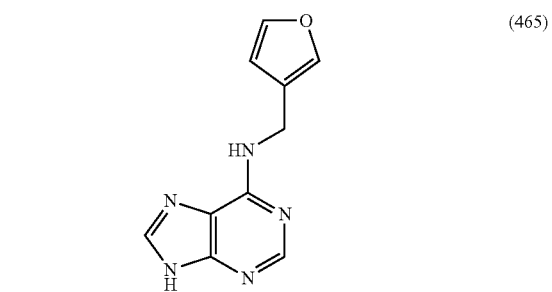
(466) 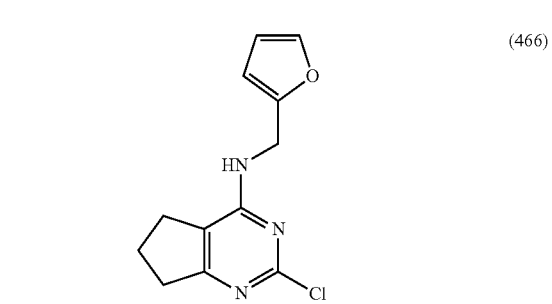
(467) 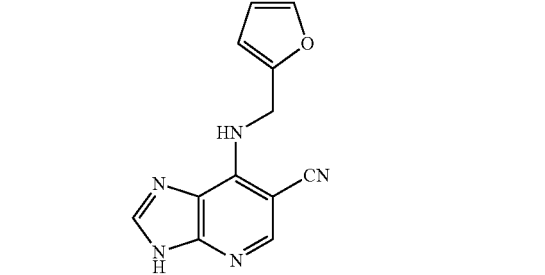 [SMILES: N#Cc1cnc2[nH]cnc2c1NCc1ccco1]

TABLE A-continued
(468) 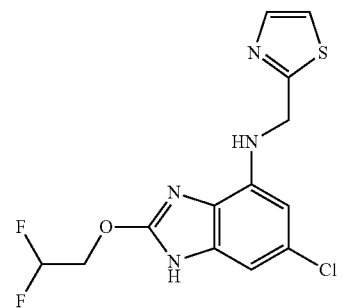 [SMILES: FC(F)COc1nc2c(NCc3nccs3)cc(Cl)cc2[nH]1]
(469) 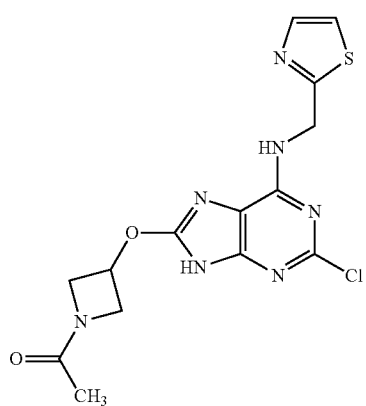 [SMILES: CC(=O)N1CC(Oc2nc3c(NCc4nccs4)nc(Cl)nc3[nH]2)C1]
(470) 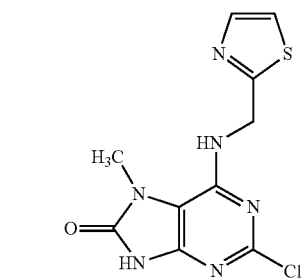 [SMILES: Cn1c(=O)[nH]c2nc(Cl)nc(NCc3nccs3)c21]
(471) 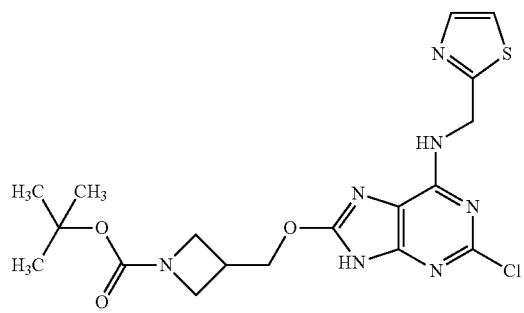 [SMILES: CC(C)(C)OC(=O)N1CC(COc2nc3c(NCc4nccs4)nc(Cl)nc3[nH]2)C1]
(472) 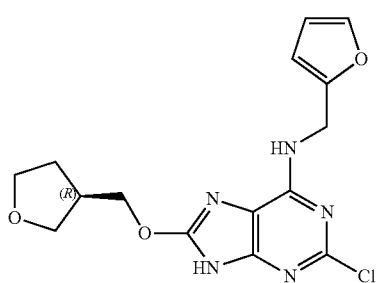
TABLE A-continued
(473) 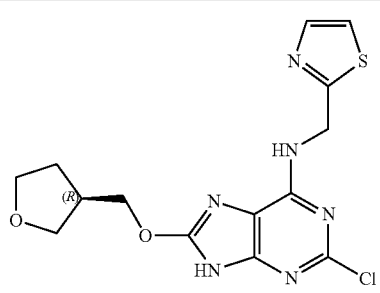
(474) 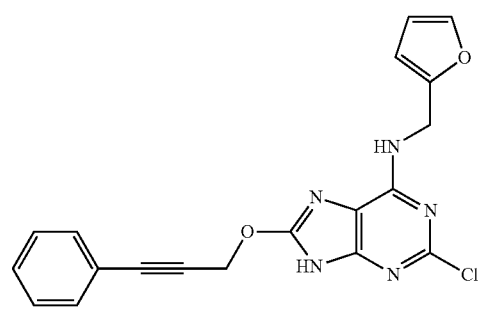 [SMILES: Clc1nc(NCc2ccco2)c2nc(OCC#Cc3ccccc3)[nH]c2n1]
(475) 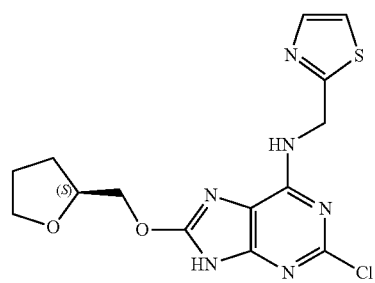
(476) 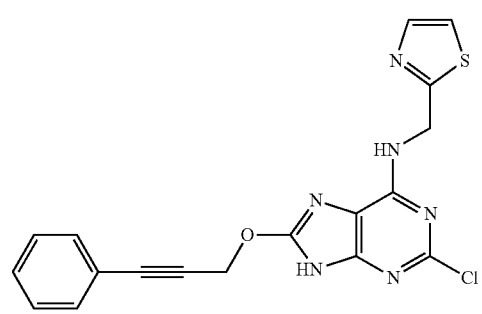 [SMILES: Clc1nc(NCc2nccs2)c2nc(OCC#Cc3ccccc3)[nH]c2n1]
(477) 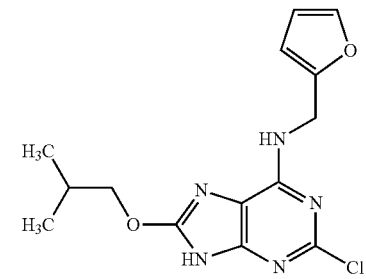 [SMILES: CC(C)COc1nc2c(NCc3ccco3)nc(Cl)nc2[nH]1]

TABLE A-continued
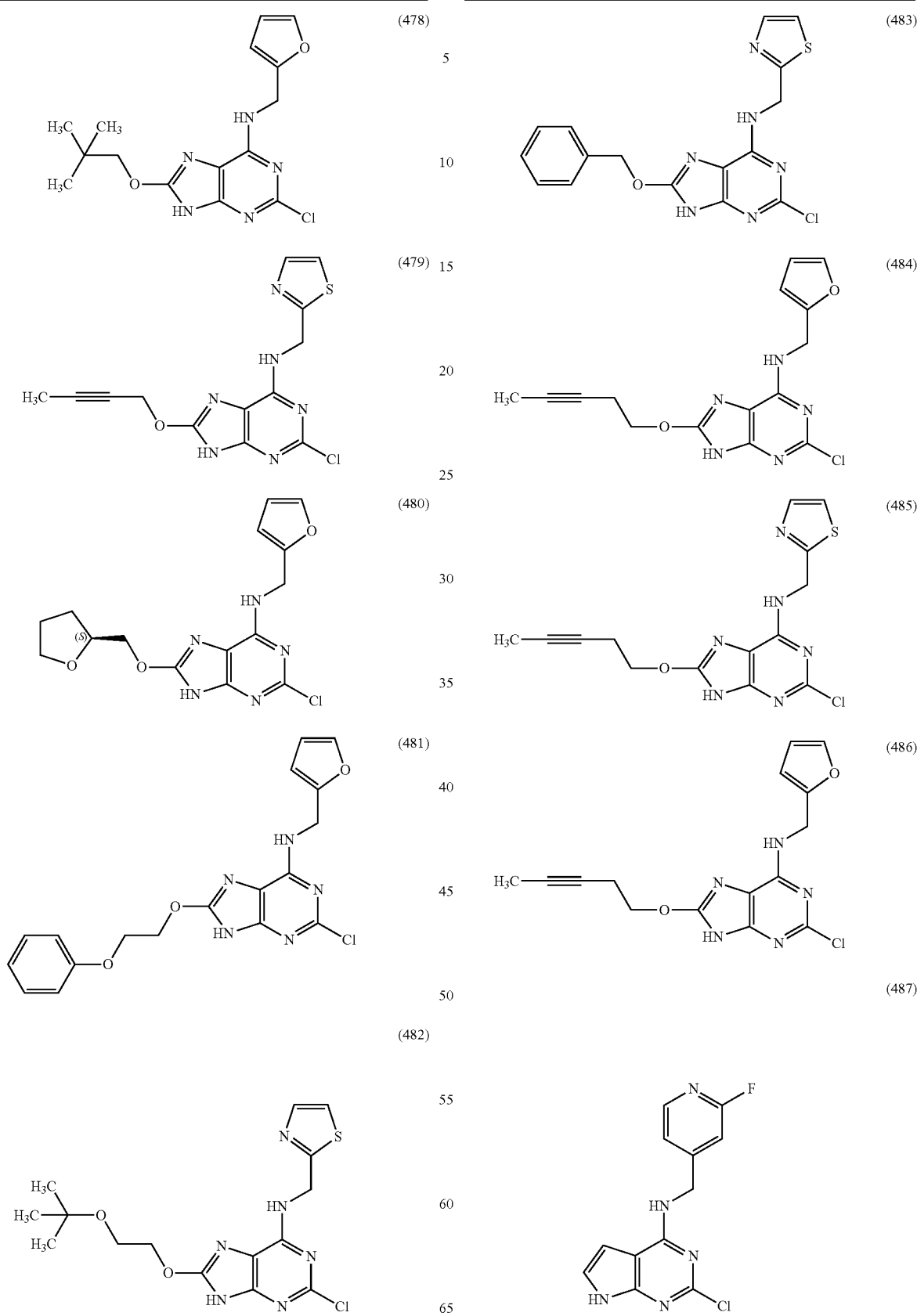

TABLE A-continued
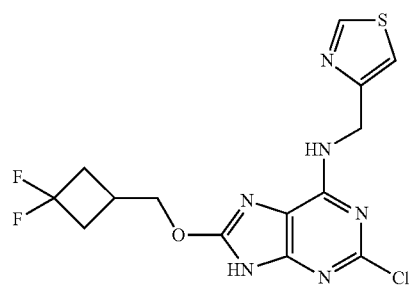 [SMILES: FC1(F)CC(COc2nc3c(NCc4cscn4)nc(Cl)nc3[nH]2)C1] (488)
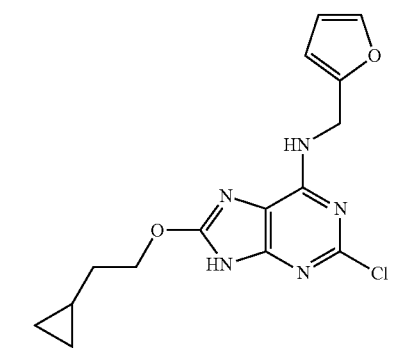 [SMILES: Clc1nc(NCc2ccco2)c2nc(OCCC3CC3)[nH]c2n1] (489)
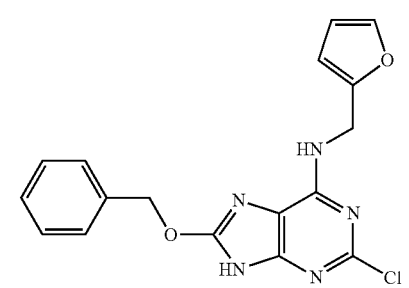 (490)
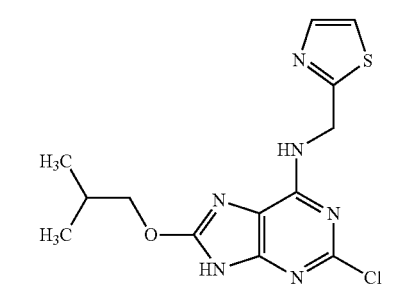 (491)
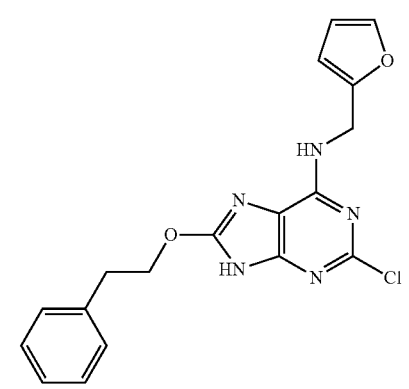 [SMILES: Clc1nc(NCc2ccco2)c2nc(OCCc3ccccc3)[nH]c2n1] (492)
TABLE A-continued
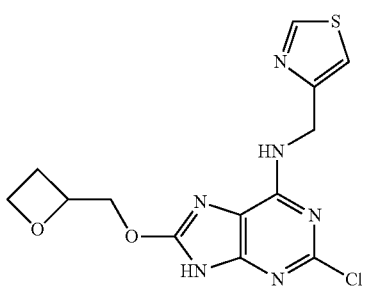 [SMILES: Clc1nc(NCc2cscn2)c2nc(OCC3CCO3)[nH]c2n1] (493)
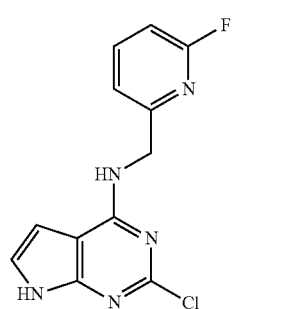 [SMILES: Fc1cccc(CNc2nc(Cl)nc3[nH]ccc23)n1] (494)
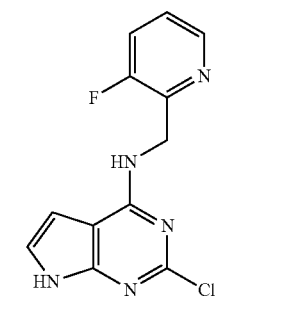 (495)
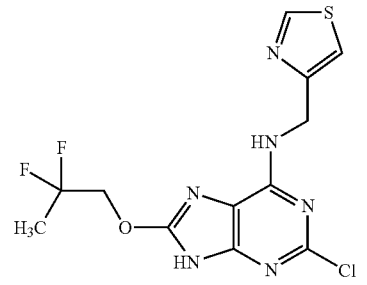 [SMILES: CC(F)(F)COc1nc2c(NCc3cscn3)nc(Cl)nc2[nH]1] (496)
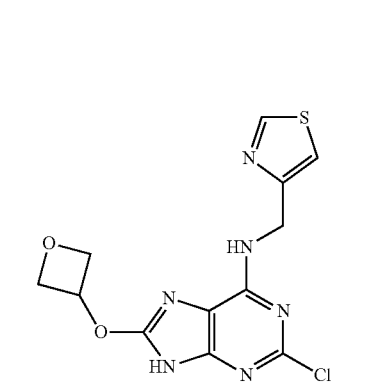 [SMILES: Clc1nc(NCc2cscn2)c2nc(OC3COC3)[nH]c2n1] (497)

TABLE A-continued
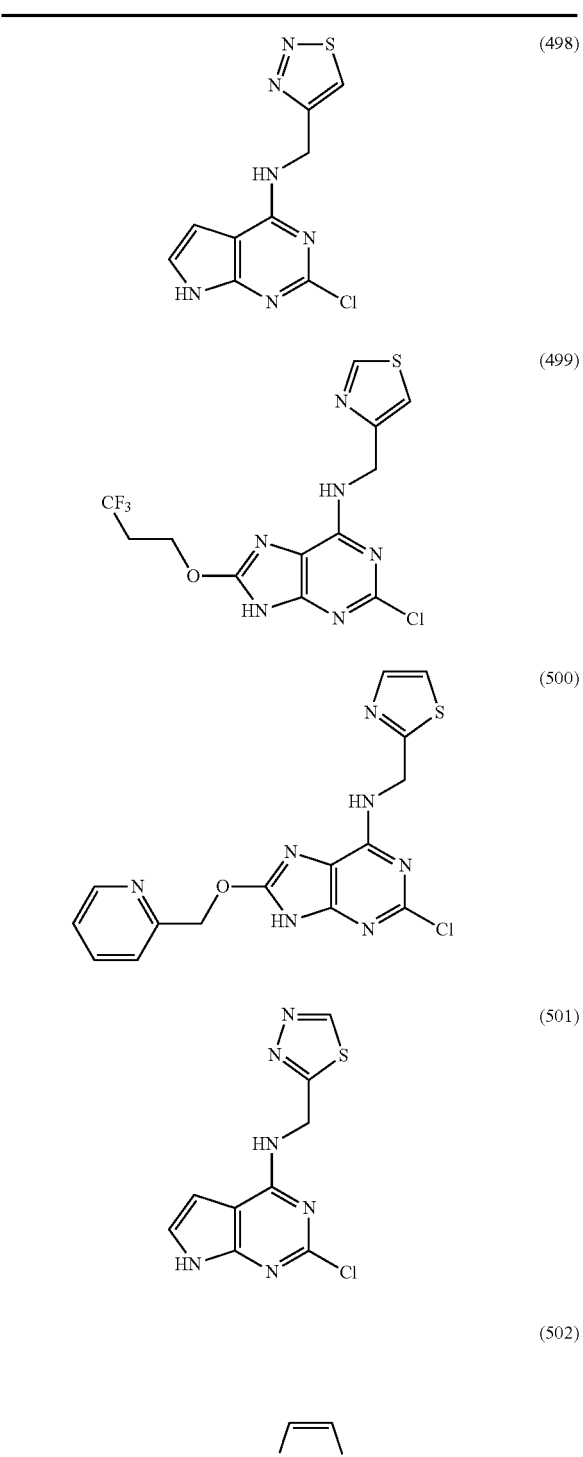
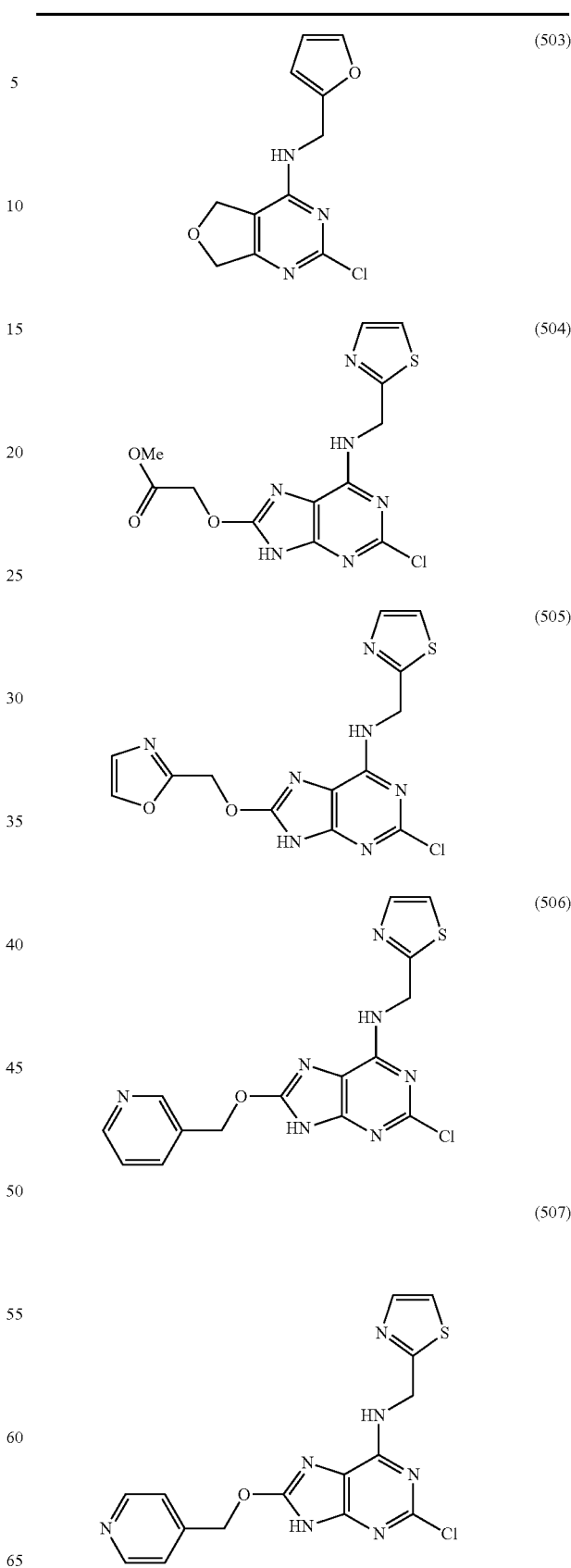

TABLE A-continued
(508) 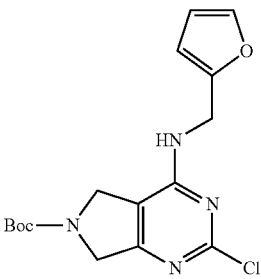 [SMILES: CC(C)(C)OC(=O)N1Cc2nc(Cl)nc(NCc3ccco3)c2C1]
(509) 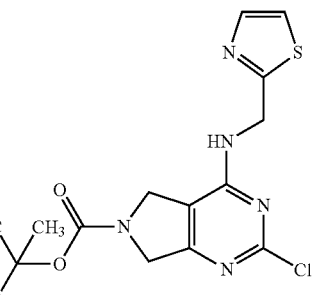
(510) 
(511) 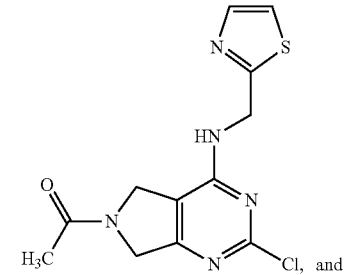 [SMILES: CC(=O)N1Cc2nc(Cl)nc(NCc3nccs3)c2C1 ; "and"]
In some embodiments, the compound of Formula (I) is selected from the group of compounds provided in Table A-2, or a pharmaceutically acceptable salt thereof.
TABLE A-2
(302) 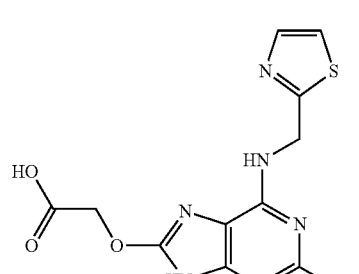
TABLE A-2-continued
(230) 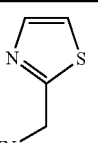
(271) 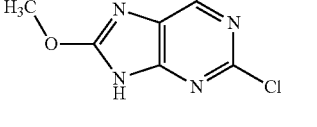
(269) 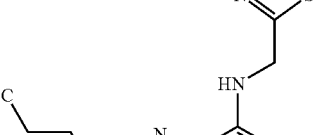
(270) 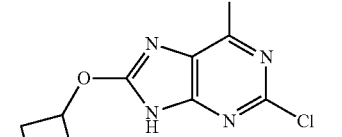
(275) 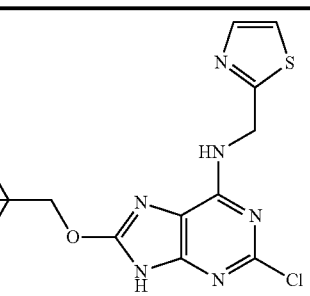

TABLE A-2-continued

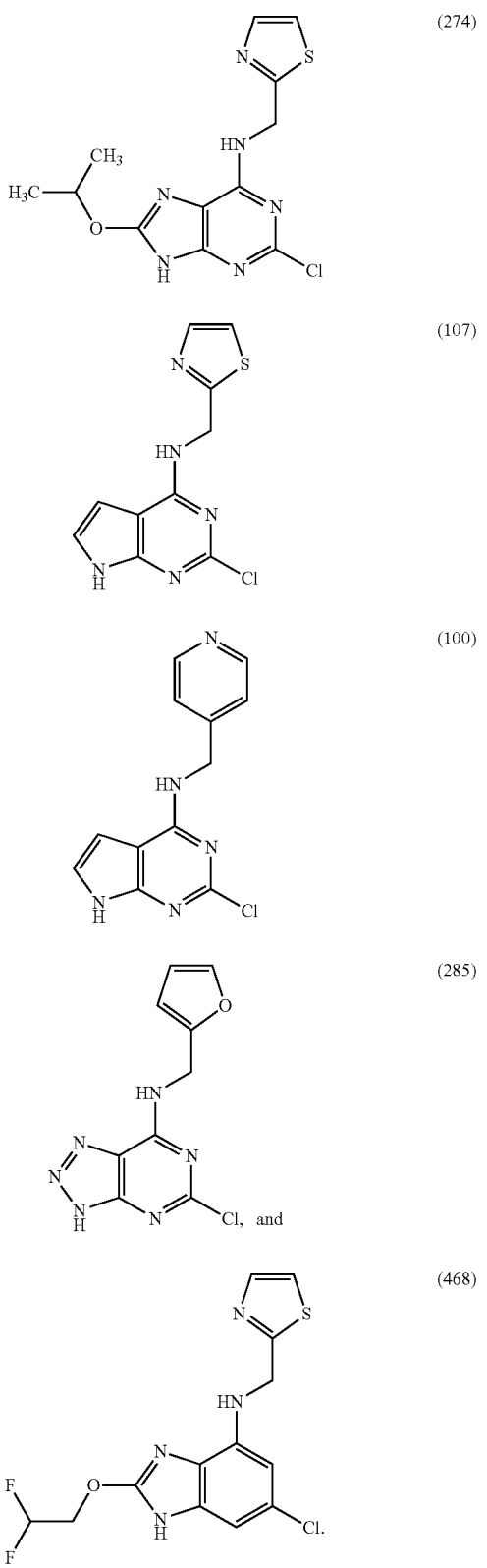

In some embodiments, the compound of Formula (I) is selected from the group of compounds provided in Table A-3, or a pharmaceutically acceptable salt thereof.

TABLE A-3

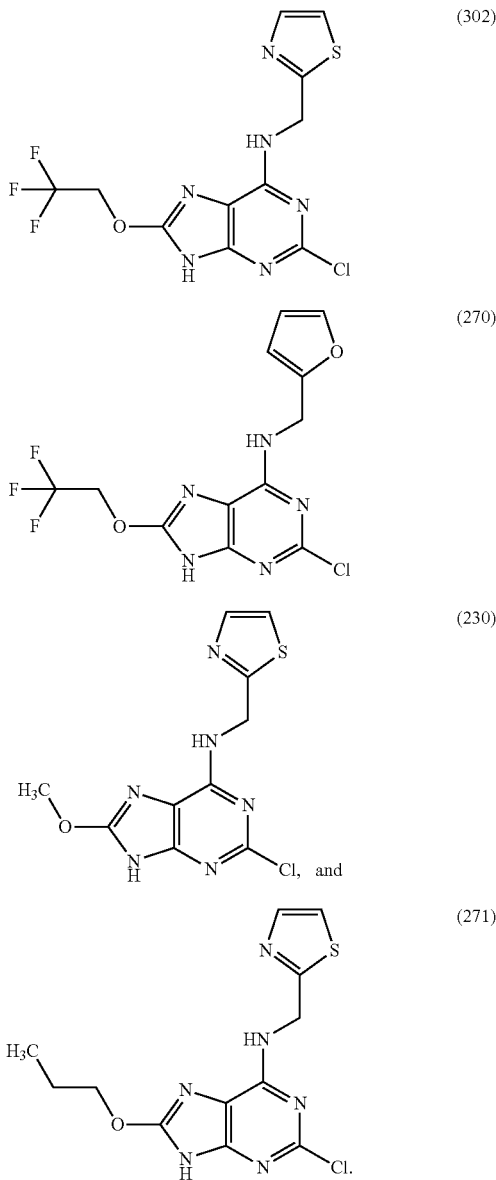

The present application further provides compounds of Formula (II):

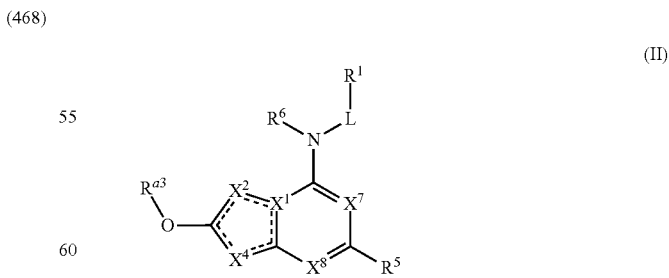

or a pharmaceutically acceptable salt thereof, wherein:

$X^1$ is N or C;

$X^2$ is selected from the group consisting of S, N, $NR^2$, $CR^2$, and $CHR^2$;

$X^4$ is selected from the group consisting of S, N, $NR^4$, $CR^4$, and $CHR^4$;

$X^7$ is N or $CR^7$;

$X^8$ is N or $CR^8$;

L is absent or selected from the group consisting of $C_{1-6}$ alkylene, $C_{2-6}$ alkenylene, and $C_{2-6}$ alkynylene, wherein the $C_{1-6}$ alkylene, $C_{2-6}$ alkenylene, and $C_{2-6}$ alkynylene are each optionally substituted by 1, 2, 3, or 4 independently selected $R^{20}$ groups;

$R^1$ is selected from the group consisting of a $C_{6-10}$ aryl, $C_{3-10}$ cycloalkyl, 5-10 membered heteroaryl, and a 4-10 membered heterocycloalkyl, each optionally substituted by 1, 2, 3, or 4 independently selected $R^{1A}$ groups;

each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;

$R^2$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a2}$, $C(=O)R^{b2}$, $C(=O)OR^{b2}$, $NR^{c2}R^{d2}$, $C(=O)NR^{c2}R^{d2}$, —$OC(=O)NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}S(=O)_2NR^{c2}R^{d2}$, $S(O)NR^{c2}R^{d2}$, and $S(O)_2NR^{c2}R^{d2}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^4$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a4}$, $C(=O)R^{b4}$, $C(=O)OR^{b4}$, $NR^{c4}R^{d4}$, $C(=O)NR^{c4}R^{d4}$, —$OC(=O)NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, $S(O)NR^{c4}R^{d4}$, and $S(O)_2NR^{c4}R^{d4}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^5$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^5$, $SR^{a5}$, $C(=O)R^{b5}$, $C(=O)OR^{b5}$, $NR^{c5}R^{d5}$, $C(=O)NR^{c5}R^{d5}$, —$OC(=O)NR^{c5}R^{d5}$, $NR^{c5}C(=O)R^{b5}$, $NR^{c5}C(=O)OR^{b5}$, $NR^{c5}C(=O)NR^{c5}R^{d5}$, $NR^{c5}S(=O)_2R^{b5}$, $NR^{c5}S(=O)_2NR^{c5}R^{d5}$, $S(O)NR^{c5}R^{d5}$, and $S(O)_2NR^{c5}R^{d5}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^6$ is selected from the group consisting of H, $C_{1-6}$ alkyl, $C_{1-6}$ haloalkyl, $C_{1-6}$ hydroxyalkyl, and $C_{1-6}$ alkoxy, wherein the $C_{1-6}$ alkyl is optionally substituted by 1, 2, 3, or 4 independently selected $R^{20}$ groups;

$R^7$ is selected from the group consisting of H, $C_{1-6}$ alkyl, CN, $NO_2$, $OR^{a7}$, $C(=O)R^{b7}$, $C(=O)OR^{b7}$, $NR^{c7}R^{d7}$, $C(=O)NR^{c7}R^{d7}$, —$OC(=O)NR^{c7}R^{d7}$, $NR^{c7}C(=O)R^{b7}$, $NR^{c7}C(=O)OR^{b7}$, $NR^{c7}C(=O)NR^{c7}R^{d7}$ $NR^{c7}S(=O)_2R^{b7}$, and $NR^{c7}S(=O)_2NR^{c7}R^{d7}$;

$R^8$ is selected from the group consisting of H, $C_{1-6}$ alkyl, CN, $NO_2$, $OR^{a8}$, $C(=O)R^{b8}$, $C(=O)OR^{b8}$, $NR^{c8}R^{d8}$, $C(=O)NR^{c8}R^{d8}$, —$OC(=O)NR^{c8}R^{d8}$, $NR^{c8}C(=O)R^{b8}$, $NR^{c8}C(=O)OR^{b8}$, $NR^{c8}C(=O)NR^{c8}R^{d8}$, $NR^{c8}S(=O)_2R^{b8}$, and $NR^{c8}S(=O)_2NR^{c8}R^{d8}$;

$R^{a3}$ is selected from the group consisting of H, $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}C(=O)R^{4e}$, wherein said $C_{1-6}$ alkyl, $C_{6-10}$ aryl, —($C_{1-6}$ alkylene)-$C_{6-10}$ aryl, $C_{3-10}$ cycloalkyl, —($C_{1-6}$ alkylene)-$C_{3-10}$ cycloalkyl, 5-10 membered heteroaryl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups;

each $R^{a2}$, $R^{b2}$, $R^{c2}$, $R^{d2}$, $R^{a4}$, $R^{b4}$, $R^{c4}$, $R^{d4}$, $R^{a5}$, $R^{b5}$, $R^{c5}$, $R^{d5}$, $R^{a7}$, $R^{b7}$, $R^{c7}$, $R^{d7}$, $R^{a8}$, $R^{b8}$, $R^{c8}$, and $R^{d8}$ is independently selected from the group consisting of H, $C_{1-6}$ alkyl, $C_{2-6}$ alkenyl, $C_{2-6}$ alkynyl, $C_{1-6}$ hydroxyalkyl, $C_{1-6}$ haloalkyl, $C_{1-6}$ alkoxy, —($C_{1-6}$ alkylene)-$C_{1-6}$ alkoxy, $C_{3-10}$ cycloalkyl, —($C_{1-6}$ alkylene)-$C_{3-10}$ cycloalkyl, $C_{6-10}$ aryl, 5-10 membered heteroaryl, 4-10 membered heterocycloalkyl, wherein the $C_{1-6}$ alkyl, $C_{2-6}$ alkenyl, $C_{2-6}$ alkynyl, $C_{3-10}$ cycloalkyl, —($C_{1-6}$ alkylene)-$C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

or $R^{c2}$ and $R^{d2}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c4}$ and $R^{d4}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

each $R^{3e}$ and $R^{3f}$ is independently selected from the group consisting of H and $C_{1-6}$ alkyl;

each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl) amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino;

wherein the ring comprising $X^1$, $X^2$, and $X^4$ forms a cycloalkyl, heteroaryl or heterocycloalkyl ring.

In some embodiments, $X^1$ is N. In some embodiments, $X^1$ is C.

In some embodiments, $X^2$ is N. In some embodiments, $X^2$ is $NR^2$. In some embodiments, $X^2$ is $CR^2$. In some embodiments, $X^2$ is $CHR^2$. In some embodiments, $X^2$ is S.

In some embodiments, $X^4$ is N. In some embodiments, $X^4$ is $NR^4$. In some embodiments, $X^4$ is $CR^4$. In some embodiments, $X^4$ is $CHR^4$. In some embodiments, $X^4$ is S.

In some embodiments, $X^7$ is N. In some embodiments, $X^7$ is $CR^7$.

In some embodiments, $X^8$ is N. In some embodiments, $X^8$ is $CR^8$.

In some embodiments, L is $C_{1-6}$ alkylene optionally substituted by 1, 2, 3, or 4 independently selected $R^{20}$ groups. In some embodiments, L is unsubstituted $C_{1-6}$ alkylene. In some embodiments, L is unsubstituted methylene or unsubstituted ethylene.

In some embodiments, $R^1$ is selected from the group consisting of $C_{6-10}$ aryl, 5-6 membered heteroaryl, and 5-6 membered heterocycloalkyl, each optionally substituted by 1, 2, 3, or 4 independently selected $R^{14}$ groups. In some embodiments, $R^1$ is selected from the group consisting of 5-6 membered heteroaryl, and 5-6 membered heterocycloalkyl, each optionally substituted by 1, 2, 3, or 4 independently selected $R^{14}$ groups.

In some embodiments, $R^1$ is selected from the group consisting of:

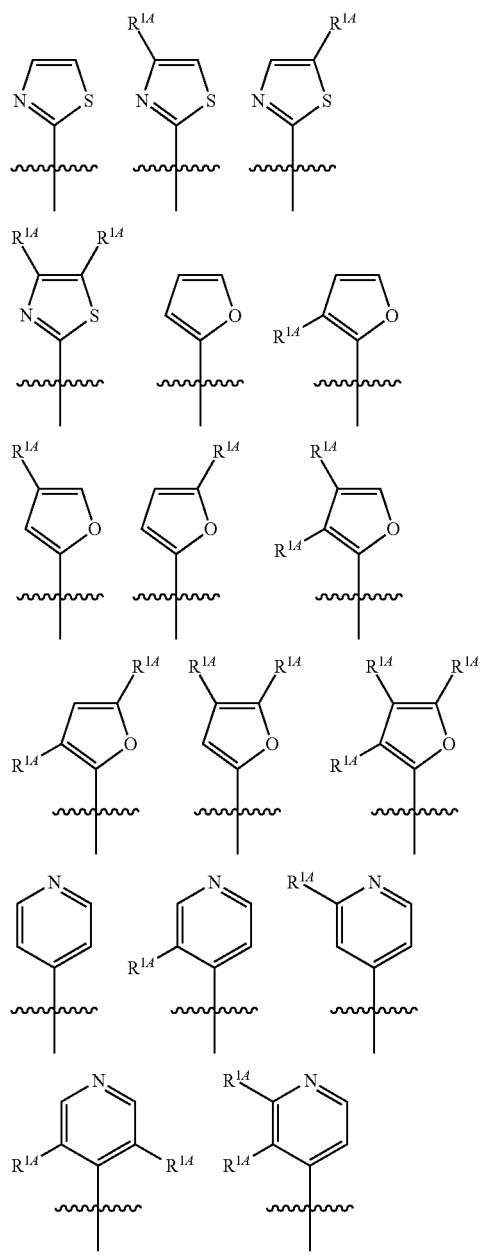

-continued

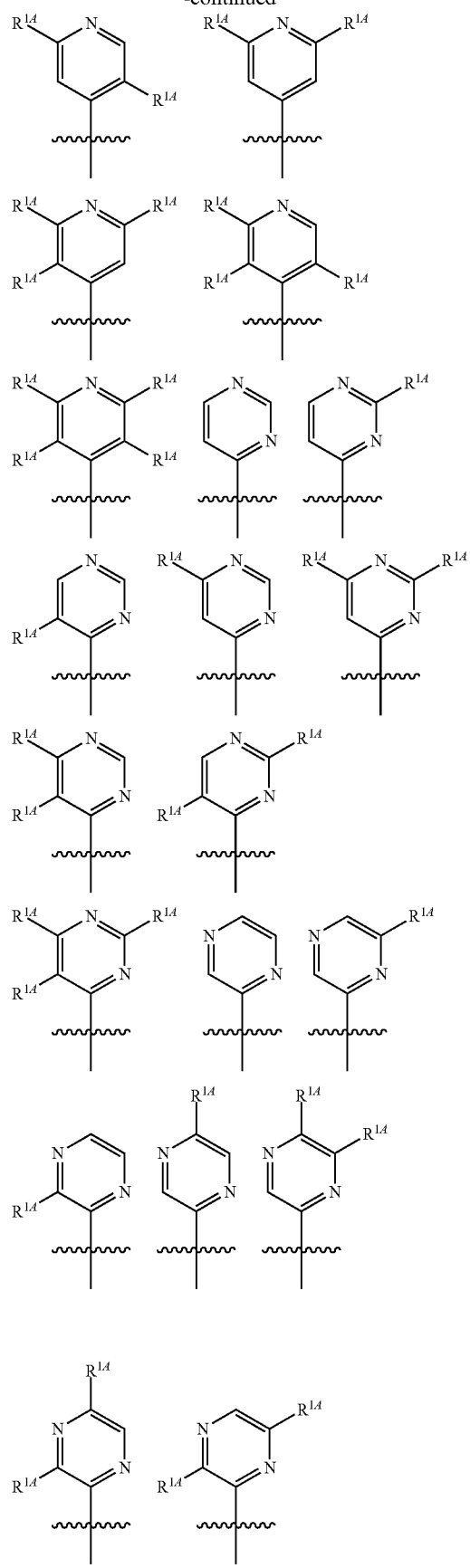

-continued

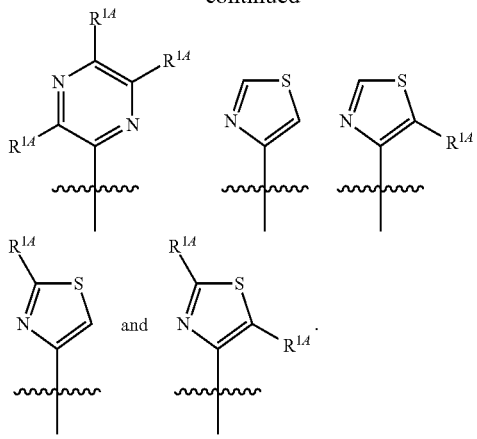

In some embodiments, R¹ is selected from the group consisting of:

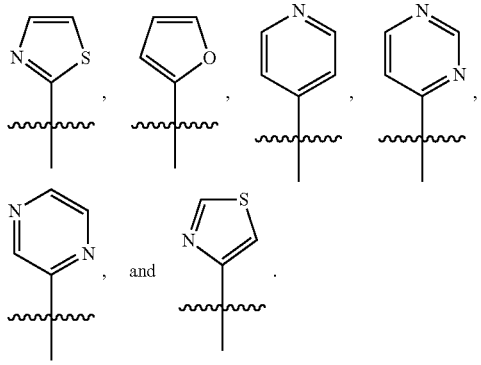

In some embodiments, R² is H or $C_{1-6}$ alkyl. In some embodiments, R² is H or methyl.

In some embodiments, R⁴ is H or $C_{1-6}$ alkyl, wherein the $C_{1-6}$ alkyl is optionally substituted by 1, 2, 3, or 4 independently selected $R^{20}$ groups. In some embodiments, R⁴ is H or —$CH_2CH_2OH$.

In some embodiments, R⁵ is selected from the group consisting of H, halo, CN, and $OR^{a4}$. In some embodiments, R⁵ is selected from the group consisting of H, Cl, CN, and —$OCH_3$.

In some embodiments, R⁶ is H or $C_{1-6}$ alkyl, wherein the $C_{1-6}$ alkyl is optionally substituted by 1, 2, 3, or 4 independently selected $R^{20}$ groups. In some embodiments, R⁶ is selected from the group consisting of H, methyl, and —$CH_2CH_2OH$.

In some embodiments, $R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}C(=O)R^{4e}$, wherein said $C_{1-6}$ alkyl, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups. In some embodiments, $R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{5-6}$ aryloxy, $C_{4-6}$ cycloalkyl, —($C_{1-6}$ alkylene)-$C_{4-6}$ cycloalkyl, —($C_{1-6}$ alkylene)-(5-6 membered heteroaryl), 4-6 membered heterocycloalkyl, -(4-6 membered heterocycloalkyl)-C(=O)$OR^{3f}$, —($C_{1-6}$ alkylene)-(4-6 membered heterocycloalkyl), —$NR^{3e}R^{3f}$, —($C_{1-6}$ alkylene)-$NR^{3e}R^{3f}$, and —($C_{1-6}$ alkylene)-$NR^{3e}C(=O)R^{4e}$, wherein the —($C_{1-6}$ alkylene)-$C_{1-6}$ alkoxy is substituted by phenyl. In some embodiments, $R^{a3}$ is selected from the group consisting of methyl, ethyl, n-propyl, isopropyl, n-butyl, —$CH_2CH_2OH$, —$CH_2CH_2CH_2OH$, —$CH_2CHF_2$, —$CH_2CF_3$, —$CH_2CH_2CF_3$, —$CH_2CHF_2CH_3$, —$CH_2CH_2OCH_3$, —$CH_2CH_2CH_2OCH_3$, —$NHCH_3$, —$CH_2CH_2NHC(=O)CH_3$, cyclobutyl, —$CH_2$-cyclobutyl, —$CH_2$-cyclopentyl, —$CH_2CH_2$—O-phenyl, azetidinyl, —$CH_2$-azetidinyl, oxetanyl, —$CH_2$-oxetanyl, —$CH_2$-thiazolyl,

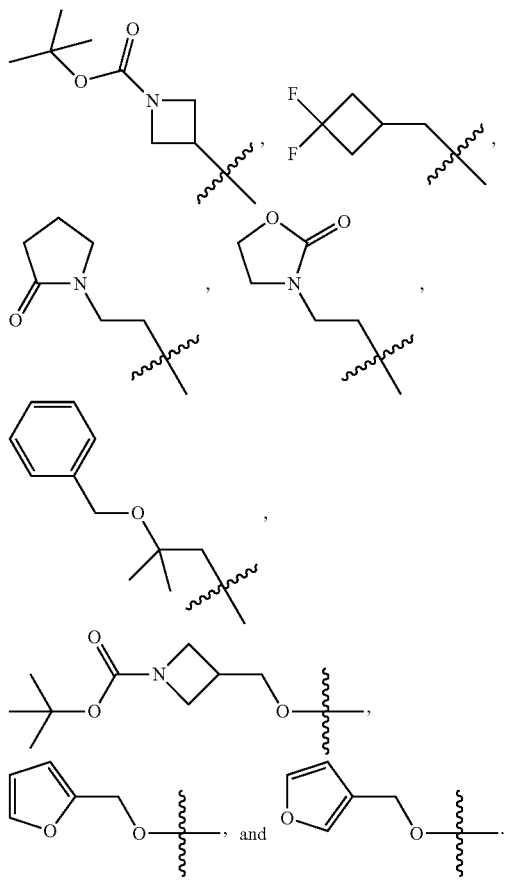

In some embodiments:
X¹ is C;
X² is N or NR²;
X⁴ N or NR⁴;
X⁷ is N; and
X⁸ is N.

In some embodiments:
X¹ is C;
X² is N or NR²;
X⁴ N or NR⁴;
X⁷ is N;
X⁸ is N;
L is $C_{1-6}$ alkylene optionally substituted by 1, 2, 3, or 4 independently selected $R^{20}$ groups;

$R^1$ is selected from the group consisting of $C_{6-10}$ aryl, 5-6 membered heteroaryl, and 5-6 membered heterocycloalkyl, each optionally substituted by 1, 2, 3, or 4 independently selected $R^{1A}$ groups;

each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;

$R^2$ is H or $C_{1-6}$ alkyl;

$R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{6-10}$ aryloxy, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, -(4-10 membered heterocycloalkyl)-C(=O)$OR^{3f}$, —($C_{1-6}$ alkylene)-(4-10 membered heterocycloalkyl), —$NR^{3e}R^{3f}$, —($C_{1-6}$ alkyl)-$NR^{3e}R^{3f}$, and —($C_{1-6}$ alkylene)-$NR^{3e}C$(=O)$R^{4e}$, wherein said $C_{1-6}$ alkyl, $C_{3-10}$ cycloalkyl, —($C_{1-6}$ alkylene)-$C_{3-10}$ cycloalkyl, —($C_{1-6}$ alkylene)-(5-10 membered heteroaryl), 4-10 membered heterocycloalkyl, and —($C_{1-6}$ alkylene)-(4-10 membered heterocycloalkyl) are each optionally substituted by 1, 2, 3, or 4 $R^{20}$ groups;

$R^4$ is H or $C_{1-6}$ alkyl, wherein the $C_{1-6}$ alkyl is optionally substituted by 1, 2, 3, or 4 independently selected $R^{20}$ groups;

$R^5$ is selected from the group consisting of H, halo, CN, and $OR^{a4}$;

$R^6$ is H or $C_{1-6}$ alkyl;

each $R^{3e}$ and $R^{3f}$ is independently selected from the group consisting of H and $C_{1-6}$ alkyl; and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments:

$X^1$ is C;

$X^2$ is N or $NR^2$;

$X^4$ N or $NR^4$;

$X^7$ is N;

$X^8$ is N;

L is unsubstituted $C_{1-6}$ alkylene;

$R^1$ is selected from the group consisting of 5-6 membered heteroaryl, and 5-6 membered heterocycloalkyl, each optionally substituted by 1, 2, 3, or 4 independently selected $R^{1A}$ groups;

each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;

$R^2$ is H or $C_{1-6}$ alkyl;

$R^4$ is H or $C_{1-6}$ alkyl, wherein the $C_{1-6}$ alkyl is optionally substituted by 1, 2, 3, or 4 independently selected $R^{20}$ groups;

$R^5$ is selected from the group consisting of H, halo, CN, and $OR^{a4}$;

$R^6$ is H or $C_{1-6}$ alkyl, wherein the $C_{1-6}$ alkyl is optionally substituted by 1, 2, 3, or 4 independently selected $R^{20}$ groups;

$R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{5-6}$ aryloxy, $C_{4-6}$ cycloalkyl, —($C_{1-6}$ alkylene)-$C_{4-6}$ cycloalkyl, —($C_{1-6}$ alkylene)-(5-6 membered heteroaryl), 4-6 membered heterocycloalkyl, -(4-6 membered heterocycloalkyl)-C(=O)$OR^{3f}$, —($C_{1-6}$ alkylene)-(4-6 membered heterocycloalkyl), —$NR^{3e}R^{3f}$, —($C_{1-6}$ alkylene)-$NR^{3e}R^{3f}$, and —($C_{1-6}$ alkylene)-$NR^{3e}C$(=O)$R^{4e}$, wherein the —($C_{1-6}$ alkylene)-$C_{1-6}$ alkoxy is substituted by phenyl;

each $R^{3e}$ and $R^{3f}$ is independently selected from the group consisting of H and $C_{1-6}$ alkyl; and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamoyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

In some embodiments:

$X^1$ is C;

$X^2$ is N or $NR^2$;

$X^4$ is N or $NR^4$;

$X^7$ is N;

$X^8$ is N;

L is unsubstituted methylene or unsubstituted ethylene;

$R^1$ is selected from the group consisting of 5-6 membered heteroaryl, and 5-6 membered heterocycloalkyl;

$R^2$ is H or $C_{1-6}$ alkyl;

$R^4$ is H or $C_{1-6}$ alkyl, wherein the $C_{1-6}$ alkyl is optionally substituted by 1 $R^{20}$ group;

$R^5$ is selected from the group consisting of H, halo, CN, and $OR^{a4}$;

$R^6$ is H or $C_{1-6}$ alkyl, wherein the $C_{1-6}$ alkyl is optionally substituted by 1 $R^{20}$ group;

$R^{a3}$ is selected from the group consisting of $C_{1-6}$ alkyl, $C_{1-6}$ haloalkyl, $C_{1-6}$ hydroxyalkyl, —($C_{1-6}$ alkylene)-$C_{1-6}$ alkoxy, —($C_{1-6}$ alkylene)-$C_{5-6}$ aryloxy, $C_{4-6}$ cycloalkyl, —($C_{1-6}$ alkylene)-$C_{4-6}$ cycloalkyl, —($C_{1-6}$ alkylene)-(5-6 membered heteroaryl), 4-6 membered heterocycloalkyl, -(4-6 membered heterocycloalkyl)-C(=O)$OR^{3f}$, —($C_{1-6}$ alkylene)-(4-6 membered heterocycloalkyl), —$NR^{3e}R^{3f}$, —($C_{1-6}$ alkylene)-$NR^{3e}R^{3f}$, and —($C_{1-6}$ alkylene)-$NR^{3e}C$(=O)$R^{4e}$, wherein the —($C_{1-6}$ alkylene)-$C_{1-6}$ alkoxy is substituted by phenyl;

$R^{a4}$ is $C_{1-6}$ alkyl;

each $R^{3e}$ and $R^{3f}$ is independently selected from the group consisting of H and $C_{1-6}$ alkyl; and each $R^{20}$ is OH.

In some embodiments, the compound of Formula (II) is a compound of Formula (IIa):

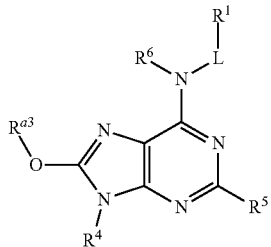

(IIa)

or a pharmaceutically acceptable salt thereof.

In some embodiments, the compound of Formula (II) is a compound of Formula (IIb):

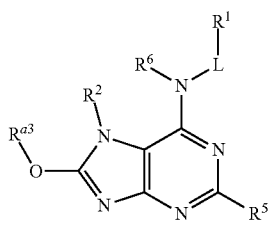

(IIb)

or a pharmaceutically acceptable salt thereof.

In some embodiments, the compound of Formula (II) is selected from the group of compounds provided in Table B, or a pharmaceutically acceptable salt thereof.

TABLE B

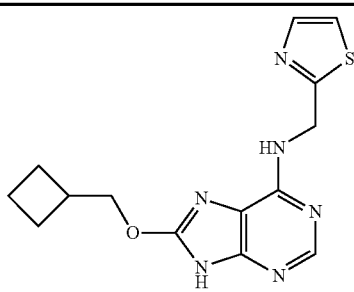

(2)

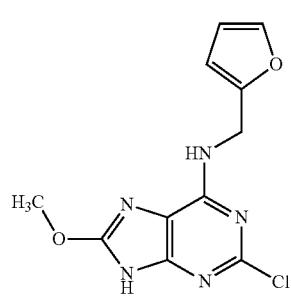 [SMILES: COc1nc2c(NCc3ccco3)nc(Cl)nc2[nH]1]

(124)

TABLE B-continued

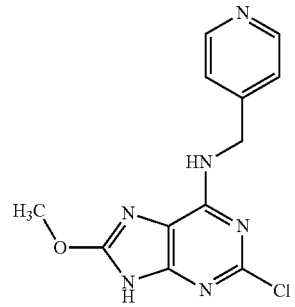 [SMILES: COc1nc2c(NCc3ccncc3)nc(Cl)nc2[nH]1]

(184)

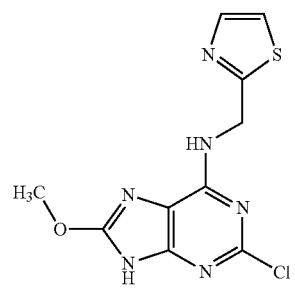 [SMILES: COc1nc2c(NCc3nccs3)nc(Cl)nc2[nH]1]

(230)

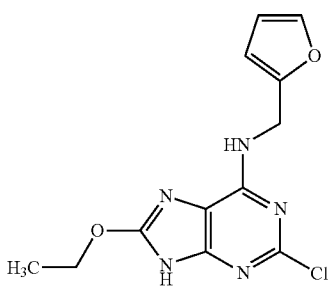 [SMILES: CCOc1nc2c(NCc3ccco3)nc(Cl)nc2[nH]1]

(233)

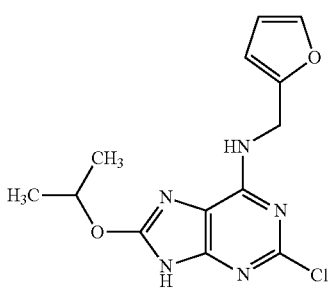 [SMILES: CC(C)Oc1nc2c(NCc3ccco3)nc(Cl)nc2[nH]1]

(239)

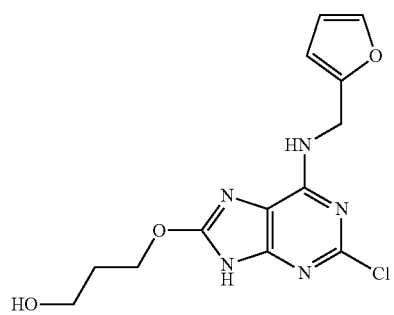

(249)

TABLE B-continued
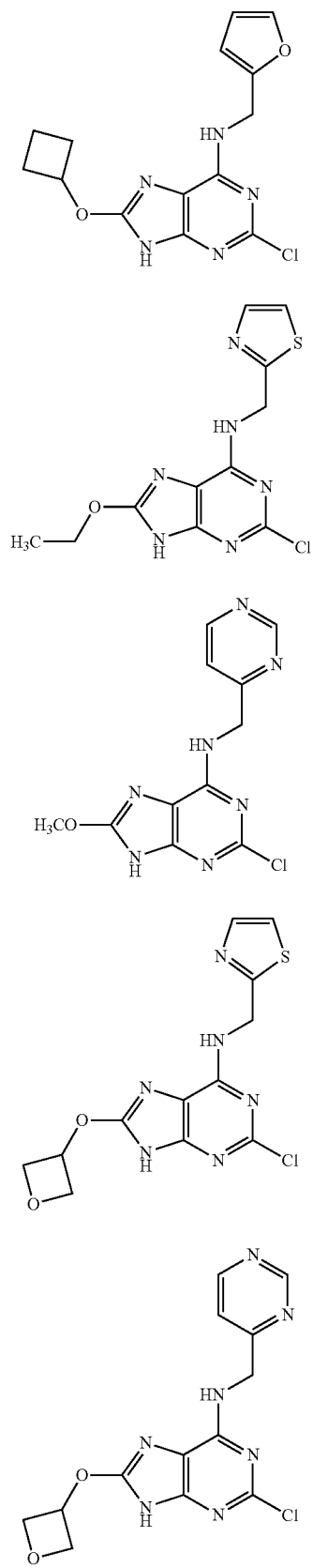
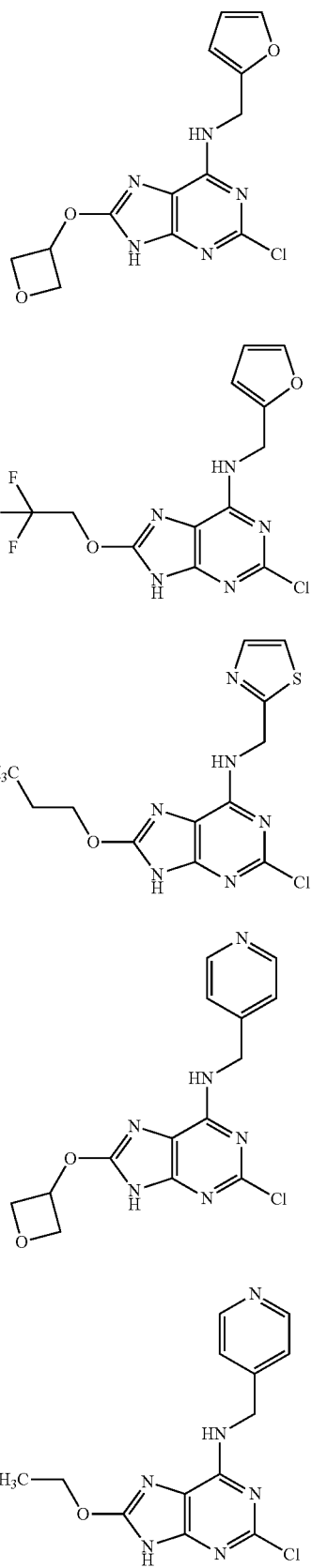

TABLE B-continued
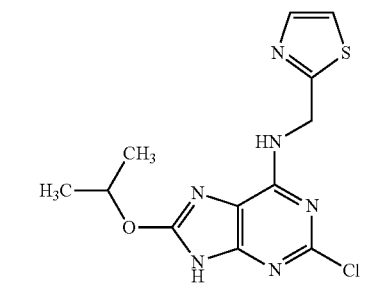 [SMILES: CC(C)Oc1nc2c(NCc3nccs3)nc(Cl)nc2[nH]1] (274)
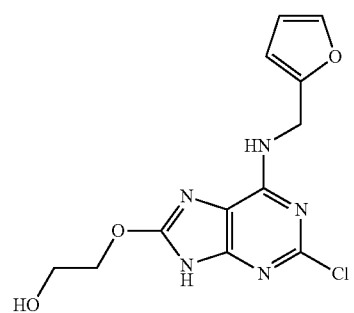 [SMILES: OCCOc1nc2c(NCc3ccco3)nc(Cl)nc2[nH]1] (275)
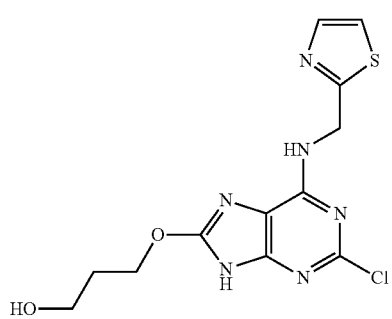 (276)
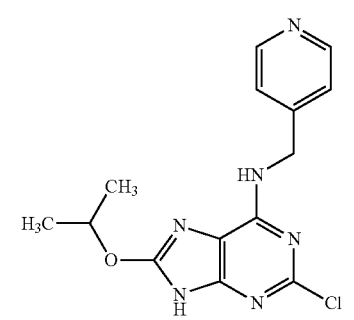 [SMILES: CC(C)Oc1nc2c(NCc3ccncc3)nc(Cl)nc2[nH]1] (277)
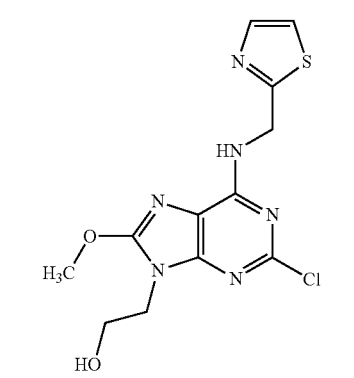 [SMILES: COc1nc2c(NCc3nccs3)nc(Cl)nc2n1CCO] (278)
TABLE B-continued
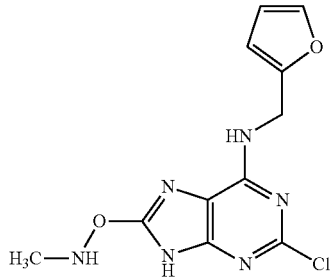 [SMILES: CNOc1nc2c(NCc3ccco3)nc(Cl)nc2[nH]1] (280)
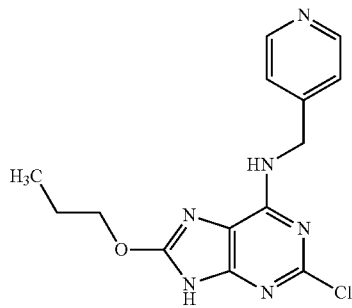 (282)
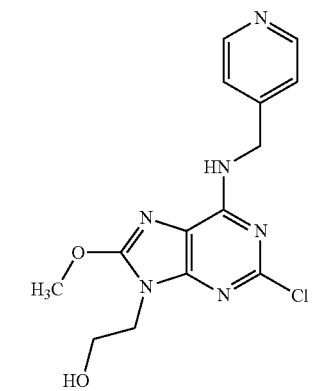 [SMILES: COc1nc2c(NCc3ccncc3)nc(Cl)nc2n1CCO] (287)
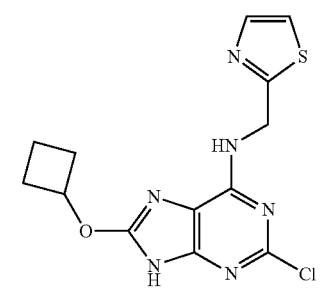 [SMILES: Clc1nc(NCc2nccs2)c2nc(OC3CCC3)[nH]c2n1] (289)
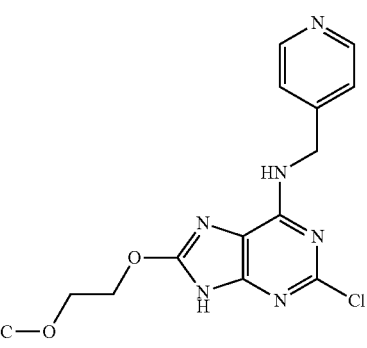 (290)

TABLE B-continued
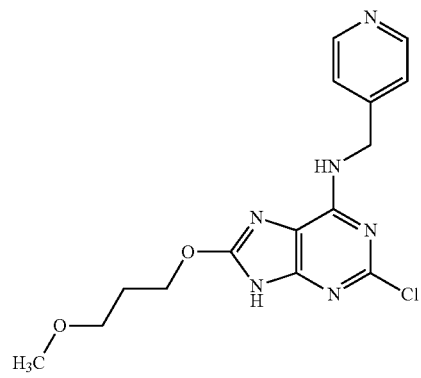 [SMILES: COCCCOc1nc2c(NCc3ccncc3)nc(Cl)nc2[nH]1]
(291)
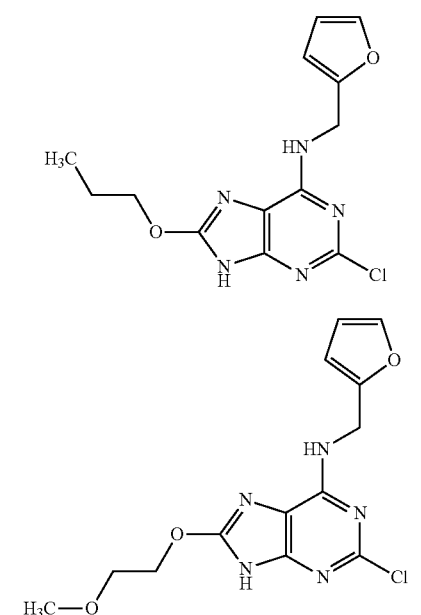
(292)
(293)
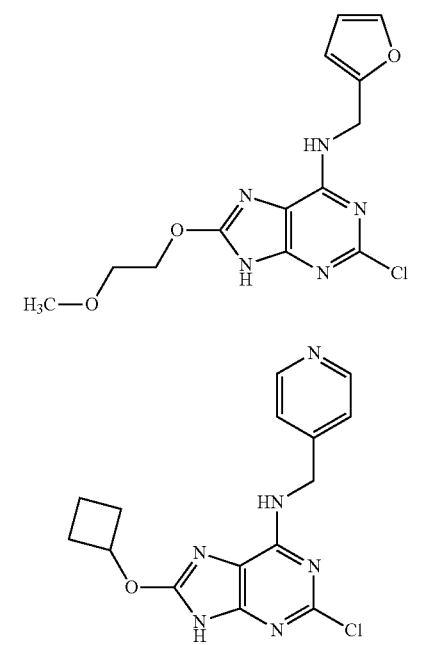
(294)
(296)
TABLE B-continued
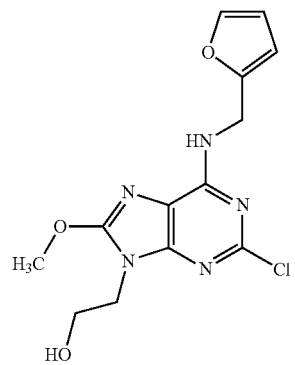 [SMILES: COc1nc2c(NCc3ccco3)nc(Cl)nc2n1CCO]
(297)
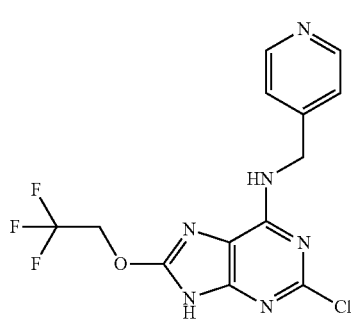 [SMILES: FC(F)(F)COc1nc2c(NCc3ccncc3)nc(Cl)nc2[nH]1]
(299)
(300)
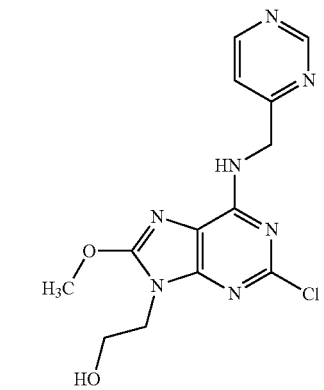 [SMILES: COc1nc2c(NCc3ccncn3)nc(Cl)nc2n1CCO]
(302)

TABLE B-continued
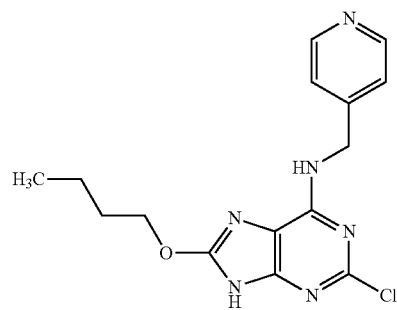 [SMILES: CCCCOc1nc2c(NCc3ccncc3)nc(Cl)nc2[nH]1] (305)
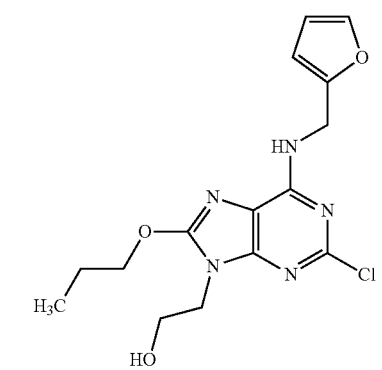 [SMILES: CCCOc1nc2c(NCc3ccco3)nc(Cl)nc2n1CCO] (306)
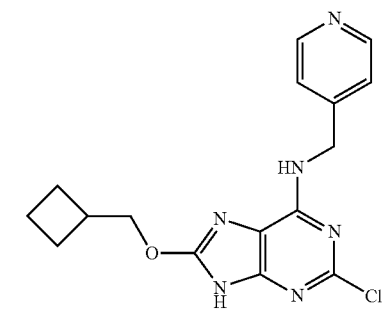 [SMILES: Clc1nc(NCc2ccncc2)c2nc(OCC3CCC3)[nH]c2n1] (307)
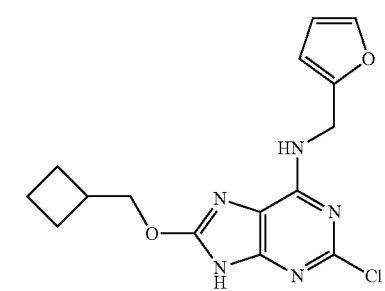 [SMILES: Clc1nc(NCc2ccco2)c2nc(OCC3CCC3)[nH]c2n1] (308)
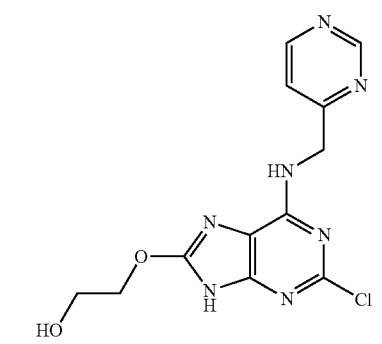 [SMILES: OCCOc1nc2c(NCc3ccncn3)nc(Cl)nc2[nH]1] (309)
TABLE B-continued
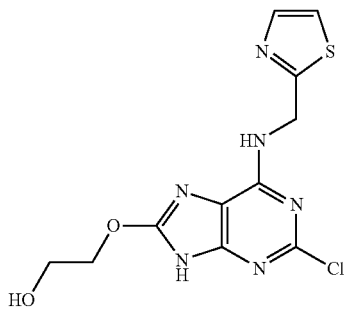 [SMILES: OCCOc1nc2c(NCc3nccs3)nc(Cl)nc2[nH]1] (310)
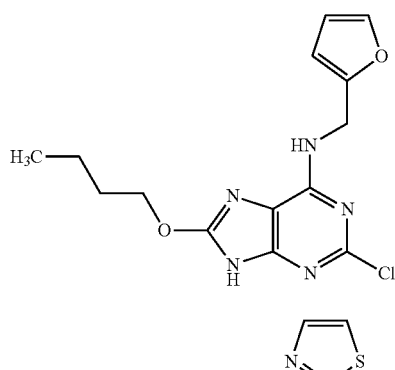 (311)
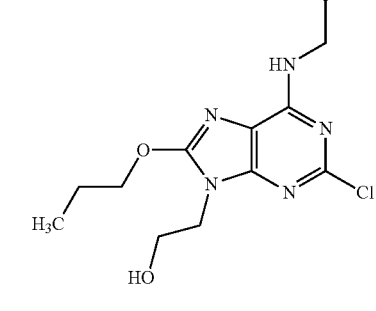 (312)
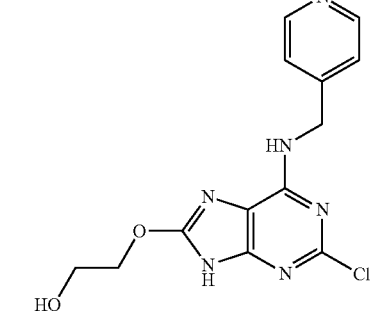 (315)
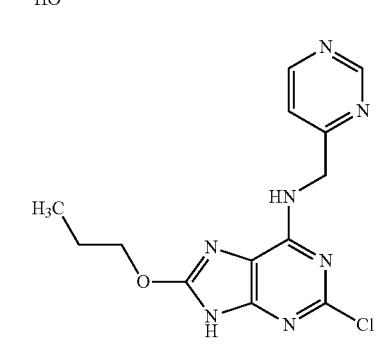 (317)

TABLE B-continued
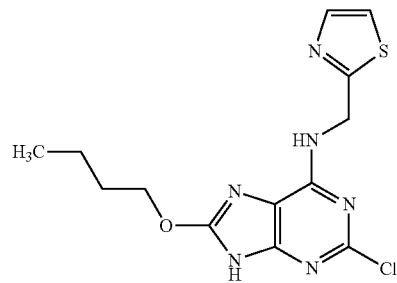 (318)
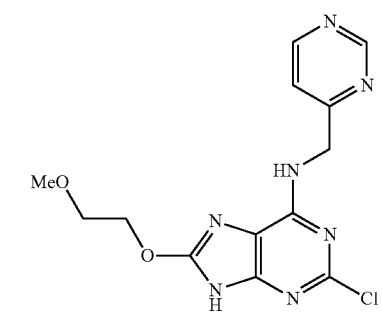 [SMILES: COCCOc1nc2c(NCc3ccncn3)nc(Cl)nc2[nH]1] (319)
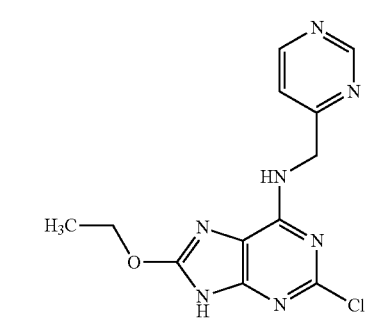 [SMILES: CCOc1nc2c(NCc3ccncn3)nc(Cl)nc2[nH]1] (320)
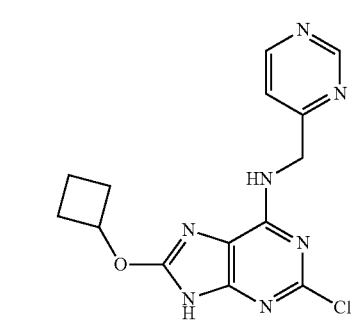 (321)
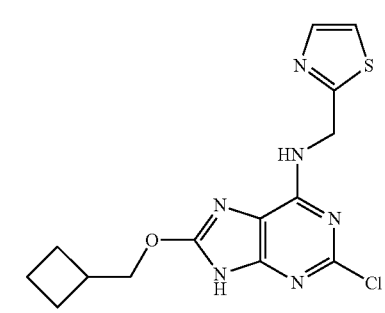 [SMILES: Clc1nc(NCc2nccs2)c2nc(OCC3CCC3)[nH]c2n1] (324)
TABLE B-continued
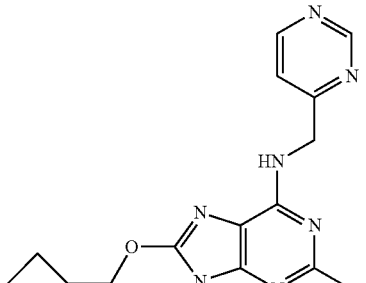 (326)
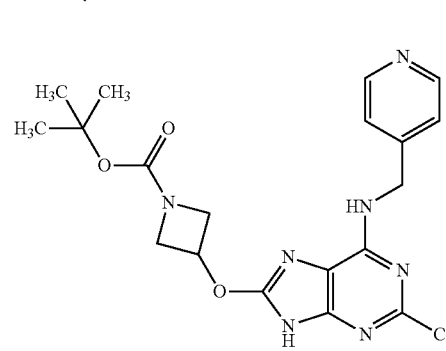 (327)
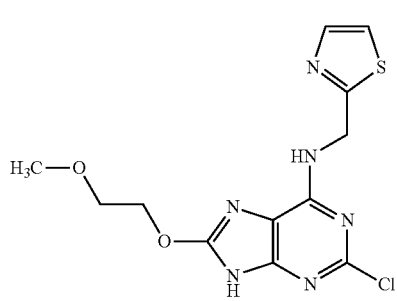 [SMILES: COCCOc1nc2c(NCc3nccs3)nc(Cl)nc2[nH]1] (328)
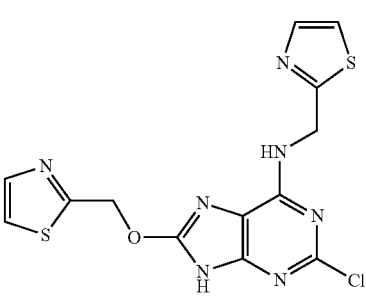 [SMILES: Clc1nc(NCc2nccs2)c2nc(OCc3nccs3)[nH]c2n1] (329)
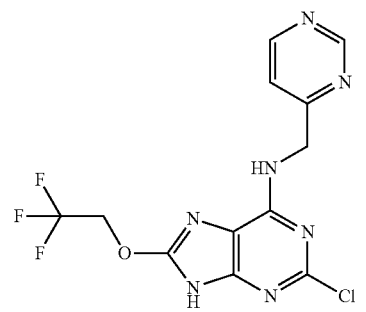 [SMILES: FC(F)(F)COc1nc2c(NCc3ccncn3)nc(Cl)nc2[nH]1] (331)

TABLE B-continued
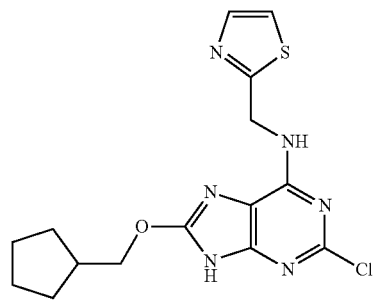 [SMILES: Clc1nc(NCc2nccs2)c2nc(OCC3CCCC3)[nH]c2n1] (332)
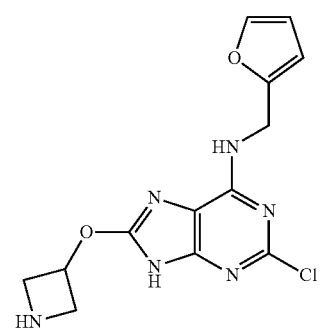 [SMILES: Clc1nc(NCc2ccco2)c2nc(OC3CNC3)[nH]c2n1] (333)
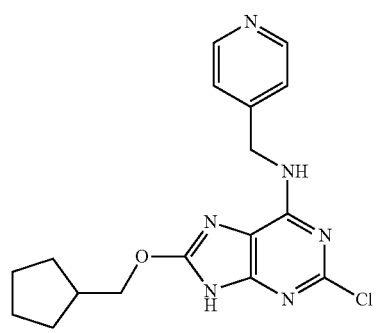 [SMILES: Clc1nc(NCc2ccncc2)c2nc(OCC3CCCC3)[nH]c2n1] (334)
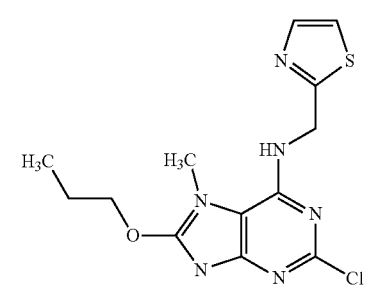 (335)
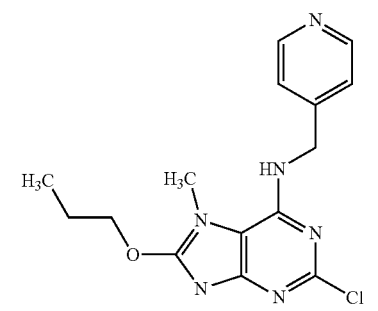 (336)
TABLE B-continued
(337)
(338)
(339)
(340)
(341)

TABLE B-continued
(346) 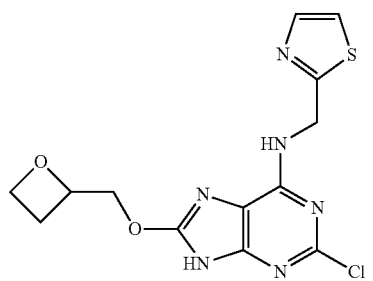 [SMILES: Clc1nc(NCc2nccs2)c2nc(OCC3CCO3)[nH]c2n1]
(347) 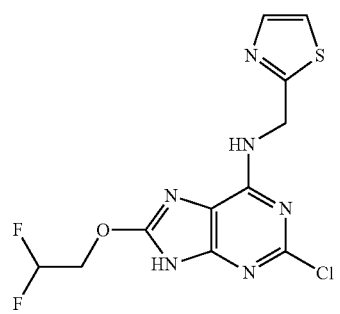
(348) 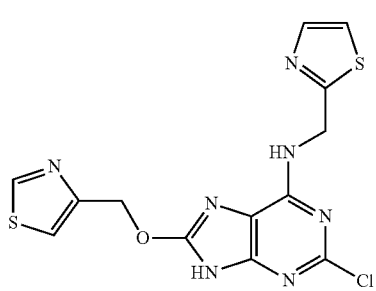 [SMILES: Clc1nc(NCc2nccs2)c2nc(OCc3cscn3)[nH]c2n1]
(349) 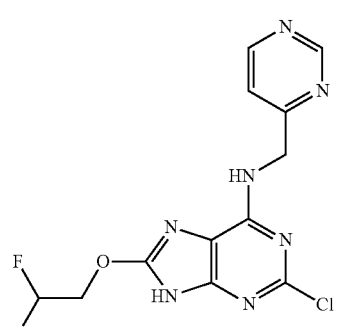
(351) 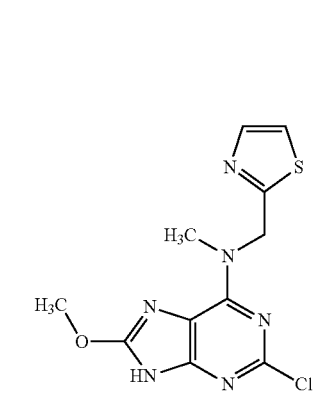 [SMILES: COc1nc2c(N(C)Cc3nccs3)nc(Cl)nc2[nH]1]
TABLE B-continued
(362) 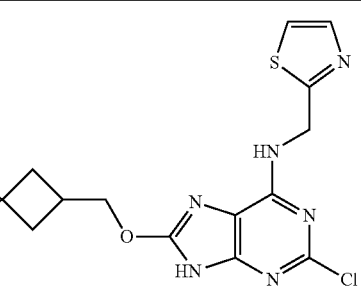
(365) 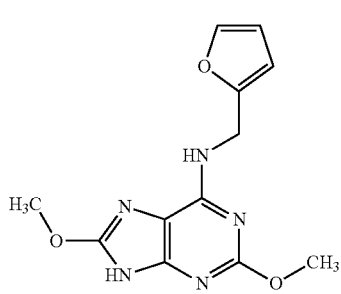
(370) 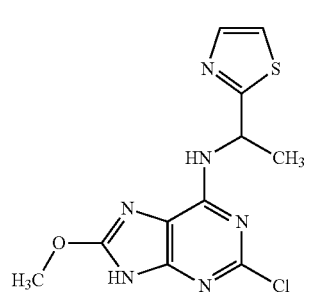 [SMILES: COc1nc2c(NC(C)c3nccs3)nc(Cl)nc2[nH]1]
(374) 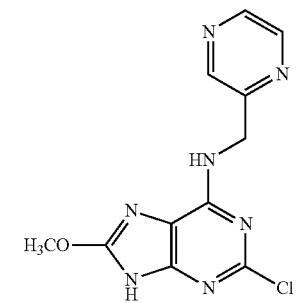 [SMILES: COc1nc2c(NCc3cnccn3)nc(Cl)nc2[nH]1]
(375) 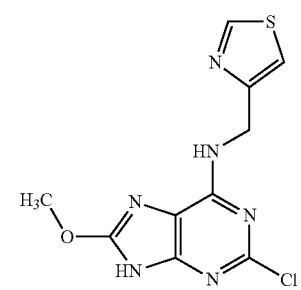 [SMILES: COc1nc2c(NCc3cscn3)nc(Cl)nc2[nH]1]

TABLE B-continued
(376) 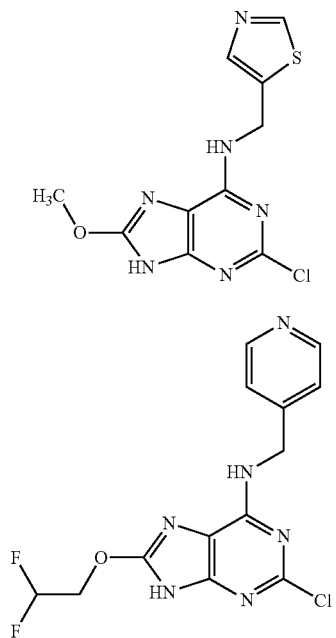
(382) 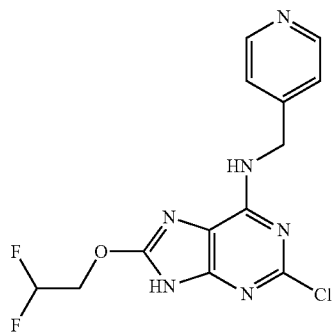 [SMILES: FC(F)COc1nc2c(NCc3ccncc3)nc(Cl)nc2[nH]1]
(384) 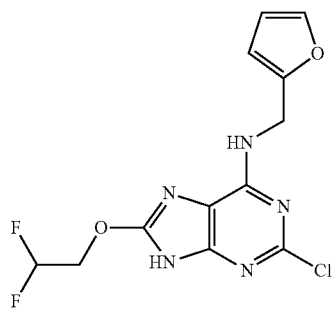 [SMILES: FC(F)COc1nc2c(NCc3ccco3)nc(Cl)nc2[nH]1]
(385) 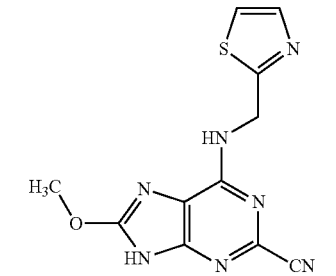 [SMILES: COc1nc2c(NCc3nccs3)nc(C#N)nc2[nH]1]
(386) 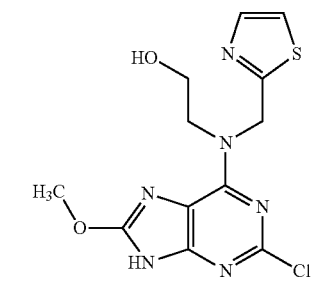 [SMILES: COc1nc2c(N(CCO)Cc3nccs3)nc(Cl)nc2[nH]1]
TABLE B-continued
(387) 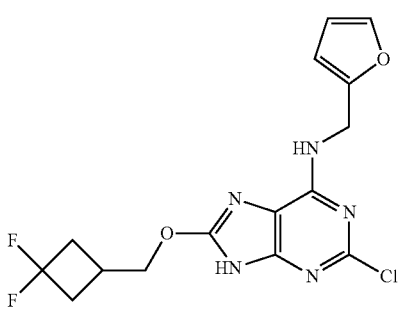 [SMILES: FC1(F)CC(COc2nc3c(NCc4ccco4)nc(Cl)nc3[nH]2)C1]
(388) 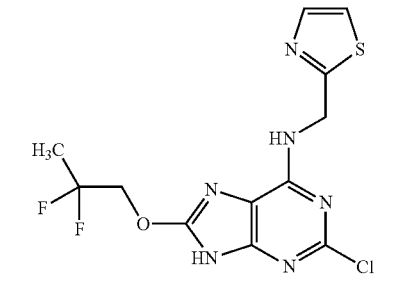 [SMILES: CC(F)(F)COc1nc2c(NCc3nccs3)nc(Cl)nc2[nH]1]
(389) 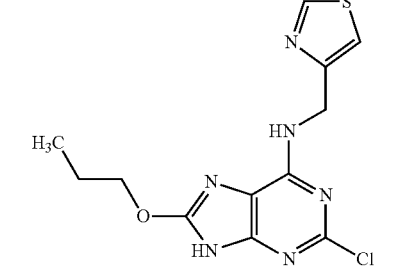
(390) 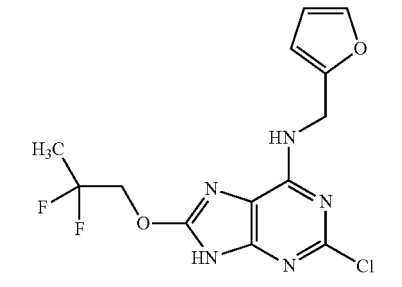
(391) 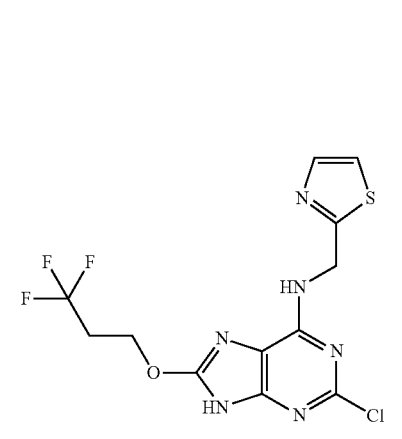 [SMILES: FC(F)(F)CCOc1nc2c(NCc3nccs3)nc(Cl)nc2[nH]1]

TABLE B-continued
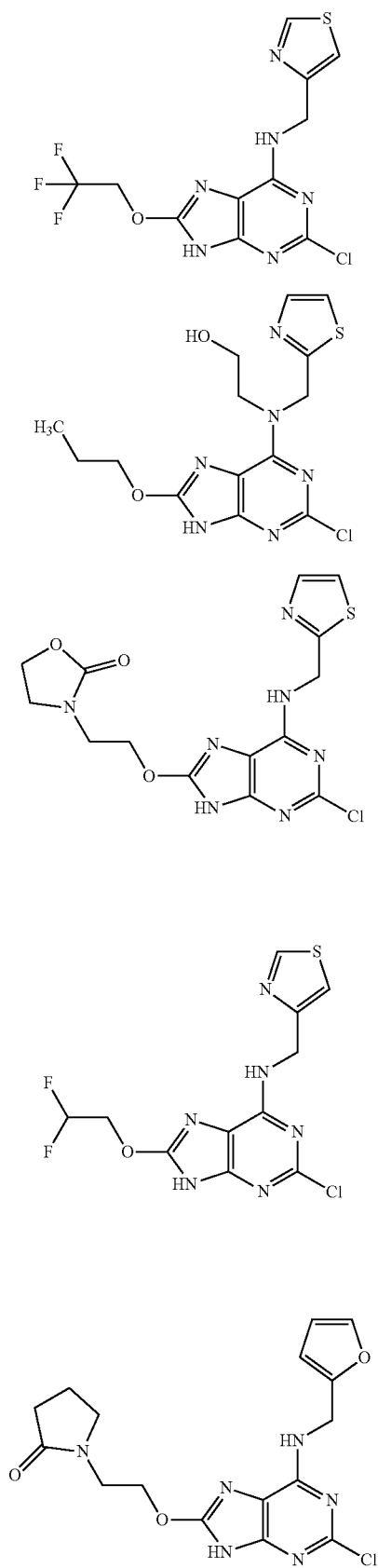
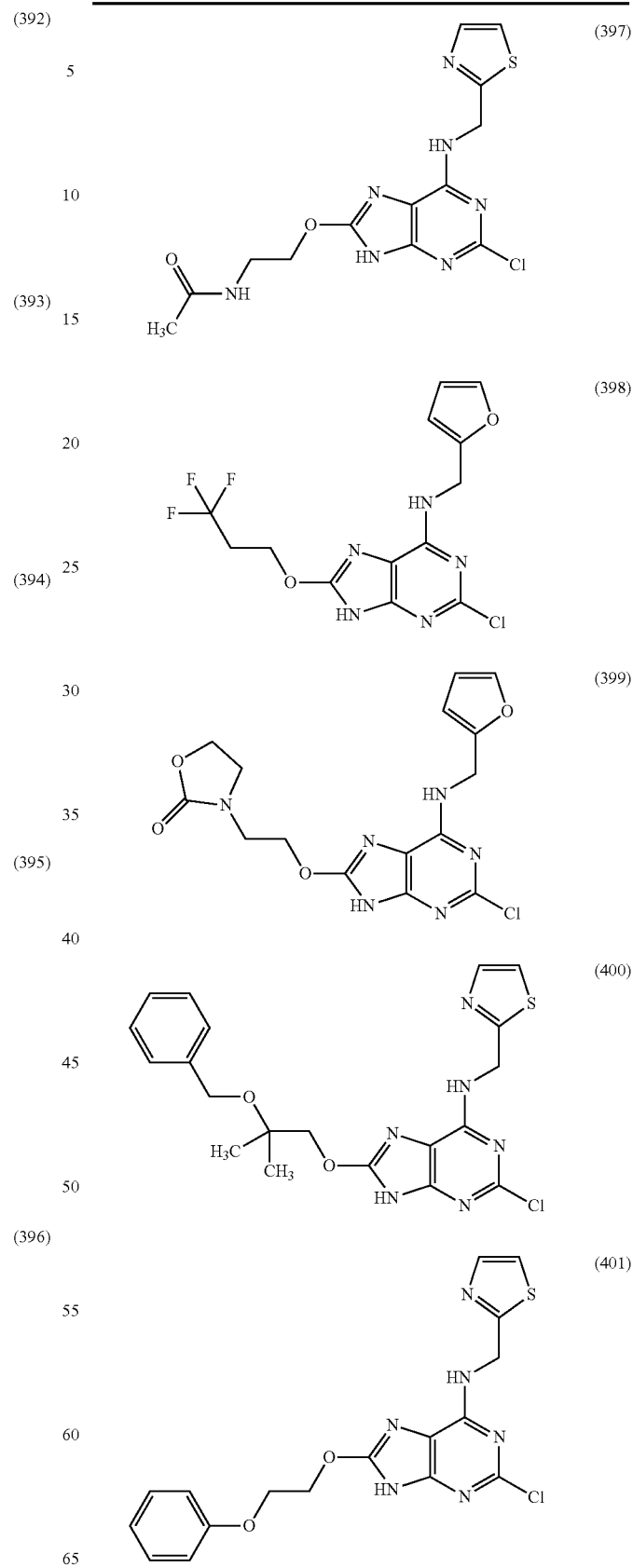

TABLE B-continued
(402)
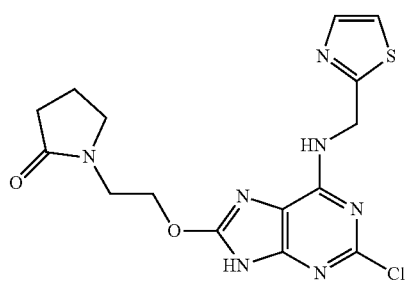 [SMILES: O=C1CCCN1CCOc1nc2c(NCc3nccs3)nc(Cl)nc2[nH]1]
(468)
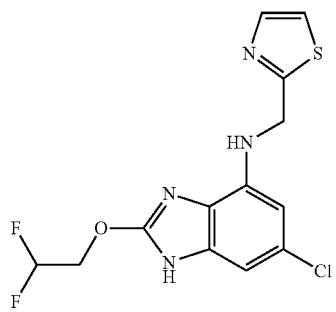 [SMILES: FC(F)COc1nc2c(NCc3nccs3)cc(Cl)cc2[nH]1]
(469)
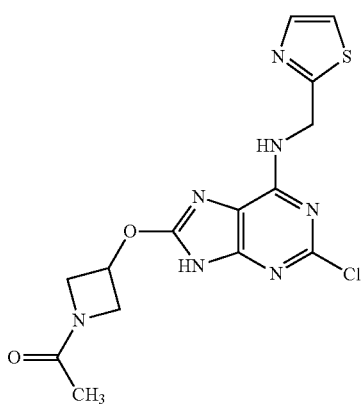
(471)
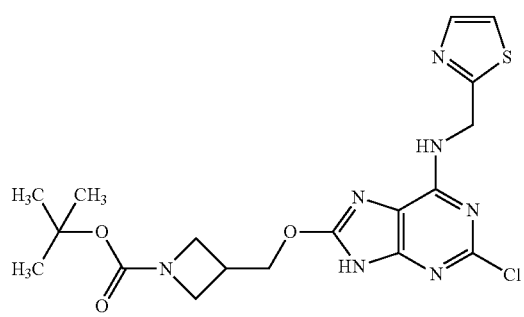 [SMILES: CC(C)(C)OC(=O)N1CC(COc2nc3c(NCc4nccs4)nc(Cl)nc3[nH]2)C1]
(472)
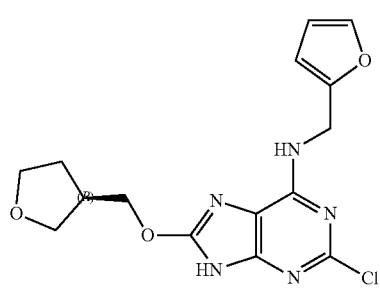
TABLE B-continued
(473)
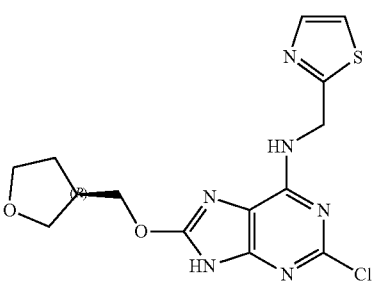
(474)
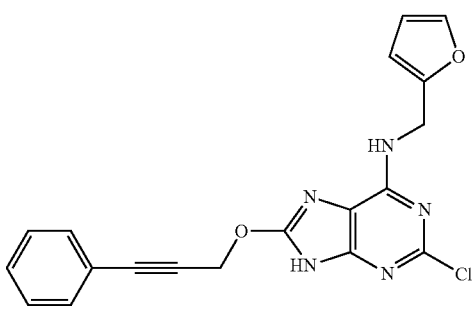 [SMILES: Clc1nc(NCc2ccco2)c2nc(OCC#Cc3ccccc3)[nH]c2n1]
(475)
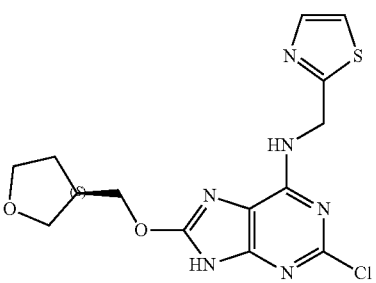
(476)
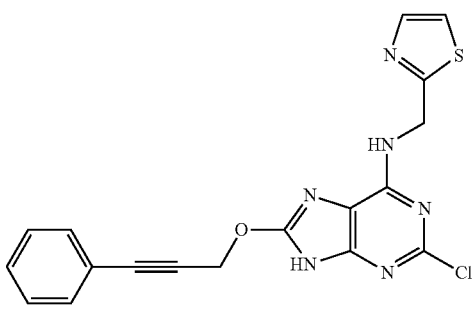 [SMILES: Clc1nc(NCc2nccs2)c2nc(OCC#Cc3ccccc3)[nH]c2n1]
(477)
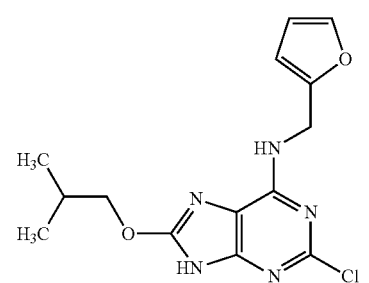 [SMILES: CC(C)COc1nc2c(NCc3ccco3)nc(Cl)nc2[nH]1]

TABLE B-continued
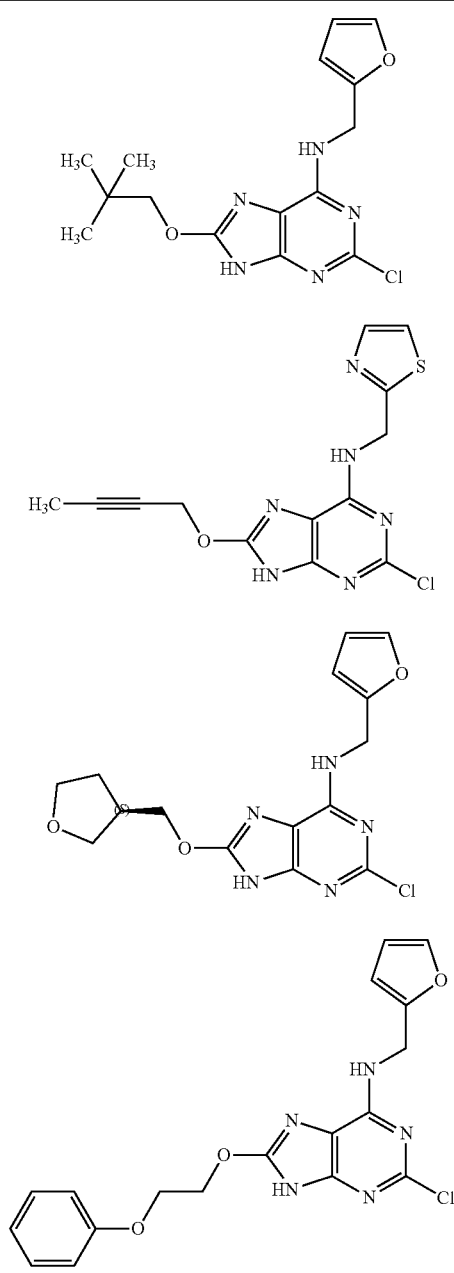
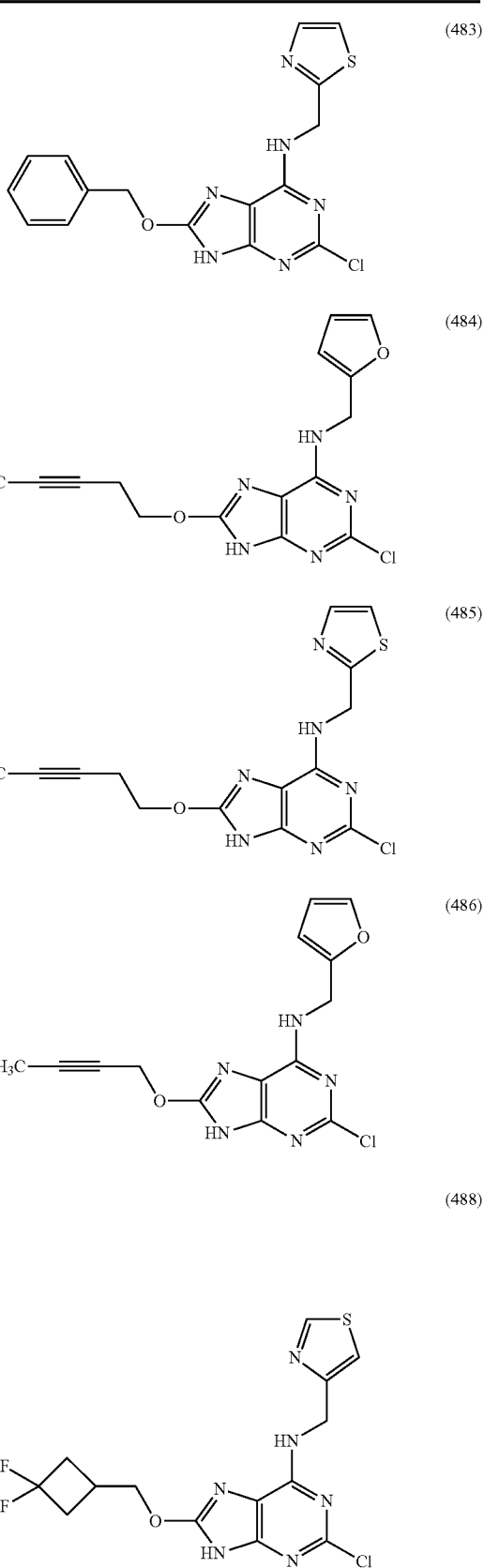

TABLE B-continued
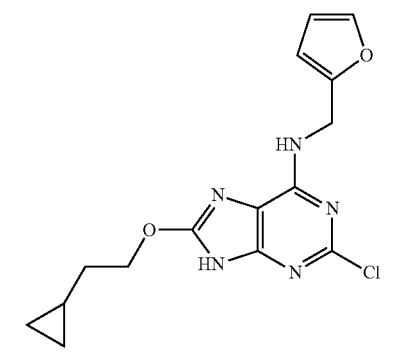 [SMILES: Clc1nc(NCc2ccco2)c2nc(OCCC3CC3)[nH]c2n1] (489)
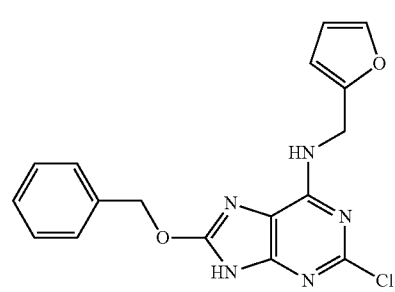 [SMILES: Clc1nc(NCc2ccco2)c2nc(OCc3ccccc3)[nH]c2n1] (490)
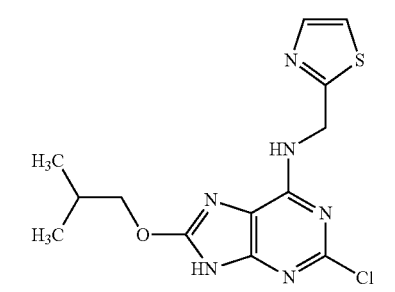 (491)
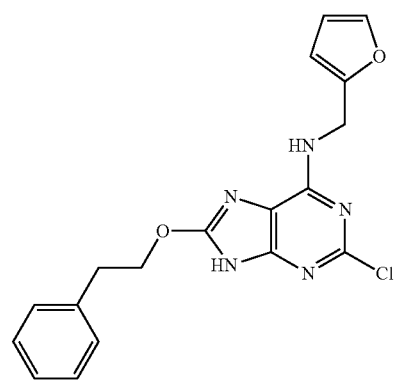 [SMILES: Clc1nc(NCc2ccco2)c2nc(OCCc3ccccc3)[nH]c2n1] (492)
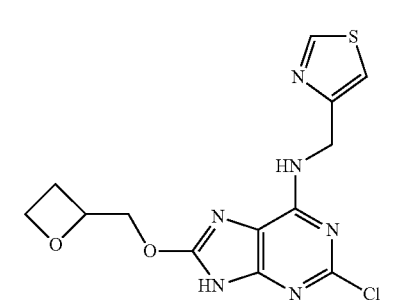 [SMILES: Clc1nc(NCc2cscn2)c2nc(OCC3CCO3)[nH]c2n1] (493)
TABLE B-continued
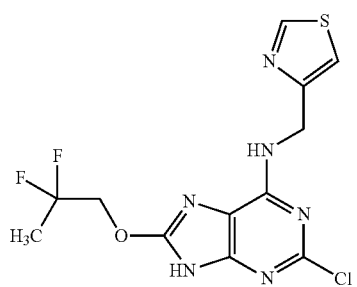 [SMILES: CC(F)(F)COc1nc2c(NCc3cscn3)nc(Cl)nc2[nH]1] (496)
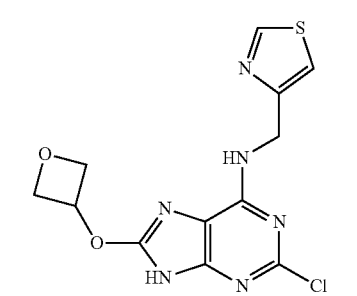 [SMILES: Clc1nc(NCc2cscn2)c2nc(OC3COC3)[nH]c2n1] (497)
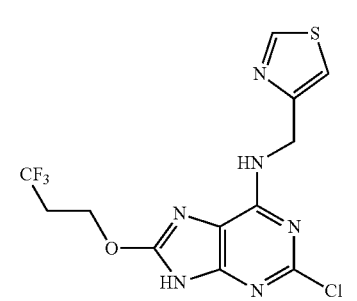 [SMILES: FC(F)(F)CCOc1nc2c(NCc3cscn3)nc(Cl)nc2[nH]1] (499)
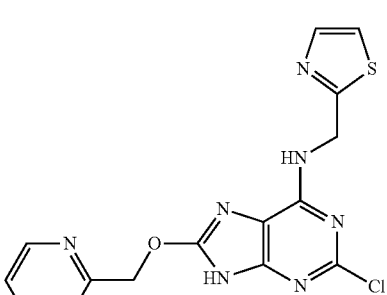 (500)
(504)
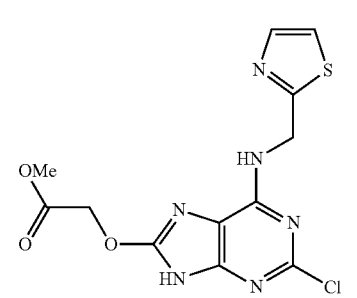 [SMILES: COC(=O)COc1nc2c(NCc3nccs3)nc(Cl)nc2[nH]1]

TABLE B-continued
(505) 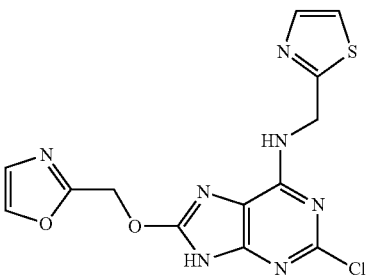 [SMILES: Clc1nc(NCc2nccs2)c2nc(OCc3ncco3)[nH]c2n1]
(506) 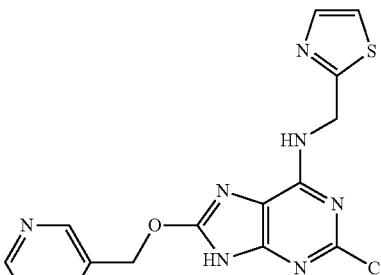
(507) 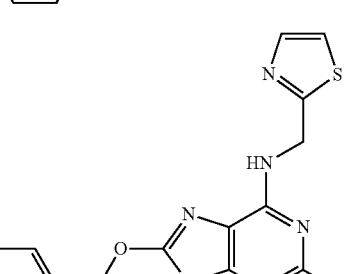
(511) 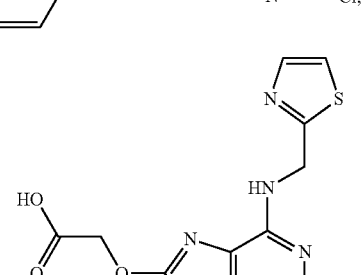
In some embodiments, the compound of Formula (II) is selected from the group of compounds provided in Table B-2, or a pharmaceutically acceptable salt thereof.
TABLE B-2
(302) 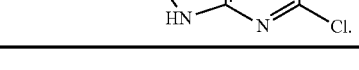
TABLE B-2-continued
(230) 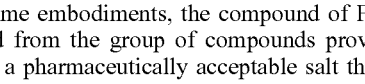
(271) 
(269) 
(270) 
(275) 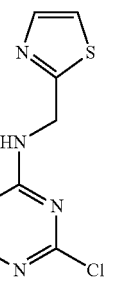

TABLE B-2-continued
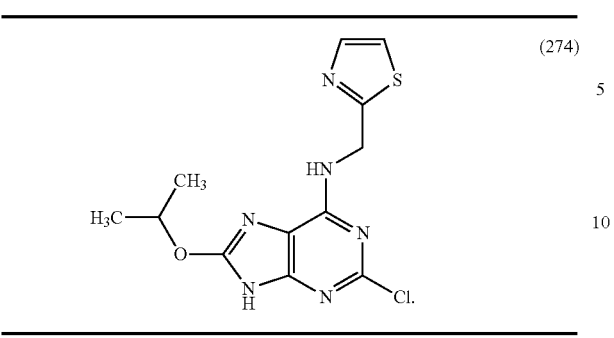
(274)
In some embodiments, the compound of Formula (II) is selected from the group of compounds provided in Table B-3, or a pharmaceutically acceptable salt thereof.
TABLE B-3
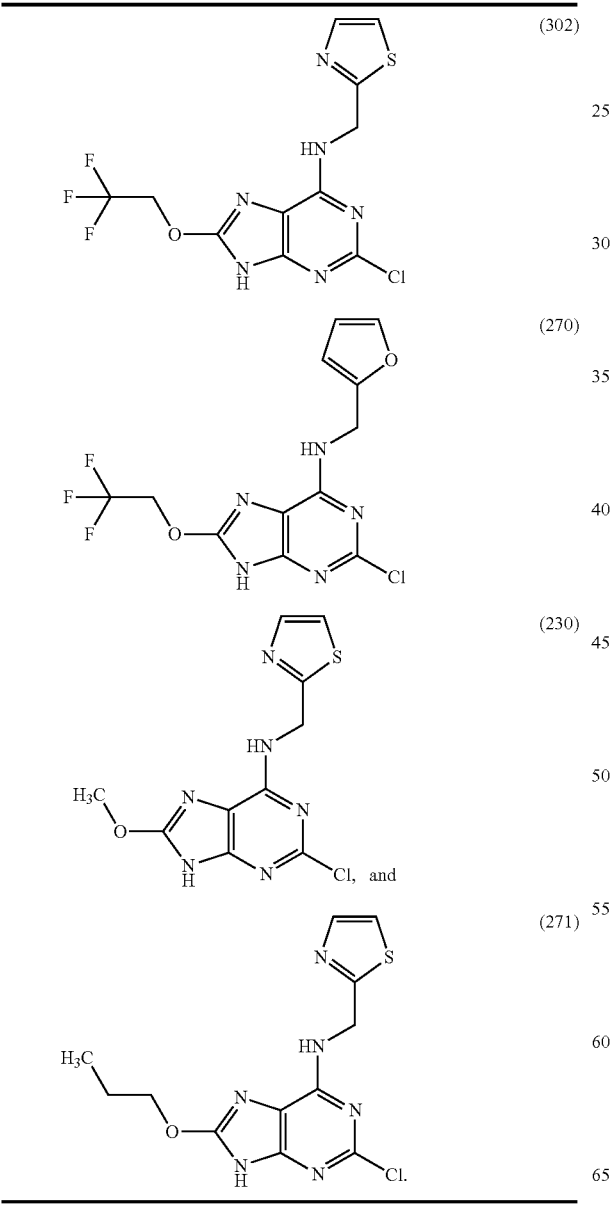
(302)
(270)
(230)
(271)
In some embodiments, the compound of Formula (I) or the compound of Formula (II) is not a compound provided in Table C.
TABLE C
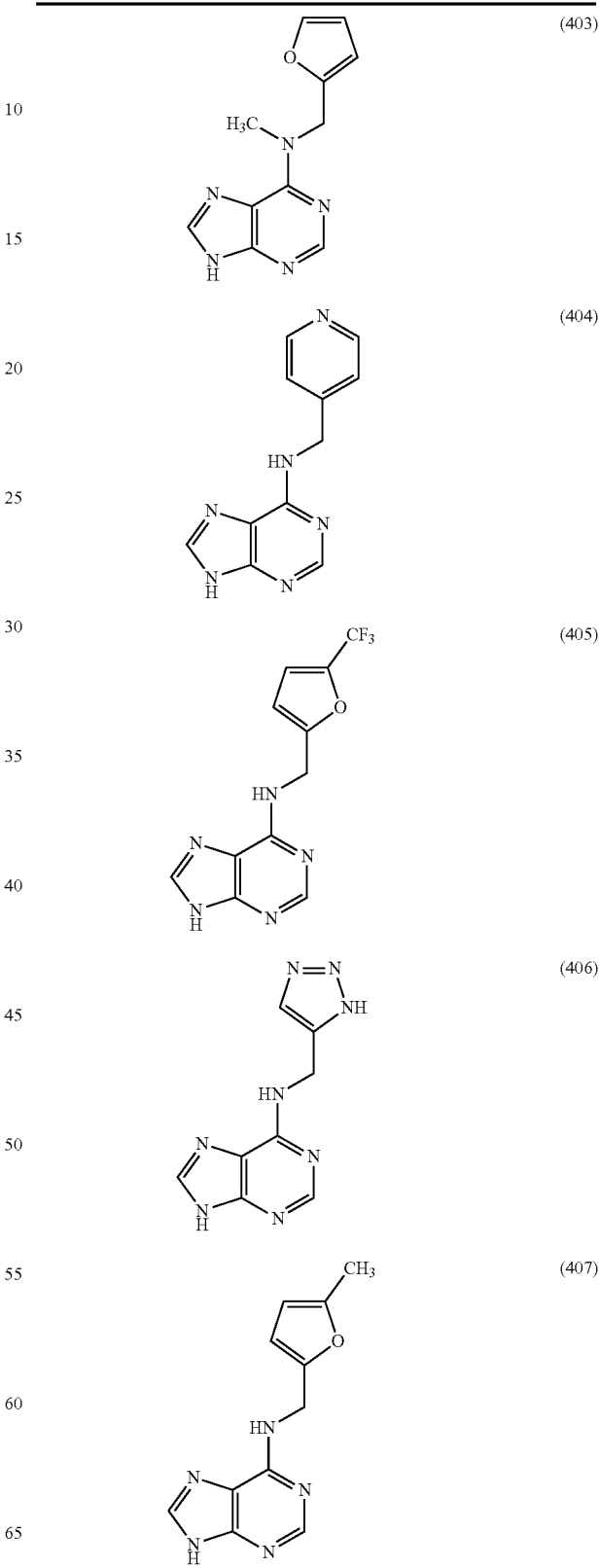
(403)
(404)
(405)
(406)
(407)

TABLE C-continued
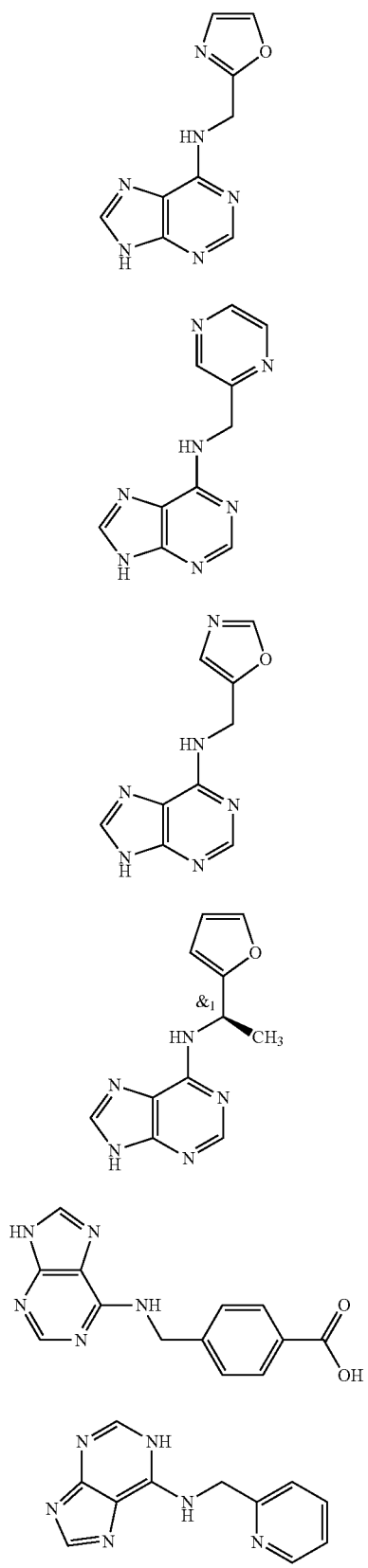
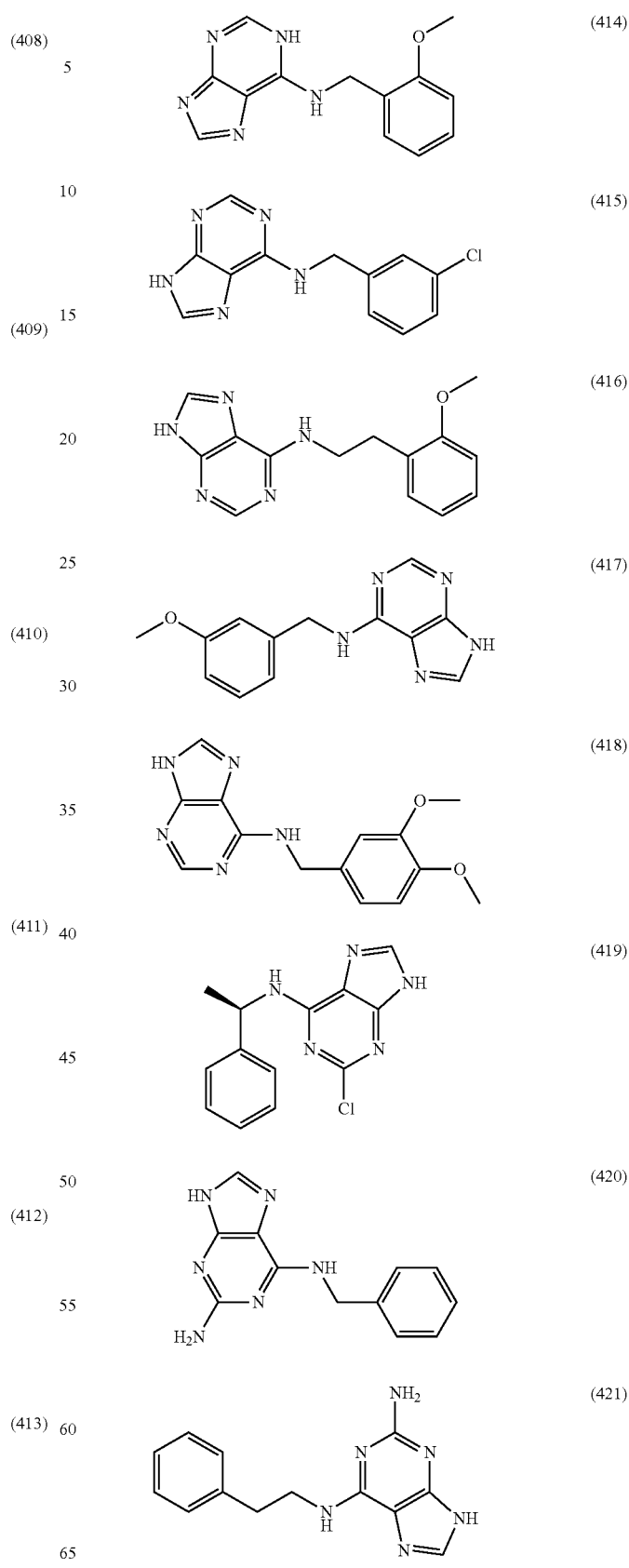

TABLE C-continued
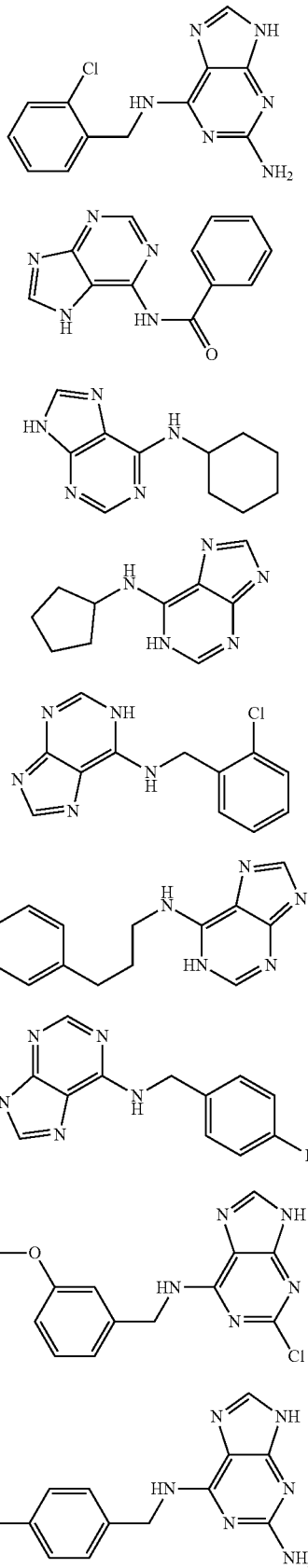
TABLE C-continued
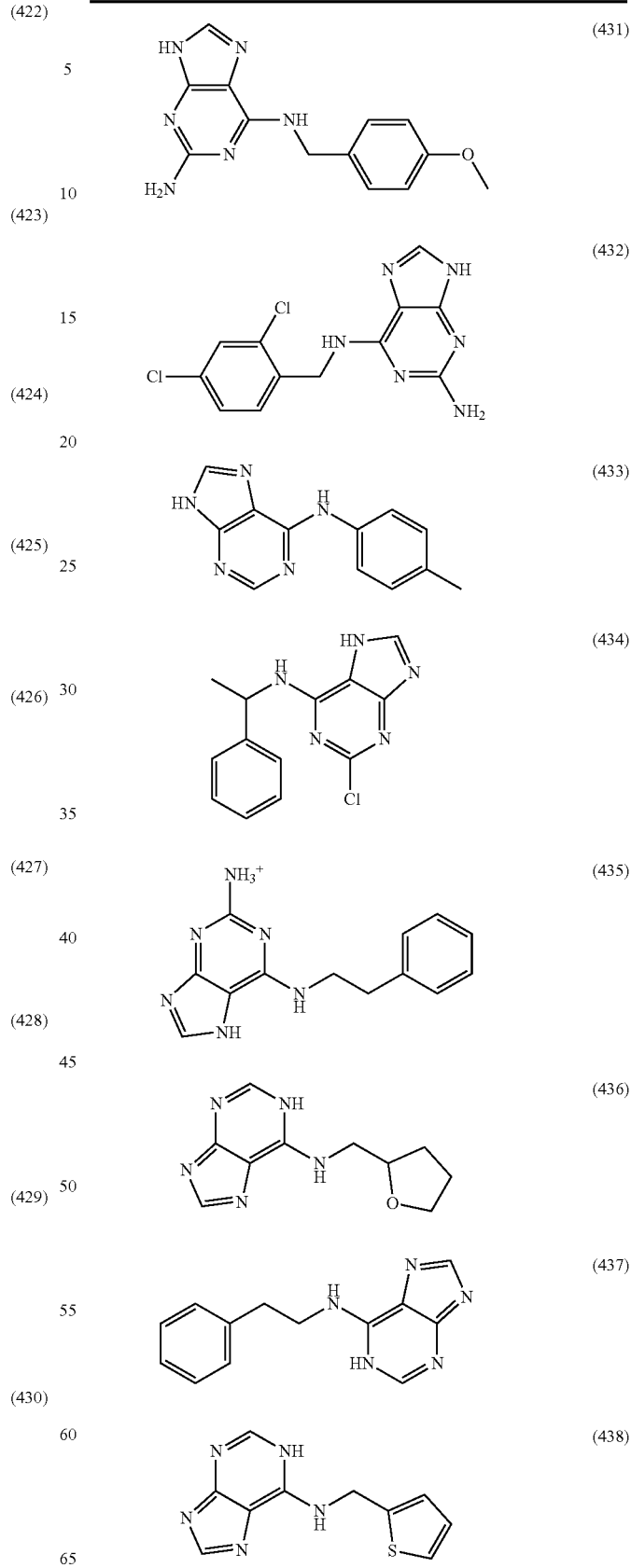

TABLE C-continued
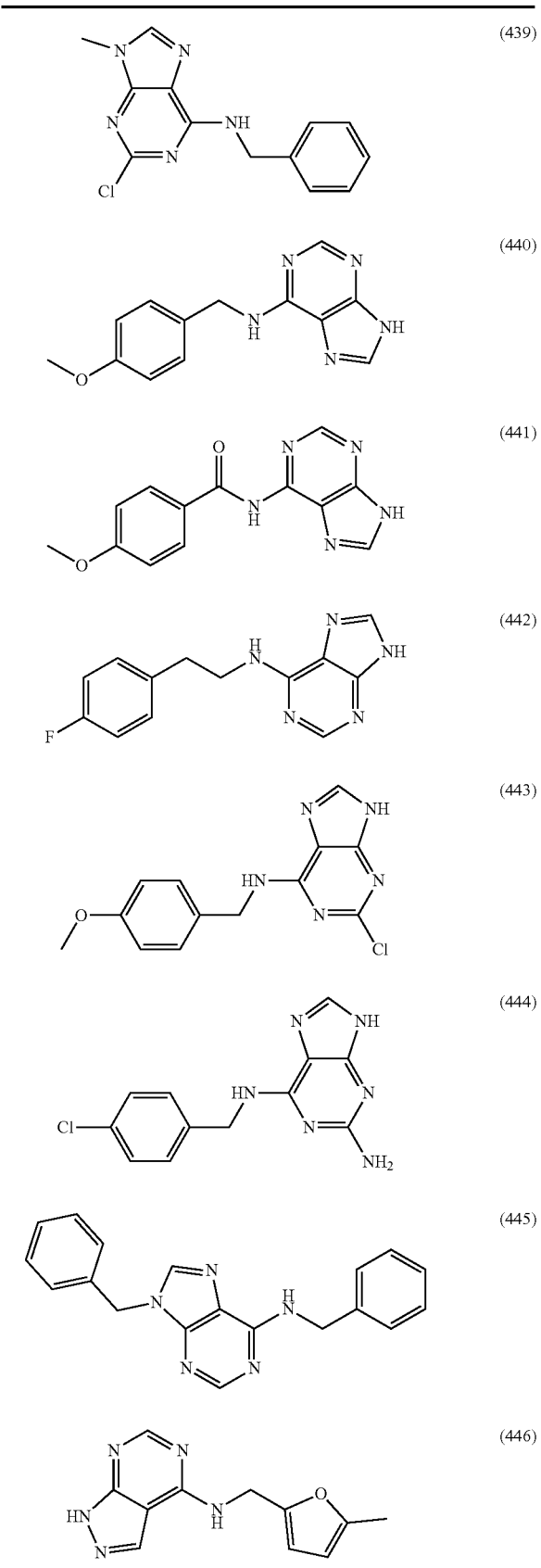
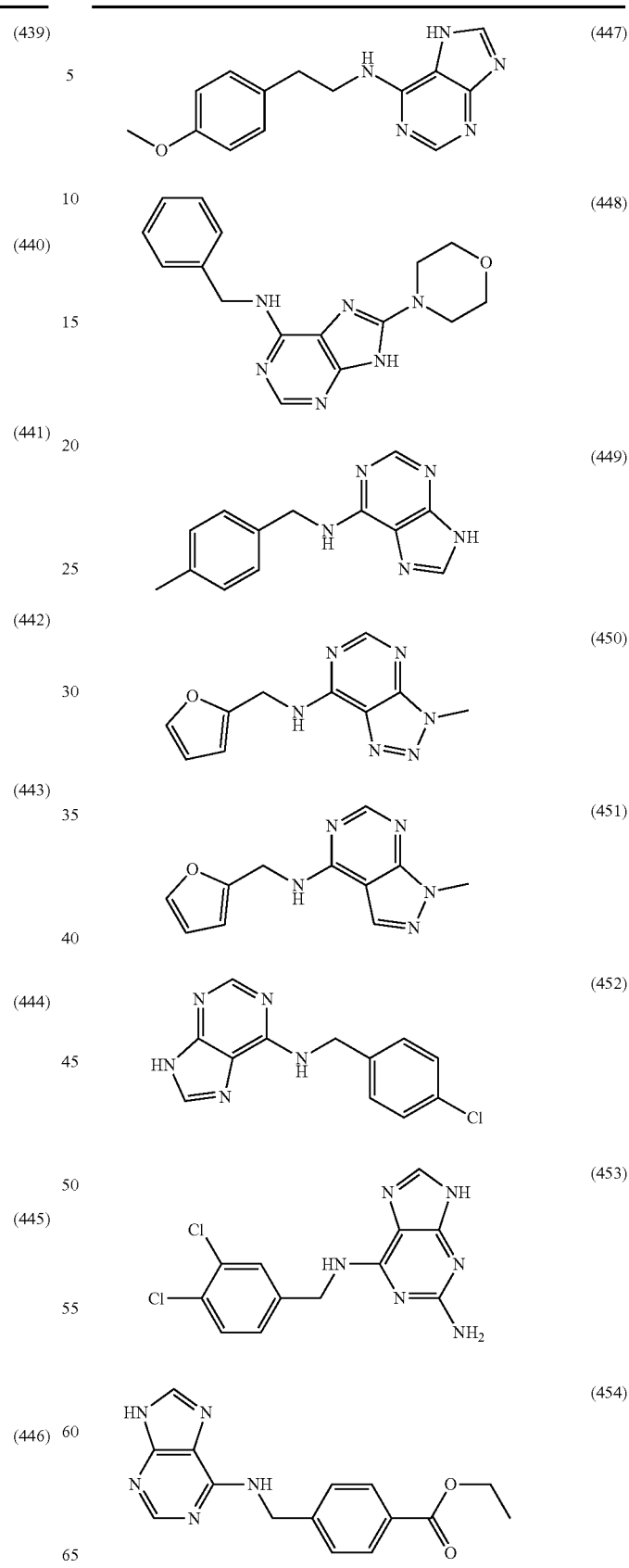

TABLE C-continued

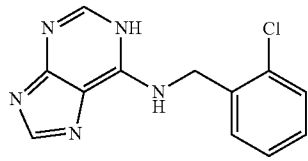 [SMILES: Clc1ccccc1CNc1[nH]cnc2ncnc1-2] (455)

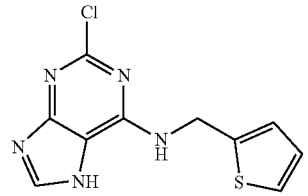 (456)

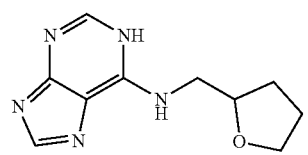 [SMILES: c1nc2nc[nH]c(NCC3CCCO3)c-2n1] (457)

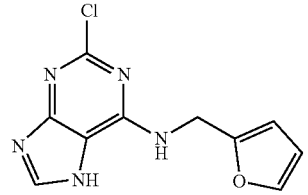 [SMILES: Clc1nc(NCc2ccco2)c2[nH]cnc2n1] (458)

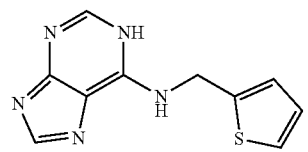 [SMILES: c1csc(CNc2[nH]cnc3ncnc2-3)c1] (459)

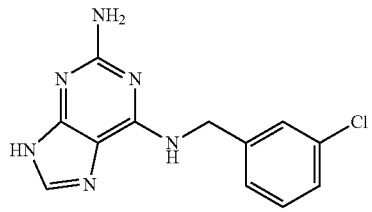 [SMILES: Nc1nc(NCc2cccc(Cl)c2)c2nc[nH]c2n1] (460)

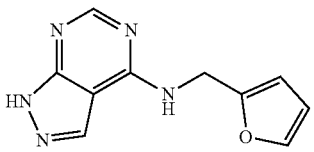 [SMILES: c1coc(CNc2ncnc3[nH]ncc23)c1] (461)

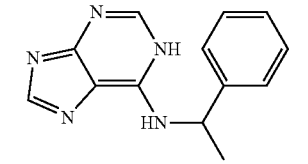 (462)

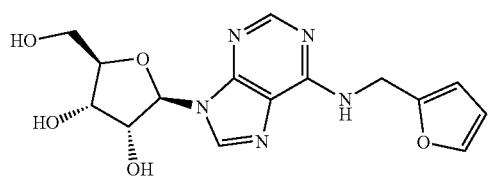 [SMILES: OC[C@H]1O[C@@H](n2cnc3c(NCc4ccco4)ncnc32)[C@H](O)[C@@H]1O] (463)

TABLE C-continued (464)

, and (512)

General Definitions

The following abbreviations may be used herein: ADME (Absorption, Distribution, Metabolism, and Excretion); aq. (aqueous); n-BuOH (n-butanol); calc. (calculated); d (doublet); dd (doublet of doublets); DBTCE (dibromotetrachloroethane); DCM (dichloromethane); DIPEA (N,N-diisopropylethylamine); DMA (dimethylacetamide); DMEM (Dulbecco's Modified Eagle's Media); DMF (N,N-dimethylformamide); eq. or equiv. (equivalents); Et (ethyl); EtOAc (ethyl acetate); EtOH (ethanol); FD (familial dysautonomia); g (gram(s)); h (hour(s)); HPLC (high performance liquid chromatography); Hz (hertz); IPA (isopropyl alcohol); J (coupling constant); KOH (potassium hydroxide); LCMS (liquid chromatography-mass spectrometry); LDA (lithium diisopropylamide); m (multiplet); M (molar); Me (methyl); MeI (methyl iodide); MeCN (acetonitrile); MeOH (methanol); mg (milligram(s)); min. (minutes(s)); mL (milliliter(s)); mmol (millimole(s)); MS (Mass spectrometry); Na$_2$SO$_4$ (sodium sulfate); nM (nanomolar); NMR (nuclear magnetic resonance spectroscopy); PBS (phosphate buffered saline); t (triplet or tertiary); TEA (triethylamine); THF (tetrahydrofuran); TLC (thin layer chromatography); g (microgram(s)); µL (microliter(s)); µM (micromolar); wt % (weight percent).

Synthesis

As will be appreciated, the compounds provided herein, including salts thereof, can be prepared using known organic synthesis techniques and can be synthesized according to any of numerous possible synthetic routes.

The compounds of Formula (I) and Formula (II) can be prepared, for example, using a process as illustrated in Scheme I. A mixture of the desired chloropyrrolopyrimidine or purine i-A, desired aminomethyl heterocycle or appropriately substituted aryl or benzyl amine ii-A, and amine base (e.g. triethylamine or diisopropylethylamine) in an appropriate solvent (e.g., 1,4-dioxane) are stirred at 50-150° C. in a sealed tube to afford a compound iii-A.

Scheme I

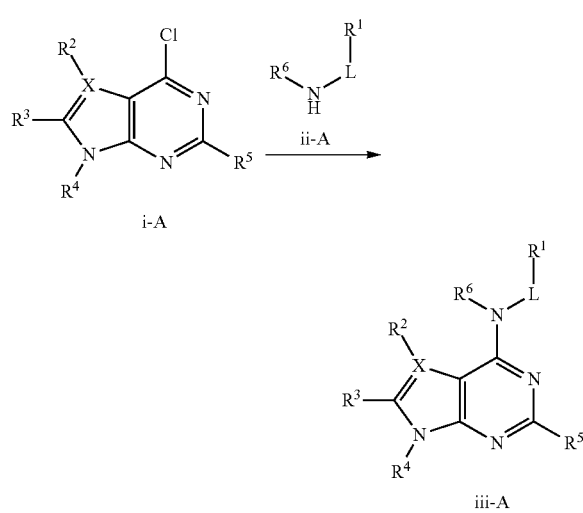

The compounds of Formula (I) can also be prepared, for example, according to the procedure illustrated in Scheme II. A mixture of the desired chloropyrazolopyrimidine i-B, desired aminomethyl heterocycle or appropriately substituted aryl or benzyl amine ii-B, and amine base (e.g., triethylamine or diisopropylethylamine) in an appropriate solvent (e.g., 1,4-dioxane) are stirred at 50-150° C. in a sealed tube to afford the desired product iii-B.

Scheme II

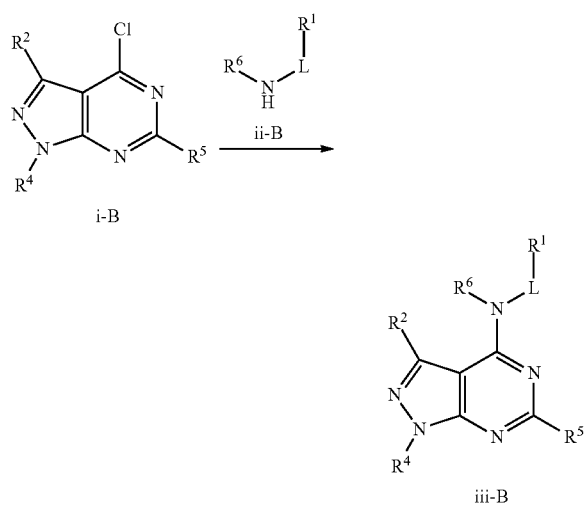

The compounds of Formula (I) can also be prepared, for example, according to the procedure illustrated in Scheme III. A mixture of 5,6-diaminouracil sulfate salt i-C, the desired carboxylic acid or acid chloride ii-C, POCl₃, and NH₄Cl are stirred at 100° C. until the reaction is complete by LC-MS and/or TLC analysis. The reaction mixture is cooled to room temperature and carefully poured over ice. Subsequent neutralization of the reaction solution and purification using standard techniques affords the desired compound iii-C. A mixture of the desired chloropurine iv-C, desired aminomethyl heterocycle or appropriately substituted aryl or benzyl amine iv-C (1.1 equiv), and amine base (e.g., triethylamine or diisopropylethylamine) in an appropriate solvent (e.g. 1,4-dioxane) are stirred at 50-150° C. in a sealed tube to afford the desired product v-C.

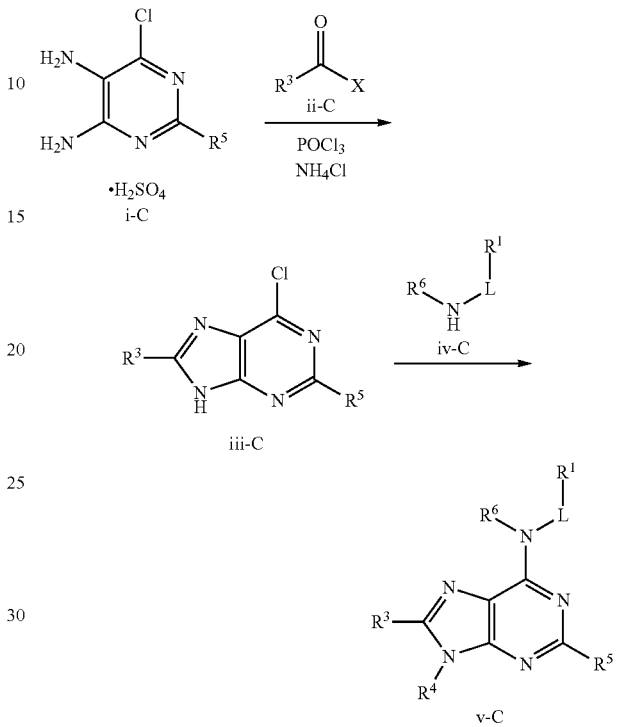

X = OH or Cl

The compounds of Formula (I) and Formula (II) can also be prepared, for example, according to the procedure illustrated in Scheme IV. 2,6-Dichloropurine i-D, dihydropyran, and para-toluenesulfonic acid in an appropriate solvent (e.g., ethyl acetate) are stirred at 65° C. overnight. After this time, the reaction is cooled to room temperature and washed with saturated basic solution (e.g., NaHCO₃ solution) followed by brine. The solution was dried over Na₂SO₄, filtered and concentrated under reduced pressure to afford a clear residue. The resulting residue is then triturated with an appropriate alcoholic solvent (e.g., MeOH) to afford ii-D.

To a solution of 2,6-dichloro-9-(tetrahydro-2H-pyran-2-yl)-9H-purine ii-D in an appropriate solvent (e.g., THF) is added LDA (3 equiv) at −78° C. and stirred for about 20 to about 40 minutes. After this time, a solution of dibromotetrachloroethane in an appropriate solvent (e.g., THF) is added slowly and stirred at −78° C. for about 90 to about 120 minutes to afford the title compound iii-D.

8-Bromo-2,6-dichloro-9-(tetrahydro-2H-pyran-2-yl)-9H-purine is reacted with an appropriately substituted heterocyclic, aryl, or benzyl amine (e.g., 2-(aminomethyl)thiazole dihydrochloride, 4-(aminomethyl)pyridine, 4-(aminomethyl)pyrimidine hydrochloride, or furfurylamine) in the presence of an amine base (e.g., trimethylamine) in an appropriate solvent (e.g., 1,4-dioxane) to afford the desired compound of iv-D. The compound iv-D is then reacted with an appropriate substituted alkyl alcohol in the presence of a base (e.g., potassium tert-butoxide, sodium hydride, or sodium hydroxide) at about 60 to about 90° C. to afford the desired compound v-D.

Lastly, the THP protected alkoxy purine v-D in an appropriate solvent (e.g., MeOH) is reated with excess strong acid (e.g. trifluoroacetic acid) at 0° C. Upon addition of the TFA, the reaction mixture is stirred and heated at about 40° C. to about 55° C. until the reaction is complete by LC-MS and/or TLC analysis. Subsequent purification affords the desired compound vi-D. The product structure was confirmed by $^1$H NMR and/or by mass analysis.

The compounds of Formula (I) and Formula (II) can also be prepared, for example, according to the procedure illustrated in Scheme V. A mixture of compound i-E and the desired amine ii-E is stirred at about 40° C. to about 60° C. until the reaction is complete by LC-MS and/or TLC analysis. Subsequent purification affords the desired compound iii-E. To a solution of THP protected amino purine iii-E in an appropriate solvent (e.g., MeOH) is added an excess of strong acid (e.g., trifluoroacetic acid) at 0° C. Upon addition of the acid, the reaction mixture is stirred and heated to about 65° C. until the reaction is complete by LC-MS and/or TLC analysis. Subsequent purification affords the desired compound iii-E.

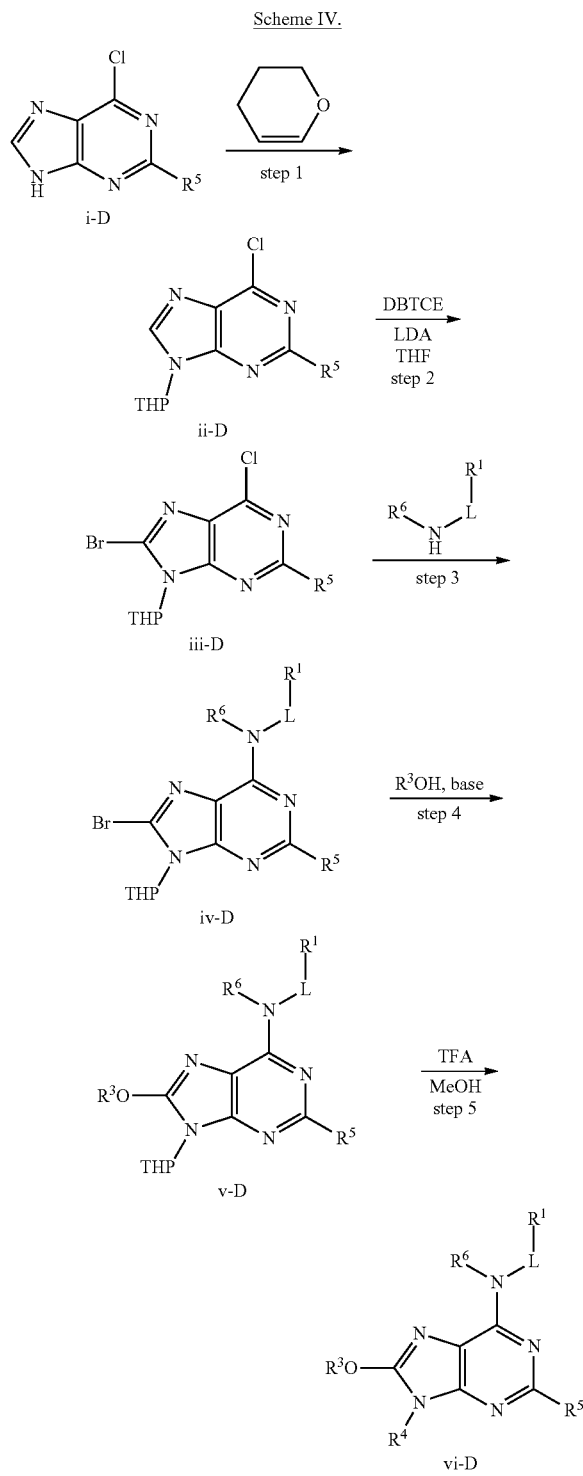

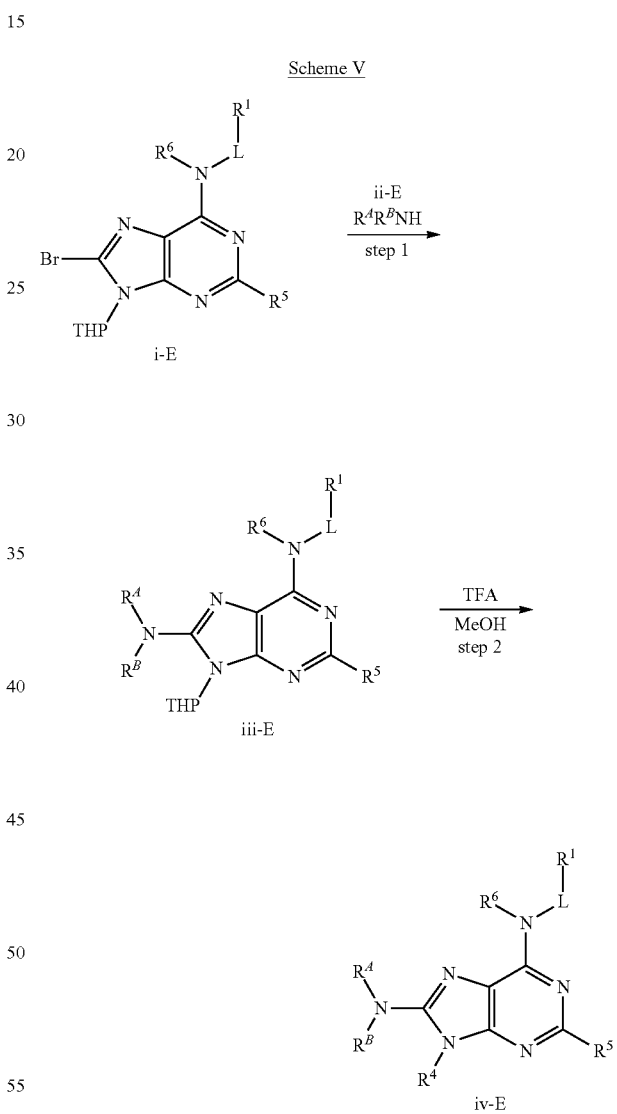

The compounds of Formula (I) can also be prepared, for example, according to the procedure illustrated in Scheme VI. A mixture of the desired chlorothiazolopyrimidines i-F, desired aminomethyl heterocycle or appropriately substituted aryl or benzylamine ii-F, and amine base (e.g., trimethylamine) in an appropriate solvent (e.g., 1,4-dioxane) is stirred at room temperature until the reaction was complete by LC-MS and/or TLC analysis. Subsequent purification affords the desired compound iii-F.

Scheme VI

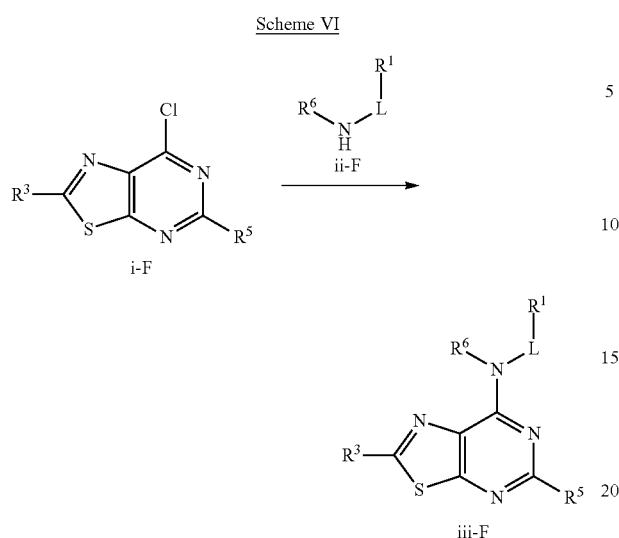

i-F iii-F

The compounds of Formula (I) and Formula (II) can also be prepared, for example, according to the procedure illustrated in Scheme VII. A mixture of the desired chlorotriazolopyrimidines i-G, desired aminomethyl heterocycle or appropriately substituted aryl or benzylamine ii-G, and amine base (e.g., triethylamine) in an appropriate solvent (e.g., 1,4-dioxane) is stirred at room temperature until the reaction is complete by LC-MS and/or TLC analysis. Subsequent purification affords the desired product iii-G.

Scheme VII.

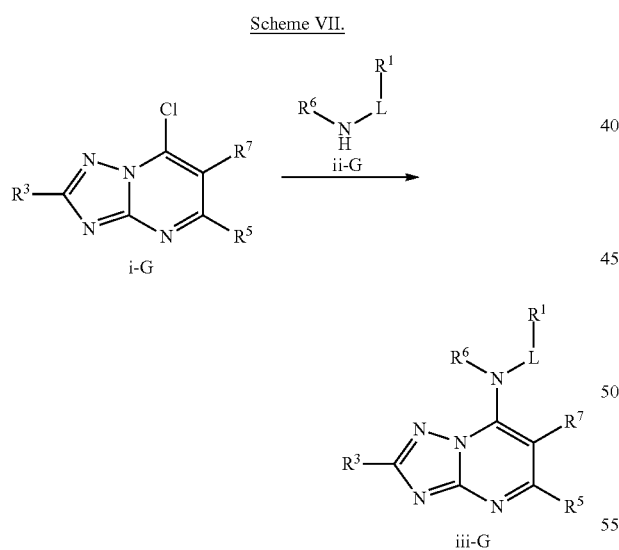

i-G iii-G

The compounds of Formula (I) and Formula (II) can also be prepared, for example, according to the procedure illustrated in Scheme VIII. A mixture of the desired chloroimidazopyrimidines i-H, desired aminomethyl heterocycle or appropriately substituted aryl or benzylamine ii-H, and amine base (e.g., triethylamine) in an appropriate solvent (e.g. 1,4-dioxane) is stirred at about 70° C. until the reaction is complete by LC-MS and/or TLC analysis. Subsequent purification afford the desired product iii-H.

Scheme VIII.

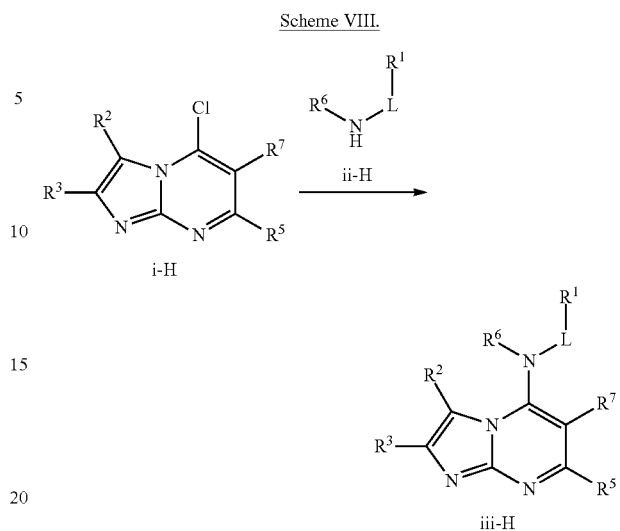

i-H iii-H

The compounds of Formula (I) and Formula (II) can also be prepared, for example, according to the procedure illustrated in Scheme IX. A mixture of the dichloroimidazopyrimidines i-J, desired aminomethyl heterocycle i-J, and amine base (e.g., trimethylamine) in an appropriate solvent (e.g., 1,4-dioxane) is stirred at about 55° C. until the reaction is complete by LC-MS and/or TLC analysis. Subsequent purification affords the desired product iii-J.

Scheme IX.

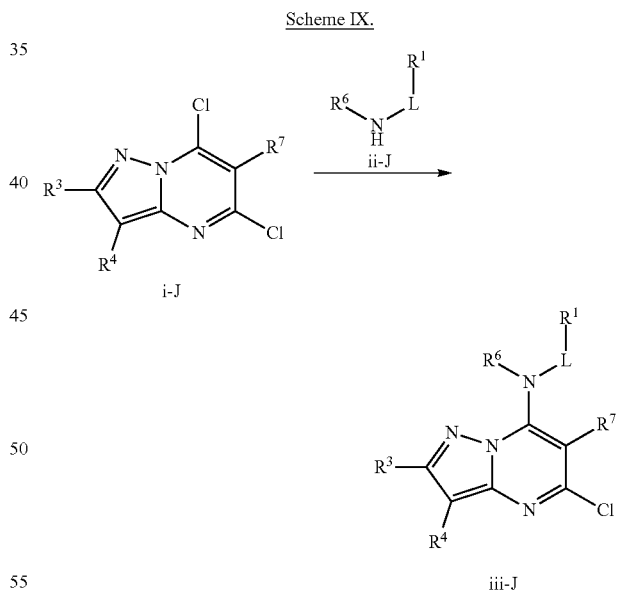

i-J iii-J

It will be appreciated by one skilled in the art that the processes described herein are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in*

*Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ aryloxy", employed alone or in combination with other terms, refers to a group of formula —O-aryl, wherein the aryl group has n to m carbon atoms. Example aryloxy group include, phenoxy and naphthyloxy.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "C$_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "C$_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "C$_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "C$_{n-m}$ alkylcarbamoyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "C$_{n-m}$ alkylcarbamoyl" refers to a group of formula —OC(O)NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "C$_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "C$_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carbamoyl" refers to a group of formula —OC(O)NH$_2$.

As used herein, the term "cyano-C$_{1-3}$ alkyl" refers to a group of formula —(C$_{1-3}$ alkylene)-CN.

As used herein, the term "HO—C$_{1-3}$ alkyl" refers to a group of formula —(C$_{1-3}$ alkylene)-OH.

As used herein, the term "di(C$_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di(C$_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di(C$_{n-m}$-alkyl)carbamoyl" refers to a group of formula —OC(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, Br, or I. In some embodiments, a halo is F, Cl, or Br. In some embodiments, a halo is Cl. In some embodiments, a halo is F.

As used herein, "C$_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "C$_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons (C$_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-on-yl, 1,3-isoxazolidin-2-on-yl, pyranyl, tetrahydropyranyl, oxetanyl, azetidinyl, morpholinyl, thiomorpholinyl, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., a furan ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pyroglutamic acid, gulonic acid, pentanoic acid, hexanoic acid, heptanoic acid, octanoic acid, nonanoic acid, and decanoic acid. Also included are organic diacids such as malonic, fumaric and maleic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Methods of Use

Provided herein are methods of treating a disease in a subject in need thereof. As used herein, the term "subject," refers to any animal, including mammals. For example, mice, rats, other rodents, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of Formula (I)), or a pharmaceutically acceptable salt thereof. In some embodiments, the disease is a disease associated with one or more mRNA splicing defects.

The present application further provides a method of treating a disease associated with one or more mRNA splicing defects in a subject in need thereof, comprising administering to the subject a therapeutically effective amount of a compound provided herein (i.e., a compound of Formula (I)). In some embodiments, the disease associated with the one or more mRNA splicing defects is a disease of the central nervous system.

In some embodiments of the methods provided herein, the compound is selected from the group of compounds provided in Table A, or a pharmaceutically acceptable salt thereof. In some embodiments, the compound is selected from the group of compounds provided in Table A-2, or a pharmaceutically acceptable salt thereof. In some embodiments, the compound is selected from the group of compounds provided in Table A-3, or a pharmaceutically acceptable salt thereof. In some embodiments, the compound is selected from the group of compounds provided in Table B, or a pharmaceutically acceptable salt thereof. In some embodiments, the compound is selected from the group of compounds provided in Table B-2, or a pharmaceutically acceptable salt thereof. In some embodiments, the compound is selected from the group of compounds provided in Table B-3, or a pharmaceutically acceptable salt thereof. In some embodiments, the compound is selected from the group of compounds provided in Table C, or a pharmaceutically acceptable salt thereof.

Example diseases of the central nervous system include, but are not limited to, Alzheimer's disease, amyotrophic lateral sclerosis (ALS), attention deficit/hyperactivity disorder (ADHD), atypical cystic fibrosis, autism, autism spectrum disorders, Bell's Palsy, bipolar disorder, catalepsy, Cerebal Palsy, Charcot-Marie-Tooth disease, Charge syndrome, depression, dementia, epilepsy, epileptic encephalopathy, encephalitis, familial dysautomonia (FD), familial isolated growth hormone deficiency type II (IGHD II), Frasier syndrome, frontotemporal dementia and Parkinson's linked to Chromosome 17 (FTDP-17), Huntington's disease, locked-in syndrome, major depressive disorder, Marfan syndrome, meningitis, mental retardation, Menkes Disease (MD), migraine, multiple sclerosis (MS), muscular dystrophies (e.g., Duchenne Muscular Dystrophy, Becker Muscular Dystrophy, Ullrich congenital muscular dystrophy, Asphyxiating thoracic dystrophy, Fukuyama Muscular dystrophy, Spinal muscular atrophy with respiratory distress 1, Congenital Muscular dystrophy 1A, Muscular dystrophy with epidermolysis bullosa, Facioscapulohumeral-like muscular dystrophy), myopathies (e.g., Bethlem myopathy, Collagen VI myopathy, Myotubular myopathy, Nemaline myopathy, Proximal myopathy and learning difficulties, Desmin related Myopathy and Congenital Myopathy with cores), neurofibromatosis 1 (NF1, von Recklinghausen NF; peripheral NF), neurofibromatosis 2 (NF2), occipital horn syndrome, Parkinson's disease, retinoblastoma, Rett syndrome, schizophrenia, tropical spastic paraparesis, Tourette's syndrome, and tuberous sclerosis. In some embodiments, the disease associated with one or more mRNA splicing defects is a disease listed in Table 1.

In some embodiments, the disease associated with one or more mRNA splicing defects is selected from the group consisting of amyotrophic lateral sclerosis (ALS), atypical cystic fibrosis, autism, autism spectrum disorders, Charcot-Marie-Tooth disease, Charge syndrome, dementia, epilepsy, epileptic encephalopathy, familial dysautonomia (FD), familial isolated growth hormone deficiency type II (IGHD II), Frasier syndrome, frontotemporal dementia and Parkinson's linked to Chromosome 17 (FTDP-17), Huntington's disease, Marfan syndrome, mental retardation, Menkes Disease (MD), muscular dystrophies (e.g., Duchenne Muscular Dystrophy, Becker Muscular Dystrophy, Ullrich congenital muscular dystrophy, Asphyxiating thoracic dystrophy, Fukuyama Muscular dystrophy, Spinal muscular atrophy with respiratory distress 1, Congenital Muscular dystrophy 1A, Muscular dystrophy with epidermolysis bullosa, Facioscapulohumeral-like muscular dystrophy), myopathies (e.g., Bethlem myopathy, Collagen VI myopathy, Myotubular myopathy, Nemaline myopathy, Proximal myopathy and learning difficulties, Desmin related Myopathy and Congenital Myopathy with cores), myotonic dystrophy type 1 (DM1), myotonic dystrophy type 2 (DM2), neurofibromatosis 1 (NF1, von Recklinghausen NF; peripheral NF), occipital horn syndrome, Parkinson's disease, retinoblastoma, schizophrenia, and tuberous sclerosis.

In some embodiments, the disease associated with one or more mRNA splicing defects is a disease listed in Table 1; for example, bilateral temporooccipital polymicrogyria; amyotrophic lateral sclerosis; Charcot-Marie-Tooth disease; Yunis-Varon syndrome; juvenile onset Parkinson disease 19; juvenile-onset neurodegeneration with brain iron accumulation; Parkinson disease 8; autosomal recessive spastic paraplegia 43; periventricular heterotopia with microcephaly; X linked mental retardation 46; Coach syndrome; Joubert syndrome 9; Meckel syndrome 6; X linked mental retardation syndromic 15, Cabezas type; X linked mental retardation syndromic, Claes-Jensen type; autosomal dominant mental retardation 1; X linked mental retardation, with cerebellar hypoplasia and distinctive facial appearance; autosomal recessive mental retardation 42; arthrogryposis; hypokalemic periodic paralysis, type 1; malignant hyperthermia susceptibility 5; susceptibility to thyrotoxic periodic paralysis 1; Angelman syndrome-like; early infantile epileptic encephalopathy; Fragile X syndrome; Fragile X-tremor/ataxia syndrome; premature ovarian failure 1; Cornelia de Lange syndrome 5; Wilson-Turner syndrome; Angelman syndrome; neonatal severe encephalopathy; X-linked syndromic, Lubs type mental retardation; X-linked syndromic mental retardation 13; Rett syndrome; preserved speech variant Rett syndrome; X-linked autism susceptibility 3; cerebral creatine deficiency syndrome 1; autosomal dominant mental retardation 5; childhood onset epileptic encephalopathy; epilepsy; Dravet syndrome; primary erythermalgia; familial febrile seizures 3B; autosomal recessive HSAN2D; paroxysmal extreme pain disorder/small fiber neuropathy; Dravet syndrome modifier of epileptic encephalopathy; early infantile 4 and 18; dilated cardiomyopathy 3B; Bethlem myopathy; short-rib thoracic dysplasia 3 with or without polydactyly cardiomyopathy, dilated, 1X; neuronopathy type VI; epidermolysis bullosa simplex with pyloric atresia; epidermolysis bullosa simplex, Ogna type; King-Denborough syndrome; minicore myopathy with external ophthalmoplegia; congnenital neuromuscular disease with uniform type 1 fiber; malignant hyperthermia susceptibility 1; Taylor balloon cell type focal cortical dysplasia; lymphangioleiomyomatosis; tuberous sclerosis-1; somatic lymphangioleiomyomatosis; tuberous sclerosis-2; acromicric dysplasia; ascending and dissection aortic aneurysm; familial ectopia lentis; Mass syndrome; stiff skin syndrome; dominant Weill-Marchesani syndrome 2; somatic bladder cancer; somatic osteosarcoma; retinoblastoma; small cell lung cancer; somatic Charge syndrome; hypogonadotropic hypogonadism 5 with or without anosmia; and, idiopathic scoliosis 3.

In some embodiments, the disease associated with one or more mRNA splicing defects is selected from familial dysautonomia and neurofibromatosis 1. In some embodiments, the disease associated with one or more mRNA splicing defects is familial dysautonomia. In some embodiments, the disease associated with one or more mRNA splicing defects is neurofibromatosis 1.

In some embodiments, the one or more mRNA splicing defects is associated with one or more genes comprising at least one exon comprising the nucleotide sequence CAA. In some embodiments, the one or more genes comprising at least one exon comprising the nucleotide sequence CAA is associated with a disease of the central nervous system. In some embodiments, the one or more genes comprising at least one exon comprising the nucleotide sequence CAA is selected from the group provided in Table 1, wherein all references cited herein are incorporated by reference herein in their entirety.

TABLE 1

| Human Gene Name | GeneBank Acc. No. for Human Gene | Associated Diseases | References |
| --- | --- | --- | --- |
| Inhibitor of kappa light polypeptide gene enhancer in B cells, kinase complex-associated protein (IKBKAP) | NG_008788.1 | Dysautonomia, familial | Anderson et al., Am. J. Hum. Genet. 68: 753-758, 2001; Slaugenhaup et al. Am. J., Hum. Genet. 68: 598-605, 2001 |
| SAC domain-containing inositol phosphatase 3 (FIG. 4) | NG_007977.1 | Polymicrogyria, bilateral temporooccipital, Amyotrophic lateral sclerosis 11, Charcot-Marie-Tooth disease, type 4J, Yunis-Varon syndrome | Chow et al Nature 448: 68-72, 2007; Chow et al., Am. J. Hum. Genet. 84: 85-88, 2009; Campeau et al., Am. J. Hum. Genet. 92: 781-791, 2013; Baulac et al., Neurology 82: 1068-1075, 2014 |
| DNAJ/HSP40 homology subfamily C member 6 (DNAJC6) | NG_033843.1 | Parkinson disease 19, juvenile-onset | Edvardson et al., PLoS One 7: e36458, 2012; Koroglu et al., Parkinsonism Relat. Disord. 19: 320-324, 2013 |
| WD40 repeat-containing protein 45 (WDR45) | NG_033004.1 | Neurodegeneration with brain iron accumulation 5 | Haack et al., Am. J. Hum. Genet. 91: 1144-1149, 2012; Saitsu et al., Nature Genet. 45: 445-449, 2013. |
| Leucine-rich repeat kinase 2 (LRRK2) | NG_011709.1 | Parkinson disease 8 | Zimprich et al., Neuron 44: 601-607, 2004; Tan et al., Hum. Mutat. 31: 561-568, 2010 |
| Leucine-rich repeat- and sterile alpha motif-containing 1 (LRSAM1) | NG_032008.1 | Charcot-Marie-Toothe disease, axonal, type 2P | Guernsey et al., PLOS Genet. 6: e1001081, 2010; Nicolaou et al., Europ. J. Hum. Genet. 21: 190-194, 2013 |
| SET-binding factor 2 (SBF2) | NG_008074.1 | Charcot-Marie-Tooth disease, type 4B2 | Senderek et al., Hum. Molec. Genet. 12: 349-356, 2003; Azzedine et al., Am. J. Hum. Genet. 72: 1141-1153, 2003 |

TABLE 1-continued

| Human Gene Name | GeneBank Acc. No. for Human Gene | Associated Diseases | References |
| --- | --- | --- | --- |
| Chromosome 10 open reading frame 12 (C19orf12) | NG_031970.1 | Spastic paraplegia 43, autosomal recessive; Neurodegeneration with brain iron accumulation 4 | Hogarth et al., Neurology 80: 268-275, 2013; Meilleur et al., Neurogenetics 11: 313-318, 2010 |
| ADP-ribosylation factor guanine nucleotide-exchange factor 2 (brefeldin A-inhibited) (ARFGEF2) | NG_011490.1 | Periventricular heterotopia with microcephaly | Banne et al., J. Med. Genet. 50: 772-775, 2013 |
| RHO guanine nucleoside exchange factor 6(ARHGEF6) | NG_008873.1 | Mental retardation, X-linked 46 | Yntema et al., J. Med. Genet. 35: 801-805, 1998; Kutsche et al., Nature Genet. 26: 247-250, 2000 |
| Coiled-coil and C2 domain-containing protein 2A (CC2D2A) | NG_013035.1 | COACH syndrome; Joubert syndrome 9; Meckel syndrome 6 | Noor et al., DNA Res. 7: 65-73, 2000; Tallila et al., Am. J. Hum. Genet. 82: 1361-1367, 2008; Doherty et al., J. Med. Genet. 47: 8-21, 2010 |
| Chromodomain helicase DNA-binding protein 8 (CHD8) | NG_021249.1 | Autism, susceptibility | O'Roak et al., Science 338: 1619-1622, 2012 |
| Cullin 4b (CUL4B) | NG_009388.1 | Mental retardation, X-linked, syndromic 15 (Cabezas type) | Tarpey et al., Nature Genet. 41: 535-543, 2009 |
| Lysine-specific demethylase 5C (KDM5C) | NG_008085.1 | Mental retardation, X-linked, syndromic, Claes-Jensen type | Jensen et al., Am. J. Hum. Genet. 76: 227-236, 2005 |
| Methyl-CpG-binding domain protein 5 (MBD5) | NG_017003.1 | Mental retardation, autosomal dominant 1 | Wagenstaller et al., Am. J. Hum. Genet. 81: 768-779, 2007 |
| Oligophrenin1 (OPHN1) | NG_008960.1 | Mental retardation, X-linked, with cerebellar hypoplasia and distinctive facial appearance | Zanni et al., Neurology 65: 1364-1369, 2005 |
| Post-GPI attachment to proteins 1 (PGAP1) | NC_000002.12 Range: 196833004 . . . 196926995 | Mental retardation, autosomal recessive 42 | Murakami et al., PLoS Genet. 10: e1004320, 2014 |
| Solute carrier family 9 (sodium/hydrogen exchanger) member 9 (SLC9A9) | NG_017077.1 | Autism susceptibility | Morrow et al., Science 321: 218-223, 2008 |
| Solute carrier family 35 (UDP-N-acetylglucosamine transporter) member 3 (SLC35A3) | NG_033857.1 | Arthrogryposis, mental retardation, and seizures | Edvardson et al., J. Med. Genet. 50: 733-739, 2013. |
| Calcium channel, voltage-dependent, L Type, alpha-1S subunit (CACNA1S) | NG_009816.1 | Hypokalemic periodic paralysis, type 1; Malignant hyperthermia susceptibility 5; Thyrotoxic periodic paralysis, susceptibility to, 1 | Ptacek et al., Cell 77: 863-868, 1994; Monnier et al., Am. J. Hum. Genet. 60: 1316-1325, 1997; Kung et al., J. Clin. Endocr. Metab. 89: 1340-1345, 2004 |
| Cyclin-dependent kinase-like 5 (CDKL5) | NG_008475.1 | Angelman syndrome-like; Epileptic encephalopathy, early infantile, 2 | Van Esch et al., Am. J. Med. Genet. 143A: 364-369, 2007; Nemos et al., Clin. Genet. 76: 357-371, 2009. |
| Fragile X mental retardation protein (FMR1) | NG_007529.1 | Fragile X syndrome; Fragile X tremor/ataxia syndrome; Premature ovarian failure 1 | Devys et al., Nature Genet. 4: 335-340, 1993; Allingham-Hawkins et al., Am. J. Med. Genet. 83: 322-325, 1999; Leehey et al., Arch. Neurol. 60: 117-121, 2003 |
| Histone deacetylase 8 (HDAC8) | NG_015851.1 | Cornelia de Lange syndrome 5; Wilson-Turner syndrome | Harakalova et al., J. Med. Genet. 49: 539-543, 2012; Deardorff et al., Nature 489: 313-317, 2012 |

TABLE 1-continued

| Human Gene Name | GeneBank Acc. No. for Human Gene | Associated Diseases | References |
|---|---|---|---|
| Methyl-CpG-binding protein 2 (MECP2) | NG_007107.2 | Angelman syndrome; Encephalopathy, neonatal severe; Mental retardation, X-linked syndromic, Lubs type; Mental retardation, X-linked, syndromic 13; Rett syndrome; Rett syndrome, preserved speech variant; Autism susceptibility, X-linked 3 | Wan et al., Hum. Molec. Genet. 10: 1085-1092, 2001; Xiang et al., J. Med. Genet. 37: 250-255, 2000; Meloni et al., Am. J. Hum. Genet. 67: 982-985, 2000; Watson et al., J. Med. Genet. 38: 224-228, 2001; Carney et al., Pediat. Neurol. 28: 205-211, 2003 |
| Solute carrier family 6 (neurotransmitter transporter creatine) member 8(SLC6A8) | NG_012016.1 | Cerebral creatine deficiency syndrome 1 | Salomons et al., Am. J. Hum. Genet. 68: 1497-1500, 2001 |
| Synaptic RAS-GTPase-activating protein 1 (SYNGAP1) | NG_016137.1 | Mental retardation, autosomal dominant 5 | Hamdan et al., Biol. Psychiat. 69: 898-901, 2011 |
| Chromodomain helicase DNA-binding protein 2 (CHD2) | NG_012826.1 | Epileptic encephalopathy, childhood-onset | Carvill et al., Nature Genet. 45: 825-830, 2013 |
| Cholinergic receptor, neuronal nicotinic, alpha polypeptide 4 (CHRNA4) | NG_011931.1 | Epilepsy, nocturnal frontal lobe, 1; Nicotine addiction, susceptibility to | Steinlein et al., Nature Genet. 11: 201-203, 1995; Li et al., Hum. Molec. Genet. 14: 1211-1219, 2005 |
| DEP domain-containing protein 5 (DEPDC5) | NG_034067.1 | Epilepsy, familial focal, with variable foci | Dibbens et al., Nature Genet. 45: 546-551, 2013 |
| Golgi SNAP receptor complex member 2 (GOSR2) | NG_031806.1 | Epilepsy, progressive myoclonic 6 | Corbett et al., Am. J. Hum. Genet. 88: 657-663, 2011 |
| Glutamate receptor, ionotropic, N-methyl-D-aspartate, subunit 2A (GRIN2A) | NG_011812.1 | Epilepsy, focal, with speech disorder and with or without mental retardation | Carvill et al., Nature Genet. 45: 1073-1076, 2013 |
| Sodium channel, neuronal type 1, alpha subunit (SCN1A) | NG_011906.1 | Dravet syndrome; Epilepsy, generalized, with febrile seizures plus, type 2; Febrile seizures, familial, 3A; Migraine, familial hemiplegic, 3 | Baulac et al., Am. J. Hum. Genet. 65: 1078-1085, 1999; Claes et al., Am. J. Hum. Genet. 68: 1327-1332, 2001; Ohmori et al., Biochem. Biophys. Res. Commun. 295: 17-23, 2002 |
| Sodium channel, voltage-gated, type 1X, alpha subunit (SCN9A) | NG_012798.1 | Epilepsy, generalized, with febrile seizures plus, type 7; Erythermalgia, primary; Febrile seizures, familial, 3B; HSAN2D, autosomal recessive; Paroxysmal extreme pain disorder, Small fiber neuropathy; Dravet syndrome, modifier of | Yang et al., J. Med. Genet. 41: 171-174, 2004; Faber et al., Ann. Neurol. 71: 26-39, 2012; Goldberg et al., Clin. Genet. 71: 311-319, 2007; Catterall et al., Neuron 52: 743-749, 2006; Singh et al., PLoS Genet. 5: e1000649, 2009 |
| Syntaxin-binding protein 1 (STXBP1) | NG_016623.1 | Epileptic encephalopathy, early infantile, 4 | Saitsu et al., Nature Genet. 40: 782-788, 2008 |
| Seizure threshold 2 (SZT2) | NG_029091.1 | Epileptic encephalopathy, early infantile, 18 | Basel-Vanagaite et al., Am. J. Hum. Genet. 93: 524-529, 2013 |

TABLE 1-continued

| Human Gene Name | GeneBank Acc. No. for Human Gene | Associated Diseases | References |
|---|---|---|---|
| Dystrophin (DMD) | NG_012232.1 | Becker muscular dystrophy; Cardiomyopathy, dilated, 3B; Duchenne muscular dystrophy | Gurvich et al., Hum. Mutat. 30: 633-640, 2009; Muntoni et al., Am. J. Hum. Genet. 56: 151-157, 1995; Daoud et al., Hum. Molec. Genet. 18: 3779-3794, 2009 |
| Collagen type VI, alpha-3 (COL6A3) | NG_008676.1 | Bethlem myopathy; Ullrich congenital muscular dystrophy | Demir et al., Am. J. Hum. Genet. 70: 1446-1458, 2002; Lampe et al., J. Med. Genet. 42: 108-120, 2005 |
| Dynein, cytoplasmic 2 heavy chain 1 (DYNC2H1) | NG_016423.1 | Short-rib thoracic dysplasia 3 with or without polydactyly | Dagoneau et al., Am. J. Hum. Genet. 84: 706-711, 2009 |
| Fukutin (FKTN) | NG_008754.1 | Cardiomyopathy, dilated, 1X; Muscular dystrophy-dystroglycanopathy (congenital with brain and eye anomalies), type A4, B4 and C4 | Taniguchi-Ikeda et al., 478: 127-131, 2011 |
| Immunoglobin 2 MU-binding protein2 (IGHMBP2) | NG_007976.1 | Charcot-Marie-Tooth disease, axonal, type 2S; Neuronopathy, distal hereditary motor, type VI | Grohmann et al., Nature Genet. 29: 75-77, 2001; Cottenie et al., Am. J. Hum. Genet. 95: 590-601, 2014 |
| Laminin alpha-2 (LAMA2) | NG_008678.1 | Muscular dystrophy, congenital merosin-deficient; Muscular dystrophy, congenital, due to partial LAMA2 deficiency | Tezak et al., Hum. Mutat. 21: 103-111, 2003; Oliveira et al., Clin. Genet. 74: 502-512, 2008 |
| Myotubularin 1 (MTM1) | NG_008199.1 | Myotubular myopathy, X-linked | Tanner et al., Hum. Mutat. 11: 62-68, 1998 |
| Nebulin (NEB) | NG_009382.2 | Nemaline myopathy 2, autosomal recessive | Donner et al., Europ. J. Hum. Genet. 12: 744-751, 2004; Lehtokari et al., Hum. Mutat. 27: 946-956, 2006 |
| Plectin (PLEC) | NG_012492.1 | Epidermolysis bullosa simplex with pyloric atresia; Epidermolysis bullosa simplex, Ogna type; Muscular dystrophy with epidermolysis bullosa simplex; Muscular dystrophy, limb-girdle, type 2Q | Pulkkinen et al., Hum. Molec. Genet. 5: 1539-1546, 1996; Pfendner et al., J. Invest. Derm. 124: 111-115, 2005 |
| Mitochondrial calcium uptake protein 1 (MICU1) | NG_033179.1 | Myopathy with extrapyramidal signs | Logan et al., Nature Genet. 46: 188-193, 2014 |
| Structural maintenance of chromosomes flexible hinge domain-containing protein 1 (SMCHD1) | NG_031972.1 | Fascioscapulohumeral muscular dystrophy 2, digenic | Lemmers et al., Nature Genet. 44: 1370-1374, 2012 |
| Desmin (DES) | NG_008043.1 | Muscular dystrophy, limb-girdle, type 2R; Cardiomyopathy, dilated, 1I; Myopathy, myofibrillar, 1; Scapuloperoneal syndrome, neurogenic, Kaeser type | Dalakas et al., New Eng. J. Med. 342: 770-780, 2000; Li et al., Circulation 100: 461-464, 1999; Walter et al., Brain 130: 1485-1496, 2007; Cetin et al., J. Med. Genet. 50: 437-443, 2013 |

TABLE 1-continued

| Human Gene Name | GeneBank Acc. No. for Human Gene | Associated Diseases | References |
|---|---|---|---|
| Ryanodine receptor 1 (RYR1) | NG_008866.1 | Central core disease; King-Denborough syndrome; Minicore myopathy with external ophthalmoplegia; Neuromuscular disease, congenital, with uniform type 1 fiber; Malignant hyperthermia susceptibility 1 | Sambuughin et al., Am. J. Hum. Genet. 69: 204-208, 2001; Tilgen et al., Hum. Molec. Genet. 10: 2879-2887, 2001; Monnier et al., Hum. Molec. Genet. 12: 1171-1178, 2003; D'Arcy et al., Neurology 71: 776-777, 2008 |
| Hamartin(TSC1) | NG_012386.1 | Focal cortical dysplasia, Taylor balloon cell type; Lymphangioleiomyomatosis; Tuberous sclerosis-1 | Iyer et al., Science 338: 222, 2012; Becker et al., Ann. Neurol. 52: 29-37, 2002; Jones et al., Hum. Molec. Genet. 6: 2155-2161, 1997 |
| Tuberin (TSC2) | NG_005895.1 | Lymphangioleiomyomatosis, somatic; Tuberous sclerosis-2 | Carbonara et al., Genes Chromosomes Cancer 15: 18-25, 1996; Carsillo et al., Proc. Nat. Acad. Sci. 97: 6085-6090, 2000 |
| Fibrillin 1 (FBN1) | NG_008805.2 | Acromicric dysplasia; Aortic aneurysm, ascending, and dissection; Ectopia lentis, familial; Marfan syndrome; MASS syndrome; Stiff skin syndrome; Weill-Marchesani syndrome 2, dominant | Dietz et al., Nature 352: 337-339, 1991; Faivre et al., J. Med. Genet. 40: 34-36, 2003; Loeys et al., Sci. Transl. Med. 2: 23ra20, 2010; Le Goff et al., Am. J. Hum. Genet. 89: 7-14, 2011 |
| Retinoblastoma 1 (RB1) | NG_009009.1 | Bladder cancer, somatic; Osteosarcoma, somatic; Retinoblastoma; Retinoblastoma, trilateral; Small cell cancer of the lung, somatic | Yandell et al., New Eng. J. Med. 321: 1689-1695, 1989; Harbour et al., Science 241: 353-357, 1988 |
| Chromodomain helicase DNA-binding protein 7 (CHD7) | NG_007009.1 | CHARGE syndrome; Hypogonadotropic hypogonadism 5 with or without anosmia; Scoliosis, idiopathic 3 | Lalani et al., Am. J. Hum. Genet. 78: 303-314, 2006; Kim et al., Am. J. Hum. Genet. 83: 511-519, 2008; Gao et al., Am. J. Hum. Genet. 80: 957-965, 2007; Felix et al., Am. J. Med. Genet. 140A: 2110-2114, 2006; Pleasance et al., Nature 463: 184-190, 2010 |

Figure 4A:
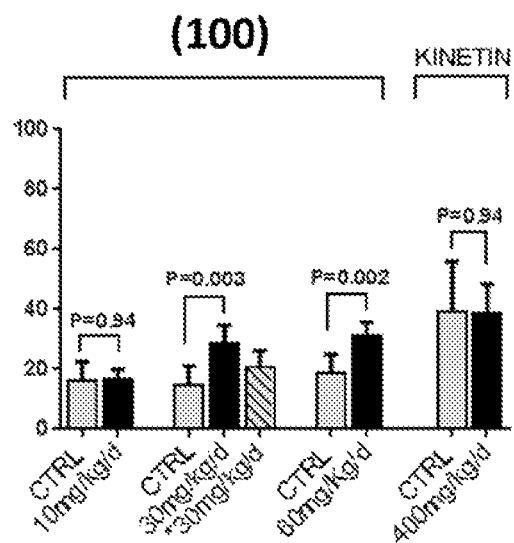
FIG. 4A shows percent exon 20 inclusion in C57Bl6-FD mouse brain after administration of compound (100) at 10 mg/kg/day; 30 mg/kg/day; and 60 mg/kg/day; and administration of kinetin at 400 mg/kg/day.
Figure 4B:
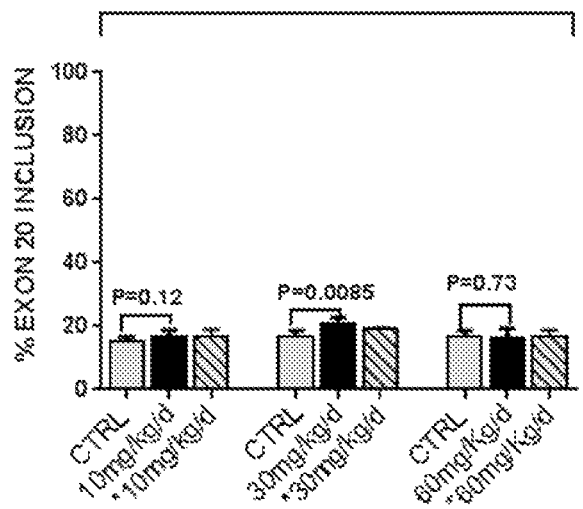
FIG. 4B shows percent exon 20 inclusion in C57BI6-FD mouse brain after administration of compound (230) at 10 mg/kg/day; 30 mg/kg/day; and 60 mg/kg/day.
Figure 4C:
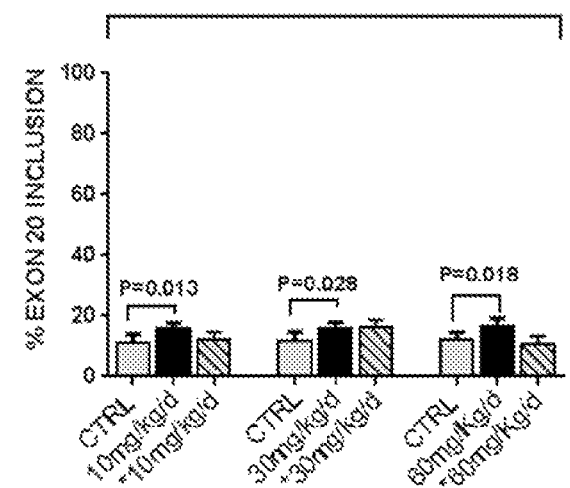
FIG. 4C shows percent exon 20 inclusion in C57BI6-FD mouse brain after administration of compound (270) at 10 mg/kg/day; 30 mg/kg/day; and 60 mg/kg/day.
Figure 5:
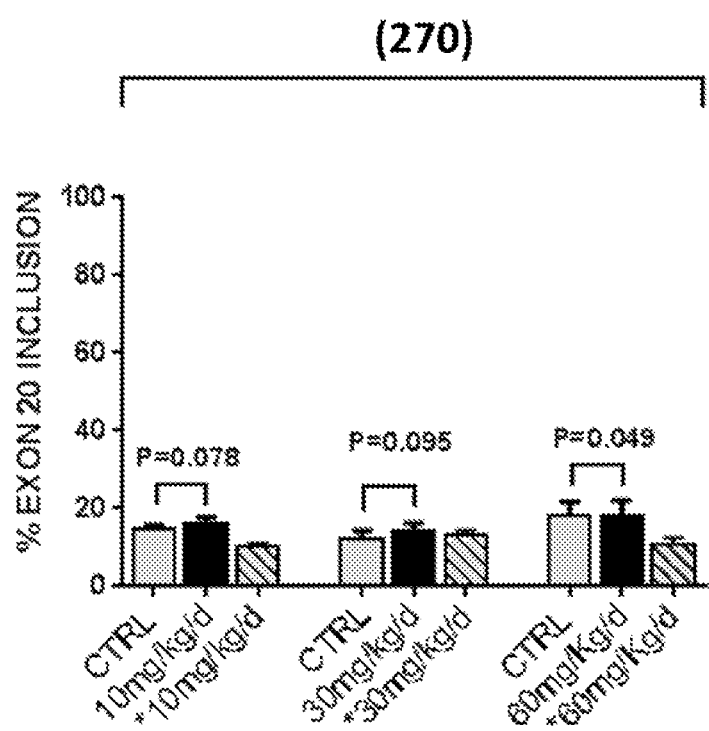
FIG. 5 shows percent exon 20 inclusion in C57BI6-FD mouse trigeminal nerve after administration of compound (270) at 10 mg/kg/day; 30 mg/kg/day; and 60 mg/kg/day.
Figure 6:
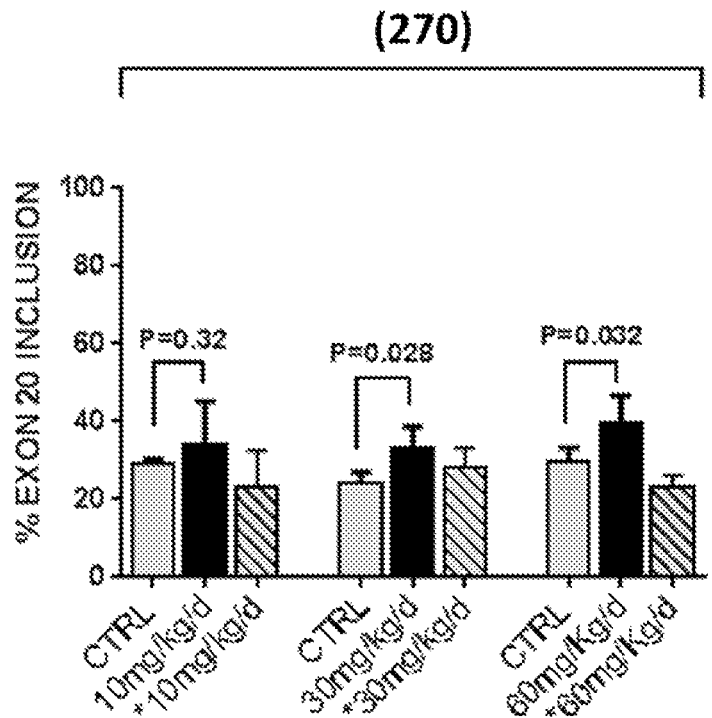
FIG. 6 shows percent exon 20 inclusion in C57BI6-FD mouse sciatic nerve after administration of compound (270) at 10 mg/kg/day; 30 mg/kg/day; and 60 mg/kg/day.

In some embodiments, the one or more mRNA splicing defects is associated with one or more genes selected from the group consisting of BMP2K, ABI2, IKBKAP, FIG4, DNAJC6, WDR45, LRRK2, LRSAM1, SBF2, C19orf12, ARFGEF2, ARHGEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD7. In some embodiments, the one or more mRNA splicing defects is associated with one or more genes selected from the group provided in Table 1; in some embodiments, the mRNA splicing defect causes or contributes to a disease listed in Table 1.

The present application further provides a method of improving mRNA splicing of a gene, e.g., in a cell or a subject, e.g., in a cell or subject who has an mRNA splicing defect, e.g., a genetic mutation associated with an mRNA splicing defect or a disease associated with an mRNA splicing defect. In some embodiments, the gene comprises at least one exon comprising the nucleotide sequence CAA. In some embodiments, the method of improving mRNA splicing of a gene comprises contacting the gene (e.g., in a cell or subject expressing the gene) with a compound provided herein (e.g., a compound of Formula (I)). In some embodiments, the method of improving mRNA splicing of a gene comprises contacting a gene (e.g., a cell expressing a gene) selected from the group consisting of BMP2K, ABI2, IKBKAP, FIG4, DNAJC6, WDR45, LRRK2, LRSAM1, SBF2, C19orf12, ARFGEF2, ARHGEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD7 with a compound provided herein (e.g., a compound of Formula (I)); in some embodiments, the cell has an mRNA splicing defect in processing transcripts from the gene, e.g., the cell has a mutation that causes a mRNA splicing defect in processing transcripts from the gene. In some embodiments, the method of improving mRNA splicing of a gene comprises improving exon inclusion (e.g., wherein the mRNA splicing defect results in aberrant exon exclusion when compared to a wild-type cell or mRNA).

In some embodiments, the method of improving mRNA splicing of a gene comprises improving exon inclusion, wherein the gene is selected from the group consisting of BMP2K, ABI2, IKBKAP, FIG4, DNAJC6, WDR45, LRRK2, LRSAM1, SBF2, C19orf12, ARFGEF2, ARHGEF6, CC2D2A, CHD8, CUL4B, KDM5C, MBD5, OPHN1, PGAP1, SLC9A9, SLC35A3, CACNA1S, CDKL5, FMR1, HDAC8, MECP2, SLC6A8, SYNGAP1, CHD2, CHRNA4, DEPDC5, GOSR2, GRIN2A, SCN1A, SCN9A, STXBP1, SZT2, DMD, COL6A3, DYNC2H1, FKTN, IGHMBP2, LAMA2, MTM1, NEB, PLEC, MICU1, SMCHD1, DES, RYR1, TSC1, TSC2, FBN1, RB1, and CHD. In some embodiments, the method of improving mRNA splicing of a gene comprises improving exon inclusion, wherein the gene is selected from the group provided in Table 1.

In some embodiments, contacting the gene is performed in vitro. In some embodiments, contacting the gene is performed in vivo, e.g., in a subject who has a disease described herein and/or listed in Table 1.

In some embodiments, the compound (i.e., a compound of Formula (I)) for use in the methods described herein may be used in combination with one or more of the compounds provided and described in the present disclosure.

As used herein, the expression "$EC_k$" refers to the compound concentration at which the maximum kinetin efficacy (200 μM) is reached.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a subject or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Also provided herein are methods for increasing IKAP protein expression in a patient in need thereof, the method comprising administering an effective amount of a compound provide herein, (i.e., a compound of Formula (I), or a pharmaceutically acceptable salt thereof), to the patient. For example, such methods include increasing IKAP protein expression in serum samples from the patient. Further provided herein are methods for increasing the mean percentage of IKAP protein expression in a patient in need thereof, the method comprising administering an effective amount of a compound provided herein (i.e., a compound of Formula (I), or a pharmaceutically acceptable salt thereof, to the patient.

Also provided herein are methods for increasing IKAP protein expression in a cell (e.g., ex vivo or in vivo), the method comprising contacting the cell with a therapeutically effective amount of a compound provided herein, (i.e., a compound of Formula (I), or a pharmaceutically acceptable salt thereof). In some embodiments the method is an in vitro method. In some embodiments, the method is an in vivo method. In some embodiments, the amount IKAP protein expression is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some embodiments thereof, the amount of IKAP protein expression is increased in the plasma.

Also provided herein are methods for increasing IKAP protein level in a patient in need thereof, the method comprising administering an effective amount of a compound provide herein, (i.e., a compound of Formula (I), or a pharmaceutically acceptable salt thereof), to the patient. For example, such methods include increasing IKAP protein level in serum samples from the patient. Further provided herein are methods for increasing the mean percentage of IKAP protein level in a patient in need thereof, the method comprising administering an effective amount of a compound provided herein (i.e., a compound of Formula (I), or a pharmaceutically acceptable salt thereof, to the patient.

Also provided herein are methods for increasing IKAP protein level in a cell (e.g., ex vivo or in vivo), the method comprising contacting the cell with a therapeutically effective amount of a compound provided herein, (i.e., a compound of Formula (I), or a pharmaceutically acceptable salt thereof). In some embodiments the method is an in vitro method. In some embodiments, the method is an in vivo method. In some embodiments, the amount IKAP protein level is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some embodiments thereof, the amount of IKAP protein level is increased in the plasma.

Also provided herein are methods for increasing WT IKBKAP mRNA in a patient in need thereof, the method comprising administering an effective amount of a compound provide herein, (i.e., a compound of Formula (I), or a pharmaceutically acceptable salt thereof), to the patient. For example, such methods include increasing WT IKBKAP mRNA concentration in serum samples from the patient. Further provided herein are methods for increasing the mean percentage exon inclusion (i.e. the percentage of correctly spliced or WT IKBKAP mRNA) in a patient in need thereof, the method comprising administering an effective amount of a compound provided herein (i.e., a compound of Formula (I), or a pharmaceutically acceptable salt thereof, to the patient.

In some embodiments, WT IKBKAP mRNA can be measured in the serum, for example, in blood samples obtained from the patient prior to administration of a compound as provided herein and in blood samples obtained from the patient following administration of a compound as provided herein. In some embodiments, the blood samples obtained from the patient following administration are obtained after one day, two days, three days, four days, five days, six days, seven days, eight days, nine days, ten days, fourteen days, twenty-one days, twenty-eight days, and/or thirty days of administration of the compound as provided herein. See, for example, F. B. Axelrod et al., *Pediatr Res* (2011) 70(5): 480-483; and R. S. Shetty et al., *Human Molecular Genetics* (2011) 20(21): 4093-4101, both of which are incorporated by reference in their entirety.

Further provided herein is a method of increasing WT IKBKAP mRNA in a cell, the method comprising contacting the cell with a therapeutically effective amount of a compound provided herein (i.e., a compound of Formula (I)). The amount of WT IKBKAP mRNA in the treated cell is increased relative to a cell in a subject not administered a compound provided herein. The method of increasing the amount of WT IKBKAP mRNA in a cell may be performed by contacting the cell with a compound provided herein (i.e., a compound of Formula (I), or a pharmaceutically acceptable salt form thereof), in vitro, thereby increasing the amount WT IKBKAP mRNA of a cell in vitro. Uses of such an in vitro method of increasing the amount of WT IKBKAP mRNA include, but are not limited to, use in a screening assay (for example, wherein a compound provided herein is used as a positive control or standard compared to a compound or compounds of unknown activity or potency in increasing the amount WT IKBKAP mRNA). In some embodiments, the amount of WT IKBKAP mRNA is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof. In some embodiments thereof, the amount of WT IKBKAP mRNA is increased in the plasma.

The method of increasing WT IKBKAP mRNA in a cell may be performed, for example, by contacting a cell, (e.g., a lung cell, a muscle cell, a liver cell, a heart cell, a brain cell, a kidney cell, or a nerve cell), with a compound provided herein (i.e. a compound of Formula (I), or a pharmaceutically acceptable salt thereof), in vivo, thereby increasing the amount of WT IKBKAP mRNA in a subject in vivo. The contacting is achieved by causing a compound provided herein, or a pharmaceutically acceptable salt form thereof, to be present in a subject in an amount effective to achieve an increase in the amount of WT IKBKAP mRNA. This may be achieved, for example, by administering an effective amount of a compound provided herein, or a pharmaceutically acceptable salt form thereof, to a subject. Uses of such an in vivo method of increasing the amount of WT IKBKAP mRNA include, but are not limited to, use in methods of treating a disease or condition, wherein an increase in the amount of WT IKBKAP mRNA is beneficial. In some embodiments thereof, the amount of WT IKBKAP mRNA is increased in a cell selected from the group consisting of a lung cell, a muscle cell, a liver cell, a heart cell, a brain cell, a kidney cell, and a nerve cell (e.g., a sciatic nerve cell or a trigeminal nerve cell), or any combination thereof, for example in a patient suffering from a disease or disorder provided herein (e.g., familial dysautonomia or neurofibromatosis 1). The method is preferably performed by administering an effective amount of a compound provided herein, or a pharmaceutically acceptable salt form thereof, to a subject who is suffering from familial dysautonomia or neurofibromatosis 1.

Combination Therapies

In some embodiments, one or more of the compounds provided herein may be administered to a subject in need thereof in combination with at least one additional pharmaceutical agent. In some embodiments, the additional pharmaceutical agent is a compound provided herein (e.g., a compound of Formula (I)).

Additional examples of suitable additional pharmaceutical agents for use in combination with the compounds of the present application for treatment of the diseases provided herein include, but are not limited to, antioxidants, anti-inflammatory agents, steroids, immunosuppressants, or other agents such as therapeutic antibodies. In some embodiments, the compounds provided herein may be administered to a subject in need thereof in combination with at least one additional pharmaceutical agent for the treatment of familial dysautonomia. In some embodiments, the additional pharmaceutical agent is phosphatidylserine.

Pharmaceutical Compositions and Formulations

When employed as pharmaceuticals, the compounds provided herein can be administered in the form of pharmaceutical compositions; thus, the methods described herein can include administering the pharmaceutical compositions. These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable. In some embodiments, the compounds provided herein are suitable for oral and parenteral administration. In some embodiments, the compounds provided herein are suitable for oral administration. In some embodiments, the compounds provided herein are suitable for parenteral administration. In some embodiments, the compounds provided herein are suitable for intravenous administration. In some embodiments, the compounds provided herein are suitable for transdermal administration (e.g., administration using a patch or microneedle). Pharmaceutical compositions for topical administration may include transdermal patches (e.g., normal or electrostimulated), ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein (e.g., a compound of Formula (I)), or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

Kits

Also provided herein are kits including a compound provided herein, more particularly to a compound of Formula (I) or Formula (II), or a pharmaceutically acceptable salt thereof. In some embodiments, a kit can include one or more delivery systems, e.g., for a compound provided herein, or a pharmaceutically acceptable salt thereof, and directions for use of the kit (e.g., instructions for treating a subject). In some embodiments, a kit can include a compound provided herein, or a pharmaceutically acceptable salt thereof, and one or more additional agents as provided herein.

In some embodiments, the compound is selected from the group of compounds provided in Table A, or a pharmaceutically acceptable salt thereof. In some embodiments, the compound is selected from the group of compounds provided in Table A-2, or a pharmaceutically acceptable salt thereof. In some embodiments, the compound is selected from the group of compounds provided in Table A-3, or a pharmaceutically acceptable salt thereof. In some embodiments, the compound is selected from the group of compounds provided in Table B, or a pharmaceutically acceptable salt thereof. In some embodiments, the compound is selected from the group of compounds provided in Table B-2, or a pharmaceutically acceptable salt thereof. In some embodiments, the compound is selected from the group of compounds provided in Table B-3, or a pharmaceutically acceptable salt thereof. In some embodiments, the compound is selected from the group of compounds provided in Table C, or a pharmaceutically acceptable salt thereof.

In some embodiments, the kit can include one or more compounds or additional pharmaceutical agents as provided herein, or a pharmaceutically acceptable salt thereof, and a label that indicates that the contents are to be administered to a subject resistant to a standard of care agent or adjuvant used for the treatment of familial dysautonomia or neurofibromatosis 1. In some embodiments, the additional pharmaceutical agent is phosphatidylserine. In another embodiment, the kit can include a compound provided herein, or a pharmaceutically acceptable salt thereof, and a label that indicates that the contents are to be administered to a subject with cells expressing abnormal WT IKBKAP mRNA splicing. In another embodiment, the kit can include one or more compounds or additional pharmaceutical agents as provided herein, or a pharmaceutically acceptable salt thereof, and a label that indicates that the contents are to be administered to a subject having a disease of the central nervous system resulting from abnormal mRNA splicing. In another embodiment, the kit can include one or more compounds or additional pharmaceutical agents as provided herein, or a pharmaceutically acceptable salt thereof, and a label that indicates that the contents are to be administered to a subject having familial dysautonomia or neurofibromatosis 1. In some embodiments, a kit can include one or more compounds as provided herein, or a pharmaceutically acceptable salt thereof, and a label that indicates that the contents are to be administered with one or more additional pharmaceutical agents as provided herein.

Examples

The invention is further described in the following examples, which do not limit the scope of the invention described in the claims.

General Methods

All reactions were performed under a dry atmosphere of nitrogen unless otherwise specified. Indicated reaction temperatures refer to the reaction bath, while room temperature (rt) is noted as 25° C. Commercial grade reagents and anhydrous solvents were used as received from vendors and no attempts were made to purify or dry these components further. Removal of solvents under reduced pressure was accomplished with a Buchi rotary evaporator at approximately 28 mm Hg pressure using a Teflon-linked KNF vacuum pump. Thin layer chromatography was performed using 1"×3" AnalTech No. 02521 silica gel plates with fluorescent indicator. Visualization of TLC plates was made by observation with either short wave UV light (254 nm lamp), 10% phosphomolybdic acid in ethanol or in iodine vapors. Preparative thin layer chromatography was performed using Analtech, 20×20 cm, 1000 micron preparative TLC plates. Flash column chromatography was carried out using a Teledyne Isco CombiFlash Companion Unit with RediSep®Rf silica gel columns. If needed, products were purified by reverse phase chromatography, using a Teledyne Isco CombiFlash Companion Unit with RediSep®Gold C18 reverse phase column. Proton NMR spectra were obtained either on 300 MHz Bruker Nuclear Magnetic Resonance Spectrometer or 500 MHz Bruker Nuclear Magnetic Resonance Spectrometer and chemical shifts Bruker Nuclear Magnetic Resonance Spectrometer and chemical shifts (6 are reported in parts per million (ppm) and coupling constant (J) values are given in Hz, with the following spectral pattern designations: s, singlet; d, doublet; t, triplet; q, quartet; dd, doublet of doublets; m, multiplet; br, broad. Tetramethylsilane was used as an internal reference. Melting points are uncorrected and were obtained using a MEL-TEMP Electrothermal melting point apparatus. Mass spectroscopic analyses were performed using positive mode electron spray ionization (ESI) on a Varian ProStar LC-MS with a 1200 L quadrupole mass spectrometer. High pressure liquid chromatography (HPLC) purity analysis was performed using a Varian Pro Star HPLC system with a binary solvent system A and B using a gradient elusion [A, $H_2O$ with 0.1% trifluoroacetic acid (TFA); B, $CH_3CN$ with 0.1% TFA] and flow rate=1 mL/min, with UV detection at 254 nm. All final compounds were purified to ≥95% purity by the Varian Pro Star HPLC system using the following methods:

A) Phenomenex Luna C18(2) column (4.60×250 mm); mobile phase, A=H₂O with 0.1% TFA and B=CH₃CN with 0.1% TFA; gradient: 10-100% B (0.0-20.0 min); UV detection at 254 nm.

B) Phenomenex Luna C18(2) column (4.60×250 mm); mobile phase, A=H₂O with 0.1% TFA and B=CH₃CN with 0.1% TFA; gradient: 10-95% B (0.0-10.0 min); hold 95% B (6.0 min); UV detection at 254 nm.

Intermediate 1. 2-(4,6-Dichloro-1H-pyrazolo[3,4-d]pyrimidin-1-yl)ethanol

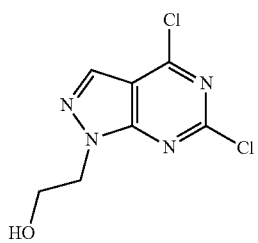 [SMILES: OCCn1ncc2c(Cl)nc(Cl)nc21]

A solution of 2,4,6-trichloropyrimidine-5-carboxaldehyde (414 mg, 1.96 mmol) in EtOH (14 mL) at −78° C. was treated with a solution of (2-hydroxyethyl)hydrazine (0.15 mL, 2.2 mmol) and TEA (0.57 mL, 4.1 mmol) in EtOH (2 mL) via dropwise addition and stirred for 30 min. The mixture was then allowed to warm to 0° C. while stirring for an additional 30 min, and then 2N HCl was added dropwise until pH=6. The solvents were removed by rotary evaporation and the crude residue was purified by chromatography on silica gel (gradient 0-100% EtOAc in hexanes) to afford the title compound (262 mg, 57%): ¹H NMR (300 MHz, CDCl₃) δ 8.57 (s, 1H), 4.87 (t, J=5.4 Hz, 1H), 4.48-4.43 (m, 2H), 3.87-3.80 (m, 2H).

Intermediate 2. 4,6-Dichloro-1-(2-fluoroethyl)-1H-pyrazolo[3,4-d]pyrimidine

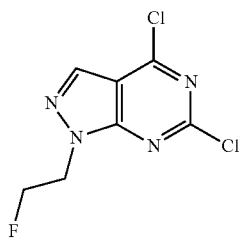 [SMILES: FCCn1ncc2c(Cl)nc(Cl)nc21]

A solution of 2-(4,6-dichloro-1H-pyrazolo[3,4-d]pyrimidin-1-yl)ethanol (100.4 mg, 0.431 mmol) in dichloromethane (2 mL) at −78° C. was treated with Deoxo-Fluor (0.09 mL, 0.49 mmol) via dropwise addition and stirred for 30 min. The mixture was then allowed to warm to room temperature while stirring for an additional 30 min, then water (5 mL) and sat. aq. NaHCO₃ (3 mL) were added. The layers were separated, and the aqueous layer was extracted with dichloromethane (2×10 mL). The combined organic extracts were dried over Na₂SO₄, filtered and concentrated to dryness. The crude residue was purified by chromatography on silica gel (gradient 0-10% methanol in DCM) to afford the title compound (18.3 mg, 18%) as an off-white solid: ¹H NMR (300 MHz, DMSO-d₆) δ 8.63 (s, 1H), 4.95 (t, J=4.4 Hz, 1H), 4.82-4.75 (m, 2H), 4.73-4.69 (m, 2H).

Intermediate 3. Ethyl N-((1H-1,2,4-triazol-5-yl)carbamothioyl)carbamate

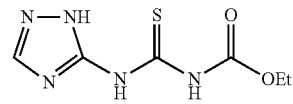 [SMILES: CCOC(=O)NC(=S)Nc1ncn[nH]1]

A solution of 3-amino-1,2,4-triazole (521 mg, 6.20 mmol) in DMF (7 mL) at 10° C. was treated with ethoxycarbonyl isothiocyanate (0.70 mL, 6.19 mmol) via dropwise addition, and the mixture was allowed to room temperature while stirring for 16 h. Water (75 mL) was added, and the mixture was extracted with EtOAc (3×50 mL). The combined organic extracts were dried over Na₂SO₄, filtered and concentrated in vacuo to afford the title compound (960 mg, 72%) as a yellow solid: ¹H NMR (500 MHz, DMSO-d₆) δ 13.99 (br s, 1H), 12.10-11.71 (br d, 1H), 11.45 (br s, 1H), 8.53 (s, 1H), 4.27-4.16 (m, 2H), 1.25 (t, J=7.1 Hz, 3H).

Intermediate 4. Disodium 5-sulfido-[1,2,4]triazolo[1,5-a][1,3,5]triazin-7-olate

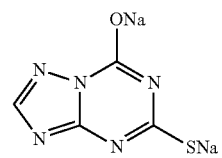

A solution of ethyl N-((1H-1,2,4-triazol-5-yl)carbamothioyl)carbamate (960 mg, 4.46 mmol) in EtOH (18 mL) was treated with aqueous NaOH (2N, 5.0 mL, 10 mmol), warmed to reflux for 30 min, then cooled to room temperature. The precipitated solid was collected on a fritted funnel and rinsed with cold EtOH (2×20 mL), then dried under vacuum at 60° C. for 1 h to afford the title compound (913 mg, 96%) as an off-white solid: ¹H NMR (500 MHz, DMSO-d₆) δ 7.57 (s, 1H).

Intermediate 5. 5-thioxo-5,6-dihydro-[1,2,4]triazolo[1,5-a][1,3,5]triazin-7(4H)-one

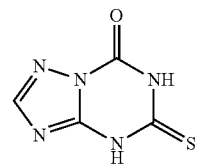 [SMILES: O=c1[nH]c(=S)[nH]c2ncnn12]

A solution of 5-sulfido-[1,2,4]triazolo[1,5-a][1,3,5]triazin-7-olate disodium salt (721 mg, 3.38 mmol) in water (21 mL) was treated with aq. HCl solution (2N, 7 mL, 14 mmol) and stirred for 10 min. The precipitated solid was collected on a fritted funnel dried under vacuum at 60° C. for 1 h to afford the title compound (480 mg, 84%) as an off-white solid: $^1$H NMR (500 MHz, DMSO-$d_6$) δ 14.23 (br s, 1H), 13.04 (br s, 1H), 8.17 (s, 1H).

Intermediate 6. 5-(methylthio)-[1,2,4]triazolo[1,5-a][1,3,5]triazin-7(6H)-one

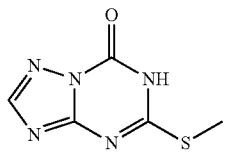

A solution of 5-thioxo-5,6-dihydro-[1,2,4]triazolo[1,5-a][1,3,5]triazin-7(4H)-one (149 mg, 0.881 mmol) in THF (0.6 mL) was treated with sodium methoxide solution (0.5 M in methanol, 1.85 mL, 0.925 mmol) and stirred for 2 min. Iodomethane solution (1.0 M in THF, 0.92 mL, 0.92 mmol) was added and the mixture was stirred for 16 h. The solvents were removed by rotary evaporation, and the residue was suspended in water (5 mL) and filtered. The collected solid was washed with additional water (5 mL) and dried under vacuum at 60° C. for 1 h to afford the title compound (80.5 mg, 50%) as a white solid: $^1$H NMR (500 MHz, DMSO-$d_6$) δ 13.40 (br s, 1H), 8.31 (s, 1H), 2.57 (s, 3H).

Intermediate 7. Triethyl ethane-1,1,2-tricarboxylate

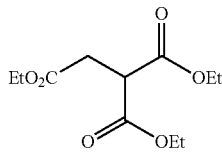 [SMILES: CCOC(=O)CC(C(=O)OCC)C(=O)OCC]

Diethyl malonate (20 mL, 132 mmol) was added dropwise to a solution of ethanolic sodium ethoxide (21% by weight, approx. 2.65 M, 50 mL, 133 mmol) in EtOH (80 mL) at 0° C. and stirred for 30 min. Ethyl chloroacetate (14 mL, 131 mmol) was added dropwise, the mixture was heated to reflux for 3.25 h and then cooled to room temperature. All volatiles were removed by rotary evaporation, the residue was partitioned between EtOAc (400 mL) and water (300 mL), and the layers were separated. The organic layer was washed with sat. aq. NaCl solution (200 mL), dried over Na$_2$SO$_4$, filtered and concentrated in vacuo to afford the title compound (30.5 g, 94% crude) as an orange oil: $^1$H NMR (300 MHz, CDCl$_3$) δ 4.25-4.14 (m, 6H), 3.83 (t, J=7.3 Hz, 1H), 2.92 (d, J=7.4 Hz, 2H), 1.31-1.23 (m, 9H).

Intermediate 8. Ethyl 2-(2,4,6-trioxohexahydropyrimidin-5-yl)acetate

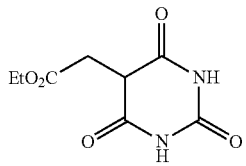

A mixture of triethyl ethane-1,1,2-tricarboxylate (30.5 g, 124 mmol), urea (7.44 g, 124 mmol) and ethanolic sodium ethoxide solution (21% by weight, approx. 2.65 M, 73 mL, 194 mmol) in EtOH (180 mL) was heated to reflux for 17 h, then cooled to room temperature. All volatiles were removed by rotary evaporation, and water (400 mL) was added. Aqueous 2N HCl was added to adjust the solution to pH=3, and the mixture was extracted with EtOAc (3×150 mL). The combined organic extracts were dried over Na$_2$SO$_4$, filtered and concentrated in vacuo to afford the title compound (8.0 g, 30%) as a tan solid: $^1$H NMR (300 MHz, CDCl$_3$) δ 8.28 (br s, 1H), 8.18 (br s, 1H), 4.80 (br s, 1H), 4.18-4.08 (m, 2H), 1.30-1.25 (m, 3H).

Intermediate 9. Ethyl 2-(2,4,6-trichloropyrimidin-5-yl)acetate

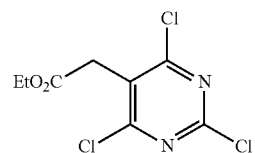

A mixture of ethyl 2-(2,4,6-trioxohexahydropyrimidin-5-yl)acetate (8.0 g, 37.4 mmol) and DIPEA (10 mL, 57 mmol) in phosphorous(V) oxychloride (50 mL) was heated to reflux for 3 h, then carefully poured onto ice water (500 g) and stirred for 1 h. Potassium carbonate was added to adjust pH to 3, and the mixture was extracted with EtOAc (3×200 mL). The combined organic extracts were dried over Na$_2$SO$_4$, filtered and concentrated in vacuo. The crude residue was purified by chromatography on silica gel (gradient 0-50% EtOAc in hexanes) to afford the title compound (3.20 g, 32%) as an off white solid: $^1$H NMR (300 MHz, CDCl$_3$) δ 4.23 (q, J=7.1 Hz, 2H), 3.94 (s, 2H), 1.29 (t, J=7.1 Hz, 3H).

Intermediate 10. Ethyl 2-(4-amino-2,6-dichloropyrimidin-5-yl)acetate

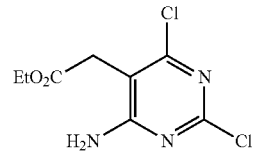

A solution of ethyl 2-(2,4,6-trichloropyrimidin-5-yl)acetate (880 mg, 3.27 mmol) in DMF (15 mL) was treated with sodium azide (213 mg, 3.28 mmol) and stirred at room temperature for 2 h. Water (200 mL) was added, and the mixture was extracted with EtOAc (3×50 mL). The combined organic extracts were dried over Na$_2$SO$_4$, filtered and concentrated in vacuo. The crude residue (1.02 g, quant.) was dissolved in THF (7 mL) and water (3.5 mL), then treated with trimethylphosphine solution (1.0 M in THF, 3.5 mL, 3.5 mmol) and stirred at room temperature for 20 h. EtOAc (75 mL) was added, and the organic layer was washed with water (2×20 mL), dried over Na$_2$SO$_4$, filtered and concentrated in vacuo. The crude residue was purified by chromatography on silica gel (gradient 0-80% EtOAc in hexanes) to afford the title compound (517 mg, 64% over 2 steps) as a white solid: ¹H NMR (300 MHz, CDCl₃) δ 5.73 (br s, 2H), 4.20 (q, J=7.1 Hz, 2H), 3.66 (s, 2H), 1.29 (t, J=7.1 Hz, 3H).

Intermediate 11. 2,4-dichloro-5H-pyrrolo[2,3-d]pyrimidin-6(7H)-one

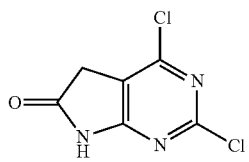 [SMILES: O=C1Cc2c(Cl)nc(Cl)nc2N1]

A solution of ethyl 2-(4-amino-2,6-dichloropyrimidin-5-yl)acetate (197 mg, 0.788 mmol) in DMF (8 mL) at 0° C. was treated with sodium hydride (60% dispersion in mineral oil, 70 mg, 1.75 mmol) and stirred for 40 min. Aqueous lithium chloride solution (5% solution, 40 mL) was added, and the mixture was extracted with EtOAc (3×50 mL). The combined organic extracts were dried over Na₂SO₄, filtered and concentrated in vacuo. The residue was purified by chromatography on silica gel (gradient 0-10% methanol in DCM) to afford the title compound (46 mg, 29%) as a yellow solid: ¹H NMR (300 MHz, DMSO-d₆) δ 12.02 (br s, 1H), 3.65 (s, 2H).

Intermediate 12. 2,6-Dichloro-7-methyl-7H-purine

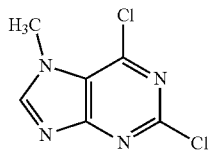

To a solution of 2,6-dichloro-7H-purine (1.05 g, 5.56 mmol) in THF (8 mL) at 0° C. under nitrogen was added NaH (60% in mineral oil, 525 mg, 13.1 mmol) in one portion and, after stirring for 30 min at 0° C., iodomethane (0.38 mL, 6.12 mmol) was added. The mixture was stirred at 0° C. for 1 h and then at room temperature for 16 h. After this time, the reaction mixture was diluted with EtOAc and washed with water and brine. The organic layer was concentrated under reduced pressure and the residue obtained was purified by column chromatography (silica, 0-30% EtOAc in CH₂Cl₂) to provide isomers 2,6-dichloro-9-methyl-9H-purine (491 mg, 43%) and 2,6-dichloro-7-methyl-7H-purine (312 mg, 28%): ESI MS (M+H) 203; 2,6-dichloro-9-methyl-9H-purine ¹H NMR (300 MHz, DMSO-d₆) δ 8.69 (s, 1H), 3.83 (s, 3H) and 2,6-dichloro-7-methyl-7H-purine ¹H NMR (300 MHz, DMSO-d₆) δ 8.81 (s, 1H), 4.07 (s, 3H).

Intermediate 13.
8-Bromo-2,6-dichloro-7-methyl-7H-purine

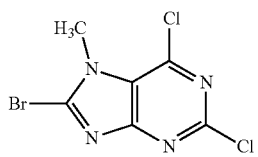

A suspension of 2,6-dichloro-7-methyl-7H-purine (250 mg, 1.23 mmol) in THF (10 mL) under nitrogen was cooled to −78° C., and then LDA (2.0 M in THF/heptane/ethylbenzene, 1.80 mL, 3.60 mmol) was added to obtain a dark solution, which was stirred for 15 min. After this time, a solution of 1,2-dibromo-1,1,2,2-tetrachloroethane (1.20 g, 3.69 mmol) in THF (2 mL) was added and the reaction mixture was stirred at −78° C. for 1 h. A saturated solution of NH₄Cl was added, and then the mixture was extracted with EtOAc. The organic layer was dried over sodium sulfate and then concentrated. The residue was purified by column chromatography (silica, 0-3% MeOH in CH₂Cl₂) to provide 8-bromo-2,6-dichloro-7-methyl-7H-purine (135 mg, 39%): ESI MS (M+H) 281; ¹H NMR (500 MHz, DMSO-d₆) δ 4.02 (s, 3H).

Intermediate 14.
2,6-Dichloro-7-methyl-8-propoxy-7H-purine

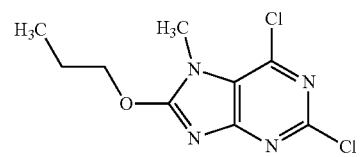 [SMILES: CCCOc1nc2nc(Cl)nc(Cl)c2n1C]

Sodium hydride (60% in mineral oil, 20 mg, 0.50 mmol) was carefully added to n-propanol (35 mg, 0.58 mmol) to obtain a solution which was added to a solution of 8-bromo-2,6-dichloro-7-methyl-7H-purine (125 mg, 0.44 mmol) in THF (2 mL). The resulting mixture was stirred at room temperature for 1.5 h. After this time the mixture was concentrated and the residue purified by column chromatography (silica, 0-10% EtOAc in CH₂Cl₂) to provide 2,6-dichloro-7-methyl-8-propoxy-7H-purine (68 mg, 59%): ESI MS (M+H) 261; ¹H NMR (500 MHz, DMSO-d₆) δ 4.58 (t, J=6.5 Hz, 2H), 3.74 (s, 3H), 1.87-1.81 (m, 2H), 1.01 (t, J=7.4 Hz, 3H).

Intermediate 15. 2-Bromo-5,7-dichlorothiazolo[5,4-d]pyrimidine

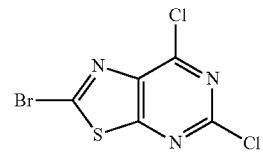 [SMILES: Clc1nc(Cl)c2nc(Br)sc2n1]

A solution of 2-bromo-5,7-dichlorothiazolo[5,4-d]pyrimidine (180 mg, 0.87 mmol) in THF (8 mL) under nitrogen was cooled to −78° C. LDA (2.0 M in THF/heptane/ethylbenzene, 1.30 mL, 2.60 mmol) was added slowly and the mixture was stirred for 10 min. After this time, a solution of 1,2-dibromo-1,1,2,2-tetrachloroethane (850 mg, 2.61 mmol) in THF (2 mL) was added and the reaction mixture was stirred at −78° C. for 1.5 h. A saturated solution of NH₄Cl was added, and then the mixture was extracted with EtOAc. The organic layer was dried over sodium sulfate and then concentrated. The residue was purified by column chromatography (silica, 0-20% EtOAc, hexanes) to provide 2-bromo-5,7-dichlorothiazolo[5,4-d]pyrimidine (134 mg, 54%): ESI MS (M+H) 284.

Intermediate 16. (E)-6-Chloro-5-((4-chlorophenyl)diazenyl)pyrimidine-2,4-diamine

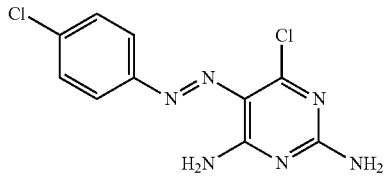 [SMILES: Nc1nc(N)c(/N=N/c2ccc(Cl)cc2)c(Cl)n1]

To a suspension of 4-chloroaniline (1.28 g, 10 mmol) in water (9 mL) was added concentrated HCl (2.75 mL, 33 mmol) and then stirred for 10 minutes. A solution of $NaNO_2$ (725 mg, 10.5 mmol) in water (9 mL) was added dropwise at 0° C. resulting in a clear solution. In a separate flask, acetic acid (45 mL, 81 mmol) and NaOAc (18 g, 216 mmol) were added to a suspension of 6-chloropyrimidine-2,4-diamine (1.3 g, 9 mmol) in water (45 mL). The clear solution from above was then added dropwise to the suspension and the reaction was allowed to stir overnight at room temperature. The resulting solid that formed was isolated by suction filtration to afford the title compound (3 g, >100%): $^1$H NMR (300 MHz, DMSO-$d_6$) δ 9.26 (s, 1H), 8.17 (s, 1H), 7.81 (d, J=8.7 Hz, 2H), 7.54 (d, J=8.7 Hz, 2H), 7.34 (br s, 2H).

Intermediate 17. 6-Chloropyrimidine-2,4,5-triamine

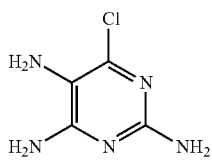

To a suspension of (E)-6-Chloro-5-((4-chlorophenyl)diazenyl)pyrimidine-2,4-diamine (2.2 g, 7 mmol) in THF (70 mL) was added acetic acid (10 mL) followed by Zn dust (3.3 g, 50 mmol) at 0° C. The reaction was stirred for 30 minutes then filtered through a pad of Celite. The filtrate was concentrated under reduced pressure and the residue was purified by silica gel chromatography (0-30% 90:9:1 mixture of $CH_2Cl_2/CH_3OH$/concentrated $NH_4OH$ in $Cl_2Cl_2$) to afford the title compound (300 mg, 27%): $^1$H NMR (500 MHz, DMSO-$d_6$) δ 6.33 (s, 2H), 5.48 (s, 2H), 3.88 (s, 2H).

Intermediate 18: 7-Chloro-3H-[1,2,3]triazolo[4,5-d]pyrimidin-5-amine

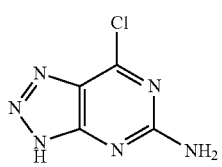 [SMILES: Nc1nc(Cl)c2nn[nH]c2n1]

To a solution of 6-chloropyrimidine-2,4,5-triamine (290 mg, 1.8 mmol) in water (25 mL) and acetic acid (6 mL) was added a solution of $NaNO_2$ (150 mg, 2.16 mmol) in water (3 mL) at 0° C. After 1 h at 0° C., a precipitate formed which was isolated by suction filtration washing with water. The solid was dissolved in EtOH and concentrated under reduced pressure to afford the title compound as a gray solid (150 mg, 49%): $^1$H NMR (300 MHz, DMSO-$d_6$) δ 15.90 (s, 1H), 7.49 (s, 2H).

Example 1. General Procedure A

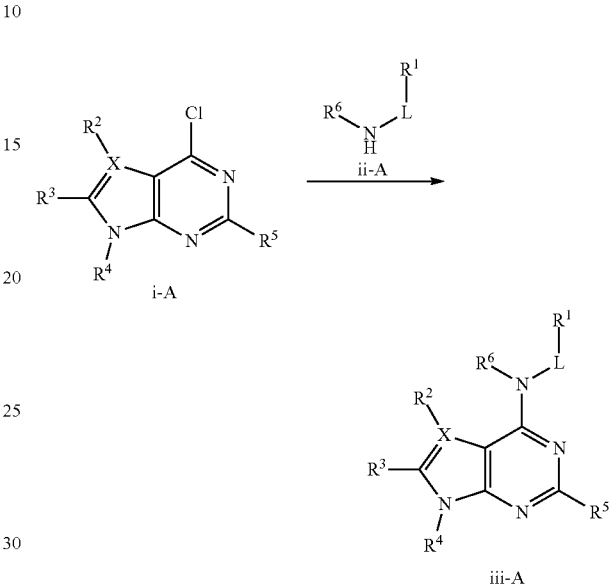

A mixture of the desired pyrrolopyrimidine or purine i-A (1 equiv), desired aminomethyl heterocycle or benzylamine ii-A (1.1 equiv), and triethylamine ($NEt_3$) or diisopropylethylamine (DIPEA) (1.5-3.5 equiv) in a suitable solvent (e.g., 1,4-dioxane, THF, EtOH, n-BuOH) was stirred at 50-150° C. in a reaction flask or sealed tube until the reaction was complete by LC-MS and/or TLC analysis. Following completion, the reaction mixture was cooled to room temperature, diluted with $CH_2Cl_2$ and washed with saturated $NaHCO_3$ solution. The organic extract was dried over $Na_2SO_4$, filtered and concentrated under reduced pressure. The resulting residue was purified by silica gel chromatography (typical eluents included, for example, a mixture of hexanes and EtOAc, or a mixture of $CH_2Cl_2$ and MeOH, or an 80:18:2 mixture of $CH_2Cl_2/CH_3OH$/concentrated $NH_4OH$) to afford the desired product iii-A. The product structures prepared according to General Procedure A were confirmed by $^1$H NMR and/or by mass analysis.

Example 2. General Procedure B

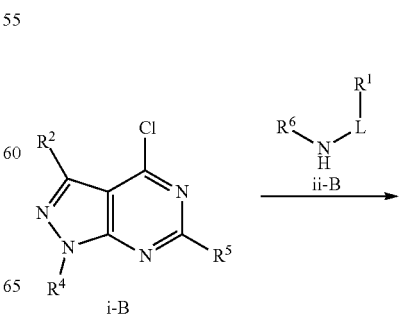

-continued

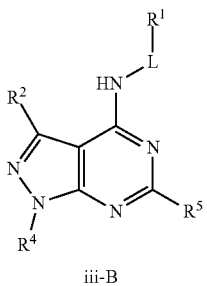

iii-B

A mixture of the desired chloropyrazolopyrimidine i-B (1 equiv), desired aminomethyl heterocycle or benzylamine ii-B (1.1 equiv), and triethylamine (NEt₃) or diisopropylethylamine (DIPEA) (1.5-3.5 equiv) in a suitable solvent (e.g. 1,4-dioxane, THF, EtOH, n-BuOH) was stirred at 50-150° C. in a sealed tube until the reaction was complete by LC-MS and/or TLC analysis. Following completion, the reaction mixture was cooled to room temperature, diluted with CH₂Cl₂, and washed with saturated NaHCO₃ solution. The organic extract was dried over Na₂SO₄, filtered and concentrated under reduced pressure. The resulting residue was purified by silica gel chromatography (typical eluents included, for example, a mixture of hexanes and EtOAc, or a mixture of CH₂Cl₂ and MeOH, or an 80:18:2 mixture of CH₂Cl₂/CH₃OH/concentrated NH₄OH) to afford the desired product iii-B. The product structures prepared according to General Procedure B were confirmed by ¹H NMR and/or by mass analysis.

Example 3. General Procedure C

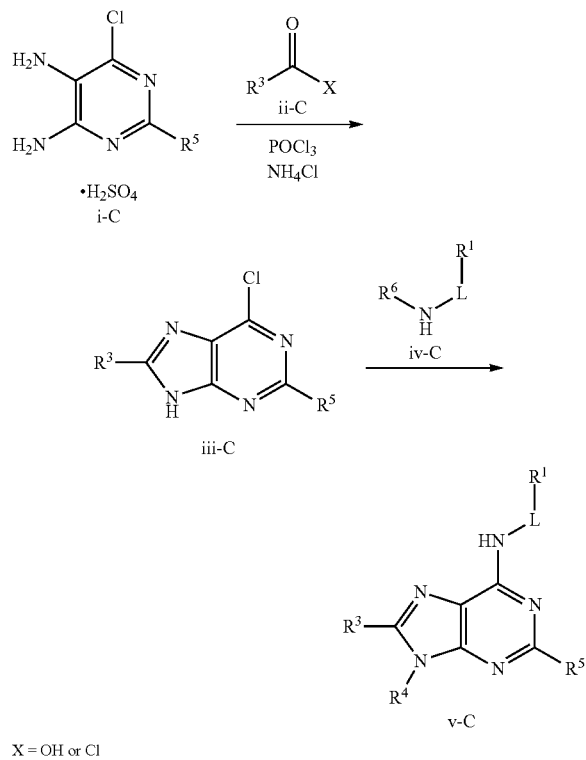

X = OH or Cl

Step 1. General Procedure C1 for Purine Ring Formation

A mixture of 5,6-diaminouracil sulfate salt i-C or 6-chloropyrimidine-4,5-diamine (1 equiv), the desired carboxylic acid or acid chloride ii-C (1.1 equiv), POCl₃ (4 mL/100 mg of i-C), and NH₄Cl (6 equiv) was stirred at 100° C. until the reaction was complete by LC-MS and/or TLC analysis. The reaction mixture was cooled to room temperature and carefully poured over ice (caution: exothermic reaction upon addition to water). The pH was adjusted to ~7 with concentrated NH₄OH then the aqueous layer was extracted with EtOAc (2×) and the combined organic extracts were dried over Na₂SO₄, filtered and concentrated under reduced pressure. The resulting residue was purified by silica gel chromatography (typical eluents included, for example, a mixture of hexanes and EtOAc, or a mixture of CH₂Cl₂ and MeOH, or an 80:18:2 mixture of CH₂Cl₂/CH₃OH/concentrated NH₄OH) to afford the desired product iii-C. The product structures prepared according to General Procedure C1 were confirmed by ¹H NMR and/or by mass analysis.

Step 2. General Procedure C2 for Amine Addition

A mixture of the desired chloropurine iii-C (1 equiv), desired aminomethyl heterocycle or benzylamine iv-C (1.1 equiv), and triethylamine (NEt₃) or diisopropylethylamine (DIPEA) (1.5 equiv) in a suitable solvent (e.g. 1,4-dioxane; ~0.25 M) was stirred at 50-150° C. in a sealed tube until the reaction was complete by LC-MS and/or TLC analysis. The reaction mixture was then cooled to room temperature, diluted with CH₂Cl₂ and washed with saturated NaHCO₃ solution. The organic extract was dried over Na₂SO₄, filtered and concentrated under reduced pressure. The resulting residue was purified by silica gel chromatography (typical eluents included, for example, a mixture of hexanes and EtOAc, or a mixture of CH₂Cl₂ and MeOH, or an 80:18:2 mixture of CH₂Cl₂/CH₃OH/concentrated NH₄OH) to afford the desired product v-C. The product structures prepared by General Procedure C2 was confirmed by ¹H NMR and/or by mass analysis.

Example 4. General Procedure D

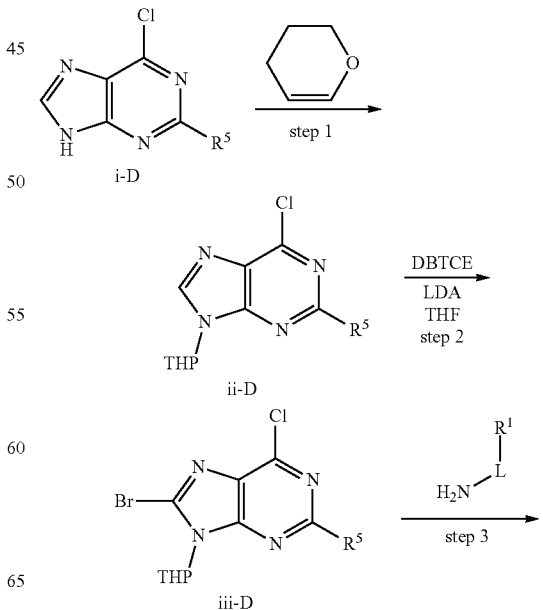

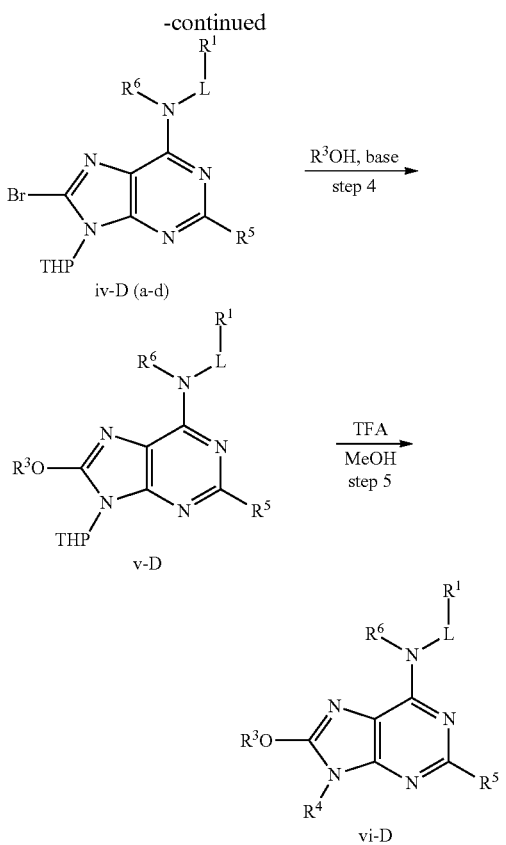

iv-D (a-d)

v-D vi-D

Step 1. 2,6-dichloro-9-(tetrahydro-2H-pyran-2-yl)-9H-purine 2,6-Dichloropurine i-D (1 equiv), dihydropyran (1.05 equiv), and para-toluenesulfonic acid (0.11 equiv) in EtOAc (~0.5 M) were stirred at 65° C. overnight. After this time, the reaction was cooled to room temperature and washed with saturated NaHCO$_3$ solution followed by brine. The solution was dried over Na$_2$SO$_4$, filtered and concentrated under reduced pressure to afford a clear residue. The resulting residue was triturated with MeOH and the resulting white solid was collected by suction filtration to afford ii-D as a white solid; ESI MS (M+H) 273.

Step 2. 8-bromo-2,6-dichloro-9-(tetrahydro-2H-pyran-2-yl)-9H-purine

To a solution of 2,6-dichloro-9-(tetrahydro-2H-pyran-2-yl)-9H-purine ii-D (1 equiv) in THF (~0.1 M) was added LDA (3 equiv) at −78° C. and stirred for 20 minutes. After this time, a solution of dibromotetrachloroethane (DBTCE, 3 equiv) in THF (~0.4 M) was added slowly and stirred at −78° C. for 90 minutes. The reaction was quenched with saturated NH$_4$Cl solution and diluted with EtOAc. The layers were separated and the organic layer was washed with brine, dried over Na$_2$SO$_4$, filtered and concentrated under reduced pressure. The resulting residue purified by silica gel chromatography (EtOAc/hexanes) to afford the title compound iii-D. $^1$H NMR (500 MHz, DMSO-d$_6$) 5.69 (dd, J=11.5, 2.5 Hz, 1H), 4.09-4.05 (m, 1H), 3.71 (td, J=11.5, 3.5 Hz, 1H), 2.83-2.75 (m, 1H), 2.02-2.00 (m, 1H), 1.96-1.93 (m, 1H), 1.78-1.69 (m, 1H), 1.66-1.58 (m, 2H).

Step 3a. 8-bromo-2-chloro-9-(tetrahydro-2H-pyran-2-yl)-N-(thiazol-2-ylmethyl)-9H-purin-6-amine 8-Bromo-2,6-dichloro-9-(tetrahydro-2H-pyran-2-yl)-9H-purine (1 equiv), 2-(aminomethyl)thiazole dihydrochloride (1.1 equiv) and triethylamine or DIPEA (3 equiv) in 1,4-dioxane (~0.4 M) were stirred at room temperature overnight. The reaction mixture was then concentrated under reduced pressure and purified by silica gel chromatography (EtOAc/hexanes) to afford the title compound (iv-D(a)) as a yellow solid. $^1$H NMR (500 MHz, DMSO-d$_6$) δ 9.29 (s, 1H), 7.73 (d, J=3.5 Hz, 1H), 7.60 (d, J=3.0 Hz, 1H), 5.58 (dd, J=11.0, 2.0 Hz, 1H), 4.89 (d, J=6.0 Hz, 2H), 4.06 (s, 1H), 3.66 (td, J=11.5, 3.5 Hz, 1H), 2.87-2.78 (m, 1H), 2.00 (s, 1H), 1.90-1.85 (m, 1H), 1.74-1.55 (m, 3H).

Step 3b. 8-bromo-2-chloro-N-(pyridin-4-ylmethyl)-9-(tetrahydro-2H-pyran-2-yl)-9H-purin-6-amine 8-Bromo-2,6-dichloro-9-(tetrahydro-2H-pyran-2-yl)-9H-purine, 4-(aminomethyl)pyridine (1.1 equiv) and triethylamine or DIPEA (1.5 equiv) in 1,4-dioxane (~0.4 M) were stirred at room temperature overnight. The reaction mixture was then concentrated under reduced pressure and purified by silica gel chromatography (EtOAc/hexanes) to afford the title compound (iv-D(b)) as a yellow solid. $^1$H NMR (500 MHz, CDCl$_3$) δ 8.57 (dd, J=4.5, 1.5 Hz, 2H), 7.253-7.250 (m, 2H), 6.08 (br s, 1H), 5.67 (dd, J=11.5, 2.5 Hz, 1H), 4.83 (br s, 2H), 4.19-4.16 (m, 1H), 3.71 (td, J=12.0, 2.5 Hz, 1H), 2.96-2.90 (m, 1H), 2.12-2.09 (m, 1H), 1.86-1.59 (m, 4H).

Step 3c. 8-bromo-2-chloro-N-(pyrimidin-4-ylmethyl)-9-(tetrahydro-2H-pyran-2-yl)-9H-purin-6-amine 8-Bromo-2,6-dichloro-9-(tetrahydro-2H-pyran-2-yl)-9H-purine (1 equiv), 4-(aminomethyl)pyrimidine hydrochloride (1.1 equiv) and triethylamine or DIPEA (2 equiv) in 1,4-dioxane (~0.4 M) were stirred at room temperature overnight. The reaction mixture was then concentrated under reduced pressure and purified by silica gel chromatography (EtOAc/hexanes) to afford the title compound (iv-D(c)) as a yellow solid. $^1$H NMR (300 MHz, CDCl$_3$) δ 9.19 (d, J=1.5 Hz, 1H), 8.70 (d, J=5.4 Hz, 1H), 7.34 (d, J=5.7 Hz, 1H), 6.94 (br s, 1H), 5.68 (dd, J=11.4, 2.4 Hz, 1H), 4.90 (br s, 2H), 4.20-4.16 (m, 1H), 3.72 (td, J=12.0, 2.7 Hz, 1H), 3.00-2.88 (m, 1H), 2.13-2.04 (m, 1H), 1.87-1.59 (m, 4H).

Step 3d. 8-bromo-2-chloro-N-(furan-2-ylmethyl)-9-(tetrahydro-2H-pyran-2-yl)-9H-purin-6-amine 8-Bromo-2,6-dichloro-9-(tetrahydro-2H-pyran-2-yl)-9H-purine (1 equiv), furfurylamine (1.1 equiv), and triethylamine or DIPEA (2 equiv) in 1,4-dioxane (~0.4 M) were stirred at room temperature overnight. The reaction mixture was then concentrated under reduced pressure and purified by silica gel chromatography (EtOAc/hexanes) to afford the title compound (iv-D(d)) as a yellow solid. $^1$H NMR (500 MHz, DMSO-d$_6$) 8.95 (s, 1H), 7.56 (s, 1H), 6.38-6.37 (m, 1H), 6.26 (d, J=2.5 Hz, 1H), 5.56 (d, J=10 Hz, 1H), 4.60 (d, J=5.5 Hz, 2H), 4.06-4.03 (m, 1H), 3.66 (td, J=11.5, 3.5 Hz, 1H), 2.85-2.78 (m, 1H), 1.98 (d, J=13.5 Hz, 1H), 1.88-1.85 (m, 1H), 1.71-1.67 (m, 1H), 1.59-1.55 (m, 2H).

Step 4a. General Procedure D1 for formation of C8-alkoxy purines

To a mixture of the desired intermediate iv-D(a-d) (1 equiv) and the desired alkyl alcohol (excess, >10 equiv) in a microwave vial was added potassium tert-butoxide (2-10 equiv). 1,4-Dioxane or THF (~0.3 M) can be used as a solvent, if necessary. The reaction vial was sealed and heated at 60-80° C. until the reaction was complete by LC-MS and/or TLC analysis. The mixture was then diluted with EtOAc, washed with water then brine. The organic layer was dried over $Na_2SO_4$, filtered, concentrated under reduced pressure, and purified by silica gel chromatography (typical eluents included either a mixture of hexanes and EtOAc or a mixture of $CH_2Cl_2$ and MeOH or an 80:18:2 mixture of $CH_2Cl_2/CH_3OH$/concentrated $NH_4OH$) to afford the desired product v-D. The product structures prepared according to General Procedure D1 were confirmed by $^1H$ NMR and/or by mass analysis.

Step 4b. General Procedure D2 for Formation of C8-Alkoxy Purines

To a mixture of the desired intermediate iv-D(a-d) (1 equiv) and the desired alkyl alcohol (2→10 equiv) in a microwave vial was added sodium hydride (2 equiv). 1,4-Dioxane or THF (~0.3 M) can be used as a solvent, if necessary. The reaction vial was sealed and heated at 85° C. until the reaction was complete by LC-MS and/or TLC analysis. The mixture was then diluted with $CH_2Cl_2$, washed with saturated $NH_4Cl$, and then extracted with $CH_2Cl_2$. The organic layers were washed with brine, dried over $Na_2SO_4$, filtered, concentrated under reduced pressure, and purified by silica gel chromatography (typical eluents included either a mixture of hexanes and EtOAc or a mixture of $CH_2Cl_2$ and MeOH or an 80:18:2 mixture of $CH_2Cl_2/CH_3OH$/concentrated $NH_4OH$) to afford the desired product v-D. The product structures prepared according to General Procedure D2 were confirmed by $^1H$ NMR and/or by mass analysis.

Step 4c. General Procedure D3 for formation of C8-alkoxy purines

To a mixture of desired intermediate iv-D(a-d) (1 equiv) and the desired alkyl alcohol (20 equiv) in 1,4-dioxane (~0.4 M) was added 2 N NaOH (1 mL). The reaction was heated at 85° C. until the reaction was complete by LC-MS and/or TLC analysis. The mixture was then diluted with $CH_2Cl_2$, washed with saturated $NH_4Cl$, and then extracted with $CH_2Cl_2$. The organic layers were washed with brine, dried over $Na_2SO_4$, filtered, concentrated under reduced pressure, and purified by silica gel chromatography (typical eluents included either a mixture of hexanes and EtOAc or a mixture of $CH_2Cl_2$ and MeOH or an 80:18:2 mixture of $CH_2Cl_2/CH_3OH$/concentrated $NH_4OH$) to afford the desired product v-D. The product structures prepared according to General Procedure D3 were confirmed by $^1H$ NMR and/or by mass analysis.

Step 5. General Procedure D4 for THP Deprotection

To a solution of THP protected alkoxy purine v-D (1 equiv) in MeOH (~0.07 M) was added TFA (excess, ≥20 equiv) at 0° C. The reaction mixture was then heated at 45-70° C. until the reaction was complete by LC-MS and/or TLC analysis. The mixture was concentrated under reduced pressure then diluted with $CH_2Cl_2$ and washed with saturated $NaHCO_3$ solution. The aqueous layer was extracted with $CH_2Cl_2$, and the combined organic layers were dried over $Na_2SO_4$, filtered, concentrated under reduced pressure and purified by silica gel chromatography (typical eluents included either a mixture of hexanes and EtOAc or a mixture of $CH_2Cl_2$ and MeOH or an 80:18:2 mixture of $CH_2Cl_2/CH_3OH$/concentrated $NH_4OH$) to afford the desired product vi-D. The product structures prepared according to General Procedure D4 were confirmed by $^1H$ NMR and/or by mass analysis.

Example 5. General Procedure E

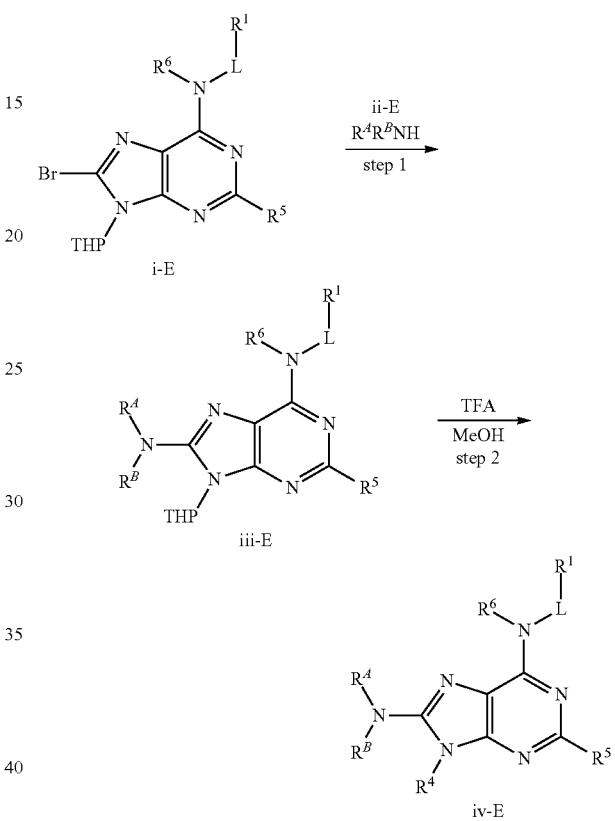

Step 1. General Procedure E1 for Formation of C8-Alkoxy Purines

A mixture of intermediate i-E (1 equiv) and the desired amine ii-E (excess), in solvent (typically NMP, DMF, or THF), was stirred at 50° C. until the reaction was complete by LC-MS and/or TLC analysis. The mixture was then diluted with $CH_2Cl_2$, washed with saturated $NH_4Cl$ solution, and then the aqueous layer was extracted with $CH_2Cl_2$. The combined organic layers were washed with brine, dried over $Na_2SO_4$, filtered, concentrated under reduced pressure, and purified by silica gel chromatography (typical eluents included, for example, a mixture of hexanes and EtOAc, or a mixture of $CH_2Cl_2$ and MeOH, or an 80:18:2 mixture of $CH_2Cl_2/CH_3OH$/concentrated $NH_4OH$).

Step 2. General Procedure E2 for THP Deprotection

To a solution of THP protected amino purine iii-E (1 equiv) in MeOH (~0.05 M) was added TFA (excess, ≥20 equiv) at 0° C. The reaction mixture stirred was then heated at 65° C. until the reaction was complete by LC-MS and/or TLC analysis. The mixture was concentrated under reduced pressure then diluted with $CH_2Cl_2$ and washed with saturated $NaHCO_3$ solution. The aqueous layer was extracted with $CH_2Cl_2$, and the combined organic layers were dried over $Na_2SO_4$, filtered, concentrated under reduced pressure and purified by silica gel chromatography to afford the desired product iv-E (typical eluents included, for example, a mixture of hexanes and EtOAc, or a mixture of $CH_2Cl_2$ and MeOH, or an 80:18:2 mixture of $CH_2Cl_2/CH_3OH/$ concentrated $NH_4OH$).

Example 6. General Procedure F

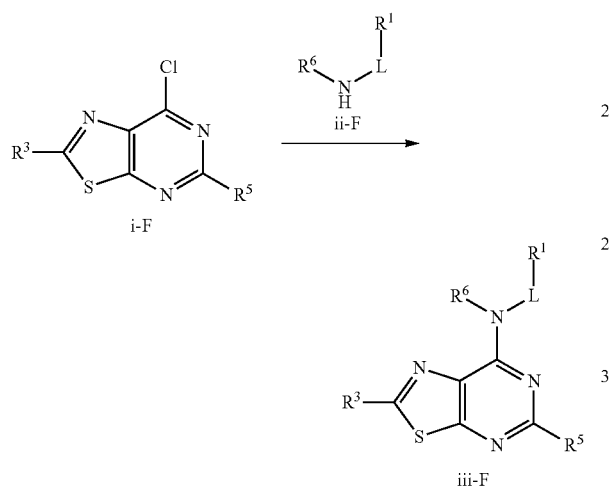

A mixture of the desired chlorothiazolopyrimidines i-F (1 equiv), desired aminomethyl heterocycle or benzylamine ii-F (1.1 equiv), and triethylamine ($NEt_3$) (1.5 equiv) in 1,4-dioxane (~0.1 M) was stirred at room temperature until the reaction was complete by LC-MS and/or TLC analysis. The reaction mixture was concentrated to dryness then re-dissolved in $CH_2Cl_2$ and washed with saturated $NaHCO_3$ solution. The organic extract was dried over $Na_2SO_4$, filtered and concentrated under reduced pressure. The resulting residue was purified by silica gel chromatography (typical eluents included, for example, a mixture of hexanes and EtOAc, or a mixture of $CH_2Cl_2$ and MeOH, or an 80:18:2 mixture of $CH_2Cl_2/CH_3OH/$concentrated $NH_4OH$) to afford the desired product iii-F. The product structures prepared according to General Procedure F were confirmed by $^1H$ NMR and/or by mass analysis.

Example 7. General Procedure G

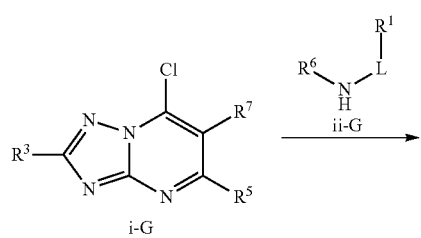

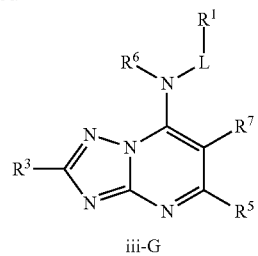

A mixture of the desired chlorotriazolopyrimidines i-G (1 equiv), desired aminomethyl heterocycle or benzylamine ii-G (1.2 equiv), and triethylamine ($NEt_3$) (1.5-3.5 equiv) in 1,4-dioxane (~0.2 M) was stirred at room temperature until the reaction was complete by LC-MS and/or TLC analysis. The crude reaction mixture was directly purified by silica gel chromatography (typical eluents included either a mixture of hexanes and EtOAc or a mixture of $CH_2Cl_2$ and MeOH or an 80:18:2 mixture of $CH_2Cl_2/CH_3OH/$concentrated $NH_4OH$) to afford the desired product iii-G. The product structures prepared according to General Procedure G were confirmed by $^1H$ NMR and/or by mass analysis.

Example 8. General Procedure H

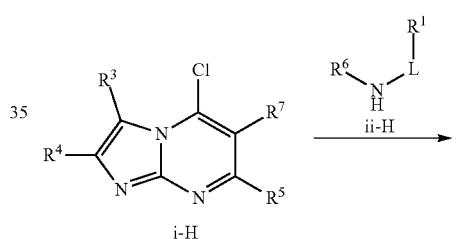

A mixture of the desired chloroimidazopyrimidines i-H (1 equiv), desired aminomethyl heterocycle or benzylamine ii-H (1.2 equiv), and triethylamine ($NEt_3$) (1.5-3.5 equiv) in 1,4-dioxane (~0.1 M) was stirred at 70° C. until the reaction was complete by LC-MS and/or TLC analysis. The crude reaction mixture was directly purified by silica gel chromatography (typical eluents included, for example, a mixture of hexanes and EtOAc, or a mixture of $CH_2Cl_2$ and MeOH, or an 80:18:2 mixture of $CH_2Cl_2/CH_3OH/$concentrated $NH_4OH$) to afford the desired product iii-H. The product structures prepared according to General Procedure H were confirmed by $^1H$ NMR and/or by mass analysis.

Example 9. General Procedure J

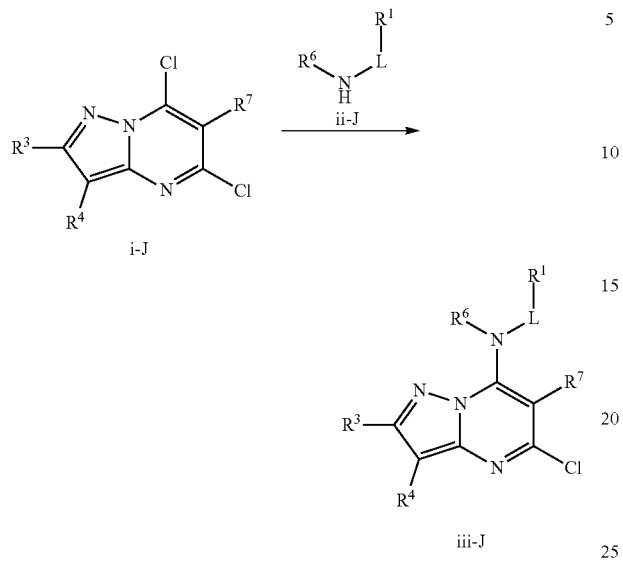

A mixture of the dichloroimidazopyrimidines i-J (1 equiv), desired aminomethyl heterocycle i-J (1.2 equiv), and triethylamine (NEt$_3$) (1.5-3.5 equiv) in 1,4-dioxane (0.2 M) was stirred at 55° C. until the reaction was complete by LC-MS and/or TLC analysis. The crude reaction mixture was directly purified by silica gel chromatography (typical eluents included either a mixture of hexanes and EtOAc or a mixture of CH$_2$Cl$_2$ and MeOH or a 90:9:1 mixture of CH$_2$Cl$_2$/CH$_3$OH/concentrated NH$_4$OH) to afford the desired product iii-J. The product structures prepared according to General Procedure J were confirmed by $^1$H NMR and/or by mass analysis.

Example 10. 6-Chloro-N-(furan-2-ylmethyl)-1H-pyrazolo[3,4-d]pyrimidin-4-amine

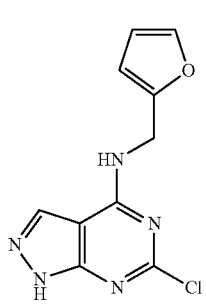

(85)

A mixture of 4,6-dichloro-1H-pyrazolo[3,4-d]pyrimidine (100 mg, 0.53 mmol), furfurylamine (0.051 mL, 0.58 mmol) and NEt$_3$ (0.11 mL, 0.79 mmol) in 1,4-dioxane (2 mL) was heated in a sealed tube at 150° C. for 30 minutes then cooled to room temperature. The solvent was removed under reduced pressure and the residue was re-dissolved in CH$_2$Cl$_2$ and washed with saturated NaHCO$_3$ solution, dried over Na$_2$SO$_4$, filtered and concentrated under reduced pressure. The crude residue was purified by silica gel chromatography (20-100% EtOAc in hexanes) to afford the title compound as a light yellow solid (65 mg, 49%): ESI MS [M+H]$^+$ 250; $^1$H NMR (300 MHz, DMSO-d$_6$) δ 13.59 (s, 1H), 9.12 (t, J=4.8 Hz, 1H), 8.14 (s, 1H), 7.63 (s, 1H), 6.44-6.38 (m, 2H), 4.84 (t, J=5.4 Hz, 2H).

Example 11. 2-(6-Chloro-4-((furan-2-ylmethyl)amino)-1H-pyrazolo[3,4-d]pyrimidin-1-yl)ethanol

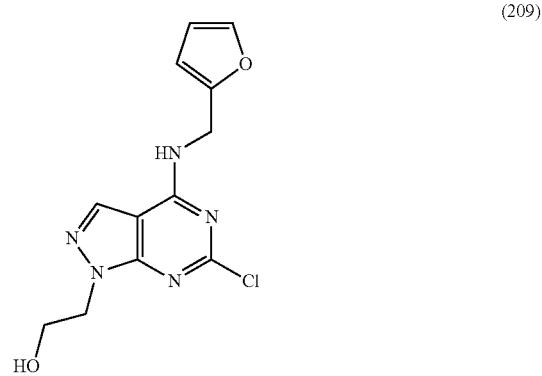 [SMILES: OCCn1ncc2c(NCc3ccco3)nc(Cl)nc21]

(209)

A mixture of 2-(4,6-dichloro-1H-pyrazolo[3,4-d]pyrimidin-1-yl)ethanol (57 mg, 0.244 mmol), furfurylamine (32 mg, 0.329 mmol) and DIPEA (0.12 mL, 0.687 mmol) in 1,4-dioxane (1.0 mL) was heated in a sealed tube at 100° C. for 1.5 h, then cooled to room temperature. The mixture was immediately concentrated and the crude residue was purified by chromatography on silica gel (gradient 0-10% methanol in DCM) to afford the title compound (67 mg, 93%) as an off-white solid: ESI MS [M+H]$^+$ 294; $^1$H NMR (300 MHz, DMSO-d$_6$) δ 9.17 (t, J=5.4 Hz, 1H), 8.15 (s, 1H), 7.63 (s, 1H), 6.44-6.38 (m, 2H), 4.84 (t, J=5.7 Hz, 1H), 4.70 (d, J=5.5 Hz, 2H), 4.26 (t, J=5.7 Hz, 2H), 3.77 (q, J=5.8 Hz, 2H).

Example 12. 6-Chloro-1-(2-fluoroethyl)-N-(furan-2-ylmethyl)-1H-pyrazolo[3,4-d]pyrimidin-4-amine

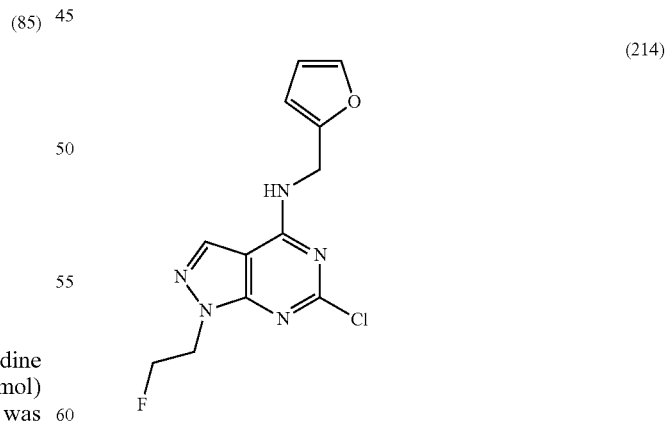

(214)

A mixture of 4,6-dichloro-1-(2-fluoroethyl)-1H-pyrazolo[3,4-d]pyrimidine (29.7 mg, 0.126 mmol), furfurylamine (36.3 mg, 0.374 mmol) and DIPEA (0.20 mL, 1.14 mmol) in 1,4-dioxane (2.4 mL) was heated in a sealed tube at 150° C. for 1 h, then cooled to room temperature. The solvents were removed by rotary evaporation, and the crude residue was purified by chromatography on silica gel (gradient 0-100% EtOAc in hexanes). The isolated chromatography product was then dissolved in acetonitrile/water, frozen and lyophilized to afford the title compound (18.2 mg, 48%) as an off-white solid: mp 125-128° C.; ESI MS [M+H]$^+$ m/z 296; $^1$H NMR (300 MHz, DMSO-d$_6$) δ 9.22 (t, J=5.4 Hz, 1H), 8.20 (s, 1H), 7.64 (dd, J=0.8, 1.8 Hz, 1H), 6.45-6.42 (m, 1H), 6.40-6.38 (m, 1H), 4.89 (t, J=4.9 Hz, 1H), 4.75-4.68 (m, 3H), 4.59 (t, J=4.9 Hz, 1H), 4.50 (t, J=4.9 Hz, 1H).

Example 13. 2-(6-Chloro-4-((pyridin-4-ylmethyl)amino)-1H-pyrazolo[3,4-d]pyrimidin-1-yl)ethanol

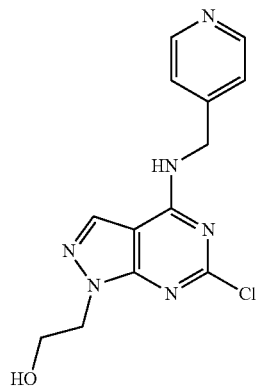

(218)

A mixture of 2-(4,6-dichloro-H-pyrazolo[3,4-d]pyrimidin-1-yl)ethanol (30 mg, 0.129 mmol), 4-(aminomethyl)pyridine (18.5 mg, 0.171 mmol) and DIPEA (0.12 mL, 0.687 mmol) in 1,4-dioxane (1.2 mL) was heated in a sealed tube at 100° C. for 45 min, then cooled to room temperature. The solvents were removed by rotary evaporation, and the crude residue was purified by chromatography on silica gel (gradient 0-100% CMA in dichloromethane). The product isolated from chromatography was dissolved in acetonitrile/water, frozen and lyophilized to afford the title compound (27.1 mg, 69%) as a light tan solid: ESI MS [M+H]$^+$ m/z 305; $^1$H NMR (300 MHz, DMSO-d$_6$) δ 9.29 (t, J=5.8 Hz, 1H), 8.52 (dd, J=1.6, 4.4 Hz, 2H), 8.18 (s, 1H), 7.34 (d, J=5.9 Hz, 2H), 4.84 (t, J=5.7 Hz, 1H), 4.74 (d, J=5.9 Hz, 2H), 4.28 (t, J=5.8 Hz, 2H), 3.78 (q, J=5.8 Hz, 2H).

Example 14. 6-Chloro-N-(pyridin-4-ylmethyl)-1H-pyrazolo[3,4-d]pyrimidin-4-amine

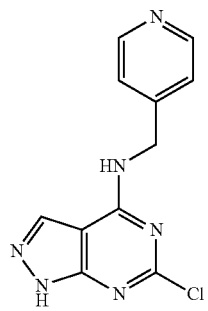

(217)

A mixture of 4,6-dichloro-1H-pyrazolo[3,4-d]pyrimidine (83 mg, 0.439 mmol), 4-(aminomethyl)pyridine (67 mg, 0.619 mmol) and DIPEA (0.30 mL, 1.72 mmol) in 1,4-dioxane (2.0 mL) was heated in a sealed tube at 100° C. for 45 min, then cooled to room temperature. The solvents were removed by rotary evaporation, and the crude residue was purified by chromatography on silica gel (gradient 0-100% CMA in dichloromethane). The product isolated from chromatography was dissolved in acetonitrile/water, frozen and lyophilized to afford the title compound (43.8 mg, 38%) as an off-white solid: ESI MS [M+H]$^+$ m/z 261; $^1$H NMR (300 MHz, DMSO-d$_6$) δ 13.63 (br s, 1H), 9.25 (t, J=6.3 Hz, 1H), 8.53 (d, J=5.9 Hz, 2H), 8.17 (s, 1H), 7.35 (d, J=5.8 Hz, 2H), 4.73 (d, J=5.7 Hz, 2H).

Example 15. 6-Chloro-N-(pyrimidin-4-ylmethyl)-1H-pyrazolo[3,4-d]pyrimidin-4-amine

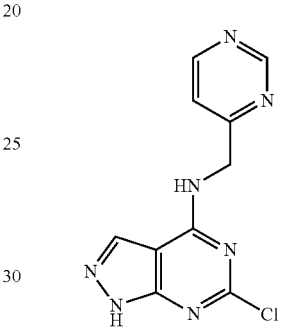

(220)

A mixture of 4,6-dichloro-1H-pyrazolo[3,4-d]pyrimidine (29 mg, 0.153 mmol), 4-(aminomethyl)pyrimidine hydrochloride (31.8 mg, 0.218 mmol) and DIPEA (0.14 mL, 0.802 mmol) in 1,4-dioxane (1.0 mL) was heated in a sealed tube at 100° C. for 90 min, then cooled to room temperature. The solvents were removed by rotary evaporation, and the crude residue was purified by chromatography on silica gel (gradient 0-10% MeOH in dichloromethane). The product isolated from chromatography was dissolved in acetonitrile/water, frozen and lyophilized to afford the title compound (35.3 mg, 88%) as an off-white solid: ESI MS [M+H]$^+$ m/z 262; $^1$H NMR (500 MHz, DMSO-d$_6$) δ 13.64 (br s, 1H), 9.34 (t, J=5.9 Hz, 1H), 9.14 (d, J=1.3 Hz, 1H), 8.74 (d, J=5.2 Hz, 1H), 8.20 (s, 1H), 7.48 (d, J=4.3 Hz, 1H), 4.79 (d, J=5.9 Hz, 2H).

Example 16. 6-Chloro-N-(thiazol-2-ylmethyl)-1H-pyrazolo[3,4-d]pyrimidin-4-amine

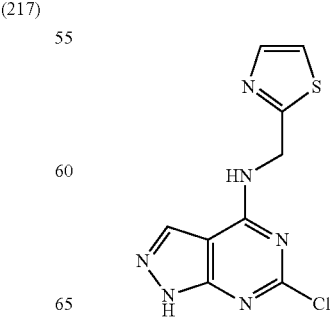

(222)

A mixture of 4,6-dichloro-1H-pyrazolo[3,4-d]pyrimidine (53.6 mg, 0.284 mmol), 2-(aminomethyl)thiazole dihydrochloride (75.4 mg, 0.403 mmol) and DIPEA (0.30 mL, 1.72 mmol) in 1,4-dioxane (1.2 mL) was heated in a sealed tube at 125° C. for 3 h, then cooled to room temperature. The solvents were removed by rotary evaporation, and the crude residue was purified by chromatography on silica gel (gradient 0-10% MeOH in dichloromethane). The product isolated from chromatography was dissolved in acetonitrile/water, frozen and lyophilized, then dried under vacuum at 75° C. for 16 h to afford the title compound (45.5 mg, 60%) as an off-white solid: ESI MS [M+H]+ m/z 267; $^1$H NMR (300 MHz, DMSO-$d_6$) δ 13.63 (br s, 1H), 9.52 (t, J=5.9 Hz, 1H), 8.17 (s, 1H), 7.77 (d, J=3.2 Hz, 1H), 7.66 (d, J=3.3 Hz, 1H), 4.98 (d, J=6.0 Hz, 2H).

Example 17. 5-(methylthio)-N-(thiazol-2-ylmethyl)-[1,2,4]triazolo[1,5-a][1,3,5]triazin-7-amine

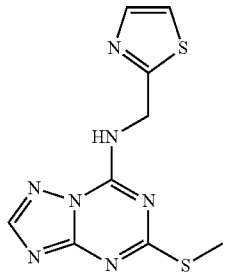

(342)

Step 1. 5-(methylthio)-[1,2,4]triazolo[1,5-a][1,3,5]triazin-7-yl trifluoromethanesulfonate

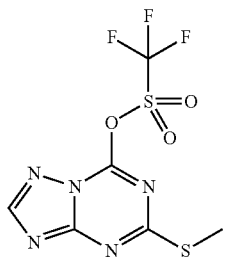 [SMILES: CSc1nc(OS(=O)(=O)C(F)(F)F)n2ncnc2n1]

A solution of 5-(methylthio)-[1,2,4]triazolo[1,5-a][1,3,5]triazin-7(6H)-one (79 mg, 0.431 mmol) in pyridine (1.0 mL) at 0° C. was treated with trifluoromethanesulfonic anhydride (0.08 mL, 0.48 mmol) and was allowed to warm to room temperature while stirring for 16 h. All volatiles were removed by rotary evaporation, and the crude residue (130 mg) was used immediately in the following step.

Step 2. 5-(methylthio)-N-(thiazol-2-ylmethyl)-[1,2,4]triazolo[1,5-a][1,3,5]triazin-7-amine A mixture of crude 5-(methylthio)-[1,2,4]triazolo[1,5-a][1,3,5]triazin-7-yl trifluoromethanesulfonate (130 mg, 0.43 mmol), 2-(aminomethyl)thiazole dihydrochloride (99 mg, 0.529 mmol) and DIPEA (0.33 mL, 1.89 mmol) in 1,4-dioxane (2.0 mL) was stirred at room temperature 16.5 h. All volatiles were removed by rotary evaporation, and the crude residue was purified by chromatography on silica gel (gradient 0-20% methanol in DCM) to afford the title compound (22 mg, 18% over 2 steps) as an off-white solid: ESI MS m/z 280 [M+H]+; $^1$H NMR (500 MHz, DMSO-$d_6$) δ 9.99 (t, J=6.0 Hz, 1H), 8.45 (s, 1H), 7.76 (d, J=3.3 Hz, 1H), 7.67 (d, J=3.3 Hz, 1H), 4.97 (d, J=6.1 Hz, 2H), 2.50 (s, 3H).

Example 18. 2-chloro-4-((pyridin-4-ylmethyl)amino)-5H-pyrrolo[2,3-d]pyrimidin-6(7H)-one (257)

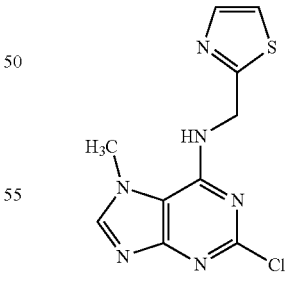

A mixture of 2,4-dichloro-5H-pyrrolo[2,3-d]pyrimidin-6(7H)-one (29.5 mg, 0.145 mmol), 4-(aminomethyl)pyridine (18.6 mg, 0.172 mmol) and DIPEA (0.04 mL, 0.23 mmol) in 1,4-dioxane (1.2 mL) was heated in a sealed tube at 60° C. for 6.5 h, then cooled to room temperature. The mixture was immediately concentrated and the crude residue was purified by chromatography on silica gel (gradient 0-100% CMA in dichloromethane). The isolated product was dissolved in acetonitrile/water, frozen and lyophilized to afford the title compound (5.0 mg, 93%) as an off-white solid: ESI MS [M+H]+ m/z 276; $^1$H NMR (300 MHz, DMSO-$d_6$) δ 11.30 (br s, 1H), 8.48 (dd, J=1.6, 4.4 Hz, 2H), 8.09 (br s, 1H), 7.26 (d, J=5.7 Hz, 2H), 4.47 (d, J=6.2 Hz, 2H), 3.41 (s, 2H).

Example 19. 2-Chloro-7-methyl-N-(thiazol-2-ylmethyl)-7H-purin-6-amine (304)

A mixture of 2,6-dichloro-7-methyl-7H-purine (60 mg, 0.30 mmol), thiazol-2-ylmethanamine dihydrochloride (67 mg, 0.36 mmol) and triethylamine (0.15 mL, 1.05 mmol) in 1,4-dioxane (2 mL) was stirred at 75° C. overnight. After this time the mixture was concentrated and the residue purified by column chromatography (silica gel, 0-6% MeOH in CH$_2$Cl$_2$) to afford the title compound as a white solid (48 mg, 58%): ESI MS (M+H) m/z 281; $^1$H NMR (300 MHz, DMSO-d$_6$) δ 8.27 (br s, 2H), 7.75 (d, J=3.3 Hz, 1H), 7.63 (d, J=3.3 Hz, 1H), 4.95 (d, J=5.7 Hz, 2H), 4.03 (s, 3H).

Example 20. 2-Chloro-N-(furan-2-ylmethyl)-7-methyl-7H-purin-6-amine

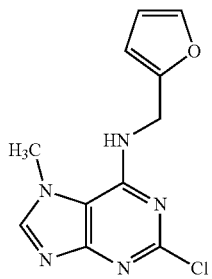

(314)

A mixture of 2,6-dichloro-7-methyl-7H-purine (60 mg, 0.30 mmol), furfurylamine (0.028 mL, 0.31 mmol) and triethylamine (0.043 mL, 0.59 mmol) in 1,4-dioxane (5 mL) was stirred at 50° C. overnight. After this time the mixture was concentrated and the residue purified by column chromatography (silica gel, 0-6% MeOH in CH$_2$Cl$_2$) to afford the title compound as an off-white solid (69 mg, 88%): ESI MS (M+H) m/z 264; $^1$H NMR (500 MHz, DMSO-d$_6$) δ 8.21 (s, 1H), 7.84 (s, 1H), 7.58 (s, 1H), 6.41-6.34 (m, 2H), 4.66 (d, J=5.5 Hz, 2H), 4.01 (s, 3H).

Example 21. 2-Chloro-7-methyl-N-(pyridin-4-ylmethyl)-7H-purin-6-amine

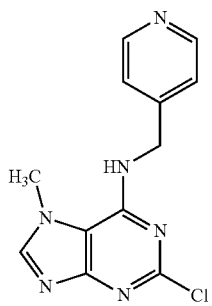

(313)

A mixture of 2,6-dichloro-7-methyl-7H-purine (60 mg, 0.30 mmol), 4-(aminomethyl)pyridine (0.031 mL, 0.31 mmol) and triethylamine (0.0.43 mL, 0.59 mmol) in 1,4-dioxane (5 mL) was stirred at 50° C. overnight. After this time the mixture was concentrated and the residue purified by column chromatography (silica gel, 0-6% MeOH, CH$_2$Cl$_2$) to afford the title compound as an off-white solid (43 mg, 53%): ESI MS (M+H) m/z 275; $^1$H NMR (500 MHz, DMSO-d$_6$) δ 8.49 (d, J=6.0 Hz, 2H), 8.24 (s, 1H), 7.97 (br s, 1H), 7.38 (d, J=6.0 Hz, 2H), 4.70 (t, J=6.0 Hz, 2H), 4.07 (s, 3H).

Example 22. 2-Chloro-7-methyl-N-(pyrimidin-4-ylmethyl)-7H-purin-6-amine

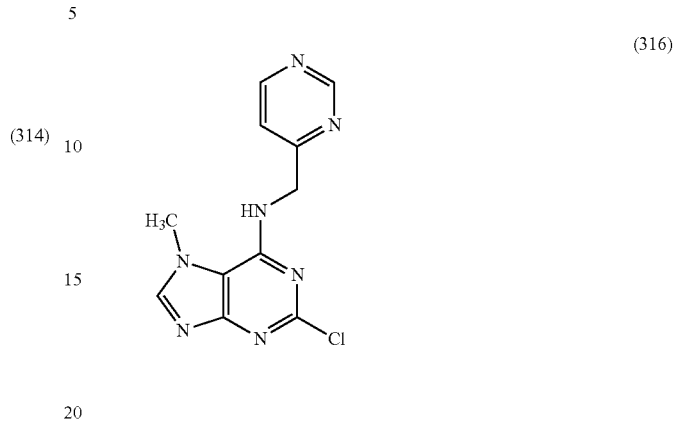

(316)

A mixture of 2,6-dichloro-7-methyl-7H-purine (60 mg, 0.30 mmol), 4-(aminomethyl)pyrimidine hydrochloride (45 mg, 0.31 mmol) and triethylamine (0.043 mL, 0.59 mmol) in 1,4-dioxane (5 mL) was stirred at 50° C. overnight. After this time the mixture was concentrated and the residue purified by column chromatography (silica gel, 0-6% MeOH, CH$_2$Cl$_2$) to afford the title compound as a tan solid (57 mg, 70%): ESI MS (M+H) m/z 276; $^1$H NMR (500 MHz, DMSO-d$_6$) δ 9.12 (d, J=1.0 Hz, 1H), 8.71 (d, J=5.5 Hz, 2H), 8.27 (s, 1H), 8.01 (s, 1H), 7.54 (d, J=5.5 Hz, 1H), 4.75 (d, J=6.0 Hz, 2H), 4.09 (s, 3H).

Example 23. 2-Chloro-7-methyl-8-propoxy-N-(pyridin-4-ylmethyl)-7H-purin-6-amine

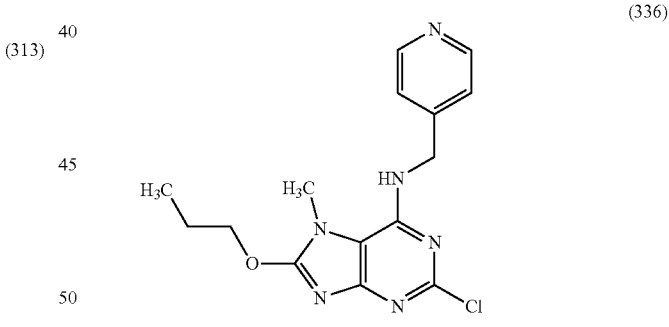

(336)

A mixture of 2,6-dichloro-7-methyl-8-propoxy-7H-purine (40 mg, 0.15 mmol), 4-(aminomethyl)pyridine (60 mg, 0.54 mmol) and triethylamine (0.04 mL, 0.29 mmol) in 1,4-dioxane was stirred at 90° C. for 8 h. After this time the mixture was concentrated and the residue purified by column chromatography (silica, 0-5% MeOH in CH$_2$Cl$_2$) to provide 2-chloro-7-methyl-8-propoxy-N-(pyridin-4-ylmethyl)-7H-purin-6-amine (9 mg, 18%): ESI MS (M+H) 333; $^1$H NMR (500 MHz, DMSO-d$_6$) δ 8.49-8.48 (m, 2H), 7.66 (t, J=5.7 Hz, 1H), 7.36-7.34 (m, 2H), 4.65 (d, J=5.7 Hz, 2H), 4.44 (t, J=6.5 Hz, 2H), 3.76 (s, 3H), 1.84-1.76 (m, 2H), 0.99 (t, J=7.4 Hz, 3H).

Example 24. 2-Chloro-7-methyl-8-propoxy-N-(thiazol-2-ylmethyl)-7H-purin-6-amine

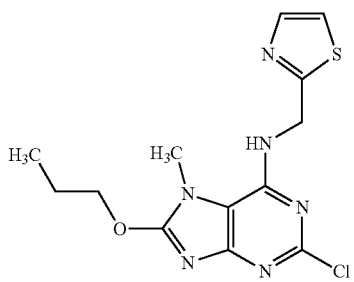

(335)

A mixture of 2,6-dichloro-7-methyl-8-propoxy-7H-purine (28 mg, 0.11 mmol), thiazol-2-ylmethanamine dihydrochloride (70 mg, 0.37 mmol) and triethylamine (0.16 mL, 1.14 mmol) in DMSO (1.5 mL) was stirred at 60° C. for 2 h. After this time the mixture was cooled to room temperature, diluted with EtOAc and washed with water and brine. The organic layer was concentrated and the resulting residue was purified by column chromatography (silica, 0-5% MeOH in CH$_2$Cl$_2$) to provide 2-chloro-7-methyl-8-propoxy-N-(thiazol-2-ylmethyl)-7H-purin-6-amine (21 mg, 56%): ESI MS (M+H) 339; $^1$H NMR (500 MHz, DMSO-d$_6$) δ 7.93 (s, 1H), 7.73 (d, J=3.3 Hz, 1H), 7.61 (d, J=3.3 Hz, 1H), 4.90 (s, 2H), 4.44 (t, J=6.5 Hz, 2H), 3.73 (s, 3H), 1.84-1.76 (m, 2H), 0.99 (t, J=7.4 Hz, 3H).

Example 25. 2-Chloro-7-methyl-8-propoxy-N-(pyrimidin-4-ylmethyl)-7H-purin-6-amine

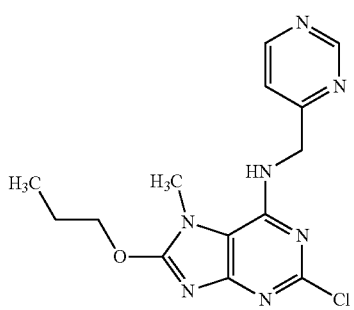

(336)

A mixture of 2,6-dichloro-7-methyl-8-propoxy-7H-purine (36 mg, 0.14 mmol), 4-(aminomethyl)pyrimidine hydrochloride (70 mg, 0.48 mmol) and triethylamine (0.20 mL, 1.43 mmol) in DMSO (1.5 mL) was stirred at 50° C. for 7 h. After this time the mixture was cooled to room temperature, diluted with EtOAc and washed with water and brine. The organic layer was concentrated and the resulting residue was purified by column chromatography (silica, 0-7% MeOH in CH$_2$Cl$_2$) to provide 2-chloro-7-methyl-8-propoxy-N-(pyrimidin-4-ylmethyl)-7H-purin-6-amine (24 mg, 51%): ESI MS (M+H) 334; $^1$H NMR (500 MHz, DMSO-d$_6$) δ 9.11 (d, J=1.3 Hz, 1H), 8.71 (d, J=5.2 Hz, 1H), 7.70 (t, J=5.8 Hz, 1H), 7.50 (dd, J=5.2, 1.3 Hz, 1H), 4.70 (d, J=5.8 Hz, 2H), 4.45 (t, J=6.5 Hz, 2H), 3.31 (s, 3H), 1.85-1.77 (m, 2H), 1.00 (t, J=7.4 Hz, 3H).

Example 26. 5-Chloro-N-(furan-2-ylmethyl)thiazolo[5,4-d]pyrimidin-7-amine

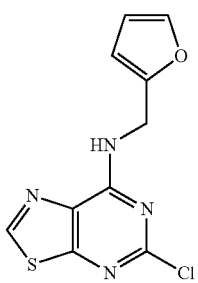

(253)

Following general procedure F, 5,7-Dichlorothiazolo[5,4-d]pyrimidine and furfurylamine were converted to 5-chloro-N-(furan-2-ylmethyl)thiazolo[5,4-d]pyrimidin-7-amine as a white solid (35 mg, 60%): ESI MS (M+H)$^+$ m/z 267; $^1$H NMR (300 MHz, DMSO-d$_6$) δ 9.27-9.21 (m, 2H), 7.58 (dd, J=1.8, 0.9 Hz, 1H), 6.40 (dd, J=3.0, 1.8 Hz, 1H), 6.31 (d, J=2.4 Hz, 1H), 4.66 (d, J=6.0 Hz, 2H).

Example 27. 5-Chloro-N-(pyridin-4-ylmethyl)thiazolo[5,4-d]pyrimidin-7-amine

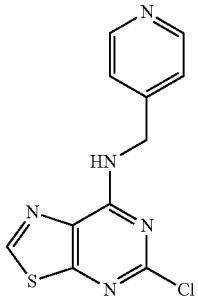

(256)

Following general procedure F, 5,7-Dichlorothiazolo[5,4-d]pyrimidine and 4-(aminomethyl)pyridine were converted to 5-chloro-N-(pyridin-4-ylmethyl)thiazolo[5,4-d]pyrimidin-7-amine as a white solid (55 mg, 83%): ESI MS (M+H)$^+$ m/z 278; $^1$H NMR (300 MHz, DMSO-d$_6$) δ 9.38 (t, J=6.3 Hz, 1H), 9.31 (s, 1H), 8.50 (d, J=6.0 Hz, 2H), 7.33 (d, J=6.0 Hz, 2H), 4.70 (d, J=6.3 Hz, 2H).

Example 28. 5-Chloro-2-(cyclobutylmethoxy)-N-(thiazol-2-ylmethyl)thiazolo[5,4-d]pyrimidin-7-amine

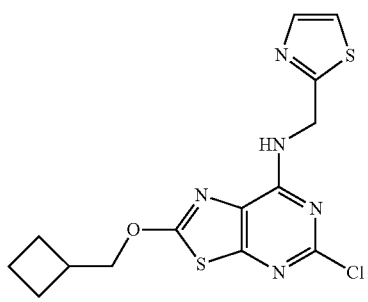

(341)

Step 1. 2-Bromo-5-chloro-N-(thiazol-2-ylmethyl)thiazolo[5,4-d]pyrimidin-7-amine

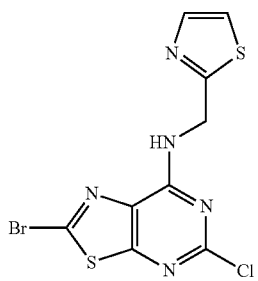 [SMILES: Clc1nc(NCc2nccs2)c2nc(Br)sc2n1]

A mixture of 2-bromo-5,7-dichlorothiazolo[5,4-d]pyrimidine (50 mg, 0.18 mmol), thiazol-2-ylmethanamine dihydrochloride (100 mg, 0.53 mmol) and triethylamine (0.23 mL, 1.65 mmol) in DMSO (3 mL) was stirred at 50° C. for 2 h. After this time the mixture was cooled to room temperature, diluted with EtOAc and washed with water and brine. The organic layer was dried over sodium sulfate, filtered and concentrated to obtain 2-bromo-5-chloro-N-(thiazol-2-ylmethyl)thiazolo[5,4-d]pyrimidin-7-amine (69 mg), which was used in the next step without further purification: ESI MS (M+H) 362; $^1$H NMR (500 MHz, DMSO-d$_6$) δ 9.65 (t, J=5.8 Hz, 1H), 7.75 (d, J=3.2 Hz, 1H), 7.64 (d, J=3.2 Hz, 1H), 4.93 (d, J=6.0 Hz, 2H).

Step 2. 5-Chloro-2-(cyclobutylmethoxy)-N-(thiazol-2-ylmethyl)thiazolo[5,4-d]pyrimidin-7-amine Sodium hydride (60% in mineral oil, 8 mg, 0.20 mmol) was carefully added to cyclobutylmethanol (1.0 mL) followed by 2-bromo-5-chloro-N-(thiazol-2-ylmethyl)thiazolo[5,4-d]pyrimidin-7-amine (69 mg, 0.19 mmol). The resulting mixture was stirred at 70° C. for 20 min. After this time the mixture was diluted with EtOAc and washed with water and brine. The organic layer was dried over sodium sulfate, filtered, and concentrated. The residue was purified by column chromatography (silica, 0-4% MeOH, CH$_2$Cl$_2$) to provide 5-chloro-2-(cyclobutylmethoxy)-N-(thiazol-2-ylmethyl)thiazolo[5,4-d]pyrimidin-7-amine (8 mg, 12% over two steps): ESI MS (M+H)$^+$ 368; $^1$H NMR (500 MHz, DMSO-d$_6$) δ 8.89 (d, J=5.8 Hz, 1H), 7.74 (d, J=3.3 Hz, 1H), 7.62 (d, J=3.3 Hz, 1H), 4.90 (d, J=5.8 Hz, 2H), 4.57 (d, J=6.8 Hz, 2H), 2.86-2.80 (m, 1H), 2.11-2.06 (m, 2H), 1.96-1.81 (m, 4H).

Example 29. N$^7$-(furan-2-ylmethyl)-3H-[1,2,3]triazolo[4,5-d]pyrimidine-5,7-diamine

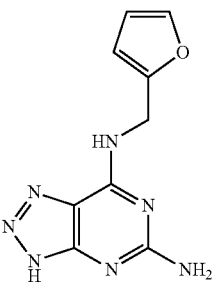

(279)

To a solution of 7-chloro-3H-[1,2,3]triazolo[4,5-d]pyrimidin-5-amine (31 mg, 0.18 mmol) in 1,4-dioxane (2 mL) was added furfurylamine (0.024 mL, 0.27 mmol) followed by triethylamine (0.075 mL, 0.54 mmol). The reaction was heated at 80° C. for 30 minutes then cooled to room temperature. The reaction mixture was partitioned between dichloromethane and saturated NaHCO$_3$ solution and the organic layer was collected and dried over sodium sulfate. The crude material was purified by silica gel chromatography (CH$_2$Cl$_2$ to 3% MeOH in CH$_2$Cl$_2$) to afford the title compound as an-off white solid (30 mg, 73%): ESI MS (M+H)$^+$ m/z 232; $^1$H NMR (500 MHz, DMSO-d$_6$) δ 14.50 (bs s, 1H), 7.91 (br s, 1H), 7.47 (dd, J=1.5, 0.5 Hz, 1H), 6.34 (dd, J=3.0, 1.5 Hz, 1H), 6.29 (dd, J=3.0, 1.0 Hz, 1H), 5.87 (br s, 2H), 4.78 (s, 2H).

Example 30. 5-Chloro-N-(furan-2-ylmethyl)-3H-[1,2,3]triazolo[4,5-d]pyrimidin-7-amine

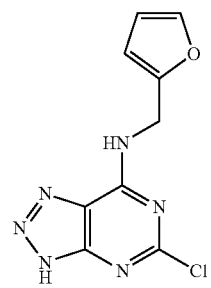

(285)

To a solution of LiCl (23 mg, 0.55 mmol) in N,N-dimethylacetamide (DMA, 1 mL) at 0° C. was added N$^7$-(furan-2-ylmethyl)-3H-[1,2,3]triazolo[4,5-d]pyrimidine-5,7-diamine (32 mg, 0.14 mmol), isoamyl nitrite (0.045 mL, 0.22 mmol), followed by thionyl chloride (0.013 mL, 0.17 mmol). The reaction was stirred overnight at room temperature. After this time, the reaction mixture was diluted with EtOAc and washed with water (3×15 mL), dried over Na$_2$SO$_4$, filtered and concentrated under reduced pressure. The crude material was purified by silica gel chromatography (CH$_2$Cl$_2$ to 4% MeOH in CH$_2$Cl$_2$) to afford the title compound as a white solid (8 mg, 23%): ESI MS (M−H)$^−$ m/z 249; $^1$H NMR (500 MHz, DMSO-d$_6$) δ 16.11 (br s, 1H), 9.07 (br s, 1H), 7.50-7.46 (m, 1H), 6.36-6.28 (m, 2H), 4.80 (br s, 2H).

Example 31. 5-Chloro-N-(thiazol-2-ylmethyl)-[1,2,4]triazolo[1,5-a]pyrimidin-7-amine

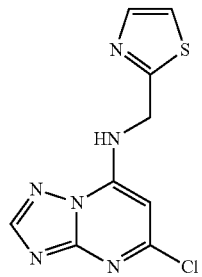

(281)

Following general procedure G, 5,7-Dichloro-[1,2,4]triazolo[1,5-a]pyrimidine and 2-(aminomethyl)thiazole dihydrochloride were converted to 5-chloro-N-(thiazol-2-ylmethyl)-[1,2,4]triazolo[1,5-a]pyrimidin-7-amine as a white solid (53 mg, 80%). ESI MS (M+H) m/z 267; $^1$H NMR (300 MHz, DMSO-d$_6$) δ 9.48 (s, 1H), 8.56 (s, 1H), 7.80 (d, J=3.3 Hz, 1H), 7.10 (d, J=3.3 Hz, 1H), 6.69 (s, 1H), 5.01 (s, 2H).

Example 32. 5-Chloro-N-(furan-2-ylmethyl)-[1,2,4]triazolo[1,5-a]pyrimidin-7-amine

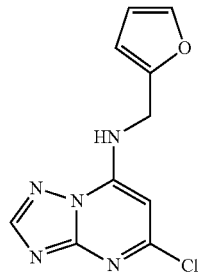

(284)

Following general procedure G, 5,7-Dichloro-[1,2,4]triazolo[1,5-a]pyrimidine and furfurylamine were converted to 5-chloro-N-(furan-2-ylmethyl)-[1,2,4]triazolo[1,5-a]pyrimidin-7-amine as a light yellow solid (20 mg, 51%). ESI MS (M+H) m/z 250; $^1$H NMR (300 MHz, DMSO-d$_6$) δ 9.25 (br s, 1H), 8.51 (s, 1H), 7.63 (dd, J=1.8, 0.9 Hz, 1H), 6.68 (s, 1H), 6.47 (d, J=2.4 Hz, 1H), 6.42 (dd, J=3.3, 1.8 Hz, 1H), 4.66 (d, J=5.1 Hz, 2H).

Example 33. 5-Chloro-N-(pyridin-4-ylmethyl)-[1,2,4]triazolo[1,5-a]pyrimidin-7-amine

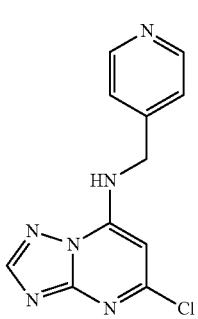

(283)

Following general procedure G, 5,7-Dichloro-[1,2,4]triazolo[1,5-a]pyrimidine and 4-(aminomethyl)pyridine were converted to 5-chloro-N-(pyridin-4-ylmethyl)-[1,2,4]triazolo[1,5-a]pyrimidin-7-amine as a light yellow solid (50 mg, 87%). ESI MS (M+H) m/z 261; $^1$H NMR (300 MHz, DMSO-d$_6$) δ 9.38 (s, 1H), 8.55-8.51 (m, 3H), 7.38 (d, J=6.0 Hz, 2H), 6.53 (s, 1H), 4.72 (s, 2H).

Example 34. 5-Chloro-N-(pyrimidin-4-ylmethyl)-[1,2,4]triazolo[1,5-a]pyrimidin-7-amine

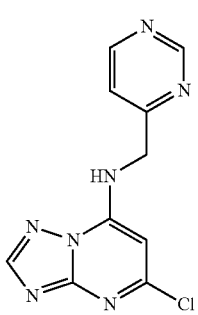

(286)

Following general procedure G, 5,7-Dichloro-[1,2,4]triazolo[1,5-a]pyrimidine and 4-(aminomethyl)pyrimidine hydrochloride were converted to 5-chloro-N-(pyrimidin-4-ylmethyl)-[1,2,4]triazolo[1,5-a]pyrimidin-7-amine as an off-white solid (41 mg, 75%). ESI MS (M+H) m/z 262; $^1$H NMR (300 MHz, DMSO-d$_6$) δ 9.22 (br s, 1H), 9.14 (d, J=1.2 Hz, 1H), 8.76 (d, J=5.4 Hz, 1H), 8.56 (s, 1H), 7.53 (dd, J=5.4, 1.5 Hz, 1H), 6.60 (s, 1H), 4.81 (d, J=5.1 Hz, 2H).

Example 35. 7-Chloro-N-(thiazol-2-ylmethyl)imidazo[1,2-a]pyrimidin-5-amine

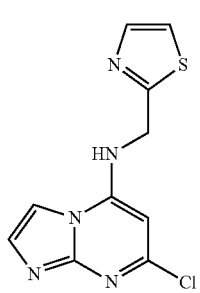

(295)

Following general procedure H, 5,7-Dichloroimidazo[1,2-a]pyrimidine and 2-(aminomethyl)thiazole dihydrochloride were converted to 7-chloro-N-(thiazol-2-ylmethyl)imidazo[1,2-a]pyrimidin-5-amine as a light yellow solid (22 mg, 40%). ESI MS (M+H) m/z 266; $^1$H NMR (300 MHz, DMSO-$d_6$) δ 9.02 (s, 1H), 7.96 (d, J=1.5 Hz, 1H), 7.81 (d, J=3.3 Hz, 1H), 7.72 (d, J=3.3 Hz, 1H), 7.58 (d, J=1.5 Hz, 1H), 6.34 (s, 1H), 5.02 (s, 2H).

Example 36. 7-Chloro-N-(furan-2-ylmethyl)imidazo[1,2-a]pyrimidin-5-amine

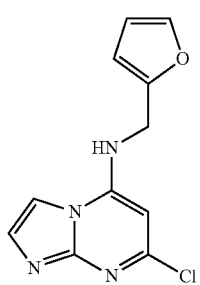

(288)

Following general procedure H, 5,7-Dichloroimidazo[1,2-a]pyrimidine and furfurylamine were converted to 7-chloro-N-(furan-2-ylmethyl)imidazo[1,2-a]pyrimidin-5-amine as a white solid (20 mg, 40%). ESI MS (M+H) m/z 249; $^1$H NMR (500 MHz, DMSO-$d_6$) δ 8.65 (br s, 1H), 7.95 (s, 1H), 7.64 (dd, J=2.0, 1.0 Hz, 1H), 7.53 (d, J=2.0 Hz, 1H), 6.51-6.44 (m, 2H), 6.34 (s, 1H), 4.65 (s, 2H).

Example 38. 7-chloro-N-(pyrimidin-4-ylmethyl)imidazo[1,2-a]pyrimidin-5-amine

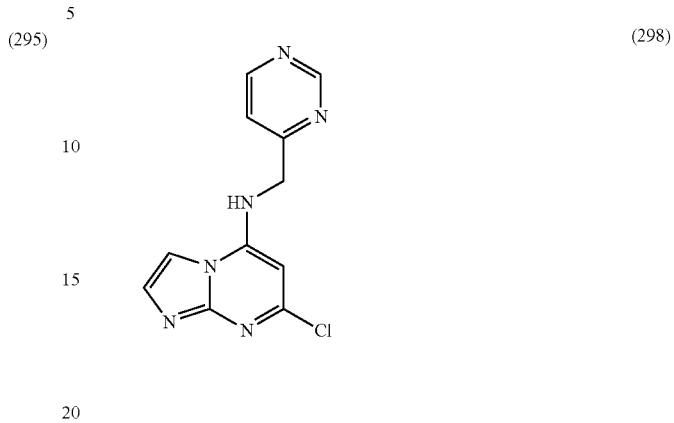

(298)

Following general procedure H, 5,7-Dichloroimidazo[1,2-a]pyrimidine and 4-(aminomethyl)pyrimidine hydrochloride were converted to 7-chloro-N-(pyrimidin-4-ylmethyl)imidazo[1,2-a]pyrimidin-5-amine as an off-white solid (22 mg, 42%). ESI MS (M+H) m/z 261; $^1$H NMR (300 MHz, DMSO-$d_6$) δ 9.14 (d, J=1.5 Hz, 1H), 8.84 (t, J=6.3 Hz, 1H), 7.78 (d, J=5.1 Hz, 1H), 7.98 (d, J=1.5 Hz, 1H), 7.58-7.56 (m, 2H), 6.18 (s, 1H), 4.80 (d, J=6.0 Hz, 2H).

Example 39. 5-chloro-N-(thiazol-2-ylmethyl)pyrazolo[1,5-a]pyrimidin-7-amine

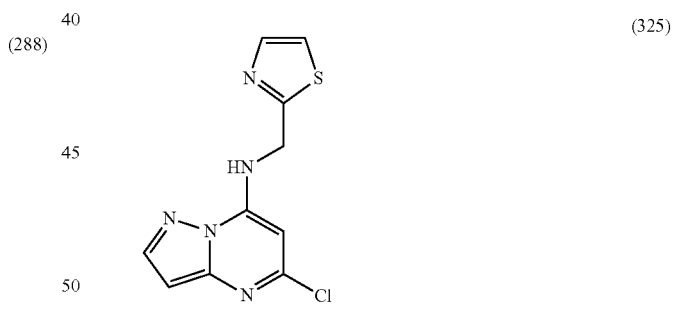

(325)

Following general procedure H, 5,7-Dichloropyrazolo[1,5-a]pyrimidine and 2-(aminomethyl)thiazole dihydrochloride were converted to 5-chloro-N-(thiazol-2-ylmethyl)pyrazolo[1,5-a]pyrimidin-7-amine as an off-white solid (82 mg, 88%). ESI MS (M+H) m/z 266; $^1$H NMR (300 MHz, DMSO-$d_6$) δ 9.14 (br s, 1H), 8.19 (d, J=2.4 Hz, 1H), 7.79 (d, J=3.3 Hz, 1H), 7.69 (d, J=3.3 Hz, 1H), 6.47 (d, J=2.1 Hz, 1H), 6.32 (s, 1H), 4.98 (br s, 2H).

Example 40. 5-Chloro-N-(furan-2-ylmethyl)pyrazolo[1,5-a]pyrimidin-7-amine

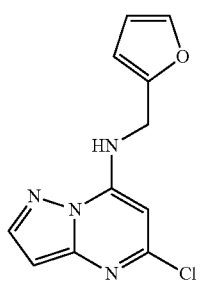

(322)

Following general procedure H, 5,7-Dichloropyrazolo[1,5-a]pyrimidine a and furfurylamine were converted to 5-chloro-N-(furan-2-ylmethyl)pyrazolo[1,5-a]pyrimidin-7-amine as a light yellow solid (62 mg, 70%). ESI MS (M+H) m/z 249; $^1$H NMR (500 MHz, DMSO-$d_6$) δ 8.65 (br s, 1H), 8.14 (d, J=2.4 Hz, 1H), 7.62 (dd, J=1.8, 0.9 Hz, 1H), 6.45-6.41 (m, 3H), 6.35 (s, 1H), 4.64 (br s, 2H).

Example 41. 5-chloro-N-(pyrimidin-4-ylmethyl)pyrazolo[1,5-a]pyrimidin-7-amine

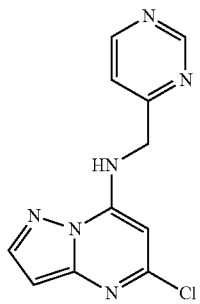

(330)

Following general procedure H, 5,7-Dichloropyrazolo[1,5-a]pyrimidine a and 4-(aminomethyl)pyrimidine hydrochloride were converted to 5-chloro-N-(pyrimidin-4-ylmethyl)pyrazolo[1,5-a]pyrimidin-7-amine as a white solid (69 mg, 77%). ESI MS (M+H) m/z 261; $^1$H NMR (300 MHz, DMSO-$d_6$) δ 9.15 (d, J=1.2 Hz, 1H), 8.90 (br s, 1H), 8.76 (d, J=5.1 Hz, 1H), 8.19 (d, J=2.4 Hz, 1H), 7.49 (dd, J=5.4, 1.5 Hz, 1H), 6.47 (d, J=2.4 Hz, 1H), 6.23 (s, 1H), 4.79 (d, J=5.4 Hz, 2H).

Example 42. 2-Chloro-N-(furan-2-ylmethyl)thieno[2,3-d]pyrimidin-4-amine

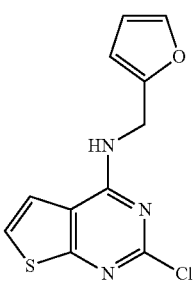

(56)

To a solution of 2,4-dichlorothieno[2,3-d]pyrimidine (142 mg, 0.69 mmol) in 1,4-dioxane (10 mL) was added furfurylamine (0.07 mL, 0.76 mmol) followed by triethylamine (0.14 mL, 1.03 mmol). The reaction was heated at 100° C. for 4 h then cooled to room temperature. The reaction mixture was partitioned between dichloromethane and saturated NaHCO$_3$ solution and the organic layer was collected and dried over sodium sulfate. The crude material was purified by silica gel chromatography (5-50% EtOAc in hexanes) to afford the title compound as a white solid (158 mg, 86%): ESI MS (M+H)$^+$ m/z 266; $^1$H NMR (300 MHz, DMSO-$d_6$) δ 8.91 (t, J=5.4 Hz, 1H), 7.65-7.60 (m, 3H), 6.43 (dd, J=3.3, 1.8 Hz, 1H), 6.37 (d, J=2.7 Hz, 1H), 4.69 (d, J=5.4 Hz, 2H).

Example 43. 2-Chloro-N-(furan-2-ylmethyl)-6,7-dihydro-5H-cyclopenta[d]pyrimidin-4-amine (466)

To a solution of 2,4-dichloro-6,7-dihydro-5H-cyclopenta[d]pyrimidine (188 mg, 0.99 mmol) in 1,4-dioxane (10 mL) was added furfurylamine (0.096 mL, 1.09 mmol) followed by triethylamine (0.14 mL, 1.48 mmol). The reaction was heated at 100° C. for 2 h then cooled to room temperature. The reaction mixture was partitioned between dichloromethane and saturated NaHCO$_3$ solution and the organic layer was collected and dried over sodium sulfate. The crude material was purified by silica gel chromatography (5-50% EtOAc in hexanes) to afford the title compound as a white solid (135 mg, 55%): ESI MS (M+H)$^+$ m/z 250; $^1$H NMR (300 MHz, DMSO-$d_6$) δ 7.85 (t, J=5.7 Hz, 1H), 7.58 (dd, J=1.8, 0.6 Hz, 1H), 6.39 (dd, J=3.3, 1.8 Hz, 1H), 6.27 (dd, J=3.3, 0.6 Hz, 1H), 4.52 (d, J=5.7 Hz, 2H), 2.72 (t, J=7.5 Hz, 2H), 2.62 (t, J=7.5 Hz, 2H), 2.05-1.95 (m, 2H).

Table 2 shows a list of representative compounds that were prepared using the methods described herein and characterized via mass spectrometry.

TABLE 2

| Cpd No. | m/z |
|---|---|
| (1) | 240 |
| (2) | 317 |
| (3) | 215 |
| (4) | 308 |
| (4) | 216 |
| (5) | 308 |
| (7) | 227 |
| (8) | 231 |
| (9) | 270 |
| (10) | 294 |
| (11) | 258 |
| (12) | 244 |
| (13) | 280 |
| (14) | 240 |
| (15) | 284 |
| (16) | 233 |
| (17) | 284 |
| (18) | 284 |
| (19) | 245 |
| (20) | 230 |
| (21) | 232 |
| (22) | 215 |
| (23) | 294 |
| (24) | 284 |
| (25) | 254 |
| (26) | 308 |
| (27) | 241 |
| (28) | 258 |
| (29) | 254 |
| (30) | 241 |
| (31) | 242 |
| (32) | 254 |
| (33) | 284 |
| (34) | 230 |
| (35) | 251 |
| (36) | 246 |
| (37) | 226 |
| (38) | 292 |
| (39) | 294 |
| (40) | 270 |
| (41) | 241 |
| (42) | 251 |
| (43) | 233 |
| (44) | 284 |
| (45) | 230 |
| (46) | 230 |
| (47) | 241 |
| (48) | 215 |
| (49) | 242 |
| (50) | 218 |
| (51) | 229 |
| (52) | 232 |
| (53) | 262 |
| (54) | 230 |
| (55) | 249 |
| (57) | 249 |
| (58) | 234 |
| (59) | 282 |
| (60) | 259 |
| (61) | 266 |
| (62) | 244 |
| (63) | 228 |
| (64) | 228 |
| (65) | 256 |
| (66) | 215 |
| (67) | 258 |
| (68) | 228 |
| (69) | 232 |
| (70) | 284 |
| (71) | 307 |
| (72) | 341 |
| (73) | 294 |
| (74) | 259 |
| (75) | 307 |
| (76) | 341 |
| (77) | 293 |
| (78) | 307 |
| (79) | 341 |

TABLE 2-continued

| Cpd No. | m/z |
|---|---|
| (80) | 260 |
| (81) | 267 |
| (82) | 229 |
| (83) | 291 |
| (84) | 263 |
| (86) | 325 |
| (87) | 230 |
| (88) | 327 |
| (89) | 326 |
| (90) | 264 |
| (91) | 306 |
| (92) | 292 |
| (93) | 326 |
| (94) | 307 |
| (95) | 290 |
| (96) | 256 |
| (97) | 292 |
| (98) | 307 |
| (99) | 341 |
| (100) | 260 |
| (101) | 289 |
| (102) | 335 |
| (103) | 275 |
| (104) | 321 |
| (105) | 307 |
| (106) | 303 |
| (107) | 266 |
| (108) | 307 |
| (109) | 279 |
| (110) | 261 |
| (111) | 311 |
| (112) | 279 |
| (113) | 279 |
| (114) | 278 |
| (115) | 263 |
| (116) | 284 |
| (117) | 321 |
| (118) | 293 |
| (119) | 274 |
| (120) | 274 |
| (121) | 318 |
| (122) | 304 |
| (123) | 280 |
| (124) | 280 |
| (125) | 324 |
| (126) | 275 |
| (127) | 305 |
| (128) | 319 |
| (129) | 262 |
| (130) | 326 |
| (131) | 267 |
| (132) | 331 |
| (133) | 291 |
| (134) | 261 |
| (135) | 322 |
| (136) | 300 |
| (136) | 275 |
| (137) | 308 |
| (138) | 323 |
| (139) | 331 |
| (140) | 293 |
| (141) | 301 |
| (142) | 307 |
| (143) | 341 |
| (144) | 302 |
| (145) | 272 |
| (146) | 265 |
| (147) | 305 |
| (148) | 291 |
| (149) | 258 |
| (150) | 295 |
| (151) | 285 |
| (152) | 284 |
| (153) | 334 |
| (154) | 307 |
| (155) | 321 |
| (156) | 289 |
| (157) | 310 |

TABLE 2-continued

| Cpd No. | m/z |
|---|---|
| (158) | 293 |
| (159) | 281 |
| (160) | 345 |
| (161) | 320 |
| (162) | 275 |
| (163) | 299 |
| (165) | 292 |
| (166) | 293 |
| (167) | 307 |
| (168) | 346 |
| (169) | 254 |
| (170) | 279 |
| (171) | 272 |
| (172) | 306 |
| (173) | 332 |
| (174) | 261 |
| (175) | 251 |
| (176) | 261 |
| (177) | 292 |
| (178) | 250 |
| (179) | 262 |
| (180) | 306 |
| (181) | 292 |
| (182) | 333 |
| (183) | 332 |
| (184) | 291 |
| (185) | 311 |
| (186) | 307 |
| (187) | 306 |
| (188) | 275 |
| (188) | 292 |
| (189) | 274 |
| (190) | 346 |
| (191) | 307 |
| (192) | 312 |
| (193) | 306 |
| (194) | 306 |
| (195) | 320 |
| (197) | 374 |
| (198) | 249 |
| (199) | 291 |
| (200) | 414 |
| (201) | 292 |
| (202) | 323 |
| (203) | 334 |
| (204) | 293 |
| (205) | 283 |
| (206) | 320 |
| (207) | 294 |
| (208) | 300 |
| (210) | 295 |
| (211) | 327 |
| (212) | 329 |
| (213) | 306 |
| (215) | 316 |
| (216) | 302 |
| (219) | 321 |
| (221) | 336 |
| (223) | 272 |
| (224) | 280 |
| (225) | 323 |
| (226) | 278 |
| (227) | 279 |
| (228) | 294 |
| (229) | 295 |
| (230) | 297 |
| (231) | 304 |
| (232) | 308 |
| (233) | 294 |
| (234) | 315 |
| (235) | 293 |
| (236) | 316 |
| (237) | 290 |
| (238) | 293 |
| (239) | 308 |
| (240) | 321 |
| (241) | 291 |
| (241) | 281 |

TABLE 2-continued

| Cpd No. | m/z |
|---|---|
| (242) | 304 |
| (243) | 293 |
| (244) | 290 |
| (245) | 296 |
| (246) | 331 |
| (247) | 291 |
| (248) | 276 |
| (249) | 324 |
| (250) | 318 |
| (251) | 260 |
| (252) | 307 |
| (254) | 293 |
| (255) | 277 |
| (258) | 319 |
| (259) | 320 |
| (260) | 309 |
| (261) | 292 |
| (262) | 307 |
| (263) | 274 |
| (264) | 342 |
| (265) | 339 |
| (266) | 294 |
| (267) | 334 |
| (268) | 275 |
| (269) | 322 |
| (270) | 348 |
| (271) | 325 |
| (272) | 333 |
| (273) | 305 |
| (274) | 325 |
| (275) | 310 |
| (276) | 341 |
| (277) | 319 |
| (278) | 341 |
| (280) | 295 |
| (282) | 319 |
| (287) | 335 |
| (289) | 337 |
| (290) | 335 |
| (291) | 349 |
| (292) | 308 |
| (293) | 324 |
| (294) | 331 |
| (296) | 338 |
| (297) | 324 |
| (299) | 359 |
| (300) | 336 |
| (302) | 365 |
| (303) | 308 |
| (305) | 333 |
| (306) | 352 |
| (307) | 345 |
| (308) | 334 |
| (309) | 322 |
| (310) | 327 |
| (311) | 322 |
| (312) | 369 |
| (315) | 321 |
| (317) | 321 |
| (318) | 339 |
| (319) | 336 |
| (320) | 306 |
| (321) | 332 |
| (323) | 251 |
| (324) | 351 |
| (326) | 346 |
| (327) | 432 |
| (328) | 341 |
| (329) | 380 |
| (331) | 360 |
| (332) | 365 |
| (333) | 321 |
| (334) | 359 |
| (338) | 348 |
| (339) | 363 |
| (340) | 375 |
| (343) | 249 |
| (344) | 367 |

TABLE 2-continued

| Cpd No. | m/z |
|---|---|
| (346) | 353 |
| (347) | 347 |
| (348) | 380 |
| (349) | 342 |
| (350) | 260 |
| (351) | 311 |
| (352) | 278 |
| (353) | 261 |
| (354) | 277 |
| (355) | 260 |
| (356) | 261 |
| (357) | 261 |
| (358) | 262 |
| (359) | 274 |
| (360) | 262 |
| (361) | 261 |
| (362) | 387 |
| (363) | 280 |
| (364) | 280 |
| (365) | 276 |
| (366) | 275 |
| (367) | 251 |
| (368) | 281 |
| (369) | 274 |
| (370) | 311 |
| (371) | 245 |
| (372) | 266 |
| (373) | 266 |
| (374) | 292 |
| (375) | 297 |
| (376) | 297 |
| (377) | 283 |
| (378) | 267 |
| (379) | 250 |
| (380) | 244 |
| (381) | 267 |
| (382) | 341 |
| (383) | 276 |
| (384) | 330 |
| (385) | 288 |
| (386) | 341 |
| (387) | 370 |
| (388) | 361 |
| (389) | 325 |
| (390) | 344 |
| (391) | 379 |
| (392) | 365 |
| (393) | 369 |
| (394) | 396 |
| (395) | 347 |
| (396) | 377 |
| (397) | 366 |
| (398) | 362 |
| (399) | 379 |
| (400) | 530 |
| (401) | 403 |
| (402) | 394 |
| (403) | 230 |
| (404) | 227 |
| (405) | 284 |
| (406) | 217 |
| (407) | 230 |
| (408) | 217 |
| (409) | 228 |
| (410) | 217 |
| (411) | 230 |
| (465) | 216 |
| (467) | 240 |
| (469) | 378 |
| (470) | 297 |
| (471) | 450 |
| (472) | 350 |
| (473) | 367 |
| (474) | 378 |
| (475) | 367 |
| (476) | 395 |
| (477) | 322 |
| (478) | 336 |
| (479) | 335 |
| (480) | 350 |
| (481) | 386 |
| (482) | 383 |
| (483) | 373 |
| (484) | 332 |
| (485) | 349 |
| (486) | 318 |
| (487) | 278 |
| (488) | 387 |
| (489) | 334 |
| (490) | 356 |
| (491) | 339 |
| (492) | 370 |
| (493) | 353 |
| (494) | 278 |
| (495) | 278 |
| (496) | 361 |
| (497) | 339 |
| (498) | 267 |
| (499) | 379 |
| (500) | 374 |
| (501) | 267 |
| (502) | 269 |
| (503) | 252 |
| (504) | 355 |
| (505) | 364 |
| (506) | 374 |
| (507) | 374 |
| (508) | 351 |
| (509) | 368 |
| (510) | 310 |
| (511) | 341 |

Example 44. Primary Splicing Assay

The primary splicing assay was carried out using human embryonic kidney 293T (HEK293T) routinely maintained in Dulbecco's Modified Eagle's media (DMEM) (GIBCO ref. 11995-065). The media was supplemented with 2 mM L-glutamine, 1% penicillin/streptomycin and 10% fetal bovine serum (SIGMA cat. 12306C). Splicing analysis was made possible by using an FD (familial dysautomonia) IKBKAP minigene which contained exon 19 through exon 21, including intervening introns, and also the T→C Thymine to cytosine transition located 6 base-pairs from the end of IKBKAP exon 20; See SEQ ID NO:3 for the complete sequence of plasmid pcDNA3.1/V5HisTOPO with Renilla-Familial Dysautonomia minigene-Firefly. Firefly luciferase (SEQ ID NO: 14) was utilized as a splicing reporter, located downstream of exon 21, and Renilla luciferase (SEQ ID NO:13) was used as a control, located upstream of exon 19. The sequence of exon 19 is presented as SEQ ID NO:7; the Intron between Exon 19 and Exon 20 is SEQ ID NO:8; exon 20 is SEQ ID NO:9; the intron between Exon 19 and Exon 20 is SEQ ID NO: 10; exon 21 is SEQ ID NO: 11, and the spliced sequence of exons 19-20-21 is SEQ ID NO: 12. HEK293T cells were plated in a 6-well plate 24 hours prior to transfection. Transfection was carried out using a mixture of Opti-MEM (GIBCO ref. 31985), IKBKAP minigene, and Fugene HD (PROMEGA ref. E2311), incubated in DMEM media containing HEK293T cells at 37° C. The ratio of Opti-MEM, minigene, and Fugene was kept at approximately 9:1.5:1, with a total volume of 150 µL of transfection mixture applied per well.

After 4 hours of transfection, the cells were then plated in a 96-well plate coated with poly-L-lysine (SIGMA cat. P4707) for treatment scheduled 24 hours later. Treatment with compounds was performed at 8 concentrations, each diluted in PBS with a final DMSO concentration of 0.5%. After 24 hours of treatment, cells were washed in the poly-L-lysine coated 96-well plate using PBS and subsequently harvested using Passive Lysis Buffer (Promega cat. E196). Cell lysate was transferred to a black and white 96-well plate and analyzed for splicing correction using a Glomax luminometer (PROMEGA GloMax® 96 Microplate Luminometer w/Dual Injectors cat. E6521) and Promega Dual Glo Firefly and Stop and Glo *Renilla* reagents (Cat. E196). The compound's ability to correct splicing and promote exon 20 inclusion was marked by an increase in Firefly signal. *Renilla* signal, which is independent of exon 20 inclusion, was used to correct for cell number. Using the ratio of Firefly to *Renilla* signal, a dose response curve was produced, which referenced kinetin and DMSO Firefly/*Renilla* ratios as positive and negative controls, respectively.

Table 3 shows $EC_k$ data for representative compounds (Cpd #) tested in the Primary Assay and Table 4 shows the max efficacy ($E_{max}$, %) for representative compounds (Cpd #) tested in the Primary Assay.

TABLE 3

| Cpd # | $EC_k$ (µM) |
|---|---|
| (5) | 63.50 |
| (15) | 157.90 |
| (25) | 9.35 |
| (28) | 122.85 |
| (32) | 60.00 |
| (34) | 26.60 |
| (37) | 36.50 |
| (48) | 72.75 |
| (49) | 42.50 |
| (55) | 1.71 |
| (56) | 8.23 |
| (57) | 31.20 |
| (58) | 17.95 |
| (73) | 17.05 |
| (77) | 1-10 (RT-PCR)[b] |
| (81) | 3.08 |
| (84) | 1-10 (RT-PCR)[a] |
| (90) | 11.85 |
| (94) | 10-31.6 (RT-PCR)[a] |
| (95) | 121.65 |
| (100) | 2.18 |
| (104) | 12.02 |
| (105) | 10.36/Firefly only[c] |
| (107) | 4.58/Firefly only[c] |
| (109) | 12.16/Firefly only[c] |
| (110) | 4.92/Firefly only[c] |
| (111) | 9.3/Firefly only[c] |
| (112) | 5.33/Firefly only[c] |
| (113) | 5.17 |
| (114) | 6.59/Firefly only[c] |
| (115) | 5.92 |
| (116) | 31.80 |
| (118) | 10.50 |
| (119) | 11.20 |
| (120) | 2.75 |
| (121) | 17.30 |
| (122) | 5.65 |
| (123) | 4.90 |
| (124) | 2.41 |
| (125) | 6.52 |
| (126) | 4.73 |
| (127) | 5.45 |
| (128) | 15.45 |
| (129) | 5.60 |
| (130) | 8.90 |
| (131) | 7.00 |
| (133) | 11.81 |
| (134) | 6.25 |
| (135) | 9.06 |
| (136) | 7.52 |

TABLE 3-continued

| Cpd # | $EC_k$ (µM) |
|---|---|
| (137) | 7.25 |
| (138) | 12.75 |
| (142) | 16.10 |
| (144) | 7.70 |
| (146) | 9.41 |
| (150) | 1-10 (RT-PCR)[a] |
| (154) | 22.25 |
| (155) | 22.25 |
| (156) | 15.80 |
| (158) | 13.40 |
| (159) | 1-10 (RT-PCR)[a] |
| (162) | 48.70 |
| (170) | 49.55 |
| (181) | 8.40 |
| (184) | 3.62 |
| (188) | 11.70 |
| (191) | 5.92 |
| (192) | 7.13 |
| (194) | 4.49 |
| (198) | 5.01 |
| (202) | 9.35 |
| (205) | 6.41 |
| (207) | 75.80 |
| (208) | 107.00 |
| (209) | 12.20 |
| (210) | 69.20 |
| (211) | 7.73 |
| (214) | 11.25 |
| (217) | 7.07 |
| (218) | 21.00 |
| (220) | 8.62 |
| (222) | 8.99 |
| (224) | 9.49 |
| (225) | 21.05 |
| (226) | 1.80 |
| (227) | 23.30 |
| (228) | 15.65 |
| (230) | 1.50 |
| (233) | 1.59 |
| (234) | 19.90 |
| (238) | 64.80 |
| (239) | 2.60 |
| (240) | 18.25 |
| (243) | 17.00 |
| (244) | 7.05 |
| (245) | 15.45 |
| (247) | 5.41 |
| (249) | 0.72 |
| (250) | 62.80 |
| (251) | 3.65 |
| (253) | 11.85 |
| (254) | 13.20 |
| (256) | 17.35 |
| (258) | 15.75 |
| (259) | 0.38 |
| (260) | 3.43 |
| (261) | 2.62 |
| (262) | 28.45 |
| (263) | 27.40 |
| (265) | 7.33 |
| (266) | 8.52 |
| (267) | 2.40 |
| (269) | 1.39 |
| (270) | 0.59 |
| (271) | 0.29 |
| (272) | 2.60 |
| (273) | 0.62 |
| (274) | 0.42 |
| (275) | 0.75 |
| (276) | 1.13 |
| (277) | 0.46 |
| (278) | 6.37 |
| (282) | 0.42 |
| (285) | 6.78 |
| (287) | 7.56 |
| (289) | 0.87 |
| (290) | 2.04 |
| (291) | 3.47 |

TABLE 3-continued

| Cpd # | EC$_k$ (μM) |
|---|---|
| (292) | 0.24 |
| (293) | 1.78 |
| (294) | 0.44 |
| (296) | 1.81 |
| (297) | 4.09 |
| (299) | 1.30 |
| (300) | 10.00 |
| (302) | 1.42 |
| (303) | 1.51 |
| (304) | 4.14 |
| (305) | 0.43 |
| (306) | 0.70 |
| (307) | 0.21 |
| (308) | 0.15 |
| (309) | 2.08 |
| (310) | 1.50 |
| (311) | 0.56 |
| (312) | 2.29 |
| (313) | 7.48 |
| (314) | 2.31 |
| (315) | 2.52 |
| (316) | 7.09 |
| (317) | 0.16 |
| (318) | 0.54 |
| (319) | 1.56 |
| (320) | 0.52 |
| (321) | 1.41 |
| (324) | 0.16 |
| (326) | 0.07 |
| (327) | 4.64 |
| (328) | 1.79 |
| (329) | 1.97 |
| (331) | 0.69 |
| (332) | 0.78 |
| (334) | 0.87 |
| (338) | 1.10 |
| (339) | 1.31 |
| (340) | 0.95 |
| (341) | 4.16 |
| (346) | 1.42 |
| (347) | 0.77 |
| (348) | 0.70 |
| (349) | 0.29 |
| (362) | 0.22 |
| (372) | 3.71 |
| (375) | 2.18 |
| (377) | 7.21 |
| (380) | 4.38 |
| (382) | 1.31 |
| (384) | 1.08 |
| (387) | 0.33 |
| (388) | 0.68 |
| (389) | 0.73 |
| (390) | 0.74 |
| (391) | 1.02 |
| (392) | 1.9 |
| (393) | 7.4 |
| (395) | 1.8 |
| (398) | 0.94 |
| (466) | 3.66 |
| (471) | 1.63 |
| (472) | 1.16 |
| (473) | 2.1 |
| (475) | 3.16 |
| (477) | 2.28 |
| (479) | 3.23 |
| (480) | 1.17 |
| (481) | 4.14 |
| (482) | 11.12 |
| (483) | 1.26 |
| (486) | 2.57 |
| (487) | 6.1 |
| (488) | 1.02 |
| (489) | 1.21 |
| (490) | 0.62 |
| (491) | 0.48 |
| (493) | 3.05 |
| (496) | 1.03 |
| (497) | 5.56 |
| (499) | 1.67 |
| (500) | 3 |
| (505) | 8.07 |
| (506) | 1.14 |
| (507) | 0.77 |

[a]Firefly inhibitor
[b]Renilla interference
[c]Renilla interference/Firefly only

TABLE 4

| Cpd # | E$_{max}$ (%) |
|---|---|
| (1) | 19 |
| (3) | 59 |
| (6) | 21 |
| (7) | 39 |
| (8) | 25 |
| (10) | 21 |
| (12) | 54[a] |
| (13) | 16 |
| (14) | 53 |
| (16) | 67 |
| (18) | 39 |
| (20) | 22 |
| (22) | 49 |
| (23) | 34 |
| (26) | 66 |
| (28) | 98 |
| (36) | 18 |
| (38) | 5 |
| (41) | 35 |
| (44) | 19 |
| (45) | 56 |
| (47) | 99 |
| (54) | 13 |
| (55) | 173 |
| (56) | 152 |
| (58) | 155 |
| (60) | 13 |
| (65) | 32 |
| (67) | 13 |
| (68) | 62 |
| (72) | 39 |
| (73) | 133 |
| (74) | 64 |
| (76) | 69 |
| (77) | 321 (RT-PCR)[b] |
| (79) | 43 |
| (83) | 4 |
| (84) | 250.6 (RT-PCR)[a] |
| (85) | 96 |
| (86) | 29 |
| (87) | 46 |
| (88) | 33 |
| (89) | 21 |
| (90) | 159 |
| (93) | 63 |
| (94) | 180.1 (RT-PCR)[a] |
| (95) | 103 |
| (96) | 65 |
| (99) | 47 |
| (100) | 235 |
| (102) | 52 |
| (104) | 246 |
| (105) | 134.5/Firefly only[c] |
| (106) | 14 |
| (107) | 183.5/Firefly only[c] |
| (108) | 172 (RT-PCR)[a] |
| (109) | 128/Firefly only[c] |
| (110) | 193/Firefly only[c] |
| (111) | 191/Firefly only[c] |
| (112) | 110.85/Firefly only[c] |
| (113) | 132 |

TABLE 4-continued

| Cpd # | $E_{max}$ (%) |
|---|---|
| (114) | 174/Firefly only[c] |
| (115) | 174 |
| (116) | 112 |
| (117) | 23 |
| (118) | 112 |
| (119) | 114 |
| (120) | 166 |
| (121) | 189 |
| (122) | 256 |
| (123) | 92 |
| (124) | 180 |
| (125) | 225 |
| (126) | 155 |
| (127) | 264 |
| (128) | 155 |
| (129) | 169 |
| (130) | 201 |
| (131) | 190 |
| (132) | 67.7 (RT-PCR)[a] |
| (133) | 143 |
| (134) | 174 |
| (135) | 194 |
| (136) | 143 |
| (137) | 214 |
| (138) | 174 |
| (139) | 52.2 (RT-PCR)[a] |
| (141) | 103 |
| (142) | 121 |
| (143) | 24 |
| (144) | 127 |
| (145) | 59 |
| (146) | 154 |
| (147) | 80 |
| (148) | 62 |
| (150) | 320 (RT-PCR)[a] |
| (151) | 73 |
| (152) | 35 |
| (153) | 20 |
| (154) | 151 |
| (155) | 151[a] |
| (156) | 73 |
| (158) | 20 |
| (159) | 228[a] |
| (160) | 85 |
| (161) | 65 |
| (162) | 103 |
| (163) | 35 |
| (164) | 68 |
| (165) | 59 |
| (166) | 80 |
| (167) | 37 |
| (168) | 54 |
| (170) | 92 |
| (171) | 48 |
| (172) | 61 |
| (173) | 30 |
| (174) | 37 |
| (175) | 29 |
| (176) | 48 |
| (177) | 60 |
| (178) | 76 |
| (179) | 49 |
| (180) | 28 |
| (181) | 122 |
| (182) | 20 |
| (184) | 169 |
| (185) | 22 |
| (186) | 17 |
| (187) | 111 |
| (188) | 145 |
| (189) | 33 |
| (190) | 68 |
| (191) | 231 |
| (192) | 210 |
| (194) | 241 |
| (195) | 81 |
| (196) | 7 |
| (197) | 14 |
| (198) | 125 |
| (199) | 22 |
| (200) | 11 |
| (201) | 27 |
| (202) | 137 |
| (203) | 27.00[a] |
| (204) | 27 |
| (205) | 27 |
| (206) | 27 |
| (207) | 109 |
| (208) | 83 |
| (209) | 176 |
| (210) | 104 |
| (211) | 204 |
| (212) | 71 |
| (213) | 36 |
| (214) | 197 |
| (216) | 16 |
| (217) | 151 |
| (218) | 154 |
| (220) | 153 |
| (221) | 86 |
| (222) | 146 |
| (223) | 95 |
| (224) | 139 |
| (225) | 114 |
| (226) | 191 |
| (227) | 163 |
| (228) | 152 |
| (229) | 55 |
| (230) | 216 |
| (231) | 77 |
| (232) | 59 |
| (233) | 152 |
| (234) | 94 |
| (235) | 80 |
| (236) | 83 |
| (237) | 21 |
| (238) | 64 |
| (239) | 147 |
| (240) | 124 |
| (241) | 13 |
| (242) | 31 |
| (243) | 120 |
| (244) | 150 |
| (245) | 122 |
| (246) | 22 |
| (247) | 215 |
| (248) | 10 |
| (249) | 256 |
| (250) | 63 |
| (251) | 258 |
| (252) | 43 |
| (253) | 187 |
| (254) | 145 |
| (255) | 42 |
| (256) | 129 |
| (257) | 62 |
| (258) | 165 |
| (259) | 109 |
| (260) | 130 |
| (261) | 143 |
| (262) | 64 |
| (263) | 105 |
| (264) | 44 |
| (265) | 119 |
| (266) | 106 |
| (267) | 183 |
| (268) | 19 |
| (269) | 119 |
| (270) | 218 |
| (271) | 206 |
| (272) | 155 |
| (273) | 254 |
| (274) | 259 |
| (275) | 230 |
| (276) | 188 |
| (277) | 197 |

TABLE 4-continued

| Cpd # | $E_{max}$ (%) |
|---|---|
| (278) | 141 |
| (279) | 54 |
| (280) | 25 |
| (281) | 17 |
| (282) | 233 |
| (283) | 29 |
| (284) | 27 |
| (285) | 115 |
| (286) | 38 |
| (287) | 106 |
| (288) | 56 |
| (289) | 128 |
| (290) | 238 |
| (291) | 165 |
| (292) | 312 |
| (293) | 169 |
| (294) | 183 |
| (295) | 54 |
| (296) | 178 |
| (297) | 150 |
| (298) | 21 |
| (299) | 216 |
| (300) | 84 |
| (301) | 45 |
| (302) | 176 |
| (303) | 243 |
| (304) | 166 |
| (305) | 284 |
| (306) | 247 |
| (307) | 292 |
| (308) | 310 |
| (309) | 194 |
| (310) | 191 |
| (311) | 221 |
| (312) | 195 |
| (313) | 102 |
| (314) | 198 |
| (315) | 165 |
| (316) | 108 |
| (317) | 223 |
| (318) | 186 |
| (319) | 204 |
| (320) | 208 |
| (321) | 197 |
| (322) | 21 |
| (323) | 26 |
| (324) | 226 |
| (325) | 20 |
| (326) | 287 |
| (327) | 145 |
| (328) | 184 |
| (329) | 209 |
| (330) | 20 |
| (331) | 209 |
| (332) | 189 |
| (333) | 51 |
| (334) | 177 |
| (335) | 35 |
| (336) | 20 |
| (337) | 23 |
| (338) | 222 |
| (339) | 188 |
| (340) | 220 |
| (341) | 155 |
| (342) | 16 |
| (344) | 18.35 |
| (346) | 181 |
| (347) | 186.5 |
| (348) | 171 |
| (349) | 227 |
| (350) | 49.5 |
| (351) | 22 |
| (352) | 25 |
| (353) | 78 |
| (354) | 57.5 |
| (355) | 26 |
| (356) | 17 |
| (359) | 31.5 |

TABLE 4-continued

| Cpd # | $E_{max}$ (%) |
|---|---|
| (360) | 12.3 |
| (361) | 9.8 |
| (362) | 250 |
| (363) | 53.2 |
| (364) | 18.2 |
| (365) | 22.4 |
| (366) | 19.2 |
| (367) | 94 |
| (368) | 2.4 |
| (369) | 57.8 |
| (370) | 33 |
| (371) | 82 |
| (372) | 125.5 |
| (373) | 25.1 |
| (374) | 34.2 |
| (375) | 133.5 |
| (376) | 23.5 |
| (377) | 101.3 |
| (378) | 31.8 |
| (379) | 95 |
| (380) | 108 |
| (381) | 63.4 |
| (382) | 192.7 |
| (383) | 30.3 |
| (384) | 151.5 |
| (385) | 46 |
| (386) | 69.2 |
| (387) | 238.4 |
| (388) | 215.3 |
| (389) | 211 |
| (390) | 201 |
| (391) | 193.2 |
| (392) | 134.5 |
| (393) | 85.2 |
| (394) | 4.8 |
| (395) | 180.5 |
| (396) | 38.7 |
| (397) | 26.3 |
| (398) | 176 |
| (400) | 11.4 |
| (401) | 41.2 |
| (402) | 21 |
| (403) | 39 |
| (404) | 51 |
| (406) | 20 |
| (411) | 55 |
| (415) | 10.9 |
| (426) | 59 |
| (438) | 44 |
| (441) | 42.8 |
| (442) | 58.6 |
| (456) | 52.3 |
| (458) | 73.1 |
| (463) | 90 |
| (465) | 26.3/RT-PCR[a] |
| (466) | 221 |
| (469) | 13.3 |
| (470) | 76.8 |
| (471) | 149 |
| (472) | 151 |
| (473) | 130.2 |
| (474) | 24.9 |
| (475) | 136.5 |
| (476) | 25.5 |
| (477) | 107.5 |
| (478) | 84.1 |
| (479) | 143.5 |
| (480) | 155.5 |
| (481) | 93.4 |
| (482) | 99.1 |
| (483) | 138 |
| (484) | 40.2 |
| (485) | 72.3 |
| (486) | 150.5 |
| (487) | 114.2 |
| (488) | 206.5 |
| (489) | 131 |
| (490) | 176.5 |

TABLE 4-continued

| Cpd # | $E_{max}$ (%) |
|---|---|
| (491) | 155 |
| (492) | 54.5 |
| (493) | 168 |
| (494) | 14.1 |
| (495) | 13.9 |
| (496) | 233 |
| (497) | 120.5 |
| (498) | 37.7 |
| (499) | 156.5 |
| (500) | 141 |
| (501) | 18.1 |
| (502) | 28 |
| (503) | 27.2 |
| (504) | 80 |
| (505) | 139.5 |
| (506) | 144.5 |
| (507) | 167 |
| (508) | 80 |
| (509) | 40.8 |
| (510) | 20 |
| (511) | 35.15 |
| (512) | 43.7 |

[a] Firefly inhibitor
[b] Renilla interference
[c] Renilla interference/Firefly only

Example 45. Secondary Assay

Compounds with an $EC_k<2$ μM in the primary assay (see Example 44) were used in a secondary assay to treat FD fibroblast. The splicing analysis of IKBKAP in the FD fibroblast was used to validate the results of the most potent compounds obtained with the primary assay in vitro. FD fibroblasts GM04663 were purchased from the Coriell Cell Repository and were grown in Dulbecco's Modified Eagle's media (DMEM) (GIBCO ref 11995-065). The media was supplemented with 2 mM L-glutamine, 1% penicillin/streptomycin and 10% fetal bovine serum (SIGMA cat. 12306C). Cells were plated in 6-wells and were treated 24 hours after plating. Compounds are added to the media using two different concentrations (0.08 μM and 0.8 μM). Cells were also treated with Kinetin 200 μM and DMSO 0.5%. Test compounds and kinetin were diluted in PBS with a final DMSO concentration of 0.5%. After 24 hours of treatment total RNA was extracted using QIAzol (QUIAGEN cat. 79306) following the manufacture's protocol. Reverse Transcription (RT) was then performed using 0.5 μg of total RNA, oligo(dT), random primers, and Superscript III (INVITROGEN cat. 18080-044) reverse transcriptase according to manufacturer's protocol. For splicing assessment, semi-quantitative PCR was used with cDNA equivalents of 75 ng of starting RNA in a 20 μL reaction mixture, with the use of Go Taq Green Master Mix (PROMEGA ref. M712C) and specific primers that recognize exon 19 (EXON19F: CCT GAG CAG CAA TCA TGT G; SEQ ID NO:1) and exon23 (EXON23R: TAC ATG GTC TTC GTG ACA TC; SEQ ID NO:2) of IKBKAP. The PCR reaction was carried out for 35 cycles (94° C. for 30 seconds; 58° C. for 30 seconds; 72° C. for 30 seconds) in a C1000 ThermoCycler (BIORAD). The PCR products were separated in a 1.5% agarose (INVITROGEN ref 16500) gel stained with Ethidium Bromide (SIGMA E1501). The bands were visualized with UV light using the AlphaImager 2200 (ALPHA INNOTECH). IKBKAP wild type band is 363 base pairs (bp) and IKBKAP mutant band is 289 bp due to exon20 skipping. Relative band intensity was determined by evaluating the integrated density values as determined by ImageJ software. Splicing correction was measured as the ratio of wild type transcript to total transcript (mutant plus wild type). These values were normalized using the splicing correction values of Kinetin and DMSO treated samples as positive and negative controls. The results were used to confirm the data obtained with the primary assay and to discriminate compounds based on their potency in vitro.

Table 5 shows % exon inclusion data (normalized) for representative compounds at various concentrations (PM) using the secondary assay.

TABLE 5

| Compound No. | Concentration (μM) | % exon Inclusion Normalized | Standard Deviation |
|---|---|---|---|
| Kinetin | 200 | 100 | 8.20 |
| (271) | 0.08 | 62.17 | 15.10 |
| (271) | 0.8 | 106.66 | 8.20 |
| (274) | 0.08 | 37.94 | 7.70 |
| (274) | 0.8 | 99.03 | 10.50 |
| (320) | 0.08 | 47.12 | 3.00 |
| (320) | 0.8 | 103.47 | 7.60 |
| (302) | 0.08 | 23.29 | 7.40 |
| (302) | 0.8 | 90.80 | 9.00 |
| (319) | 0.08 | 14.24 | 6.00 |
| (319) | 0.8 | 77.85 | 9.00 |
| (347) | 0.8 | 72.01 | 9.74 |
| (347) | 0.08 | 18.31 | 9.18 |
| (346) | 0.8 | 58.64 | 13.06 |
| (346) | 0.08 | 23.20 | 11.06 |
| (100) | 0.8 | 62.10 | 17.72 |
| (100) | 0.08 | 22.62 | 6.28 |
| (348) | 0.8 | 101.72 | 8.19 |
| (348) | 0.08 | 49.042 | 6.44 |
| (349) | 0.8 | 95.28 | 7.51 |
| (349) | 0.08 | 27.07 | 5.13 |
| (362) | 0.8 | 104.69 | 23.98 |
| (362) | 0.08 | 63.75 | 24.64 |
| Kinetin | 200 | 100 | 3.66 |
| (275) | 0.08 | 37.19 | 2.34 |
| (275) | 0.8 | 101.23 | 3.18 |
| (269) | 0.08 | 34.84 | 5.76 |
| (269) | 0.8 | 101.51 | 3.18 |
| (230) | 0.08 | 22.27 | 5.26 |
| (230) | 0.8 | 69.99 | 2.72 |
| (270) | 0.08 | 28.70 | 10.17 |
| (270) | 0.8 | 101.36 | 3.46 |
| (372) | 0.08 | 13.41 | 4.12 |
| (372) | 0.8 | 48.69 | 9.13 |
| (107) | 0.8 | 93.24 | 3.63 |
| (107) | 0.08 | 25.64 | 2.46 |
| (285) | 0.8 | 1.46 | 6.05 |
| (285) | 0.08 | 0.06 | 2.37 |

Example 46. In vivo Familial Dysautonomia Mouse Model

Compound (100)

Compound (100) was administered by oral gavage for eight days at 60 mg/kg/day, 30 mg/kg/day and 10 mg/kg/day to the mouse transgenic familial dysautonomia (FD) model. Every dosing group and the control group (vehicle) consisted of 6 mice. The mice were given food and water ad libitum, and changes in body weights were monitored on a daily basis. On the eighth day the mice were dosed for the last time and after 1 hour the mice were sacrificed and dissected. Plasma, liver, kidney, heart and brain were collected. The splicing analysis was performed in all tissues and confirmed the presence of (100) in the plasma. Compound (100) improved splicing in kidney, heart, and liver at all doses tested (doses=10, 30 and 60 mg/kg/day). In liver, compound (100) at 30 mg/kg/day reached the same level of correction observed with Kinetin treatment at 400 mg/kg/day. In heart, compound (100) at 10 mg/kg/day improved splicing better than Kinetin at 400 mg/kg/day. In kidney, there were no significant changes in splicing after treatment with kinetin at 400 mg/kg/day whereas improvements were observed using compound (100) even at 10 mg/kg/day. Compound (100) was evident in the brain and corrected splicing at 30 and 60 mg/kg whereas there was no significant change observed in the brain after 8 days of treatment with kinetin 400 mg/kg/day.

In liver, it was shown that the treatment with compound (100) at 30 mg/kg/day increased the level of the IKAP protein whereas there were no significant changes after treatment with kinetin at 400 mg/kg/day.

Compounds (230) and (270)

The following solutions were prepared daily: Compound (230) in 10% DMA/45% PEG 300/12% EtOH/33% sterile water; and Compound (270) in 10% DMA/45% PEG 300/12% EtOH/33% sterile water.

Six transgenic mice for each dose (60, mg/kg/day; 30 mg/kg/day; and 10 mg/kg/day) were fed using a 20 Gauge feeding needle (Fine Science Tools Inc., CA, USA) for a period of 8 days. Six transgenic mice were fed daily with 10% DMA/45% PEG 300/12% EtOH/33% sterile water solution for the same duration. The mice were given food and water ad libitum, and changes in body weights were monitored on a daily basis. On the eighth day the mice were dosed for the last time and after 1 hour were sacrificed and dissected. Plasma, lungs, muscle, liver, heart, brain, kidney, sciatic nerve, and trigeminal nerve were collected. Splicing was evaluating by RT-PCT and IKAP protein was evaluated using Western Blotting.

Results

The data shown in FIGS. 1A-6 for representative compounds (100), (230) and (270) demonstrate that the compounds are useful for improving inclusion of exon 20.

Example 47. Protein Isolation and Western Blot Analysis

Protein extracts were obtained by homogenizing liver or cell pellets in RIPA buffer (Tris-HCl 50 mM, pH 7.4; NaCl 150 mM; NP-40 1%; Sodium deoxycholate 0.5%; SDS 0.1%) containing protease inhibitor cocktail (Sigma), DTT (100 µM) and PMSF (100 µM). Insoluble debris were discarded after centrifugation and protein concentration was determined using Pierce® 400 BCA Protein Assay Kit (Thermo Scientific). 50 µg of protein was separated on NuPage 4-12% Bis-Tris Gel (Invitrogen) and transferred into nitrocellulose membrane (Thermo Scientific). Membrane was blocked in 5% non-fat milk for one hour at room temperature and incubated overnight at 4° C. with rabbit polyclonal antibody against the C-terminus region of the human IKAP protein (Anaspec, 1:2000) or mouse monoclonal antibody against human IKAP protein (Sigma, 1:2000) and with the rabbit polyclonal antibody against actin (Sigma, 1:2000).

Figure 7:
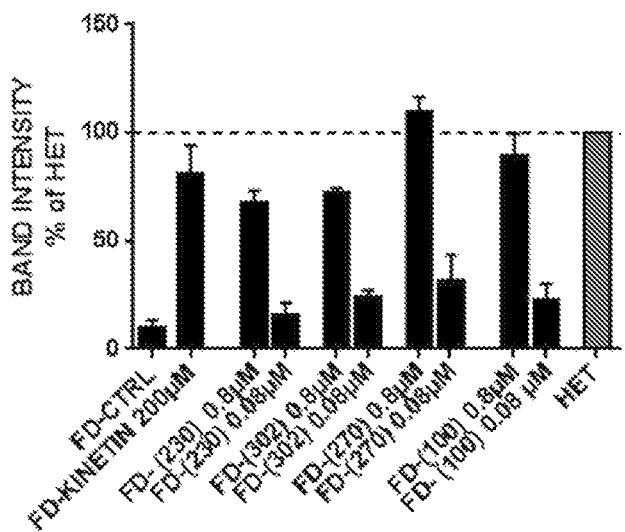
FIG. 7 shows results of a Western Blot on familial dysautonomia (FD) human fibroblast treated for five days with representative compounds (230), (302), (270), and (100).

Membranes were washed and incubated with secondary antibodies for 1 hour at room temperature. Protein bands were visualized by chemiluminescence (Pierce® 407 ECL Western 408 Blotting Substrate, Thermo Scientific) followed by exposure to autoradiographic film. IKAP levels in FD fibroblasts were compared with the level of protein found in heterozygote (HET) fibroblasts, as shown in FIG. 7.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I):

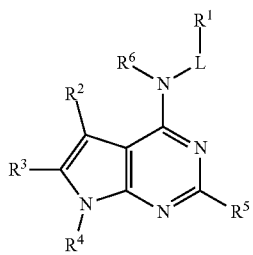

(Ia)

or a pharmaceutically acceptable salt thereof, wherein:

L is selected from the group consisting of methylene, $C_{2-6}$ alkenylene, and $C_{2-6}$ alkynylene, wherein the $C_{2-6}$ alkenylene and $C_{2-6}$ alkynylene are each optionally substituted by 1, 2, 3, or 4 independently selected $R^{20}$ groups;

$R^1$ is selected from the group consisting of $C_{6-10}$ aryl, 2-benzofuranyl, 4-quinolinyl, and a 5-6 member heteroaryl, each optionally substituted by 1, 2, 3, or 4 independently selected $R^{1A}$ groups;

each $R^{1A}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{1-6}$ alkoxy, —C(=O)OH, —C(=O)$C_{1-6}$ alkyl, —C(=O)$C_{1-6}$ haloalkyl, and —C(=O)$C_{1-6}$ alkoxy;

$R^2$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a2}$, C(=O)$R^{b2}$, C(=O)$OR^{b2}$, $NR^{c2}R^{d2}$, C(=O)$NR^{c2}R^{d2}$, —OC(=O)$NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)_2R^{b2}$, $NR^{c2}R^{d2}$, S(O)$NR^{c2}R^{d2}$, and S(O)$_2NR^{c2}R^{d2}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^3$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a3}$, $SR^{a3}$, C(=O)$R^{b3}$, C(=O)$OR^{b3}$, $NR^{c3}R^{d3}$, C(=O)$NR^{c3}R^{d3}$, OC(=O)$NR^{c3}R^{d3}$, $NR^{c3}C(=O)R^{b3}$, $NR^{c3}C(=O)OR^{b3}$, $NR^{c3}C(=O)NR^{c3}R^{d3}$, $NR^{c3}S(=O)_2R^{b3}$, $NR^{c3}S(=O)_2NR^{c3}R^{d3}$, S(O)$NR^{c3}R^{d3}$, and S(O)$_2NR^{c3}R^{d3}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^4$ is selected from the group consisting of H, oxo, azido, halo, CN, $NO_2$, $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a4}$, C(=O)$R^{b4}$, C(=O)$OR^{b4}$, $NR^{c4}R^{d4}$, C(=O)$NR^{c4}R^{d4}$, —OC(=O)$NR^{c4}R^{d4}$, $NR^{c4}C(=O)R^{b4}$, $NR^{c4}C(=O)OR^{b4}$, $NR^{c4}C(=O)NR^{c4}R^{d4}$, $NR^{c4}S(=O)_2R^{b4}$, $NR^{c4}S(=O)_2NR^{c4}R^{d4}$, S(O)$NR^{c4}R^{d4}$, and S(O)$_2NR^{c4}R^{d4}$, wherein the $C_{1-6}$ alkyl, $C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

$R^5$ is halo;

$R^6$ is selected from the group consisting of H, $C_{1-6}$ haloalkyl, $C_{1-6}$ hydroxyalkyl, and $C_{1-6}$ alkoxy;

each $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$, is independently selected from the group consisting of H, $C_{1-6}$ alkyl, $C_{2-6}$ alkenyl, $C_{2-6}$ alkynyl, $C_{1-6}$ hydroxyalkyl, $C_{1-6}$ haloalkyl, $C_{1-6}$ alkoxy, —($C_{1-6}$ alkylene)-$C_{1-6}$ alkoxy, $C_{3-10}$ cycloalkyl, —($C_{1-6}$ alkylene)-$C_{3-10}$ cycloalkyl, $C_{6-10}$ aryl, 5-10 membered heteroaryl, 4-10 membered heterocycloalkyl, wherein the $C_{1-6}$ alkyl, $C_{2-6}$ alkenyl, $C_{2-6}$ alkynyl, $C_{3-10}$ cycloalkyl, —($C_{1-6}$ alkylene)-$C_{3-10}$ cycloalkyl, $C_{6-10}$ aryl, 5-10 membered heteroaryl, and 4-10 membered heterocycloalkyl are each optionally substituted by 1, 2, 3, or 4 independently selected $R^{20}$ groups;

or $R^{c2}$ and $R^{d2}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c3}$ and $R^{d3}$ together with the N atom to which they are connected, come together to form a 5-10 membered heteroaryl or 4-10 membered heterocycloalkyl ring, each optionally substituted by 1, 2, 3, or 4 independently selected $R^{20}$ groups;

or $R^{c4}$ and $R^{d4}$ together with the N atom to which they are connected, come together to form a 5-10 membered heteroaryl or 4-10 membered heterocycloalkyl ring, each optionally substituted by 1, 2, 3, or 4 independently selected $R^{20}$ groups; and each $R^{20}$ is independently selected from the group consisting of OH, SH, CN, $NO_2$, halo, oxo, $C_{1-4}$ alkyl, $C_{2-4}$ alkenyl, $C_{2-4}$ alkynyl, $C_{1-4}$ haloalkyl, $C_{1-4}$ cyanoalkyl, $C_{1-4}$ hydroxyalkyl, $C_{1-4}$ alkoxy, —($C_{1-4}$ alkyl)-($C_{1-4}$ alkoxy), —($C_{1-4}$ alkoxy)-($C_{1-4}$ alkoxy), $C_{1-4}$ haloalkoxy, $C_{3-6}$ cycloalkyl, phenyl, 5-6 membered heteroaryl, 5-6 membered heterocycloalkyl, amino, $C_{1-4}$ alkylamino, di($C_{1-4}$ alkyl)amino, carbamyl, $C_{1-4}$ alkylcarbamyl, di($C_{1-4}$ alkyl)carbamyl, carbamoyl, $C_{1-4}$ alkylcarbamoyl, di($C_{1-4}$ alkyl)carbamoyl, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$ alkylaminosulfonyl, di($C_{1-4}$ alkyl)aminosulfonyl, aminosulfonylamino, $C_{1-4}$ alkylaminosulfonylamino, di($C_{1-4}$ alkyl)aminosulfonylamino, aminocarbonylamino, $C_{1-4}$ alkylaminocarbonylamino, and di($C_{1-4}$ alkyl)aminocarbonylamino.

2. The compound of claim 1, wherein L is methylene and $R^1$ is selected from the group consisting of:

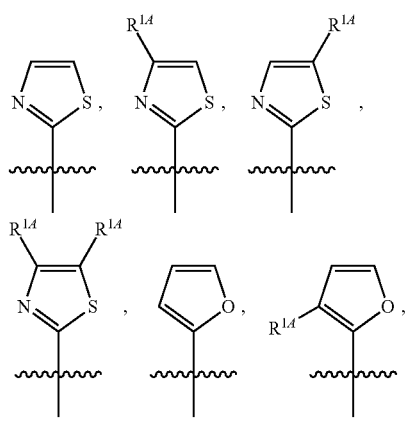

311
-continued
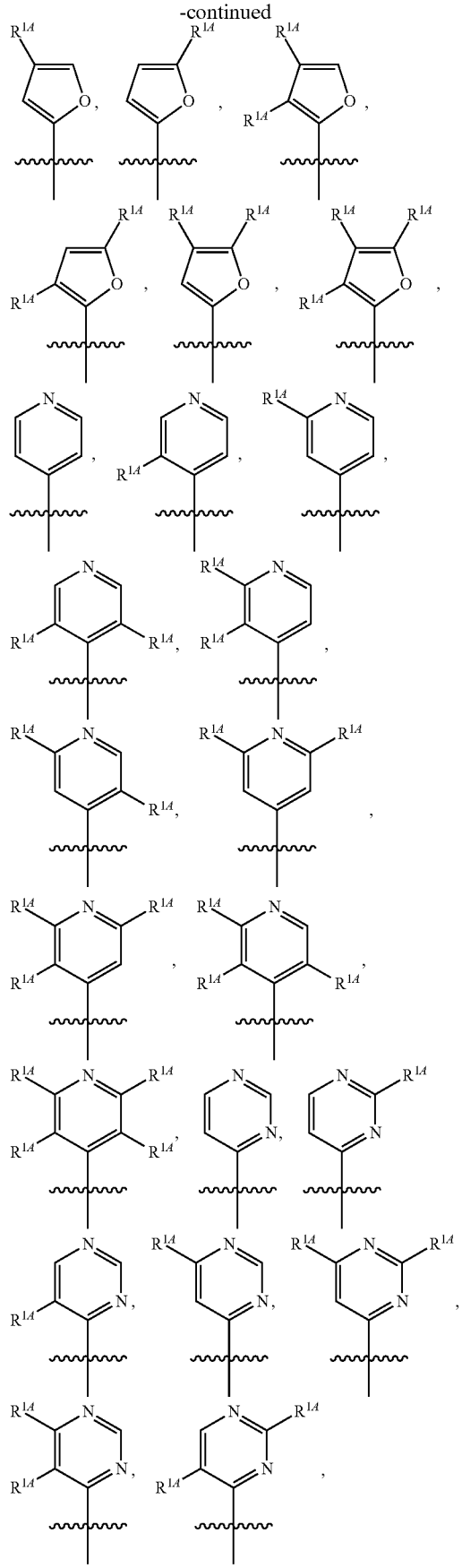
312
-continued
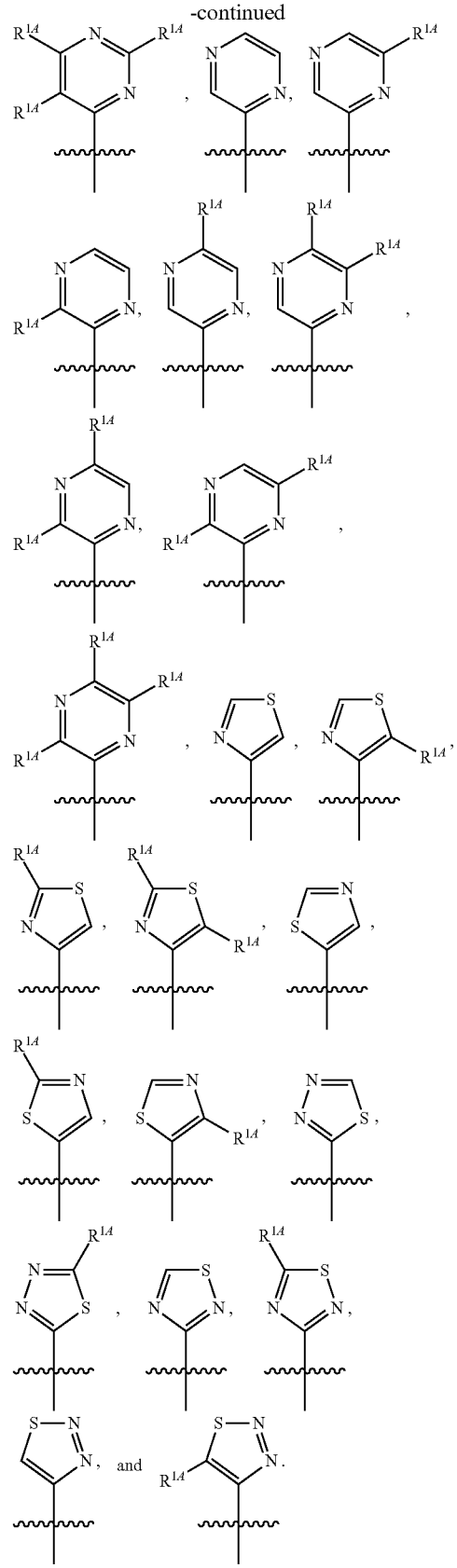
3. The compound of claim 1, wherein $R^3$ is selected from the group consisting of H, oxo, azido, CN, $C_{1-6}$ alkyl, $C_{3-6}$ cycloalkyl, phenyl, 5-6 membered heteroaryl, 5-6 membered heterocycloalkyl, OR$^{a3}$, SR$^{a3}$, NR$^{c3}$R$^{d3}$, C(=O)OR$^{a3}$, —C(=O)NR$^{c3}$R$^{d3}$, —OC(=O)R$^{b3}$, wherein the C$_{1-6}$ alkyl, C$_{3-6}$ cycloalkyl, phenyl, 5-6 membered heteroaryl and 5-6 membered heterocycloalkyl are each optionally substituted by 1, 2, 3, or 4 independently selected R$^{20}$ groups; R$^5$ is halo; and, R$^6$ is hydrogen.

4. A pharmaceutical composition comprising a compound of claim 1, or a pharmaceutically acceptable salt thereof, and at least one pharmaceutically acceptable carrier.

5. The compound of claim 1, wherein the compound is selected from the group consisting of:

(55)

(77)

(81)

(84)

(86)

(89)

(94)

(100)

(101)

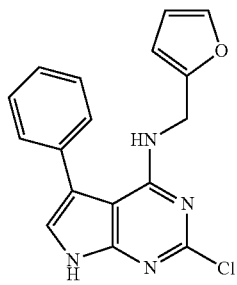
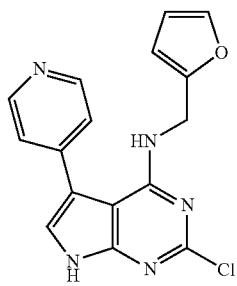
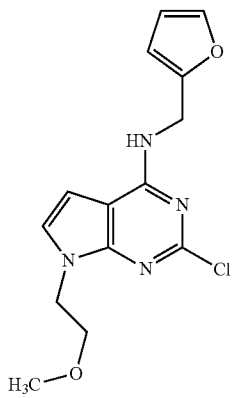
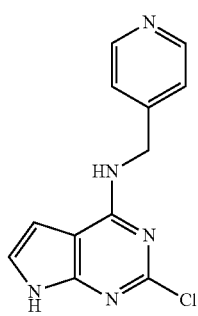
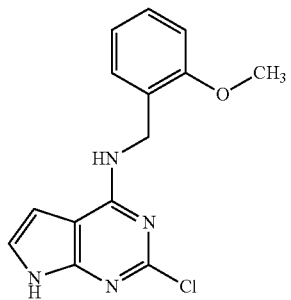

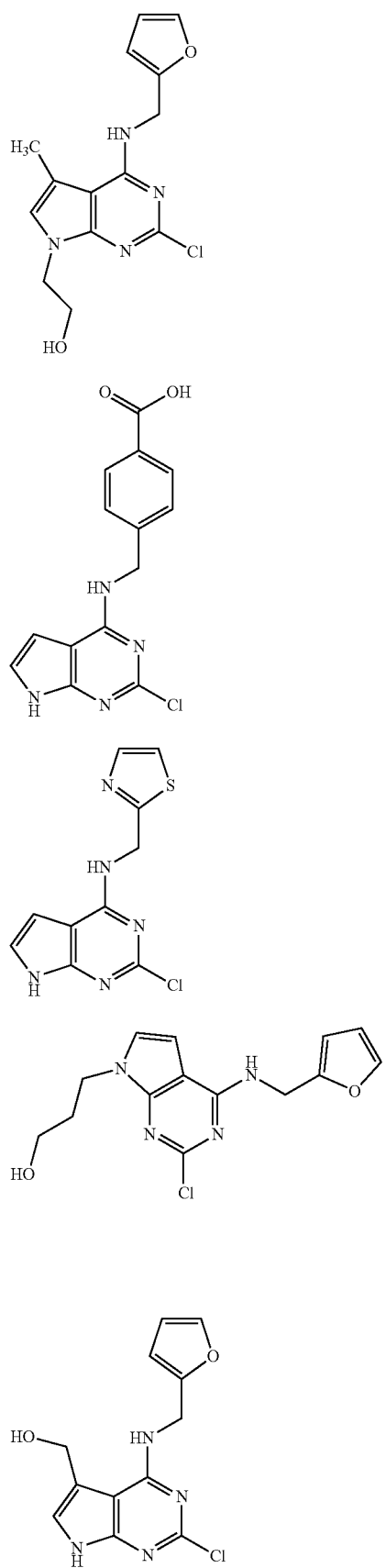

(116) 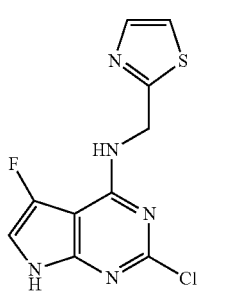
(117) 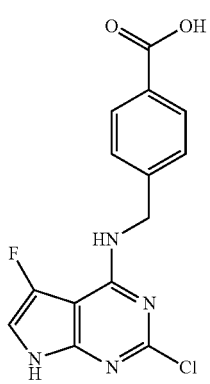
(119) 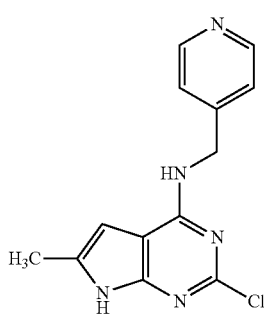
(120) 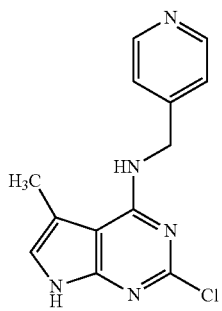
(121) 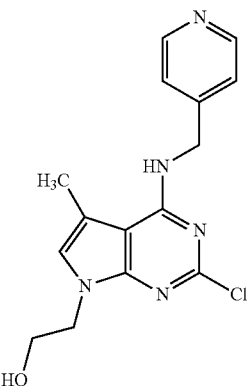
(122) 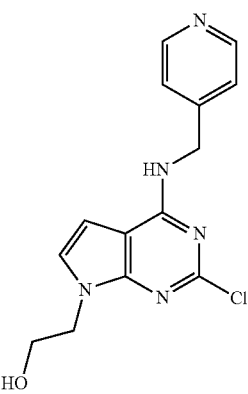
(123) 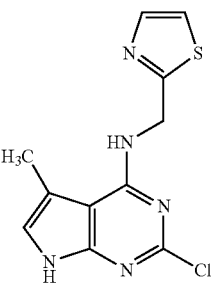
(125) 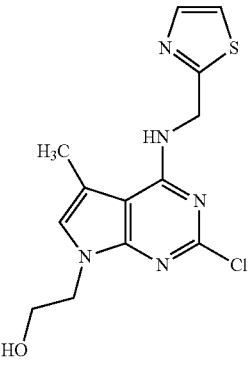

-continued
(126) 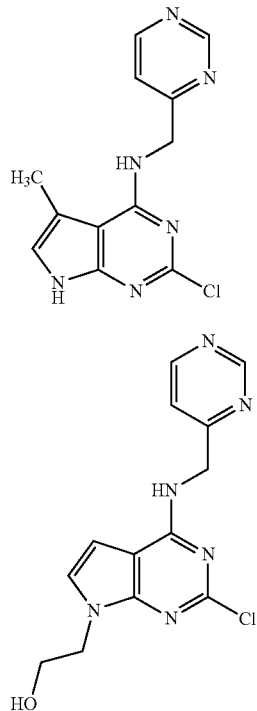
(127) 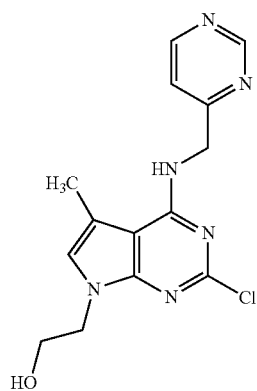
(128) 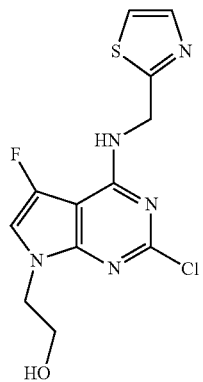
(130)
-continued
(132) 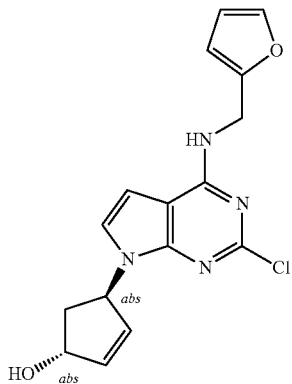
(135) 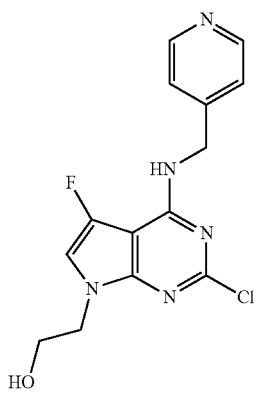
(136) 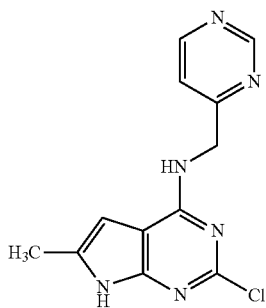
(137) 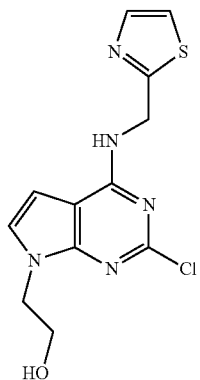

(138)
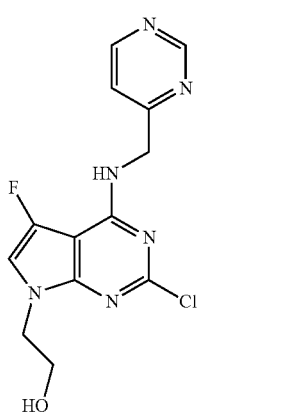
(139)
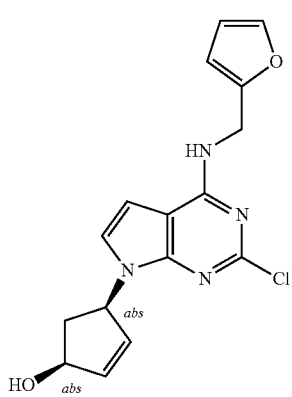
(143)
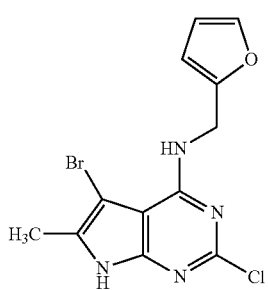
(145)
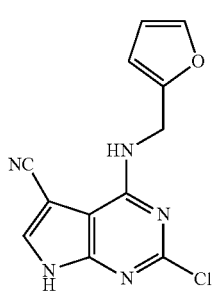
(147)
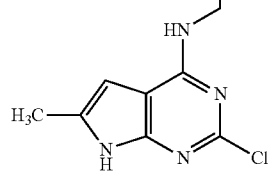
(148)
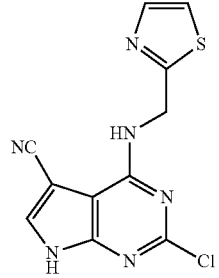
(150)
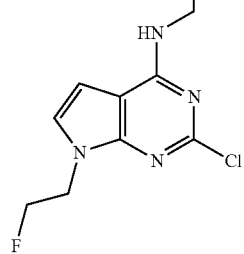
(151)
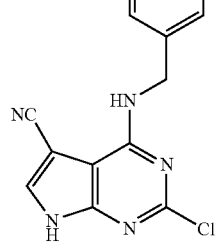
(152)
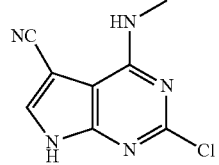

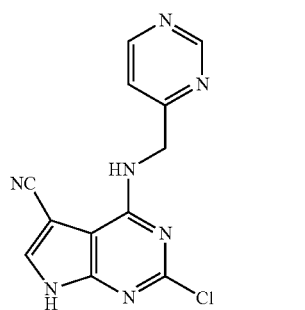
(152)
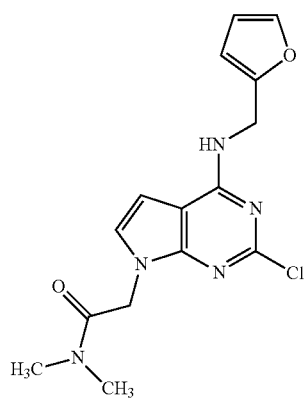
(153)
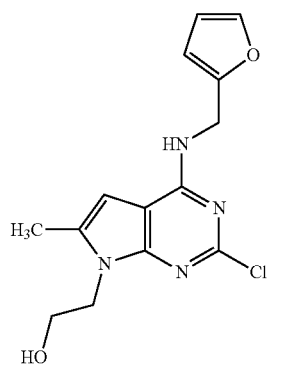
(154)
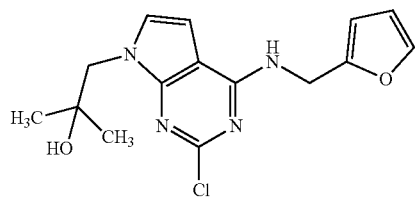
(155)
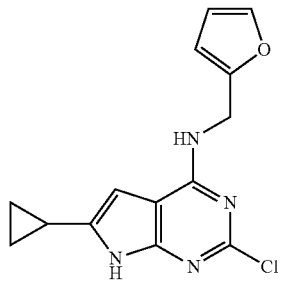
(156)
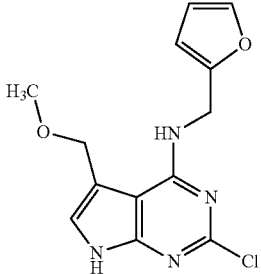
(158)
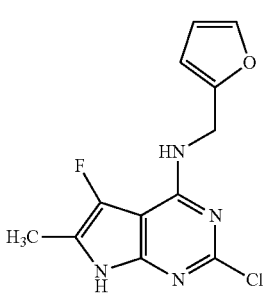
(159)
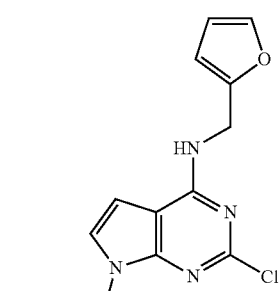
(160)
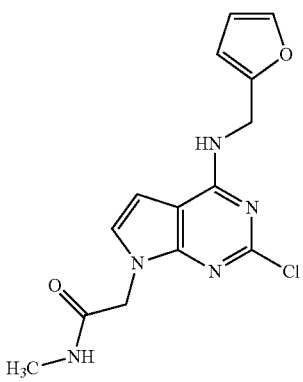
(161)

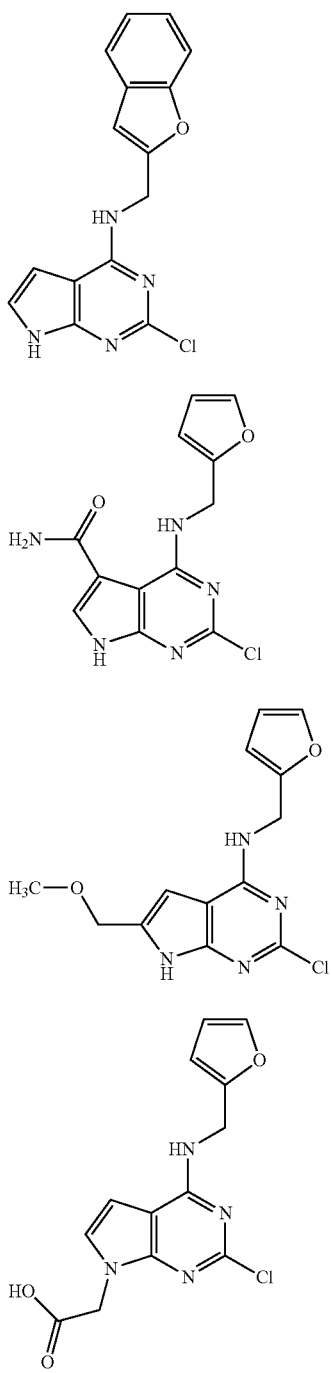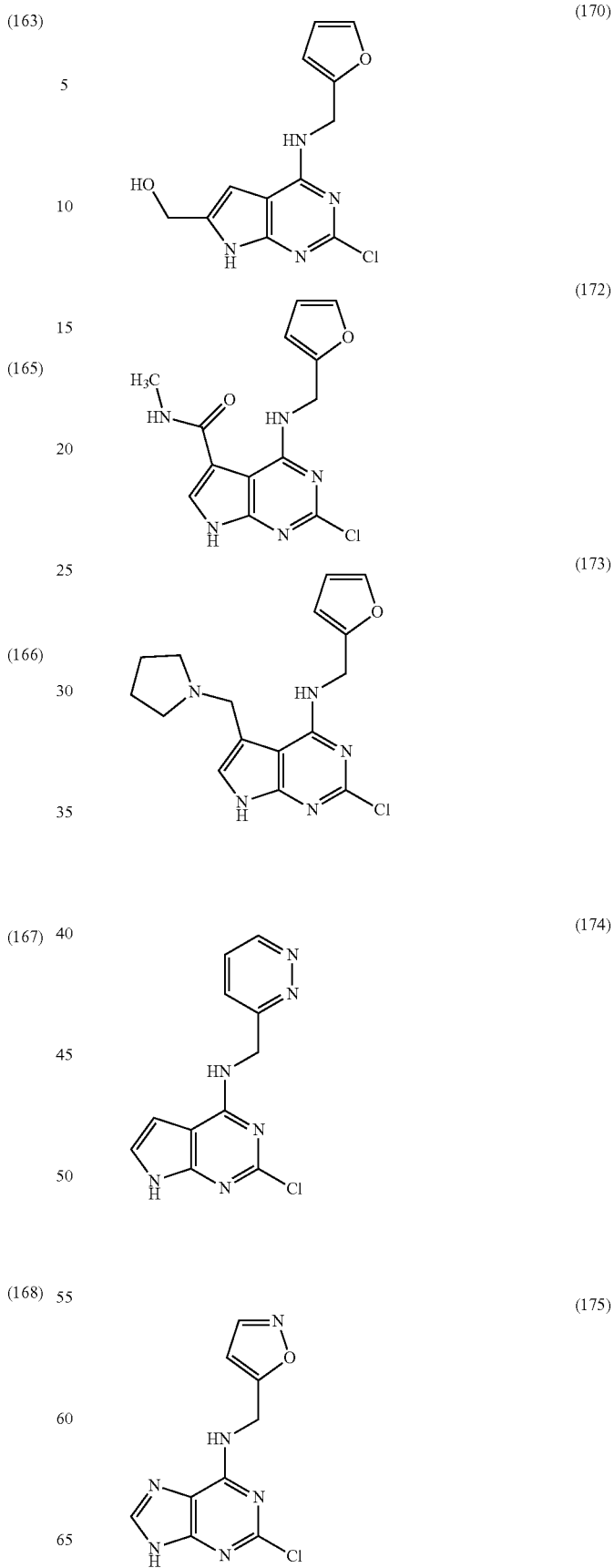

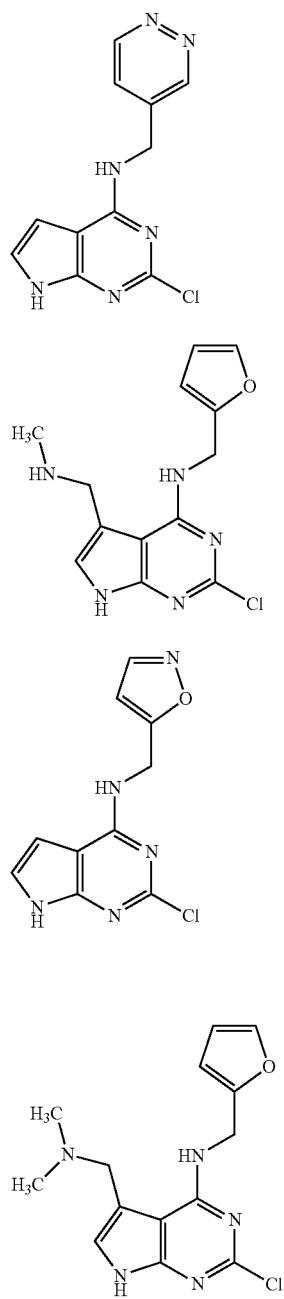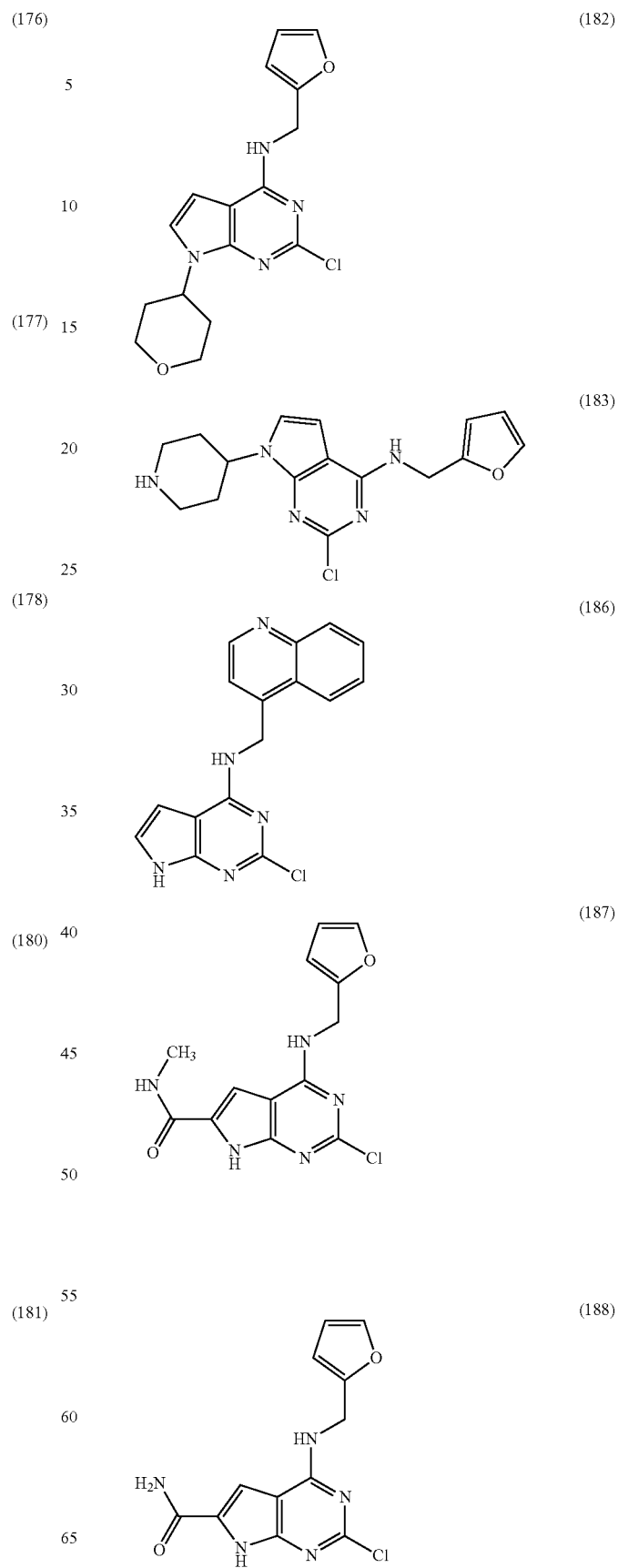

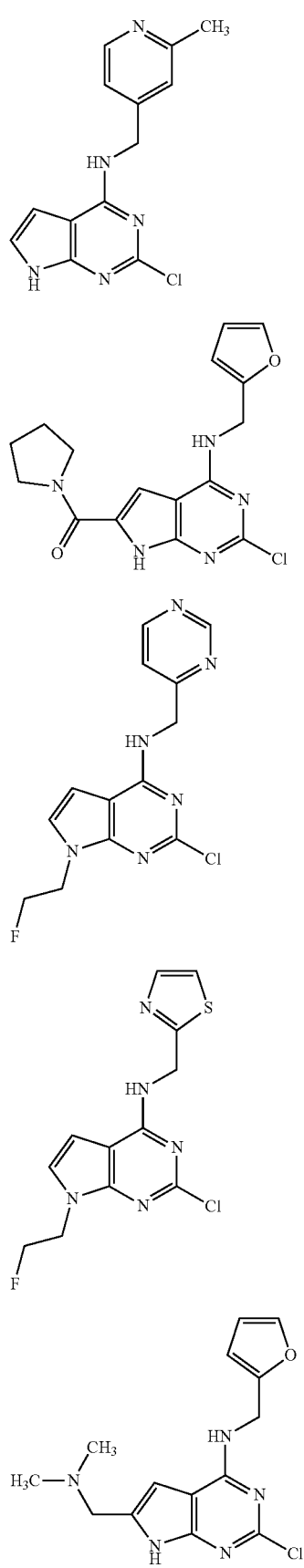
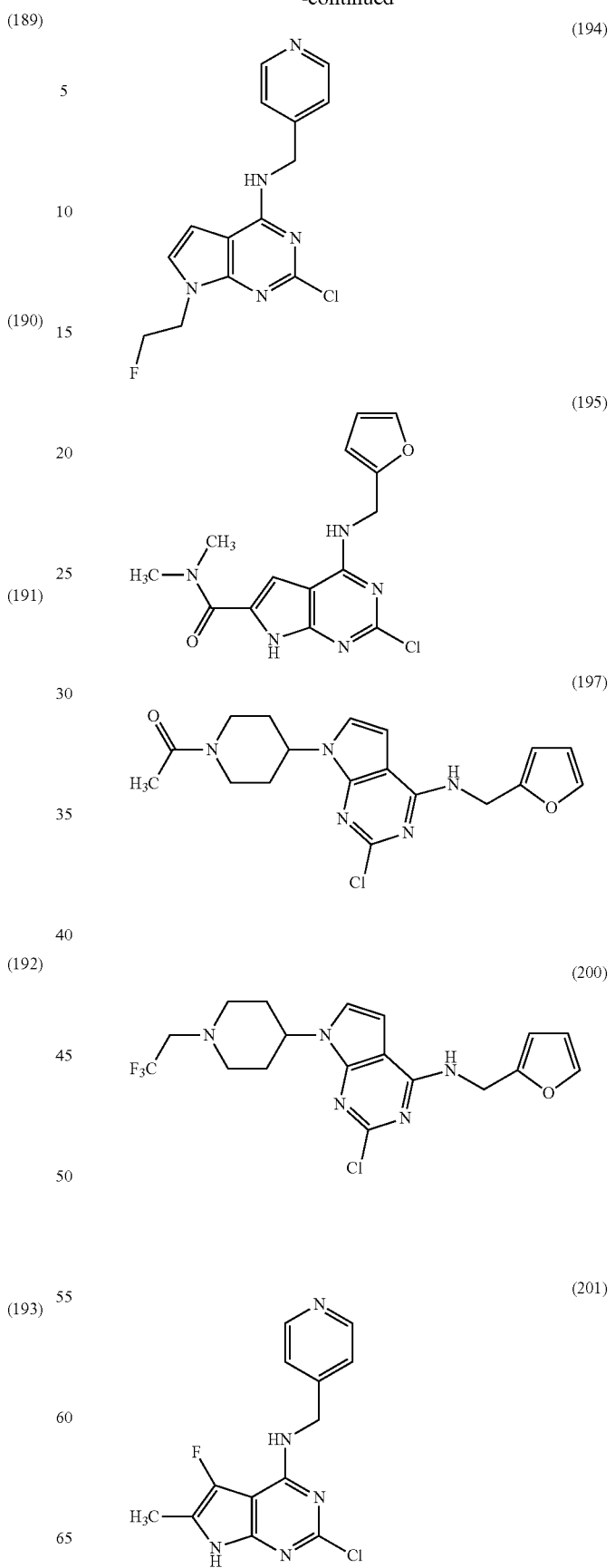

331
-continued
(203)
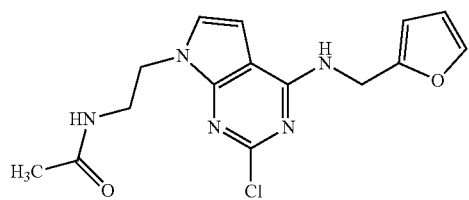
(204)
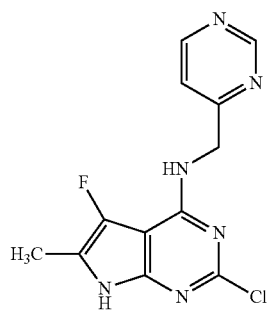
(205)
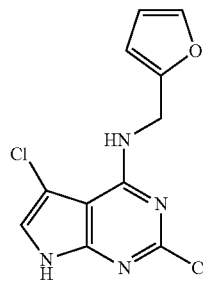
(206)
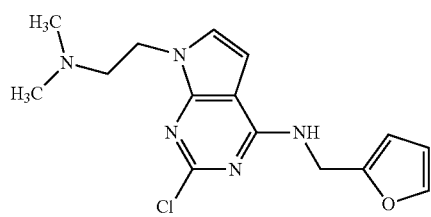
(207)
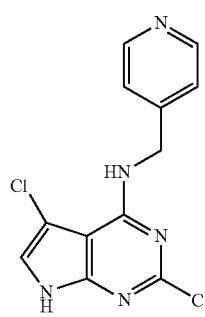
(208)
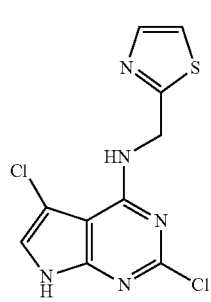
332
-continued
(210)
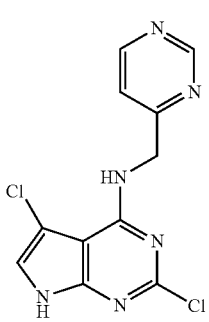
(211)
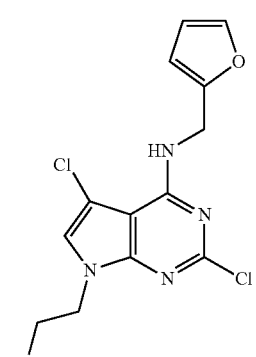
(212)
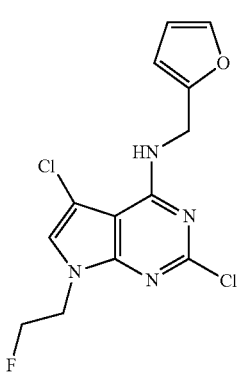
(213)
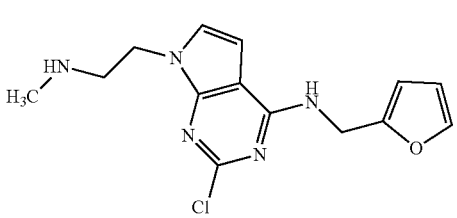
(215)
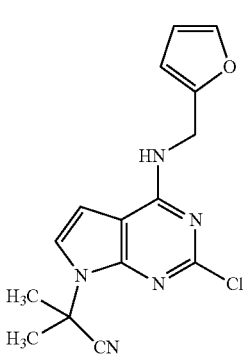

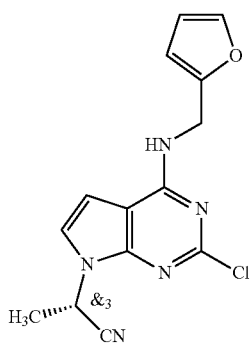
(216)
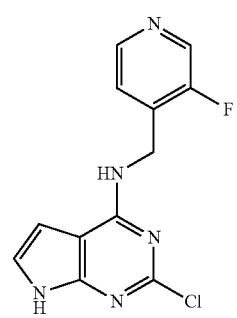
(226)
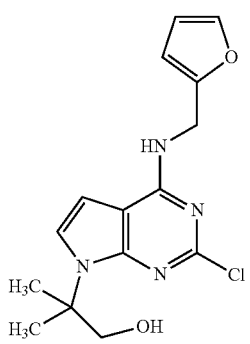
(219)
(228)
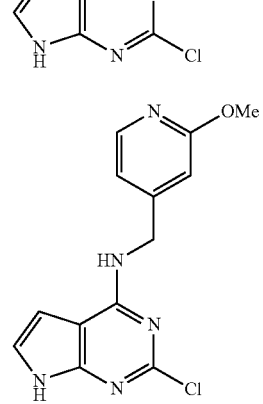
(237)
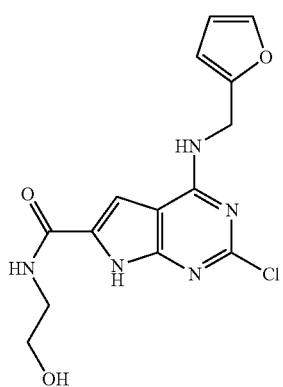
(221)
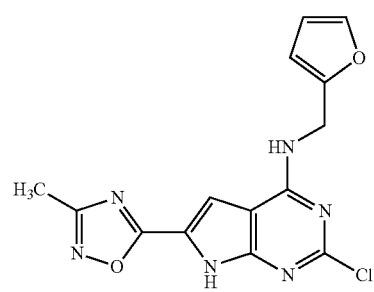
(246)
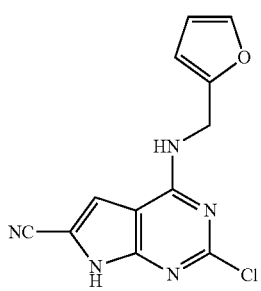
(223)
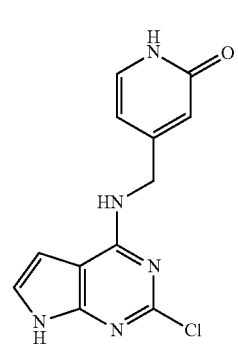
(248)

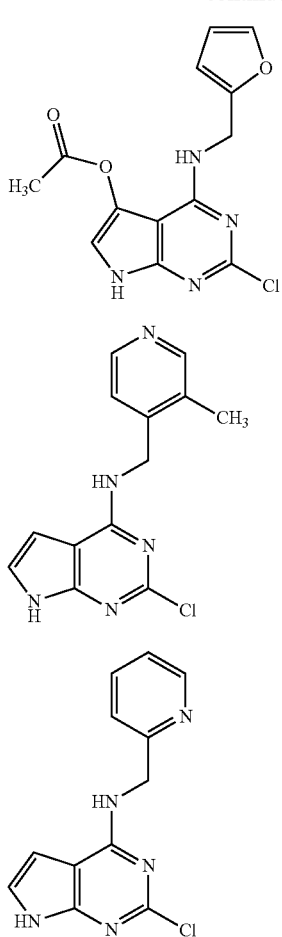
(263)
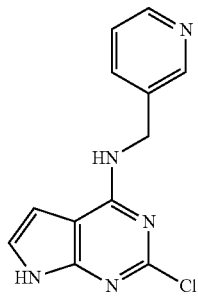
(355)
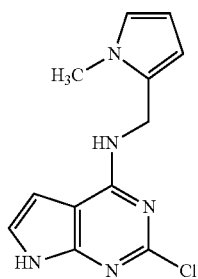
(360)
(350)
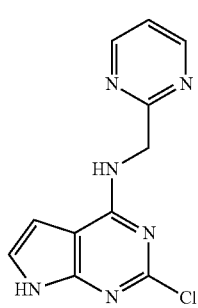
(361)
(353)
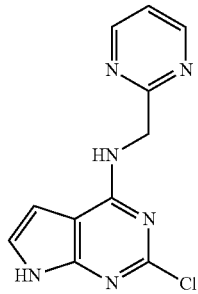
(372)
(354)
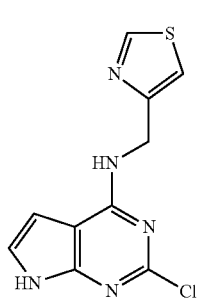
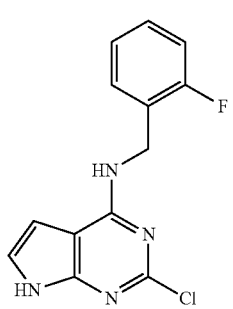
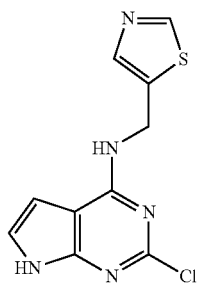
(373)

-continued
(379) 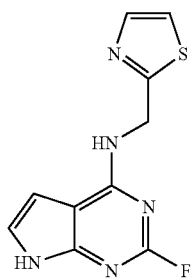
(380) 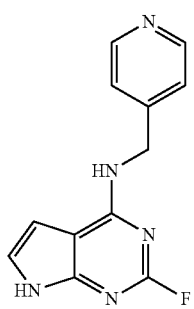
(487) 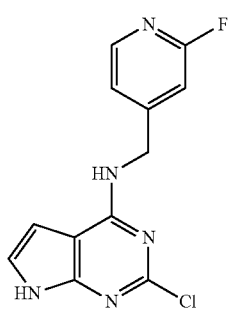
(494) 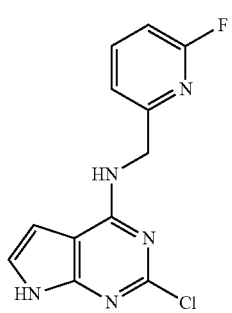
-continued
(495) 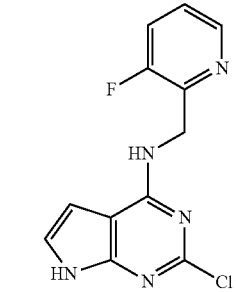
(498) 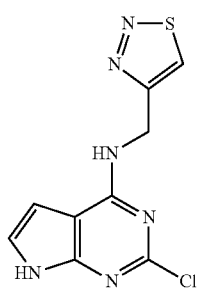
and
(501) 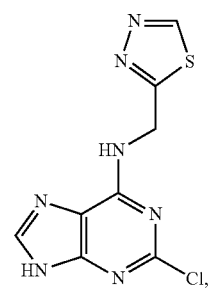
or a pharmaceutically acceptable salt thereof.
* * * * *

UNITED STATES PATENT AND TRADEMARK OFFICE
CERTIFICATE OF CORRECTION

Page 1 of 1

PATENT NO.          : 10,676,475 B2
APPLICATION NO.     : 15/543826
DATED               : June 9, 2020
INVENTOR(S)         : Susan A. Slaugenhaupt et al.

It is certified that error appears in the above-identified patent and that said Letters Patent is hereby corrected as shown below:

On the Title Page

Item (72) Column 1 (Inventors), Line 10 (approx.), delete "Hignham" and insert -- Hingham --

In the Claims

In Column 309, Line 38 (approx.), Claim 1, delete "$NR^{c2}R^{d2}$," and insert
-- $NR^{c2}S(=O)_2NR^{c2}R^{d2}$, --

In Column 309, Line 49, Claim 1, delete "$OC(=O)NR^{c3}R^{d3}$," and insert -- $-OC(=O)NR^{c3}R^{d3}$, --

Signed and Sealed this
Second Day of February, 2021

Drew Hirshfeld
*Performing the Functions and Duties of the
Under Secretary of Commerce for Intellectual Property and
Director of the United States Patent and Trademark Office*